(12) United States Patent
Kahne et al.

(10) Patent No.: US 7,473,671 B2
(45) Date of Patent: *Jan. 6, 2009

(54) GLYCOPEPTIDE ANTIBIOTICS, COMBINATORIAL LIBRARIES OF GLYCOPEPTIDE ANTIBIOTICS AND METHODS OF PRODUCING SAME

(75) Inventors: Daniel Kahne, Princeton, NJ (US); Robert Kerns, Troy, MI (US); Seketsu Fukuzawa, Tokyo (JP); Min Ge, Prineton, NJ (US); Christopher Thompson, Milford, MA (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/631,883

(22) Filed: Jul. 31, 2003

(65) Prior Publication Data

US 2004/0106772 A1 Jun. 3, 2004

Related U.S. Application Data

(63) Continuation of application No. 09/353,368, filed on Jul. 14, 1999, now Pat. No. 6,710,168.

(60) Provisional application No. 60/134,839, filed on May 19, 1999, provisional application No. 60/150,690, filed on Jul. 14, 1998.

(51) Int. Cl.
*C40B 40/14* (2006.01)
(52) U.S. Cl. .............................. 506/20; 506/18; 506/19; 514/8; 530/322
(58) Field of Classification Search ................ 514/8; 530/322
See application file for complete search history.

(56) References Cited

U.S. PATENT DOCUMENTS

| 4,548,925 | A | * | 10/1985 | Higgins et al. ................. 514/10 |
| 5,602,229 | A | | 2/1997 | Malabarba et al. ........... 530/317 |
| 5,668,272 | A | | 9/1997 | Prasad et al. ................ 536/55.3 |
| 5,684,127 | A | | 11/1997 | Malabarba et al. .......... 530/317 |
| 5,750,509 | A | | 5/1998 | Malabarba et al. ............ 514/11 |
| 5,795,958 | A | | 8/1998 | Rao et al. .................... 530/331 |
| 5,837,862 | A | | 11/1998 | Wong et al. .................... 536/53 |
| 5,843,889 | A | | 12/1998 | Cooper et al. .................. 514/8 |
| 6,498,238 | B1 | | 12/2002 | Kim et al. .................. 536/16.8 |
| 2002/0045574 | A1 | | 4/2002 | Kim et al. ....................... 514/8 |

FOREIGN PATENT DOCUMENTS

| EP | 0 802 199 A2 | 10/1997 |
| EP | 0 802 199 A3 | 11/1997 |
| EP | 0 881 229 A2 | 12/1998 |
| WO | WO 00/04044 A1 | 1/2000 |
| WO | WO 00/42067 A1 | 7/2000 |
| WO | WO 00/69893 A1 | 11/2000 |
| WO | WO 01/81373 A2 | 11/2001 |

OTHER PUBLICATIONS

Ge et al., Science vol. 284 (Apr. 16, 1999) pp. 507-511.*
Pace et al., Biochemcial Pharmacology 71:968-980 (2006).*
Li et al., Curr. Pharm. Design 11:3111-3124 (2005).*
Nicas et al., Antimicrobial Agents and Chemotherapy 33(9):1477-1481 (1989).*
Ge et al., J. Am. Chem. Soc. 120:11014-11015 (1998).*
Allen, M., et al., "The role of hydrophobic side chains as determinants of antibacterial activity of semisynthetic glycopeptide antibiotics," *J. Antibiot.*, 1997, 50, 677-684.
Beauregard, D., et al., "Dimerization and membrane anchors in extracellular targeting of vancomycin group antibiotics," *Amtimicr. Agents & Chemo.*, 1995, 39, 781-785.
Betaneli, V.I., et al., "A convenient synthesis of 1,2-O-ethylidene derivatives of carbohydrates," *Carbohydrate Research*, 1982, 107, 285-291.

(Continued)

*Primary Examiner*—J D Schultz
*Assistant Examiner*—Jeffrey S. Lundgren
(74) *Attorney, Agent, or Firm*—Woodcock Washburn LLP

(57) ABSTRACT

A glycopeptide of the formula $A_1$-$A_2$-$A_3$-$A_4$-$A_5$-$A_6$-$A_7$, in which each dash represents a covalent bond; wherein $A_1$ comprises a modified or unmodified α-amino acid residue, alkyl, aryl, aralkyl, alkanoyl, aroyl, aralkanoyl, heterocyclic, heterocyclic-carbonyl, heterocyclic-alkyl, heterocyclic-alkyl-carbonyl, alkylsulfonyl, arylsulfonyl, guanidinyl, carbamoyl, or xanthyl; wherein each of $A_2$ to $A_7$ comprises a modified or unmodified α-amino acid residue, whereby (i) $A_1$ is linked to an amino group on $A_2$, (ii) each of $A_2$, $A_4$ and $A_6$ bears an aromatic side chain, which aromatic side chains are cross-linked together by two or more covalent bonds, and (iii) $A_7$ bears a terminal carboxyl, ester, amide, or N-substituted amide group;

and wherein one or more of $A_1$ to $A_7$ is linked via a glycosidic bond to one or more glycosidic groups each having one or more sugar residues, at least one of the sugar residues bearing one or more substituents of the formula YXR, $N^+(R_1)=CR_2R_3$, $N=PR_1R_2R_3$, $N^+R_1R_2R_3$ or $P^+R_1R_2R_3$ in which Y is a single bond, O, NR, or S; X is O, $NR_1$, S, $SO_2$, C(O)O, C(O)S, C(S)O, C(S)S, C($NR_1$) O, C(O)$NR_1$, or halo (in which case Y and R are absent).

A chemical library comprising a plurality of the glycopeptides of the invention.

A method for preparing a glycopeptide by glycosylation of an aglycone derived from a glycopeptide antibiotic.

A method for preparing a glycopeptide by preparing a pseudoaglycone from a glycopeptide antibiotic and glycosylating the pseudoaglycone.

6 Claims, 26 Drawing Sheets

OTHER PUBLICATIONS

Blaakmeer, J., et al., *Int. J. Peptide Protein Res.*, 1991, 27, 556-564.

Cohen, M., *Science*, 1992, 257, 1050.

Cooper, R., et al., "Semisynthetic glycopeptide antibiotics," in Ann. Rept. In Med. Chem.-31, *Academic Press, Inc.*, 1996, Chap. 14, 131-140.

Damour, O., et al., "Cytotoxicity evaluation of antiseptics and antibiotics on cultured human fibroblasts and keratinocytes," *Burns*, 1992, 18, 479-485.

Dick, W.E., *Carbohyd. Res.*, 1972, 21, 255-268.

Felmingham, D., "Towards the ideal glycopeptide," *J. Antimicrob, Chemother.*, 1993, 32, 663-666.

Gallop, M.A., et al., "Applications of combinatorial technologies to drug discovery, 1. Background and peptide combinatorial libraries," *J. Med. Chem.*, 1994, 37, 1233-1251.

Gerhard, U., et al., "The role of the sugar and chlorine substituents in the dimerization of vancomycin antibiotics," *JACS*, 1993, 115, 232-237.

Gordon, E.M., et al., "Applications of combinatorial technologies to drug discovery, 2. Combinatorial organic synthesis, library screening strategies, and future directions," *J. Med. Chem.*, 1994, 37, 1385-1401.

Kannan R., et al., "Function of the amino sugar and N-terminal amino acid of the antibiotic vancomycin in its complexation with cell wall peptides," *JACS*, 1988, 110, 2946-2953.

Kusumoto, S., et al., *Bull. Chem. Soc. Jpn.*, 1986, 59, 1289-1298.

Link, P.A.J., et al., *J. Heterocyclic Chem.*, 1985, 22, 873-878.

Loll, P., et al., "Simultaneous recognition of a carboxylate-containing ligard and an inramolecular surrogate ligand in the crystal structure of an asymmetric vancomycin dimmer," *JACS*, 1997, 119, 1516-1522.

Mackay, J., et al., "Dissection of the contributions toward dimerization of gylcopeptide antibiotics," *JACS*, 1994, 116, 4573.

Malabarba, A., et al., "Gylcopeptide resistance in multiple antibiotic-resistant gram-positive bacteria: a current challenge for novel semisynthetic glycopeptide derivatives," *Eur. J. Med. Chem.*, 1997b, 32, 459-478.

Malabarba, A., et al., "Structural modifications of glycopeptide antibiotics," *Med. Res. Rev.*, 1997a, 17(1), 69-137.

Mercier, R-C., et al., "Pharmacodynamic evaluation of a new glycopeptide, LY333328, and in vitroactivity against *Staphylococcus aureus* and *Enterococcus faecium*," *Antimicrob. Agents Chemother*, 1997, 41, 1307-1312.

Mikami, Y., et al., "Comparison of in vitroantifungal activity of itraconazole and hydroxyl-itraconazole by colorimetric MTT assay," *MYCOSES*, 1994, 37, 27-33.

Milewski, W.M., et al., "Overproduction of a 37-Kilodalton Cytoplasmic Protein Homologous to NAD+-linked D-Lactate Dehydrogenase associated with vancomycin resistance in *Staphylococcus aureus*," *Antimicrobial Agents and Chemotherapy*, 1996, 40, 166-172.

Mosmann, T., "Rapid colorimetric assay for cellular growth and survival; application to proliferation and cytotoxicity assays," *J. Immunol. Methods.*, 1983, 65, 55-63.

Nagarajan, R., "Antibacterial activities and modes of action of vancomycin and related glycopeptides," *Antimicr. Agents Chemother.*, 1991, 35, 605-609.

Nagarajan, R., et al., "Selective cleavage of vancosamine, glucose, and N-methylleucine from vancomycin and related antibiotics," *J. Chem. Soc. Chem. Comm.*, 1988, 1306-1307.

Nagarajan, R., "Structure-activity relationships of vancomycin-type glycopeptide antibiotics," *J. Antibiotics*, 1993, 46, 1181-1195.

National Committee for clinical laboratory (NCCL) Standard, Methods for dilution antimicrobial susceptibility tests for bacteria that grow aerobically—third edition; approved standard. NCCLS document M7-A3, *National Committee for Clinical Laboratory Standard*, Villanova, PA, 1993.

Neu, H., *Science*, 1992, 257, 1064.

Pankuch, G., et al., "Study of comparative anti-pneumococcal activities of penicillin G, RP 59500, erythromycin, sparfloxacin, and cancomycin by using time-kill methodology," *Amtimicrob. Agents Chemother.*, 1994, 38, 2065-2072.

Pavlov A., et al., "Synthesis and biological activity of derivatives of glycopeptide antibiotics eremomycin and vancomycin nitrosated, acylated or carbamoylated at the N-terminal," *J. Antibiot.*, 1993, 46, 1731-1739.

Pierce, C., et al., *J. Chem. Soc. Perkins Trans.*, 1995, 2, 153-157.

Prowse, W., et al., *Biochemistry*, 1995, 34, 9632-9644.

Rodriquez, M. J., "Novel Glycopeptide Antibiotics: *N*-Alkylated Derivatives Active Against Vancomycin-Resistant Enterococci," J. Antibiotics, Jun. 1998, 51(6), 560-569.

Solenberg, P.J.,e t al., "Production of hybrid glyucopeptide antibiotics in vitro and in *Streptomyces toyocaensis*," *Chem. Biol.*, 1997, 4, 195-202.

Terrett, N.K., et al., "Combinatorial synthesis—the design of compound libraries and their application to drug discovery," *Tetrahehdron Letters*, 1995, 51, 8135-8173.

Thompson, L.A., et al., "Synthesis and applications of small molecule libraries," *Chem. Rev.*, 1996, 96, 555-600.

Walsh, C., *Science*, 1993, 261, 308.

Webb, et al., *Tetrahedron*, 1998, 54, 401-410.

Westwall, et al., *J. Antibiotics*, 1995, 48, 1292.

William, D., et al., "Toward an estimation of binding constants in aqueous solution: studies of associations of vancomycin group antibiotics," *PNAS USA*, 1993, 90, 1172-1178.

Williams, D., et al., "Molecular basis of the activity of antibiotics of the vancomycin group," *Biochem. Pharm.*, 1988, 37, 133-141.

Williams, D.H., "An analysis of the origins of a cooperative binding energy of dimerization," *Science*, 1998, 280, 711-714.

Yan, L., et al., *JACS*, 1994, 116, 6953.

Zelenitsky, S., et al., "Time-kill curves for a semisynthetic glycopeptide, LY333328, against vancomycin-susceptible and vancomycin-resistant *Enterococcus faecium* strains," *Antimicrob. Agents Chemother.*, 1997, 41, 1407-1408.

\* cited by examiner

β-Avoparcin

Ristocetin A

GLYCOPEPTIDE ANTIBIOTICS, COMBINATORIAL LIBRARIES OF GLYCOPEPTIDE ANTIBIOTICS AND METHODS OF PRODUCING SAME

RELATED APPLICATIONS

The present application is a continuing application of U.S. patent application Ser. No. 09/353,368, filed Jul. 14, 1999, now U.S. Pat. No. 6,710,168 which claims benefit of Provisional Application Ser. No. 60/134,839 filed May 19, 1999, and benefit of U.S. patent application Ser. No. 09/115,667, filed Jul. 14, 1998 (converted to Provisional Application No, 60/150,690). The disclosures of each of the foregoing are hereby incorporated by reference in their entirety.

BACKGROUND OF THE INVENTION

1. Field of the Invention

The present invention relates to glycopeptide compounds and libraries of glycopeptide compounds structurally analogous to known glycopeptide antibiotics and methods of generating those libraries. The compounds contain modified carbohydrate moieties. The libraries are generated using combinatorial chemical techniques that produce a diverse set of carbohydrate functionalities conjugated to an oligopeptide.

2. Background of the Invention

Glycopeptide antibiotics are characterized by having at least one saccharide group chemically bonded to a rigid peptide structure having a cavity or cleft which acts as a binding site for the substrate used in bacterial cell wall synthesis. The glycopeptide antibiotics are further categorized into various subclasses depending on the identity and interconnections of the amino acids comprising the peptide backbone and the number and substitution pattern of the sugar residues in the molecule. The glycopeptide antibiotics are generally active against Gram-positive bacteria but relatively ineffective against Gram-negative bacteria Most notable among the glycopeptide antibiotics is vancomycin. Vancomycin is produced by *Amycolatopsis orientalis*, and is often referred to as "the drug of last resort" because it is effective against most multi-drug-resistant gram positive bacteria. However, in recent years vancomycin-resistant strains of some bacteria have emerged. [Cohen M., (1992); Neu H., (1992)]. It is estimated that 5-25% of enterococcal strains in hospitals are now resistant to vancomycin [Axelsen, P. H. et al. (1997)]. Most feared among the bacteria is *Staphylococcus aureus*, which can result in dangerous respiratory and blood infections. Vancomycin-resistant and vancomycin-insensitive strains of this bacterium have also been recently reported [Milewski (1996)].

The structural formula of vancomycin is shown below and is characterized by a disaccharide moiety covalendy linked to a heptapeptide structure. The structure of vancomycin places it in a class of molecules referred to as the "dalbaheptides." [Malabarba A., et al. (1997a)] Dalbaheptides in general are characterized by the presence of seven amino acids linked together by peptide bonds and held in a rigid conformation by cross-links through the aromatic substituent groups of at least five of the amino acid residues. In the heptapeptide structure of vancomycin, which is commonly referred to as the "aglycone" of vancomycin, the aromatic side-chains of amino acids 2, 4, and 6 are fused together through ether linkages. The side-chains of amino acids 5 and 7 are joined via a carbon-carbon bond. Amino acids 1 and 3 arm leucine and asparaine, respectively. Other naturally-occurring glycopeptide antibiotics are similar to vancomycin in that they have a glucose residue linked to the aromatic substituent on amino acid 4 through formation of a bond with a phenolic hydroxyl group. The glucose residue, in turn, is linked through its vicinal hydroxyl position to a unique amino sugar, either L-vancosamine. The sugars have been separately removed from glycopeptide antibiotics, and it has been found that the presence of both sugars enhances the pharmacokinetic properties of this class of antibiotics. [Nagarajan R. (1988), (1991), (1993]

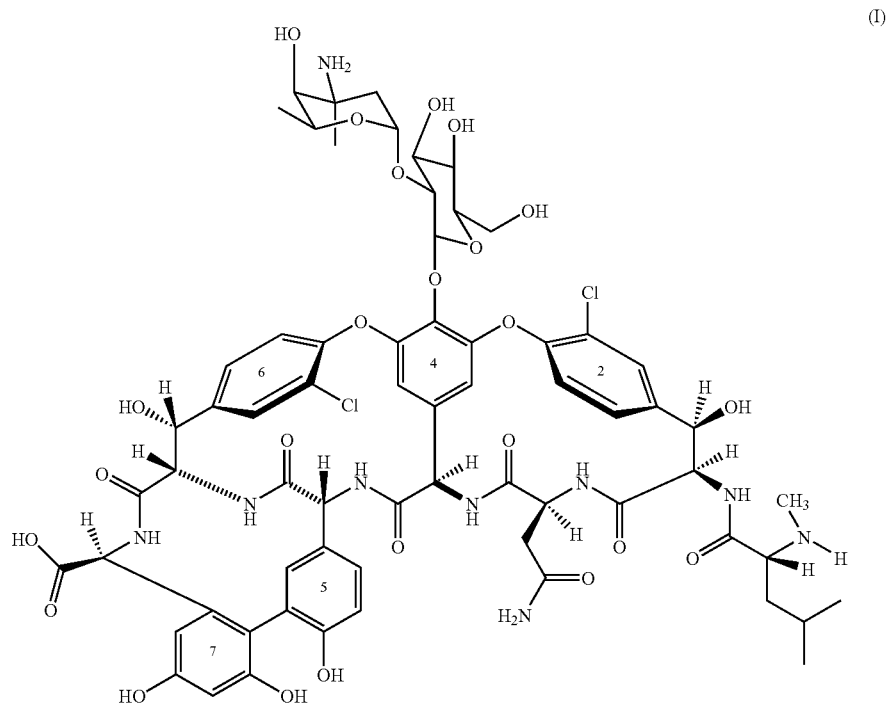

(I)

The anti-microbial activity of vancomycin is known to be due to its ability to interfere with biosynthesis of the bacterial cell wall. [Nagarajan R. (1993)]. NMR evidence shows that the heptapeptide chain of vancomycin forms a number of hydrogen bonds with the D-alanyl-D-alanine terminus of the disaccharide-pentapeptide precursors used to form the cell wall. [see, e.g., Prowse W., et al. (1995); Pierce C., et al. (1995); Williams D. et al. (1988)]. This interaction of vancomycin with cell wall precursors apparently inhibits or prevents the subsequent transglycosylation and/or transpeptidation steps of cell wall assembly. Supporting this mode of action is the fact that vancomycin-resistant strains of bacteria are found to produce a pentapeptide precursor terminating in a D-alanyl-D-lactate sequence. It is hypothesized that the reduced effectiveness of vancomycin against resistant strains is due to reduced hydrogen bonding interactions between the drug and the D-alanyl-D-lactate substrate. The affinity of vancomycin for D-alanyl-D-lactate is estimated to be 2-3 orders of magnitude (4.1 kcal/mol) less than for D-alanyl-D-alanine. [Walsh C. (1993)].

The sugar residues of the vancomycin and other glycopeptide antibiotics have been shown to affect binding activities. Structural changes in the sugar residues can produce significant changes in antibiotic activity. [Malabarba (1997), Nagarajan, R. (1993)] It has been proposed that the sugar residues on the glycopeptide antibiotics may enhance the avidity of these molecules for surface-bound peptide ligands. At least two different mechanisms for enhancing avidity have been proposed. [Kaiman (1988), Gerhard (1993), Allen (1997)]

For example, it has been proposed that the biological activity of vancomycin, along with that of many other glycopeptide antibiotics, is enhanced by dimerization due to bonding interactions at the convex (non-ligand binding) face of the molecule. [Williams D., et al. (1993); Gerhard U., et al., (1993)] Dimerization is believed to be facilitated by the disaccharide groups of the vancomycin molecule, and is thought to influence activity by increasing the avidity of vancomycin for surface-bound D-Ala-D-Ala peptide ligands. [Williams, (1998)] Structural evidence for dimerization has been obtained from both NMR and crystallographic studies, and it has been found that there are significant differences in the stability of the dimers formed in solution by different glycopeptide antibiotics. [MacKay (1994)] It is proposed that differences in the dimerization constants may account at least partially for the remarkable differences in biological activity of different glycopeptide antibiotics which otherwise have very similar binding affinities for the natural d-Ala-d-Ala substrate. [Williams (1998)]

A second mechanism for enhancing activity has also been proposed for the glycopeptide antibiotic teicoplanin, which contains an N-alkyl chain on one of the sugars. It is suggested that this N-alkyl chain increases the effective avidity of teicoplanin for surface-bound D-Ala-D-Ala ligands by interacting with the membrane, thus "anchoring" the teicoplanin molecule at the membrane surface. [Beures (1995)] It should be noted that the attachment of hydrophobic substituents to the vancomycin carbohydrate moiety appears to enhance activity against vancomycin-resistant strains. For example, attaching a hydrophobic group to the vancosamine sugar by alkylation on the amine nitrogen increases activity against vancomycin-resistant strains by two orders of magnitude. [Nagarajan (1991)] It is speculated that the lipophilic groups locate the antibiotic at the cell surface and make ligand binding an intramolecular process, which may partially overcome the decreased binding affinity for D-Ala-D-Lac. Hence, although the sugars on the glycopeptide antibiotics do not appear to interact substantially with the peptide substrates, they play a very important role in increasing the biological activity. Therefore, one potentially successful strategy for the design of new antibacterial agents based on the glycopeptide class of antibiotics involves modifying the carbohydrate portions of the molecules. [Malabarba (1997a)]

Related members of the vancomycin class of glycopeptide antibiotics include the ristocetins, the eremomycins, the avoparcins and teicoplanin. Several of these compounds are shown, together with vancomycin in FIGS. 1a and 1b. The chemical structures of all of these compounds include a dalbaheptide structure as the aglycone core, with minor differences in the amino acids and in cross-linking, but differ from each other most distinctively in terms of the nature of the sugar residues as well as the number and points of attachment of sugar residues to the aglycone core. It is known that biological activities of vancomycin-type antibiotics vary depending on the nature of the sugar residues.

One approach to obtaining new drug candidates derived from vancomycin and other glycopeptide antibiotics has involved chemical modification of one or more sugar residues of the naturally occurring glycopeptide. For instance, as noted previously, an aikyl chain can be attached to a sugar residue of the molecule, such as at the amino group of the amino sugar. [Cooper, R. et al. (1996)]. Other semi-synthetic approaches have involved traditional esterification and amidation methodologies applied to the peptide portion of the molecule. [Malabarba, A. et al. (1997b)] The attachment of lipophilic alkyl chains to the antibiotic has been proposed to afford better membrane anchoring, thereby increasing the effective activity of glycopeptide at the cell wall. [Felmingham, D. (1993)] The presence of an additional sugar has also produced compounds having enhanced activity, which may be due to their improved dimerization ability. [Malabarba A., et al. (1997a); Allen N. et al., (1997]. Other semi-synthetic approaches to modification of the vancomycin molecule have involved derivatization of the polypeptide binding pocket. [Pavlov A., et al. (1993)]

Previous efforts in producing new compounds having increased activity against vancomycin-resistant strains have typically involved a directed synthesis of a specific target derivative of a natural glycopeptide. This is a slow and relatively tedious process requiring a great deal of time and expense to obtain a suitable set of drug candidates for use in screening for activity. It is desirable to develop a combinatorial approach to the synthesis of new drug candidates based on the glycopeptide antibiotics. Recognizing this, Griffin and coworkers synthesized a combinatorial library of vancomycin derivatives in which different peptide chains were appended to the carboxylate on amino acid 7. No candidates were identified which had significantly improved activity compared with the underivatized natural product for either vancomycin-sensitive or vancomycin-resistant strains. The failure of the effort highlights a key requirement for a strategy involving the synthesis of a library related to a natural product: it is imperative to introduce substituents at positions on the molecule where there is evidence that such substitutions will have an effect on activity. In the case of the glycopeptide antibiotics, changes to the carbohydrate portions of the molecules would seem to be warranted in light of the relatively large role played by the sugar residues in increasing activity. The use of enzymes to generate glycosylated vancomycin derivatives wherein the saccharide residue carries a variety of functionalizations has been proposed and explored. [Solenberg (1997)] However, the range of compounds that can be prepared using enzymes in this manner is limited by the availability of enzymes specific to the desired functionalized saccharide residue. This has only been demonstrated for glucose and xylose; vancosamine has never been attached using the enzyme method and no compounds displaying activity have been produced using the enzyme method. No other strategies for making libraries of glycopeptide antibiotics in which the carbohydrate moieties are combinatorially varied have been reported.

Comparison of the natural products have made it clear that the nature and placement of the sugars on the glycopeptide antibiotics play critical roles in antibiotic activity. Furthermore, there is some information from semi-synthetic efforts about positions on the carbohydrates that may be important in activity. For example, we have already noted that some vancomycin derivatives containing hydrophobic substituents on the vancosamine nitrogen show improved activity against vancomycin-resistant strains. However, there have been no reports of modifications on the glucose residue of vancomycin which have affected activity. In fact, for glycopeptide antibiotics containing two or more sugars attached to amino acid 4, there is no suggestion in the literature that the sugar directly attached to the aglycone can be modified to improve activity. It has even been argued that the glucose residue "has no independent contribution to binding, and it is likely that its role with respect to the binding constant is merely to position the vancosamine optimally relative to the aglycon portion." [Kannan et al. (1988)]

The structure-activity relationships among the vancomycin-like glycopeptide antibiotics show that the presence of an amino sugar at the residue 6 benzylic position and an N-alkyl or N-aryl substituted amino sugar at the amino acid-4 position increases antibiotic activity against both VRE and VSE. However, these trends do not always hold against other gram-positive bacteria such as the Staphylococci and Streptococci. Furthermore, no studies have addressed the effects of introducing functionality on the sugar groups other than N-alkylation, N-acylation, formation of N-oxides or modification of ester groups at C-6. Because the nature and placement of the sugars on glycopeptide antibiotics play such critical roles in antibiotic activity, many more studies are needed to optimize the sugar substituents. Such studies could not only lead to better antibiotics against vancomycin-resistant bacteria, but might provide more information about the mechanism of interaction at bacterial membranes. Preparation of derivatives with different sugar substituents will not only probe the sugar's role in currently proposed interactions, but may also lead to the discovery of new specific or non-specific interactions of the glycopeptide antibiotics at the cell surface. For reviews regarding the structure activity relationships of natural and semisynthetic glycopeptide antibiotics see Malabarba et al. *Med. Res. Rev.*, 1997, 17, 69; Nagarajan, *Antimicrob. Agents Chemother.*, 1991, 35, 605; Nagarajan, *J. Antibiotics*, 1993, 46, 1181; Cooper and Thompson, *Ann. Rep. Med. Chem.*, 1996, 31, 131; Malabarba et al., *Eur. J. Med. Chem.*, 1997, 32, 459; Allen et al. *J. Antibiotics*, 1997, 50, 677.

Combinatorial strategies have been successfully applied to the synthesis of peptide, nucleic acid, and various small molecule libraries, however, they have not been extensively employed to make carbohydrate-based libraries. Most of the approaches to production of carbohydrate libraries have been conducted in solution. A solid phase approach to making diverse libraries of di- and tri-saccharide compounds has also been reported. [Liang et al. (1996)]. A solid phase method permits reactions to be driven to completion by using a large excess of reactants. The solid phase approach also permits spatial resolution of the product compounds. Glycopeptide libraries have been produced on the solid phase in which amino acids were varied. However, no suggestion has been made that glycopeptide antibiotics can be made using a solid-phase method.

SUMMARY OF THE INVENTION

This invention is directed to glycopeptide compositions which have the formula $A_1$-$A_2$-$A_3$-$A_4$-$A_5$$A_6$-$A_7$, SEQ ID NO:1 in which each dash represents a covalent bond; wherein the group $A_1$ comprises a modified or unmodified α-amino acid residue, alkyl, aryl, aralkyl, alkanoyl, aroyl, aralkanoyl, heterocyclic, heterocyclic-carbonyl, heterocyclic-alkyl, heterocyclic-alkyl-carbonyl, alkylsulfonyl, arylsulfonyl, guanidinyl, carbamoyl, or xanthyl; wherein each of the groups $A_2$ to $A_7$ comprises a modified or unmodified α-amino acid residue, whereby (i) the group $A_1$ is linked to an amino group on the group A2, (ii) each of the groups $A_2$, $A_4$, $A_6$ bears an aromatic side chain, which aromatic side chains are cross-linked together by two or more covalent bonds, and (iii) the group $A_7$ bears a terminal carboxyl, ester, amide, or N-substituted amide group.

It is further required that one or more of the groups $A_1$ to $A_7$ is linked via a glycosidic bond to one or more glycosidic groups each having one or more sugar residues; wherein at least one of said sugar residues bears one or more substituents of the formula YXR, $N^+(R_1)$=$CR_2R_3$, $N$=$PR_1R_2R_3$, $N^+R_1R_2R_3$ or $P^+R_1R_2R_3$ in which the group Y is a single bond, O, $NR_1$ or S; the group X is O, $NR_1$, S, $SO_2$, C(O)O, C(S)O, C(S)S, C($NR_1$)O, C(O)$NR_1$, or halo (in which case Y and R are absent); and R, $R_1$, $R_2$ and $R_3$ are independently hydrogen, alkyl, aryl, aralkyl, alkanoyl, aroyl, aralkanoyl, heterocyclic, heterocyclic-carbonyl, heterocyclic-alkyl, heterocyclic-alkyl-carbonyl, alkylsulfonyl or arylsulfonyl; and any pharmaceutically acceptable salts thereof; provided that: when Y is a single bond and X is O, NH or N-alkyl, then R is not hydrogen; X and Y are not both O; X and Y are not S and O, or O and S, respectively; and if two or more of said substituents are present, they can be the same or different; and provided that: when $A_4$ is linked to a glucose residue substituted at its 2-position by a group YXR in which Y is a single bond, X is NH and R is alkanoyl, then said glucose residue is further substituted by another sugar residue; when $A_4$ is linked to a disaccharide in which a glucose residue bears an N-substituted aminohexose residue, then said glucose residue bears at least one group YXR which is not alkanoyloxy; and when $A_4$ is linked to an acylaminoglucuronate residue, then said acylaminoglucuronate residue is further substituted by a sugar residue.

This invention is also directed to a chemical library comprising a plurality of glycopeptides, each having the formula described hereinabove.

This invention is further directed to a method of preparing a glycopeptide comprising:

(a) selecting: (i) an aglycone that is soluble in one or more organic solvents, is derived from a glycopeptide antibiotic, and which aglycone has exactly one free phenolic hydroxyl group; and (ii) a protected first glycosyl donor; (b) allowing a non-enzymatic glycosylation reaction to proceed in an organic solvent such that a first glycosidic bond is formed, which links said free phenolic hydroxyl group to the anomeric carbon of the first glycosyl donor to provide a pseudoaglycone having a protected first glycosyl residue;

(c) selectively removing one protecting group from the first glycosyl residue to provide a pseudoaglycone bearing exactly one free hydroxyl group on the first glycosyl residue;

(d) selecting a second protected glycosyl donor, and (e) allowing a non-enzymatic glycosylation reaction to proceed in an organic solvent such that a second glycosidic bond is formed, which links said free hydroxyl group on the pseudoaglycone to the anomeric carbon of the second glycosyl donor.

This invention is further directed to a method of preparing a glycopeptide comprising:

(a) selecting a glycopeptide antibiotic that is soluble in one or more organic solvents;

(b) contacting the glycopeptide antibiotic with a Lewis acid, and allowing a degradation reaction to proceed such that a sugar residue is removed, producing a pseudoaglycone having exactly one free hydroxyl group on a sugar residue of the pseudoaglycone;

(c) selecting a protected glycosyl donor; and (d) allowing a non-enzymatic glycosylation reaction to proceed in an organic solvent such that a glycosidic bond is formed which links the free hydroxyl group on the pseudoaglycone to the anomeric carbon of the glycosyl donor.

This invention is further directed to a method for preparing a glycopeptide comprising:

(a) selecting a protected glycopeptide having a free primary hydroxyl group only at the 6-position of a hexose residue linked to $A_4$; (b) contacting the protected glycopeptide with a compound $ArSO_2G$ in which Ar is an aryl group and G is a leaving group under conditions effective to allow reaction of the free primary hydroxyl group to form a glycopeptide sulfonate ester; (c) contacting the glycopeptide sulfonate ester with a nucleophile under conditions effective to allow displacement of a sulfonate group to produce a substituted glycopeptide.

This invention is further directed to a method for producing a chemical library by performing at least two steps in a combinatorial format to produce the chemical library, wherein each of the steps introduces a substituent on a glycopeptide.

This invention is further directed to another method for producing a chemical library by performing at least two steps which are performed in a combinatorial format; wherein at least one of the steps comprises a glycosylation reaction which introduces a substituted sugar residue.

DETAILED DESCRIPTION OF THE INVENTION

Definitions

Figure 1A:
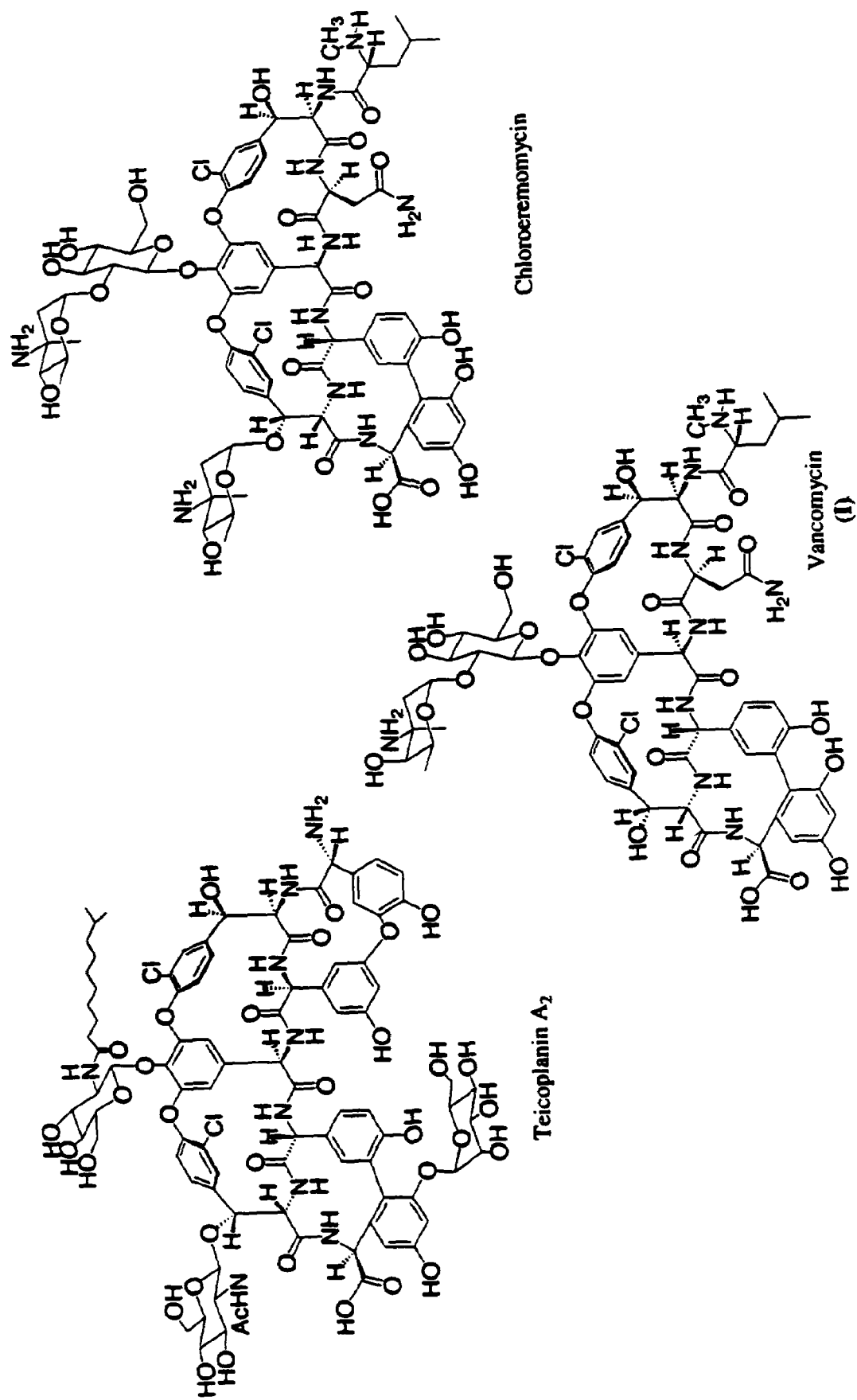
FIG. 1a contains structure diagrams of vancomycin and related glycopeptide antibiotics.

A "glycoconjugate" comprises any molecule linked to at least one carbohydrate of any size. The molecule can be a peptide or protein, a nucleic acid, a small molecule, a lipid, or another carbohydrate; it may be of natural or non-natural origin. A "glycopeptide" is a glycoconjugate comprising a peptide linked to at least one carbohydrate. A "glycopeptide antibiotic" is one of the naturally occurring glycopeptides with antibacterial activity, including, e.g., vancomycin, teicoplanin, ristocetin, chloroeremomycin and avoparicin.

An "aglycone" is the result of removing the carbohydrate residues from a glycopeptide, leaving only a peptide core. A "pseudoaglycone" is the result of removing only one of two sugar residues of a disaccharide residue linked to residue $A_4$ of a glycopeptide. Thus, a pseudoaglycone comprises an aglycone in which $A_4$ is linked to a monosaccharide residue.

A "dalbaheptide" is a glycopeptide containing a heptapeptide moiety which is held in a rigid conformation by cross-links between the aromatic substituent groups of at least five of the seven α-amino acid residues, including a cross-link comprising a direct carbon-carbon bond between the aryl substituents of amino acid residues 5 and 7, and aryl ether cross-links between the substituents of amino acid residues 2 and 4, and 4 and 6. Amino acid residues 2 and 4-7 in different dalbaheptides are those found in the naturally occurring glycopeptide antibiotics. These amino acid residues differ only in that residues 2 and 6 do not always have a chlorine substituent on their aromatic rings, and in that substitution on free hydroxyl or amino groups may be present. Amino acid residues 1 and 3 may differ substantially in different dalbaheptides; if both bear aryl substituents, these may be cross-linked. Molecules having a dalbaheptide structure include, e.g., the glycopeptide antibiotics mentioned above.

The term "alkyl" refers to an acyclic or non-aromatic cyclic group having from one to twenty carbon atoms connected by single or multiple bonds. An alkyl group may be substituted by one or more of halo, hydroxyl, protected hydroxyl, amino, nitro, cyano, alkoxy, aryloxy, aralkyloxy, COOH, aroyloxy, alkylamino, dialkylamino, trialkylammonium, alkylthio, alkanoyl, alkanoyloxy, alkanoylamido, alkylsulfonyl, arylsulfonyl, aroyl, aralkanoyl, heterocyclic, $CONH_2$, CONH-alkyl, $CON(alkyl)_2$, COO-aralkyl, COO-aryl, COO-alkyl or phosphonium substituted by any combination of alkyl, aryl, aralkyl or heterocyclic.

The term "aryl" refers to a group derived from a non-heterocyclic aromatic compound having from six to twenty carbon atoms and from one to four rings which may be fused or connected by single bonds. An aryl group may be substituted by one or more of alkyl, aralkyl, heterocyclic, heterocyclic-alkyl, heterocyclic-carbonyl, halo, hydroxyl, protected hydroxyl, amino, hydrazino, alkylhydrazino, arylhydrazino, nitro, cyano, alkoxy, aryloxy, aralkyloxy, aroyloxy, alkylamino, dialkylamino, trialkylammonium, alkylthio, alkanoyl, alkanoyloxy, alkanoylamido, alkylsulfonyl, arylsulfonyl, aroyl, aralkanoyl, COO-alkyl, COO-aralkyl, COO-aryl, $CONH_2$, CONH-alkyl, $CON(alkyl)_2$ or phosphonium substituted by any combination of alkyl, aryl, aralkyl or heterocyclic. The term "aralkyl" refers to an alkyl group substituted by an aryl group.

The term "heterocyclic" refers to a group derived from a heterocyclic compound having from one to four rings, which may be fused or connected by single bonds; said compound having from three to twenty ring atoms which may be carbon, nitrogen, oxygen, sulfur or phosphorus. A heterocyclic group may be substituted by one or more of alkyl, aryl, aralkyl, halo, hydroxyl, protected hydroxyl, amino, hydrazino, alkylhydrazino, arylhydrazino, nitro, cyano, alkoxy, aryloxy, aralkyloxy, aroyloxy, alkylamino, dialkylamino, trialkylammonium, alkylthio, alkanoyl, alkanoyloxy, alkanoylamido, alkylsulfonyl, arylsulfonyl, aroyl, aralkanoyl, COO-alkyl, COO-aralkyl, COO-aryl, $CONH_2$, CONH-alkyl, CON(alkyl)$_2$ or phosphonium substituted by any combination of alkyl, aryl, aralkyl or heterocyclic.

The terms "alkoxy," "aryloxy" and "aralkyloxy" refer to groups derived from bonding an oxygen atom to an alkyl, aryl or aralkyl group, respectively. The terms "alkanoyl," "aroyl" and "aralkanoyl" refer to groups derived from bonding a carbonyl to an alkyl, aryl or aralkyl group, respectively. The terms "heterocyclic-alkyl" and "heterocyclic-carbonyl" refer to groups derived from bonding a heterocyclic group to an alkyl or a carbonyl group, respectively. The term "heterocyclic-alkyl-carbonyl" refers to a group derived from bonding a heterocyclic-alkyl group to a carbonyl group. The term "protected hydroxyl" refers to a hydroxyl group bonded to a group which is easily removed to regenerate the free hydroxyl group by treatment with acid or base, by reduction, or by exposure to light.

The term "Lewis acid", as used herein, refers to any substance that can accept an electron pair from a base, with the exception of the mineral acids and organic carboxylic acids. The term "organic solvent", as used herein, refers to non-aqueous solvents, preferably to ketones, halogenated solvents, ethers, esters and non-heterocyclic aromatic solvents.

A "chemical library" is a synthesized set of compounds having different structures. The chemical library may be screened for biological activity to identify individual active compounds of interest.

A "glycosyl donor" is a sugar or glycosidic residue that bears an anomeric leaving group, preferably a sulfoxide, which may be activated to render the anomeric carbon susceptible to reaction with a nucleophile to displace the activated group, thereby forming a glycosidic bond.

The term "leaving group" as used herein is a group easily displaced from a sulfonyl group by a nucleophile. Examples of leaving groups are halo, alkoxy, aryloxy, alkanoyloxy and arylsulfonyloxy.

The term "DMF" refers to N,N-dimethylformamide; "THF" refers to tetrahydrofuran; "TFA" refers to trifluoroacetic acid; "EtOAc" refers to ethyl acetate; "MeOH" refers to methanol; "MeCN" refers to acetonitrile; "Tf" refers to the trifluoroacetyl group; "DMSO" refers to dimethyl sulfoxide; "DIEA" refers to diisopropylethylamine; "All" in structural formulas refers to the allyl group; "Fmoc" refers to 9-fluorenylmethyloxycarbonyl; "HOBt" refers to 1-hydroxybenzotriazole and "OBt" to the 1-oxybenzotriazolyl group; "PyBOP" refers to benzotriazol-1-yl-oxytripyrrolidine-phosphonium hexafluorophosphate; "Su" refers to the succinimidyl group; "HBTU" refers to O-benzotriazol-1-yl-N,N,N', N'-tetramethyluronium hexafluorophosphate; "aloc" refers to allyloxycarbonyl; and "CBz" refers to benzyloxycarbonyloxy.

The glycopeptide compositions of this invention have the formula $A_1$-$A_2$-$A_3$-$A_4$-$A_5$-$A_6$-$A_7$, SEQ ID NO:1 in which each dash represents a covalent bond; wherein the group $A_1$ comprises a modified or unmodified α-amino acid residue, alkyl, aryl, aralkyl, alkanoyl, aroyl, aralkanoyl, heterocyclic, heterocyclic-carbonyl, heterocyclic-alkyl, heterocyclic-alkyl-carbonyl, alkylsulfonyl, arylsulfonyl, guanidinyl, carbamoyl, or xanthyl; wherein each of the groups $A_2$ to $A_7$ comprises a modified or unmodified α-amino acid residue, whereby (i) the group $A_1$ is linked to an amino group on the group A2, (ii) each of the groups $A_2$, $A_4$, and $A_6$ bears an aromatic side chain, which aromatic side chains are cross- linked together by two or more covalent bonds, and (iii) the group $A_7$ bears a terminal carboxyl, ester, amide, or N-substituted amide group.

It is further required that one or more of the groups $A_1$ to $A_7$ is linked via a glycosidic bond to one or more glycosidic groups each having one or more sugar residues; wherein at least one of said sugar residues bears one or more substituents of the formula YXR, $N^+(R_1)=CR_2R_3$, $N=PR_1R_2R_3$, $N^+R_1R_2R_3$ or $P^+R_1R_2R_3$ in which the group Y is a single bond, O, $NR_1$ or S; the group X is O, $NR_1$, S, $SO_2$, C(O)O, C(O)S, C(S)O, C(S)S, C(NR$_1$)O, C(O)NR$_1$, or halo (in which case Y and R are absent); and R, $R_1$, $R_2$ and $R_3$ are independently hydrogen, alkyl, aryl, aralkyl, alkanoyl, aroyl, aralkanoyl, heterocyclic, heterocyclic-carbonyl, heterocyclic-alkyl, heterocyclic-alkyl-carbonyl, alkylsulfonyl or arylsulfonyl; and any pharmaceutically acceptable salts thereof; provided that: when Y is a single bond and X is O, NH or N-alkyl, then R is not hydrogen; X and Y are not both O; X and Y are not S and O, or O and S, respectively; and if two or more of said substituents are present, they can be the same or different; and provided that: when $A_4$ is linked to a glucose residue substituted at its 2-position by a group YXR in which Y is a single bond, X is NH and R is alkanoyl, then said glucose residue is further substituted by another sugar residue; when $A_4$ is linked to a disaccharide in which a glucose residue bears an N-substituted aminohexose residue, then said glucose residue bears at least one group YXR which is not alkanoyloxy; and when $A_4$ is linked to an acylaminoglucuronate residue, then said acylaminoglucuronate residue is further substituted by a sugar residue.

Modified amino acid residues include amino acid residues whose aromatic groups have been substituted by halo, alkyl, alkoxy, alkanoyl, or other groups easily introduced by electrophilic substitution reactions or by reaction of phenolic hydroxyl groups with alkylating or acylating agents; and amino acid residues which have protecting groups or other easily introduced substituents on their hydroxyl or amino groups, including, but not limited to alkyl, alkanoyl, aroyl, aralkyl, aralkanoyl, carbamoyl, alkyloxycarbonyl, aralkyloxycarbonyl, aryloxycarbonyl, alkylsulfonyl, arylsulfonyl, heterocyclic, heterocyclic-alkyl or heterocyclic-carbonyl substituents. Examples of preferred protecting groups include acetyl, allyloxycarbonyl (aloc), CBz, allyl, benzyl, p-methoxybenzyl and methyl. Modifications of hydroxyl groups occur on phenolic hydroxyl groups, benzylic hydroxyl groups, or aliphatic hydroxyl groups. Other amino acid residues, in addition to $A_2$, $A_4$ and $A_6$, may be cross-linked through their aromatic substituent groups.

Figure 1B:
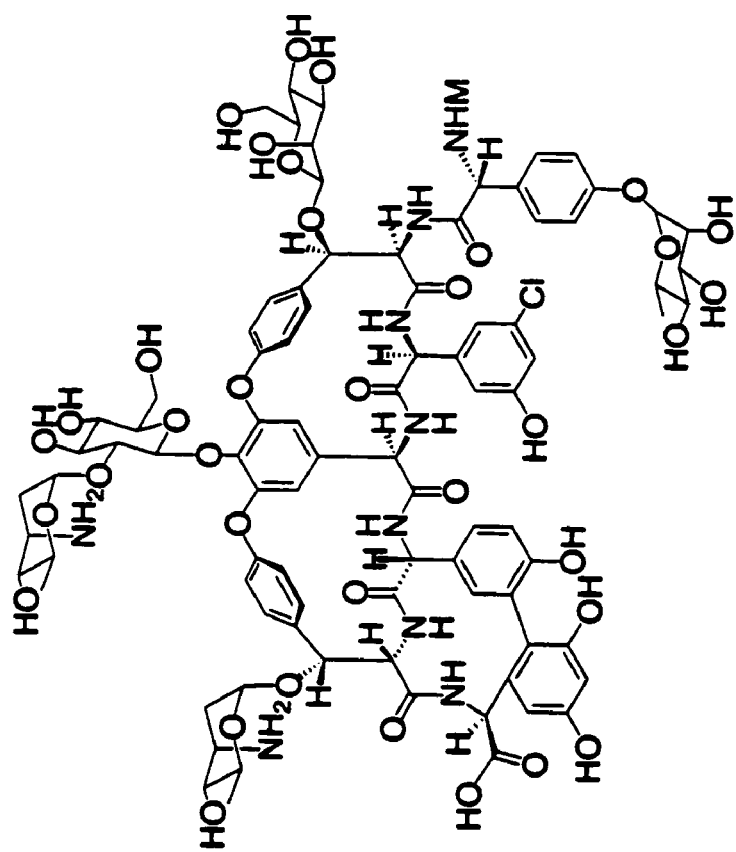
FIG. 1b contains structure diagrams of vancomycin-related glycopeptide antibiotics.
Figure 1B:
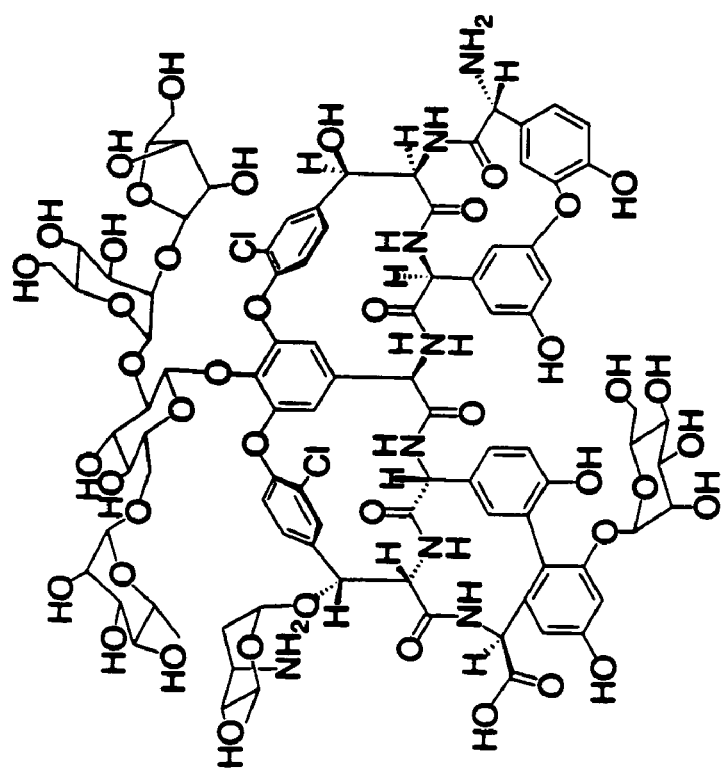

Preferably, residues $A_2$ to $A_7$ of the glycopeptide are linked sequentially by peptide bonds and are cross-linked as in a dalbaheptide, as defined hereinabove. The preferred glycopeptides thus have a peptide core in which the residues are linked as in the natural glycopeptide antibiotics, as shown in FIGS. 1a and 1b. Substitution of different amino acids at $A_3$ is permitted, as are modified amino acid residues at all positions, as described hereinabove. In a preferred embodiment of this invention, residue $A_1$ is an α-amino acid, which may be substituted on the terminal amino group by alkyl, aryl, aralkyl, alkanoyl, aroyl, aralkanoyl, heterocyclic, heterocyclic-carbonyl, heterocyclic alkyl, alkylsulfonyl, arylsulfonyl, guanidinyl, carbamoyl, or xanthyl, and the structures and interconnections of $A_1$ to $A_7$ are those of vancomycin, i.e., the glycopeptide has the heptapeptide core of vancomycin, subject to the amino acid modifications and substitutions on $A_1$ and $A_7$ described hereinabove.

The glycopeptides of this invention contain at least one glycosidic group attached through a glycosidic bond to the residues $A_1$ to $A_7$. Preferably, a glycosidic group is attached to residue $A_4$. In one preferred embodiment of the invention, a hexose residue is bonded directly to $A_4$ and is substituted by a group YXR. In the group YXR, when Y represents a single bond, XR is bonded directly to a carbon atom of the sugar residue. When X is halo, Y and R are absent and the halo group is attached directly to a carbon atom of the sugar residue, as in compounds LXX, CX, and others described hereinbelow. It is not intended that YXR represent a peroxide, OOR, or the groups OSR or SOR. The hexose residue may be a monosaccharide residue or part of a disaccharide or oligosaccharide residue. Still more preferably, the group YXR is located at the Cal position of the hexose. Most preferably, Y is a single bond and X is $NR_1$ or S, i.e., a substituted amino or thio group is attached to the C-6 position of the hexose. In one embodiment of the invention, a glycosidic group is also attached to residue $A_6$. In another preferred embodiment of the invention, a hexose residue linked to $A_4$ is substituted by an ylide group having the formula $N=PR_1R_2R_3$, in which $R_1$, $R_2$ and $R_3$ are preferably aryl.

Although this invention includes all of the compounds described hereinabove, in a preferred embodiment of this invention, the glycopeptide composition is derived from vancomycin. Accordingly, this invention includes methods for the selective derivatization of the Cal position of the glucose residue of vancomycin. We have found that substituents at this position can have a dramatic effect on biological activity. For example, replacement of the glucose C-6 hydroxyl with the substituent

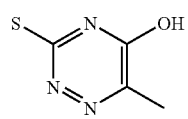

(2-thio-6-azathymine), attached to the glucose C-6 position through the sulfur, causes an increase in activity against all strains tested. Furthermore, when this position is substituted and there is an additional substitution on the vancosamine sugar, the biological activity is affected in an unpredictable and non-additive way. For example, when the above 2-thio-6-azathymine substitution at C-6 of glucose is made concurrently with substitution of a 4-(4-chlorophenyl)benzyl group on the vancosamine nitrogen, which also increases activity against all strains, the activity against some strains of bacteria is increased above the activity observed for either substitution alone, while against other strains, the activity is below that even of vancomycin.

A strategy to introduce a suitable set of protecting groups and to differentiate the C-6 hydroxyl group from all other hydroxyl groups of a glycopeptide having a hexose residue at $A_4$ is illustrated below in Scheme 1, showing functionalization of the glucose C-6 hydroxyl of vancomycin.

Scheme 1

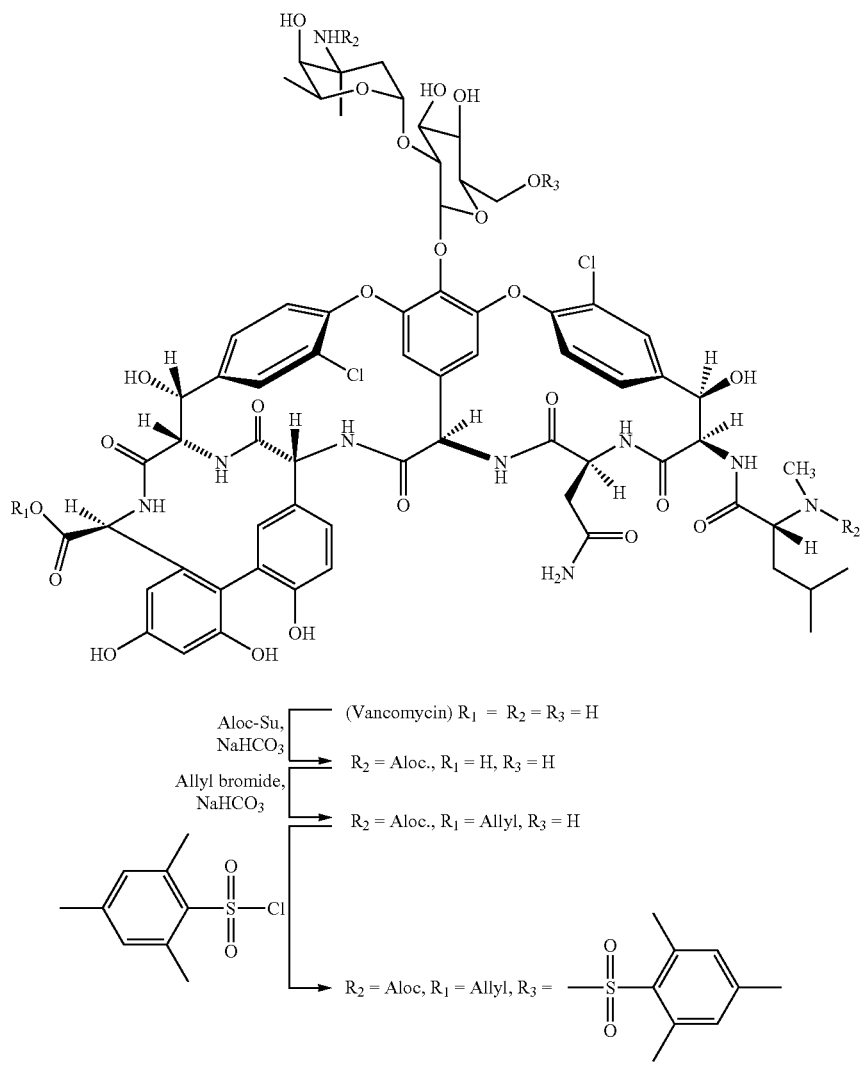

Protection of both amines by a similar group requires using excess acylation reagent while selective protection of the N-methyl leucine residue is known, allowing selective functionalization of the vancosamine amine group. See Pavlov et al., J. Antibiotics, 1993, 46, 1731. Selectively introducing the mesitylenesulfonyl group at the glucose-6-position differentiates this position from the other hydroxyl groups and allows further reaction to displace the mesitylenesulfonyl group, affording many derivatives. A variety of functional groups are introduced at the glucose-6 position by using common methods for nucleophilic displacement of primary arylsulfonyl groups directly, or by further synthetic modification of initial displacement products, including azido and iodo groups. For example, the iodo group is displaced by a variety of nucleophiles to produce additional C6-derivatives. A preferred nucleophile is a thiol compound, especially a heterocyclic thiol. Modification of an azido group at the 6-position is performed, e.g., by reducing the azido group to an amino group, which in turn is functionalized by means of reductive alkylation, nucleophilic substitution, or other amino-group reactions well known to those skilled in the art. These approaches are illustrated in FIGS. 7, 8a, 8b, 9a, 9b, 10a and 10b, and in many of the Examples. In a preferred embodiment of the invention, an azido group is partially reduced by reaction with a phosphine compound to produce an iminophosphorane.

Specific derivatives obtained by the aforementioned methods, and the antibiotic activities of these derivatives, are presented hereinafter. For example, introduction of substituted diazines or substituted triazines, e.g., 2-thio&azathymine, at the glucose-6 position affords an increase in activity against all five strains of bacteria tested, including VRE. Large hydrophobic groups, especially those bearing a full or partial positive charge, e.g., $N^+(R_1)=CR_2R_3$, $N=PR_1R_2R_3$, $N^+R_1R_2R_3$ or $P^+R_1R_2R_3$ in which one or more of $R_1$, $R_2$ and $R_3$ are bulky groups, also increase activity.

Introduction of N-decyl and N-4-(4-chlorophenyl)benzyl groups at the vancosamine amine group of glucose-6 iodo derivatives effects further enhancement of activity beyond that observed from halide substitution alone. These two hydrophobic groups were previously shown to increase the activity of glycopeptide antibiotics against VSE and VRE when introduced onto the amine group of the vancosamine or 4epi-vancosamine residues of the amino acid4 disaccharide. Since each of the hydrophobic and halide substitutions individually increases the antibiotic activity, it was anticipated that combining both changes into one structure would afford even better activity. Unexpectedly, the effects of these modifications are not additive and this result could not have been anticipated. While the individual changes increase activity, the combination of changes affords products that show bacterial strain dependence affording either a combined increase in activity or a combined decrease in activity, not only below the individual changes but below vancomycin itself. Therefore, by introducing changes in the glucose residue, a glycopeptide is produced in which the changes made to the vancosamine result in activities that could not have been anticipated in this unnatural system.

Preferred glycopeptide compounds of this invention are:
N-4-(4-chlorophenyl)benzylvancosamine-glucose-C6-2-mesitylenesulfonated vancomycin (compound XLII; see Examples).
Glucose-C6-2-thio-6-azathymine vancomycin (LXIV).
Glucose-C6-2-thio4-hydroxy-6-methylpyrimidine vancomycin (LXXVIII).
N-4-(4-chlorophenyl)benzylvancosamine-glucose-C6-2-thio-5-amino-1,3,4-thiadiazole vancomycin LXXXIII.
N-4-(4-chlorophenyl)benzylvancosamine-glucose-C6-2-thio4-amino-3-hydrazino-1,2,4-triazole vancomycin (LXXXIV).
N-4-(4-chlorophenyl)benzylvancosamine-glucose-C6-2-thio-4-hydroxy-methylpyrimidine vancomycin (LXXXV).
N-4-(4-chlorophenyl)benzylvancosamine-glucose-C6-2-thio-6-azathymine vancomycin (LXXXVI).
Vancosamine-N-4-(4-chlorophenyl)benzyl-glucose-C6-iodo vancomycin (LXXIIa).
Glucose-C6-N-2-quinoxalinyl-vancosamine-N-4-(4-chlorophenyl)benzyl vancomycin (LII).
Vancosamine-N-4-(4-chlorophenyl)benzyl-glucose-C6-S-3-amino-5-mercapto-1,2,4-triazole vancomycin (LXXIII).
Glucose-C6-mesitylenesulfonyl vancomycin (XLI).
Glucose-C6-iodo vancomycin (LXX).
Glucose-C6-azide vancomycin (XLVI).
Glucose-C6-bromo vancomycin (CX).
Glucose-C6-amine vancomycin (XLVII).
Glucose-C6-hydrazine vancomycin (XLIV).
Vancosamine-N-4-(4-chlorophenyl)benzyl-glucose-C6-iminotriphenylphosphorane vancomycin (CXXXVI).

The chemical library of compounds of this invention is prepared to explore the effects of introducing a large number of different substituents on glycopeptides on biological activity, especially substitutions on the sugar residues. In any preparation of a chemical library, at least two steps are performed, each of which introduces a substituent group on the glycopeptide. A combinatorial format is established in which many different predetermined substituent groups are introduced independently at each of at least two positions, resulting in a library containing a large number of glycopeptides, wherein each possible combination-of the predetermined substituent groups is represented. For example, if three positions are to be substituted and 36 different substituent groups (3 sets of 12) are chosen, 1 of each set of 12 to be substituted at each position, the total number of unique compounds (each of which bears 3 substituent groups) in the library will be 12×12×12=1,728. It is readily apparent that, when a combinatorial synthesis is performed in an automated system, a large number of related compounds may be prepared relatively quickly. Methods for performing combinatorial synthesis are well known and are described in several review articles. [Thompson (1996), Gallop (1994), Gordon (1994), Terrett (1995)]

Substituents are introduced on the glycopeptide library compounds of this invention through the use of two different reaction schemes. In one reaction scheme, glycosylation reactions are used to attach sugars bearing desired substituent groups to hydroxyl groups on various positions of glycopeptide antibiotics, aglycones, or pseudoaglycones, as described in detail hereinbelow. The other reaction scheme is the method for derivatizing a hexose C-6 hydroxyl group, as shown in Scheme 1, and as described in the accompanying discussion and in several of the Examples. In construction of the library of this invention, at least two steps are carried out in a combinatorial format. These steps are selected independently from the two reaction schemes outlined hereinabove, such that a library is constructed using either scheme exclusively or a combination of the two.

Figure 2:
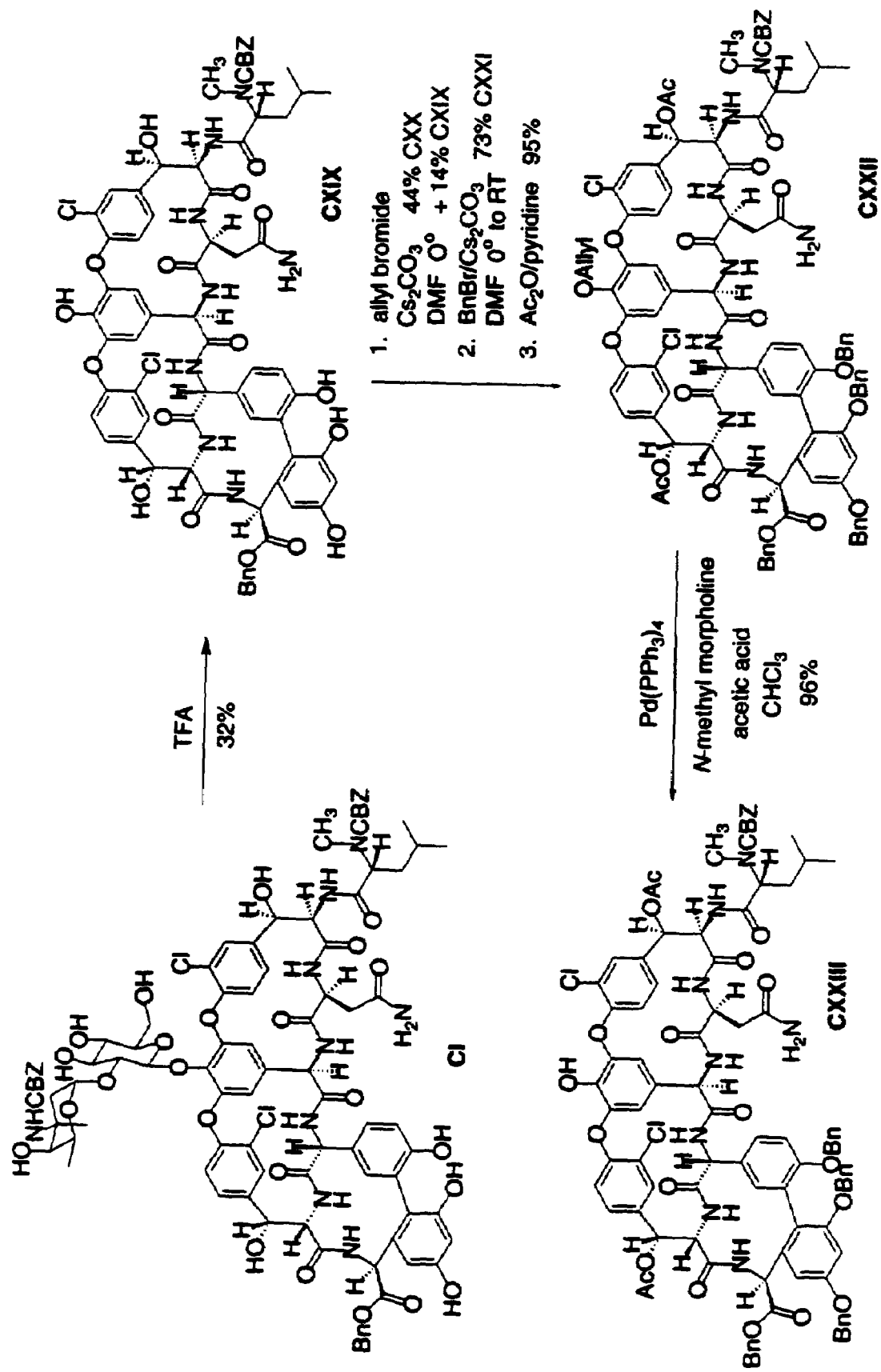
FIG. 2 illustrates a preparation of a protected aglycone of vancomycin suitable for glycosylation.
Figure 3:
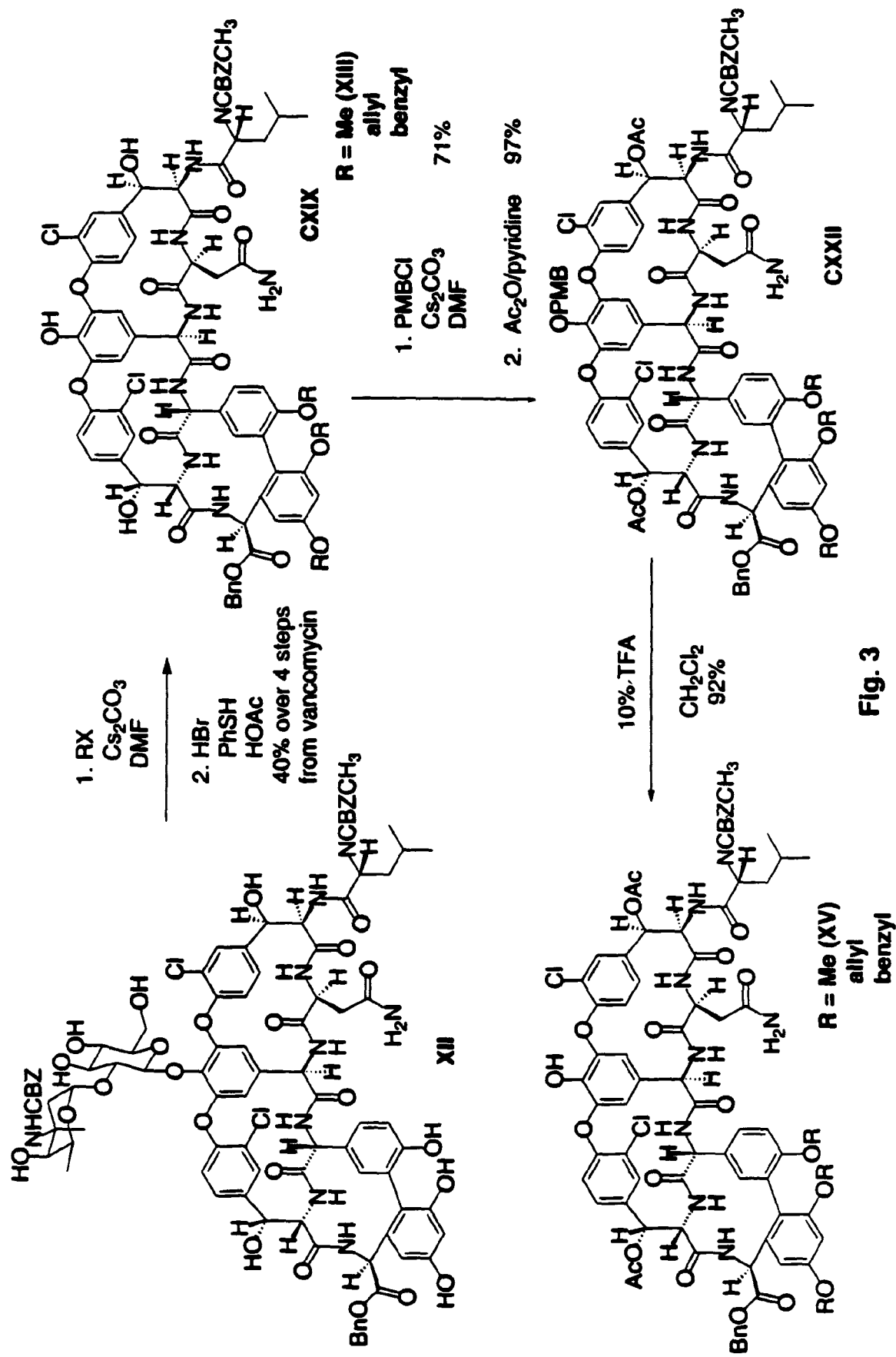
FIG. 3 illustrates another preparation of a protected aglycone of vancomycin suitable for glycosylation.
Figure 4:
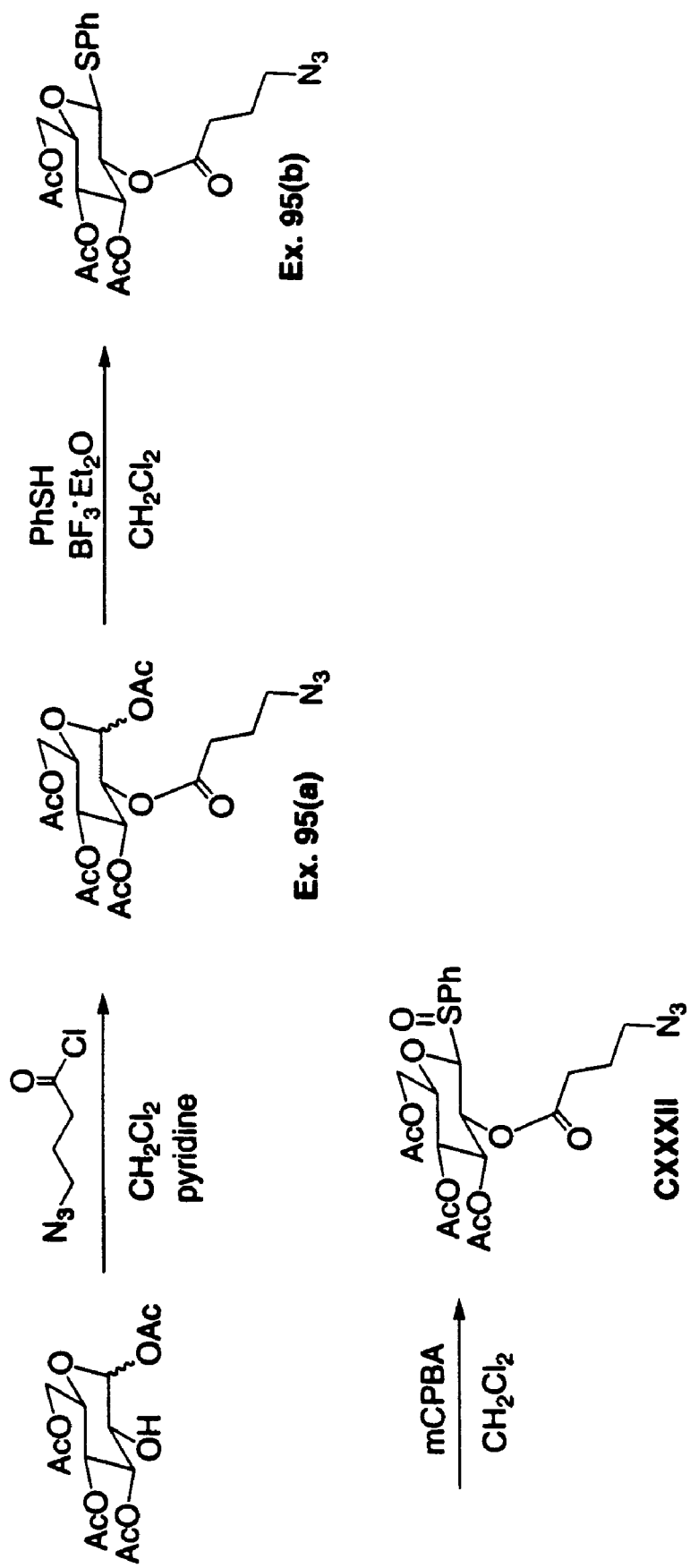
FIG. 4 illustrates preparation of a sugar useful in glycosylation of an aglycone.
Figure 5:
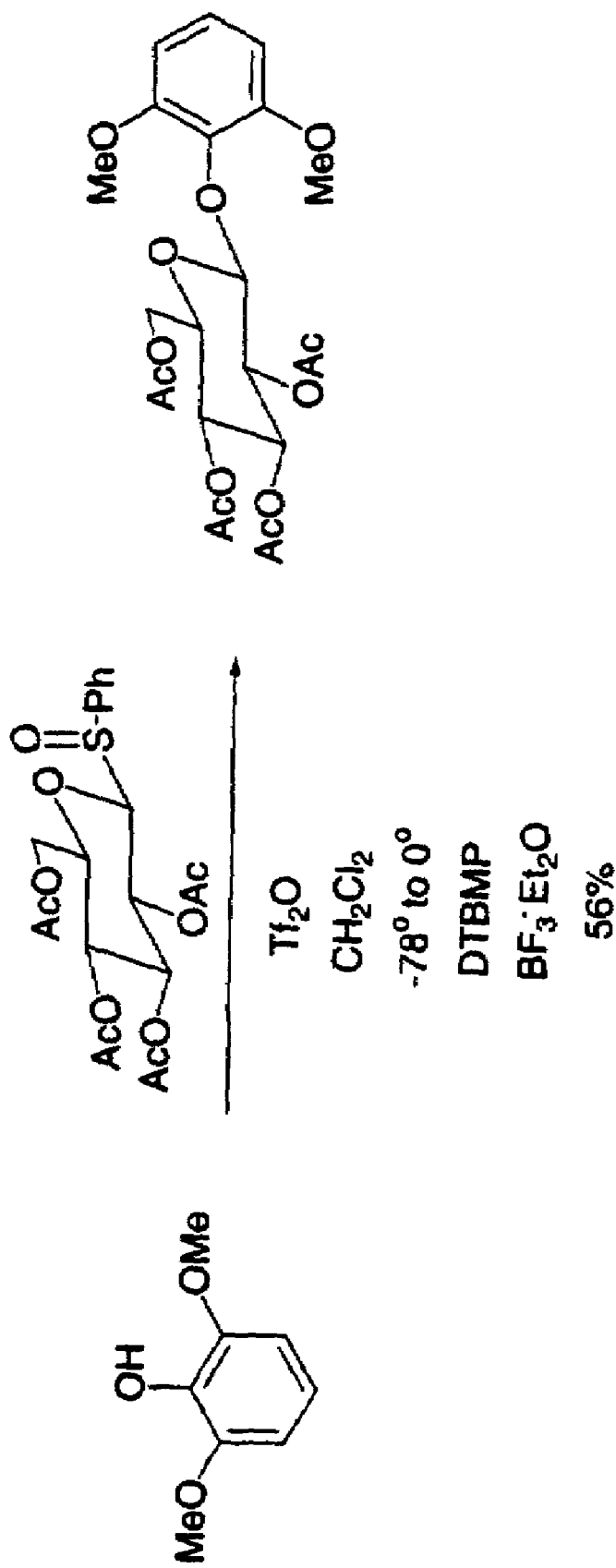
FIG. 5 illustrates glycosylation of a phenol which is a model compound for an aglycone.
Figure 6:
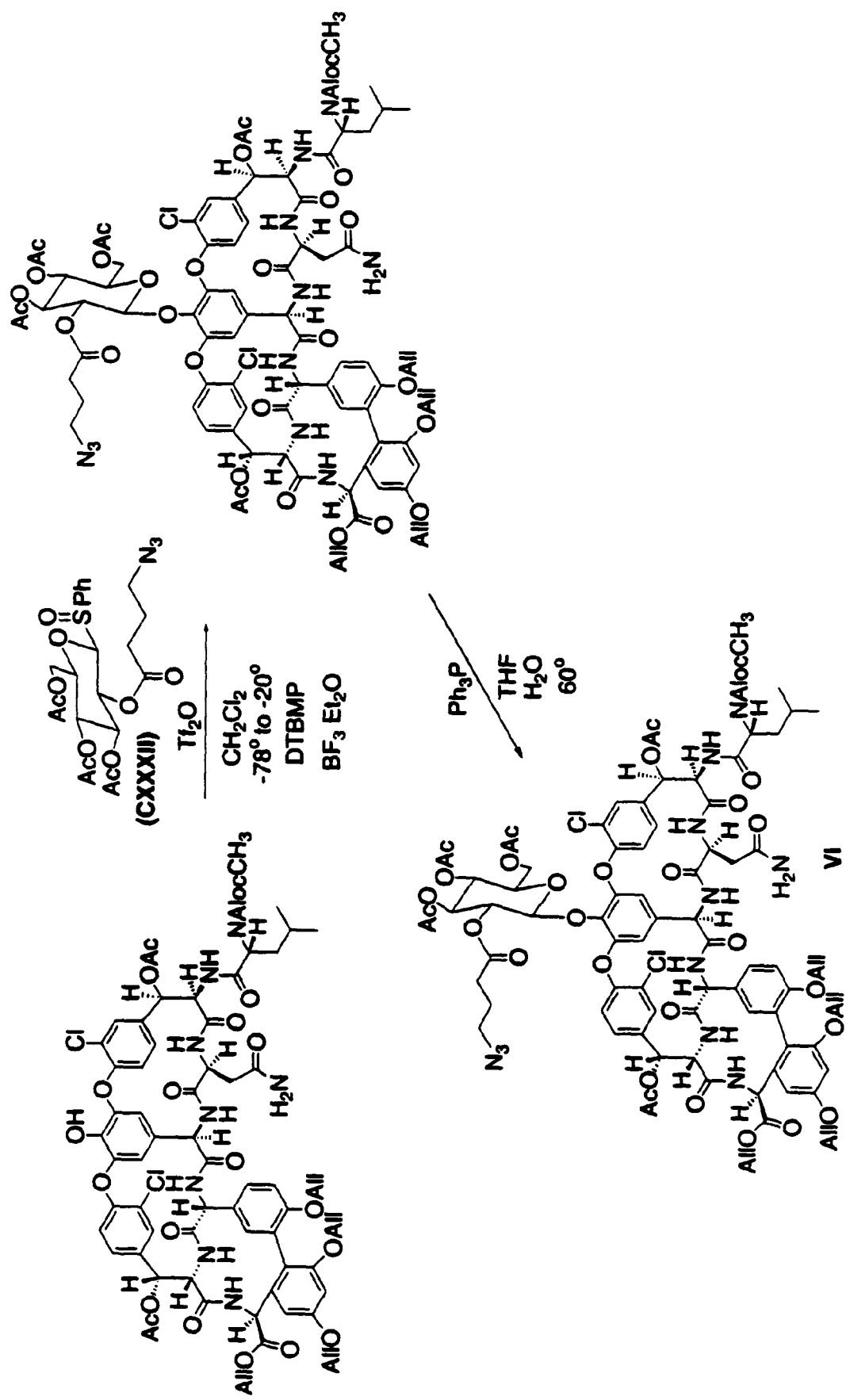
FIG. 6 illustrates glycosylation of a vancomycin aglycone.
Figure 7:
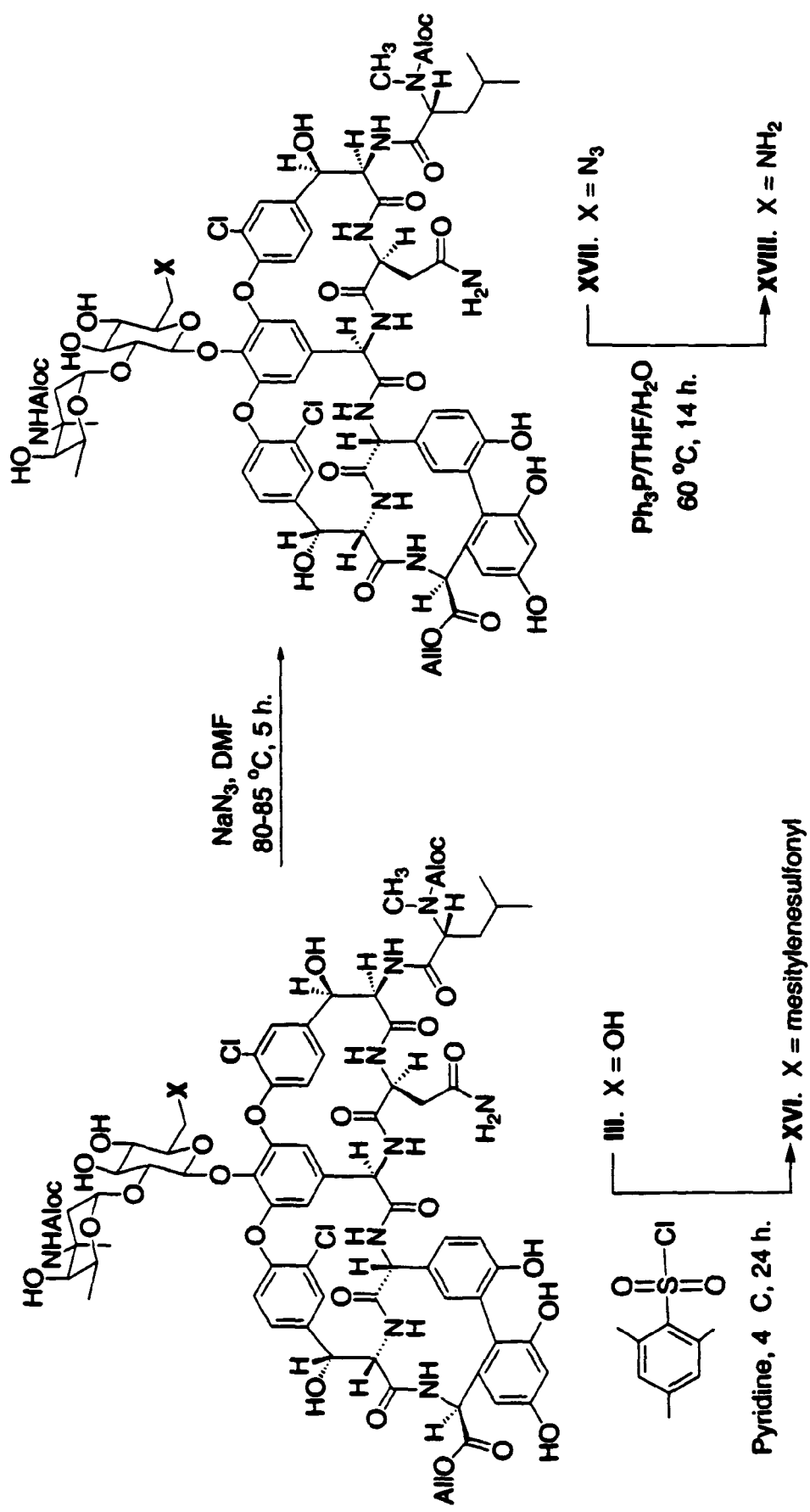
FIG. 7 is a scheme for introduction of an amino substituent onto the glucose C6 position of vancomycin.
Figure 8A:
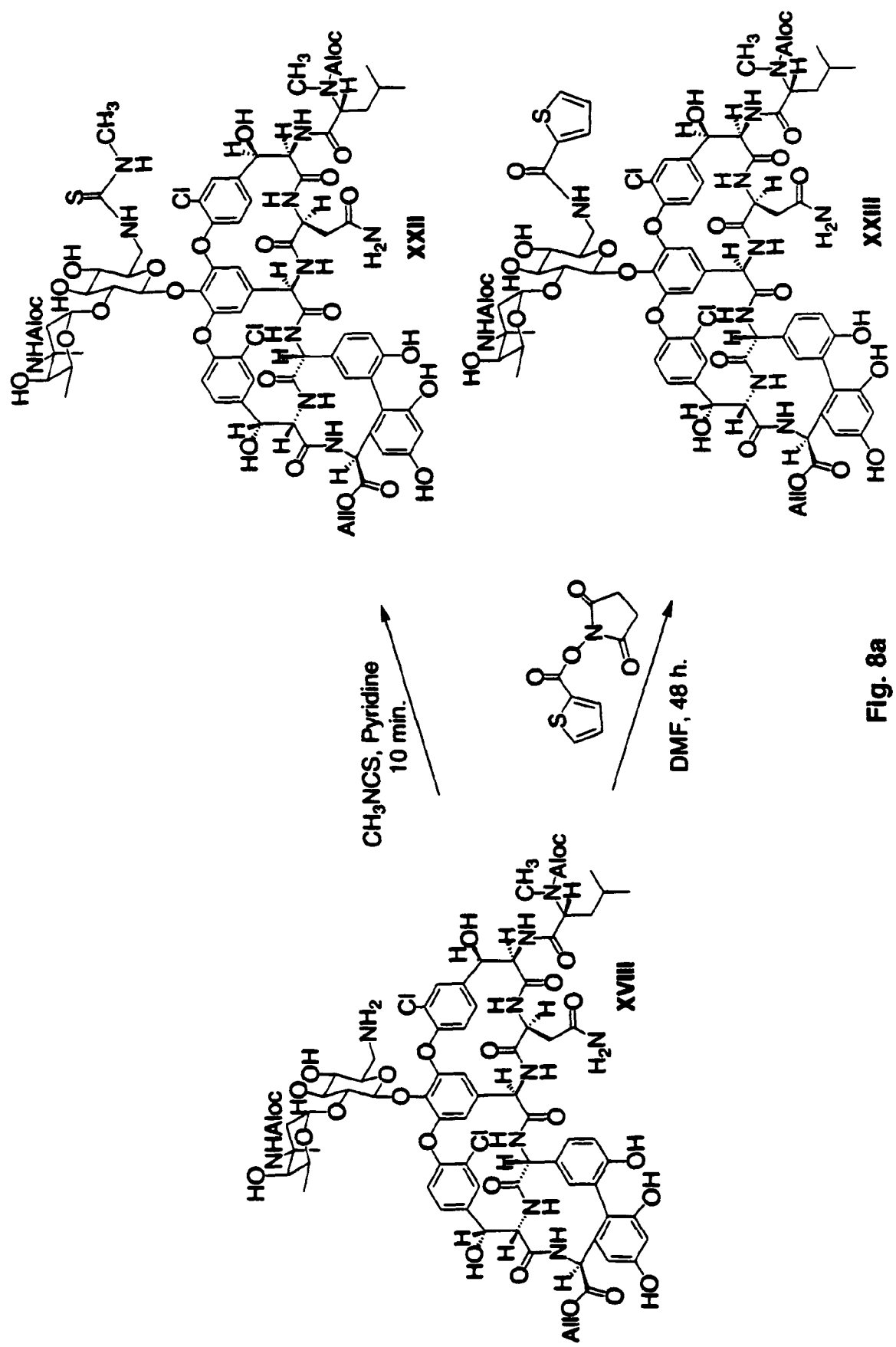
FIG. 8a illustrates further functionalization of a glucose C6 amino substituent on vancomycin.
Figure 8B:
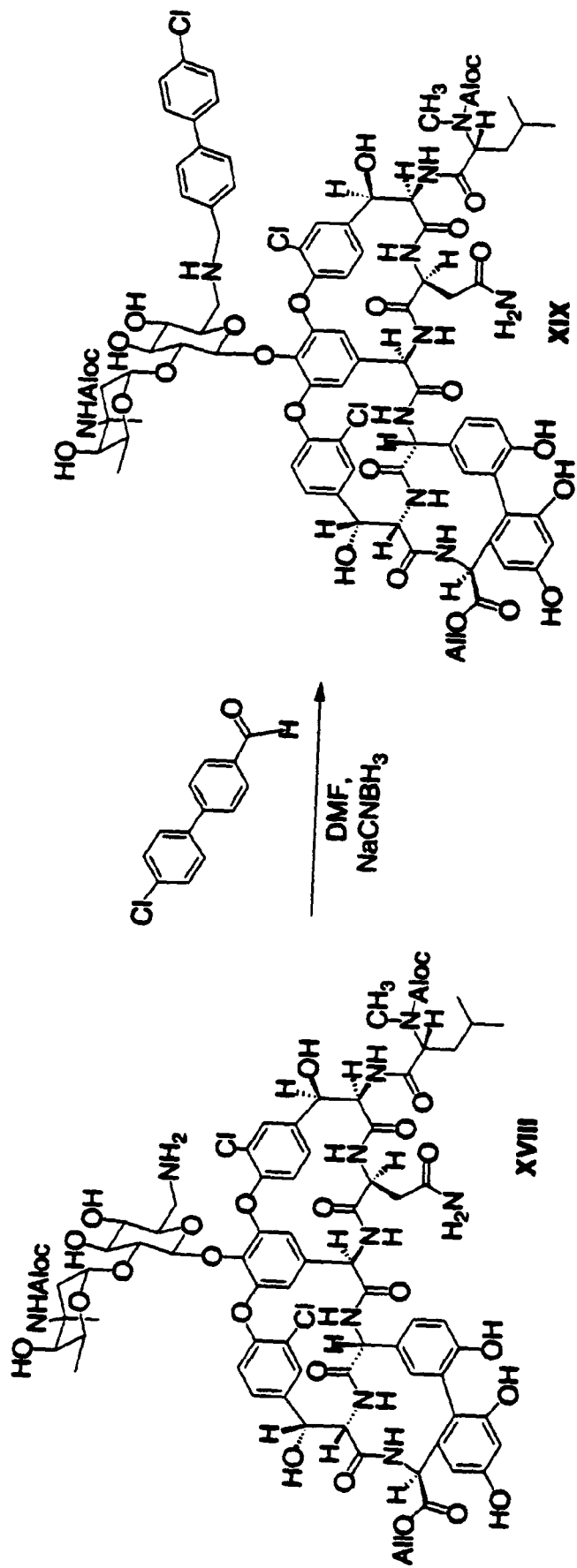
FIG. 8b illustrates further functionalization of a glucose C6 amino substituent on vancomycin.
Figure 9A:
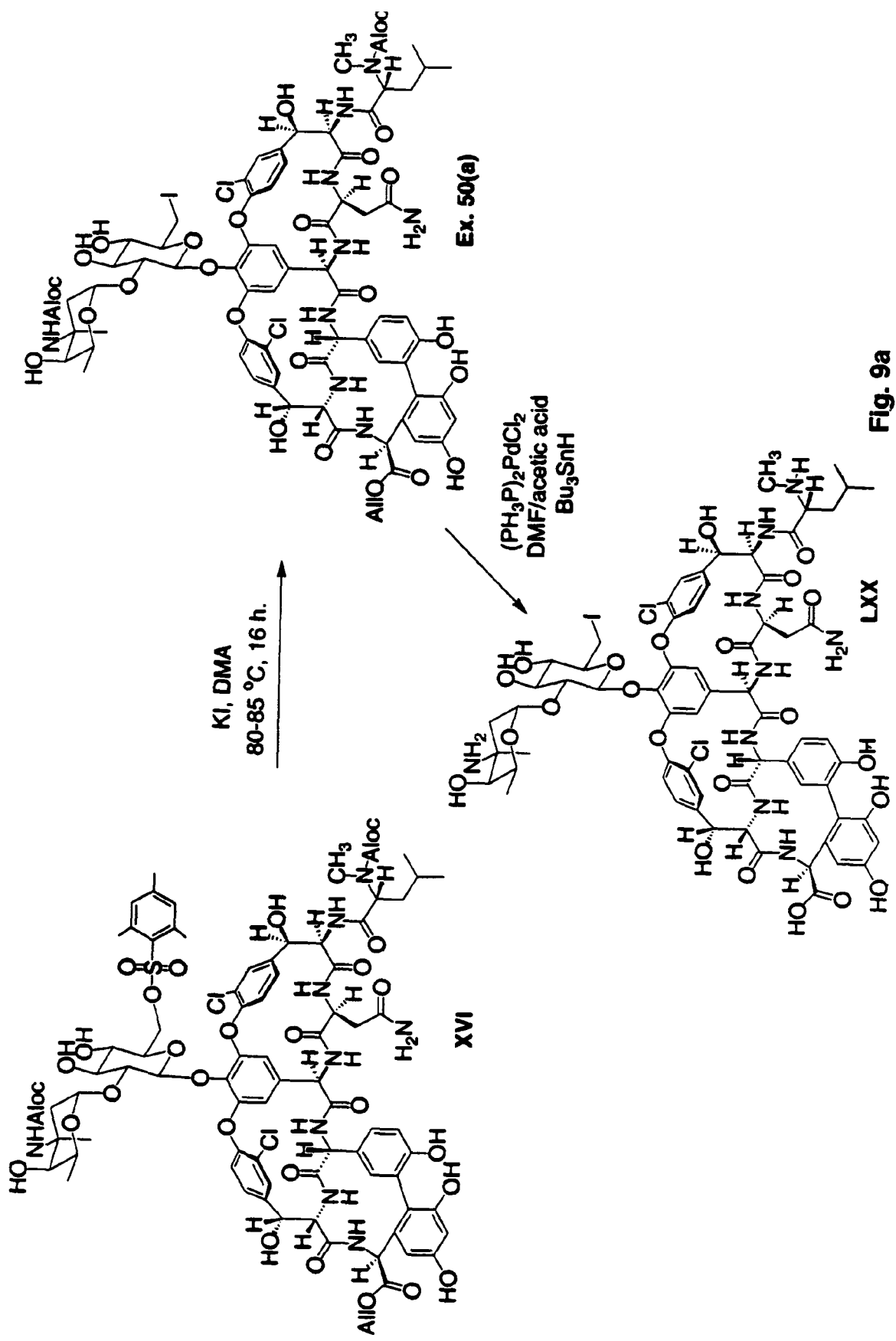
FIG. 9a illustrates substitution of the glucose C6 position.
Figure 9B:
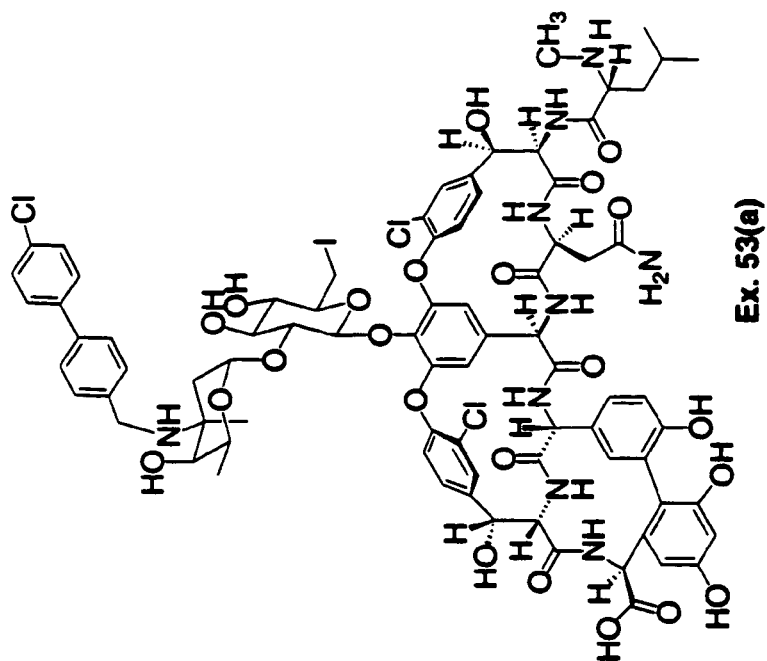
FIG. 9b further illustrates substitution of the vancosamine nitrogen.
Figure 9B:
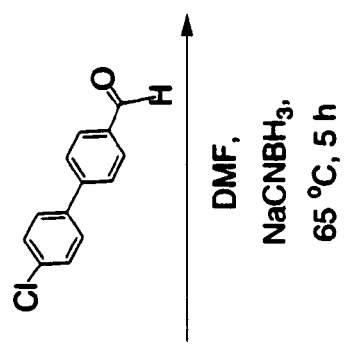
Figure 9B:
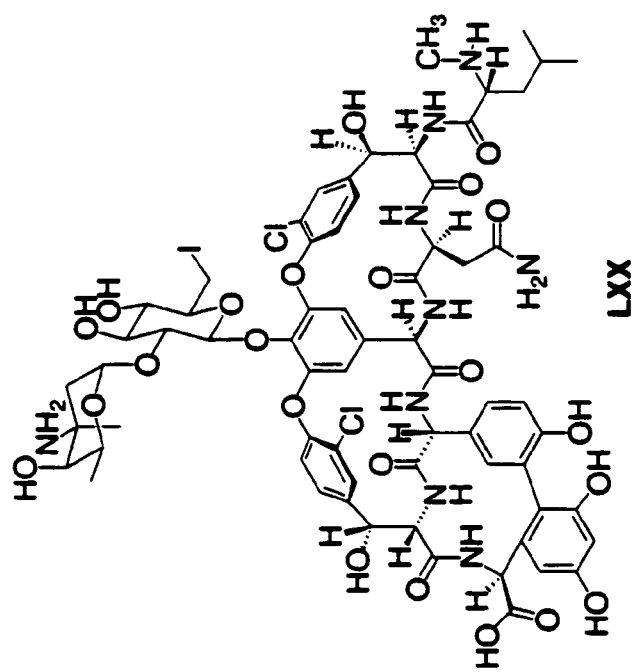
Figure 10A:
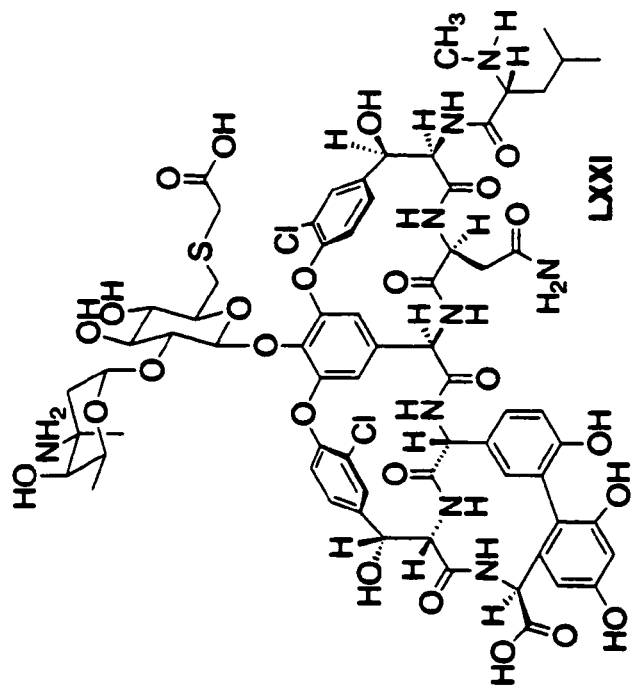
FIG. 10a illustrates introduction of a thio substituent at the glucose C6 position of vancomycin.
Figure 10A:
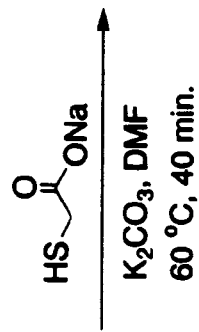
Figure 10A:
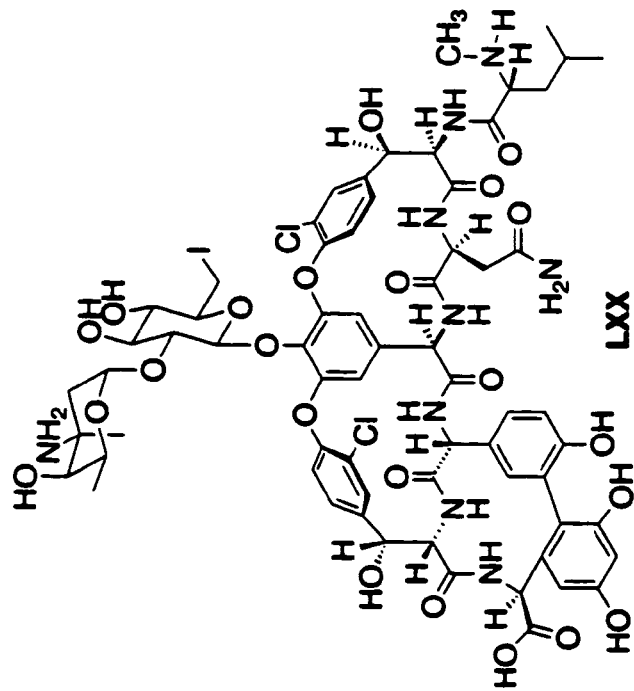
Figure 10B:
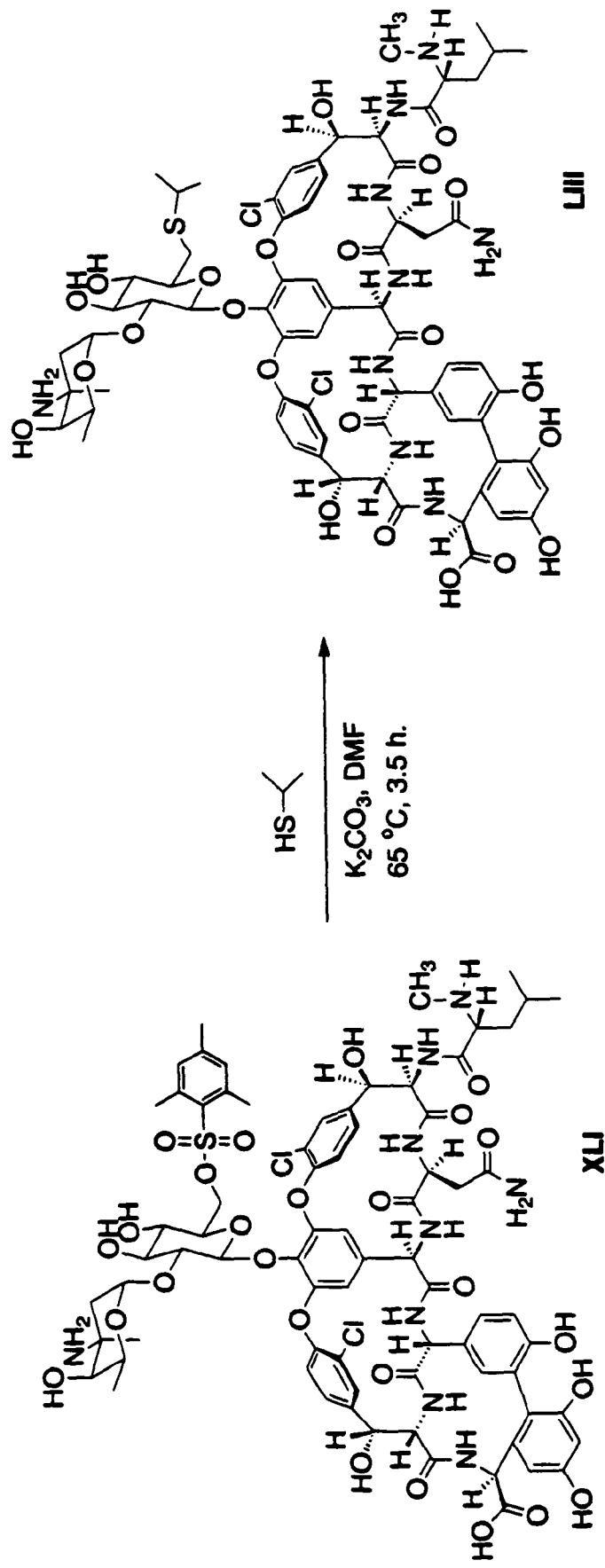
FIG. 10b illustrates introduction of a thio substituent at the glucose C6 position of vancomycin.
Figure 11A:
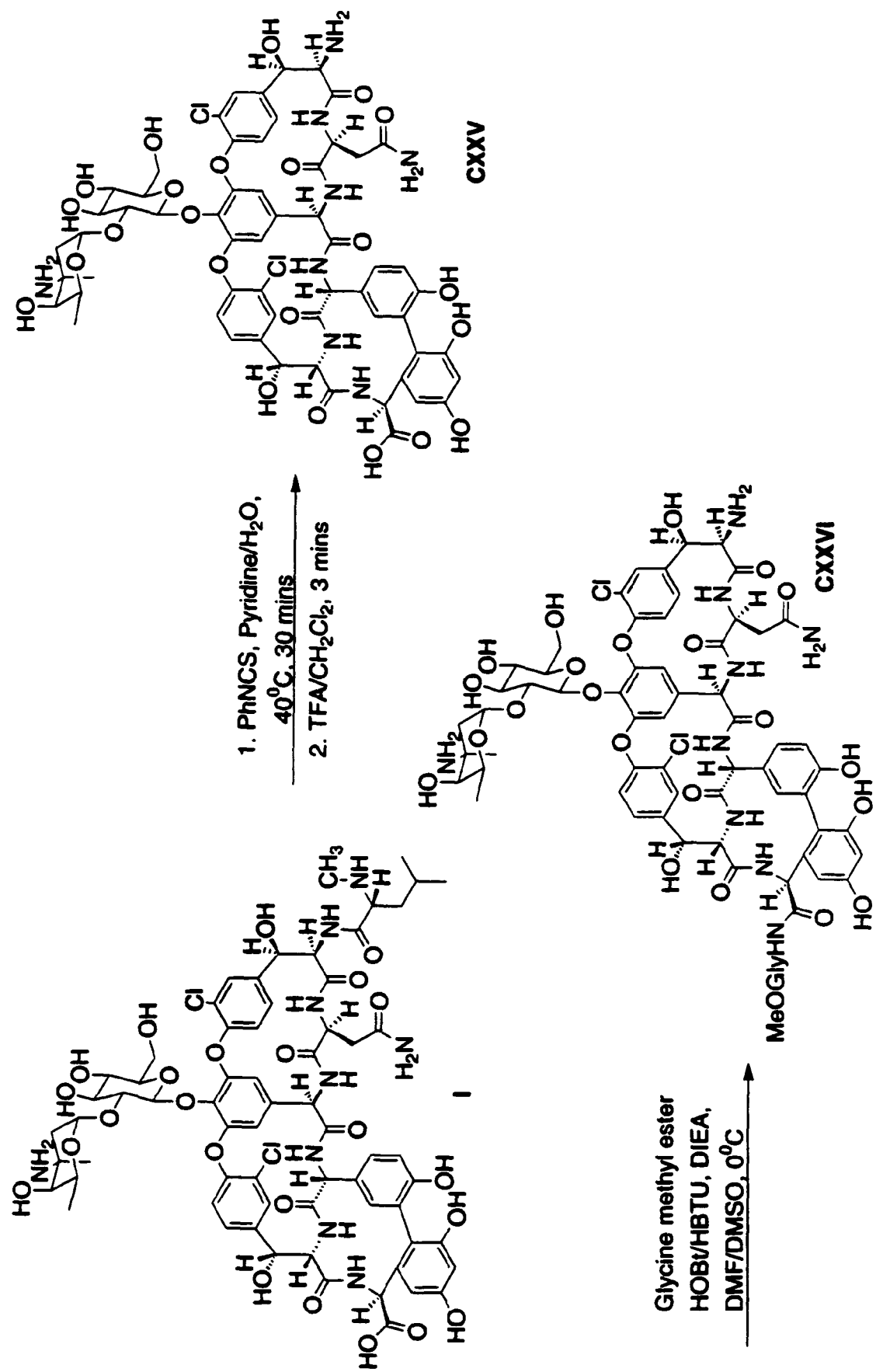
FIG. 11a illustrates removal of the $A_1$ amino acid of vancomycin and protection of the product.
Figure 11B:
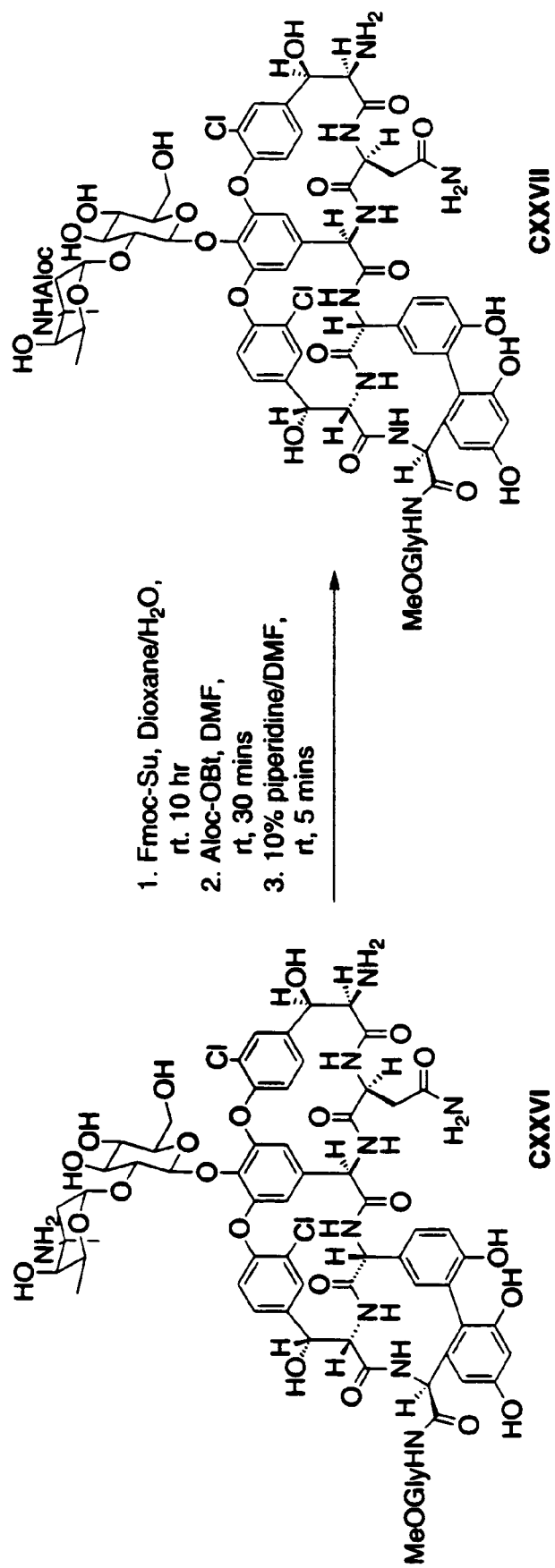
FIG. 11b illustrates the protected product formed from the removal of the $A_1$ amino acid of vancomycin and a reaction at the $A_2$ terminal amino group.

One method suitable for preparing glycopeptide compounds, individually or as part of a chemical library, starts with the synthesis of a suitably protected aglycone. All reactive functional groups of the aglycone (amine, carboxylic acid, phenols, and benzylic alcohols) are suitably protected except for the hydroxyl group on which the sugars are to be attached, preferably the phenolic hydroxyl group on residue 4. The carboxylic acid is protected with a group which is orthogonal to the other protecting groups used, i.e., the carboxylic acid protecting group is not removed under conditions suitable for removal of other protecting groups on the molecule. In addition, protecting groups are used that render the protected aglycone soluble in organic solvents. The protecting groups may either remain on the final glycopeptide compound or may be removed by exposure to acidic or basic conditions, catalytic hydrogenation, or light. When the aglycone is derived from vancomycin, it is preferred that the protecting groups are as follows: carboxybenzyl (CBz) on the amine nitrogen, a benzyl ester group; benzyl, allyl or methyl phenolic ethers on the phenolic hydroxyls of $A_5$ and $A_7$, and acetates on the aliphatic hydroxyls. Alternate methods for preparing aglycones of vancomycin are illustrated in FIGS. 2 and 3, and in the Examples.

This suitably protected aglycone is glycosylated via a non-enzymatic reaction in an organic solvent with a variety of glycosyl donors, thereby forming a glycosidic bond between the aglycone and the glycosyl donor. Preferably the glycosyl donors are activated monosaccharide anomeric sulfoxides which are functionalized at the 6 position or elsewhere. These sulfoxide donors are differentially protected so as to allow for selective deprotection of a single hydroxyl after formation of the glycosidic bond. Suitable protecting groups to allow for this selective deprotection are the 2,2-dimethyl acetoacetate group, the 4-azidobutyryl group and any other groups which can be removed in the presence of other protecting groups.

A modified sulfoxide glycosylation of the aglycone phenolic hydroxyl group may be accomplished using an acetate or other unhindered ester at C-2 of the sugar as a neighboring group. In this modified glycosylation, as in the preferred glycosylation procedure utilizing activated monosaccharide anomeric sulfoxides, the leaving group at the anomeric center is a sulfoxide moiety which is activated by trifluoromethanesulfonic anhydride ($Tf_2O$) in the presence of 2,6-di-t-butyl-methylpyridine. The modification to the glycosylation procedure involves addition of $BF_3$ to the reaction. Without being bound to theory, it is believed that the presence of $BF_3$ prevents formation of the undesired ortho-ester side product which is unstable in the presence of acid. Use of the modified procedure leads to the desired β glycosidic linkage. The use of $BF_3$ is an improvement because previously the presence of a very bulky ester at C-2 (e.g., pivalate) was required to prevent formation of the undesired ortho-ester during formation of a β glycosidic linkage by the sulfoxide method using neighboring group participation. These bulky esters can be very difficult to remove, except under strongly basic conditions.

It is preferred to perform the aforementioned glycosylation reactions on a polymeric resin, preferably after coupling the carboxylic acid functionality of these compounds to a suitable resin. In order to attach the carboxylic acid group to the resin, it must first be selectively deprotected. Use of a p-nitrobenzyl ester as a protecting group for the carboxylic acid is preferred to facilitate selective deprotection of the carboxylic acid in the presence of protected hydroxyl groups. A suitable resin is a cross-linked polymer insoluble in the reaction solvent which is suitably functionalized for attachment, e.g., SASRIN (Wang's resin). Once coupled to the resin, the differentially protected hydroxyl group on the attached sugar is deprotected. Alternatively, this hydroxyl group is freed before attachment to the resin, since the hydroxyl group does not interfere with the coupling reaction. The free hydroxyl group then serves as the nucleophile in a second glycosylation reaction. In this second glycosylation, the hydroxyl is glycosylated, preferably in a solid phase reaction, with a variety of azido sugars. Following the glycosylation reaction, the azido groups are reduced and the resulting amino groups are then derivatized. The solid phase portion of the library construction can be carried out using a parallel synthesis or a mix and split strategy. The carbohydrate-modified glycopeptide derivatives would then be deprotected and cleaved from the resin. This set of compounds would then be assayed for peptide binding and anti-bacterial activity.

When it is desired to remove protecting groups from any of the compounds of this invention, their removal is accomplished using methods well known to those skilled in the art. The preferred method for removal of protecting groups is as follows. Aloc groups on amines, and allyl esters or allyl ethers are removed by using Pd(0) mediated reactions, e.g., $[Ph_3P]_2Pd(II)Cl_2$ and $Bu_3SnH$ in 1:1 acetic acid:DMF. Acetate protecting groups are removed using hydrazine in THF/methanol.

Figure 15A:
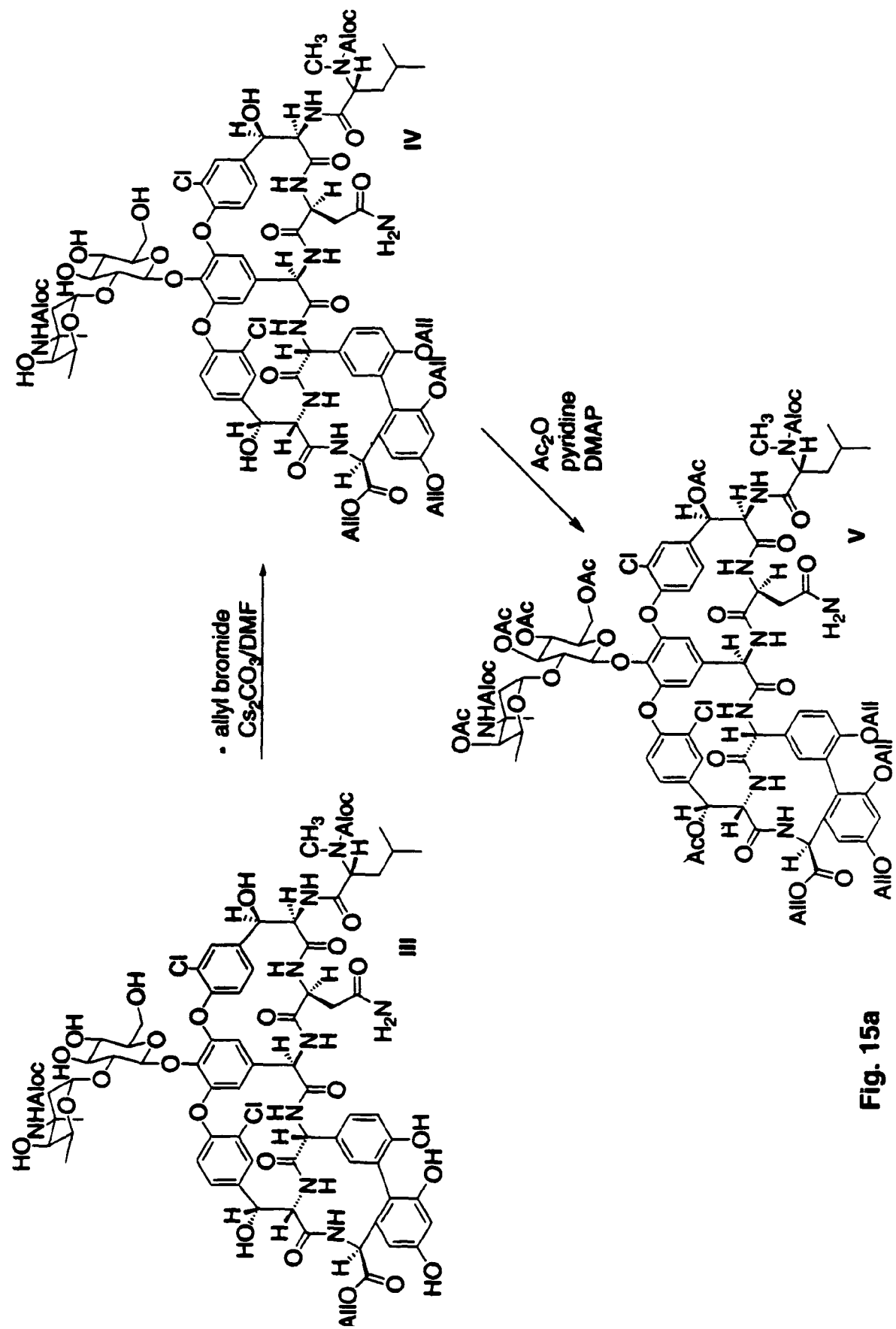
FIG. 15a illustrates a portion of a scheme for preparation of a suitably protected aglycone.
Figure 15B:
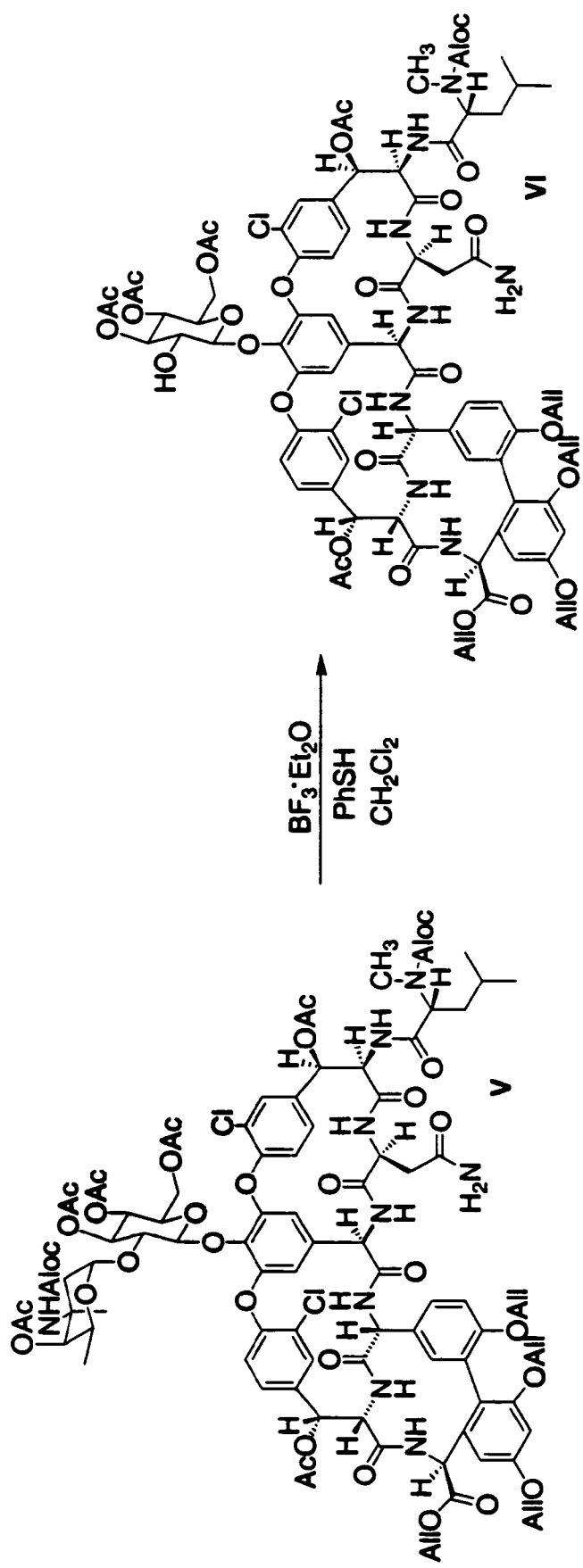
FIG. 15b illustrates a portion of a scheme for preparation of a suitably protected aglycone.
Figure 16:
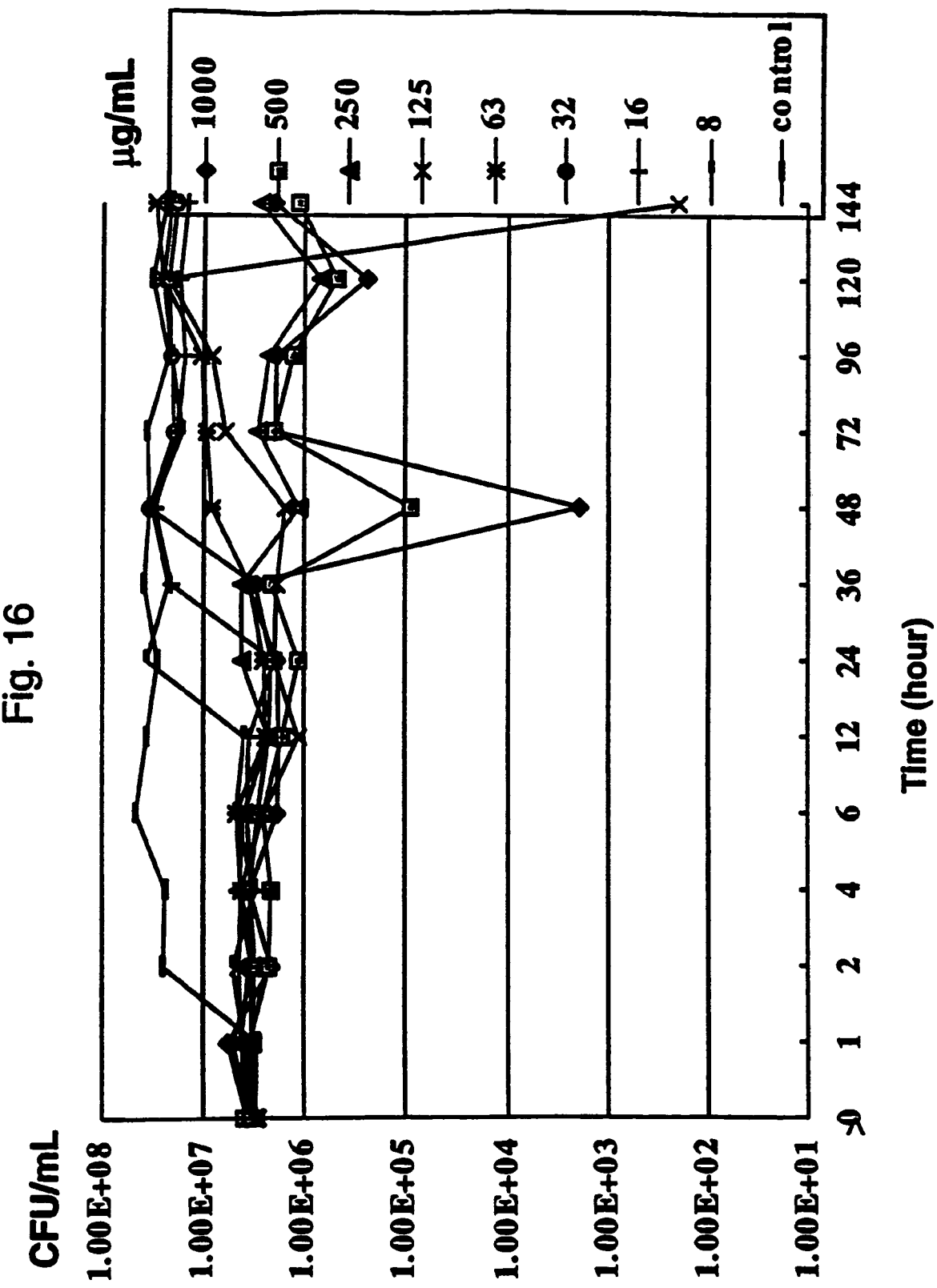
FIG. 16 is a graph of a time-kill study of N-decyl-C6-aminotriazole vancomycin against vancomycin-resistant *enterococcus faecium*.
Figure 17:
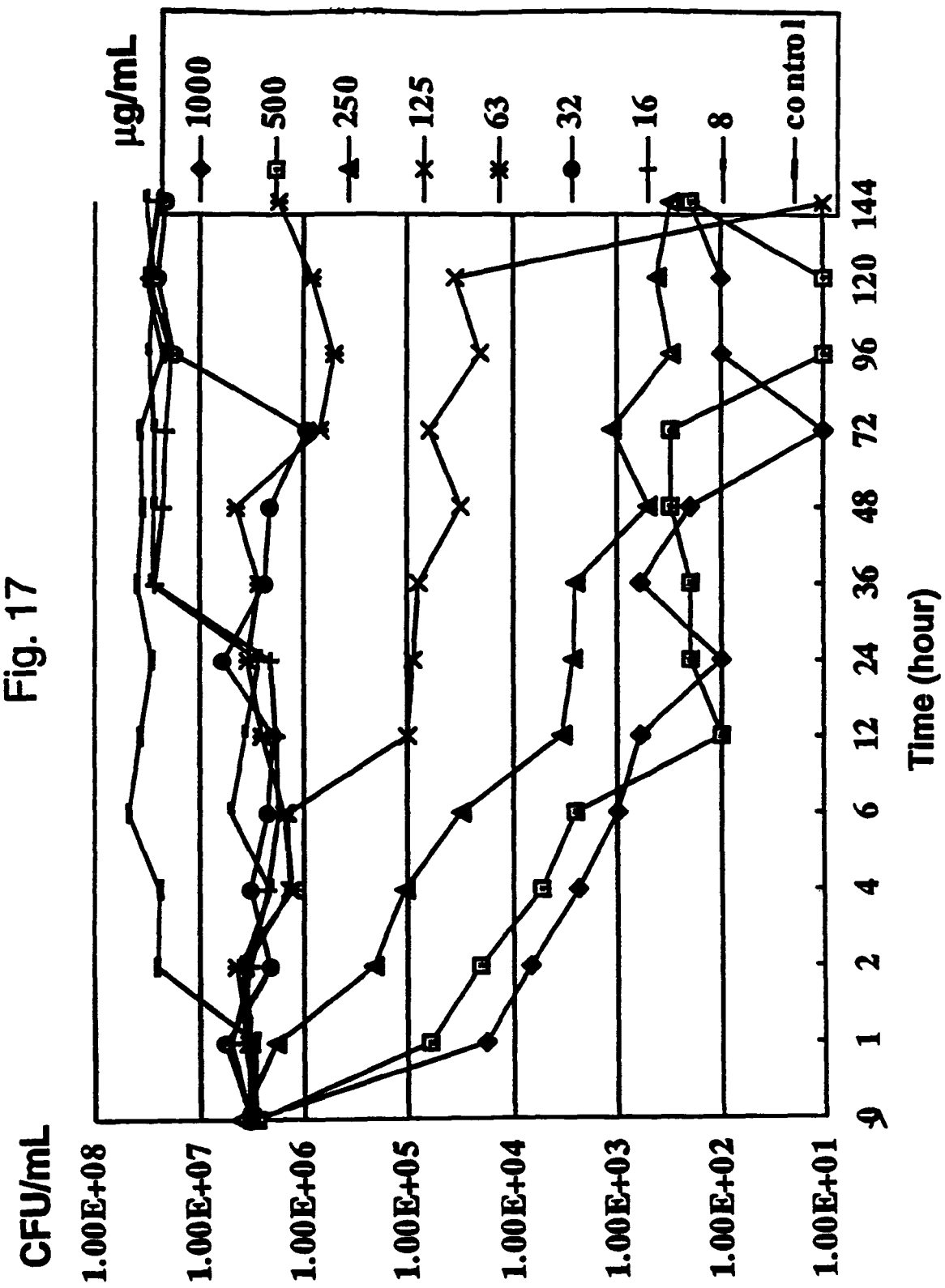
FIG. 17 is a graph of a time-kill study of N4(4-chlorophenyl)benzyl-C6-aminotriazole vancomycin against vancomycin-resistant *enterococcus faecium*.
Figure 18:
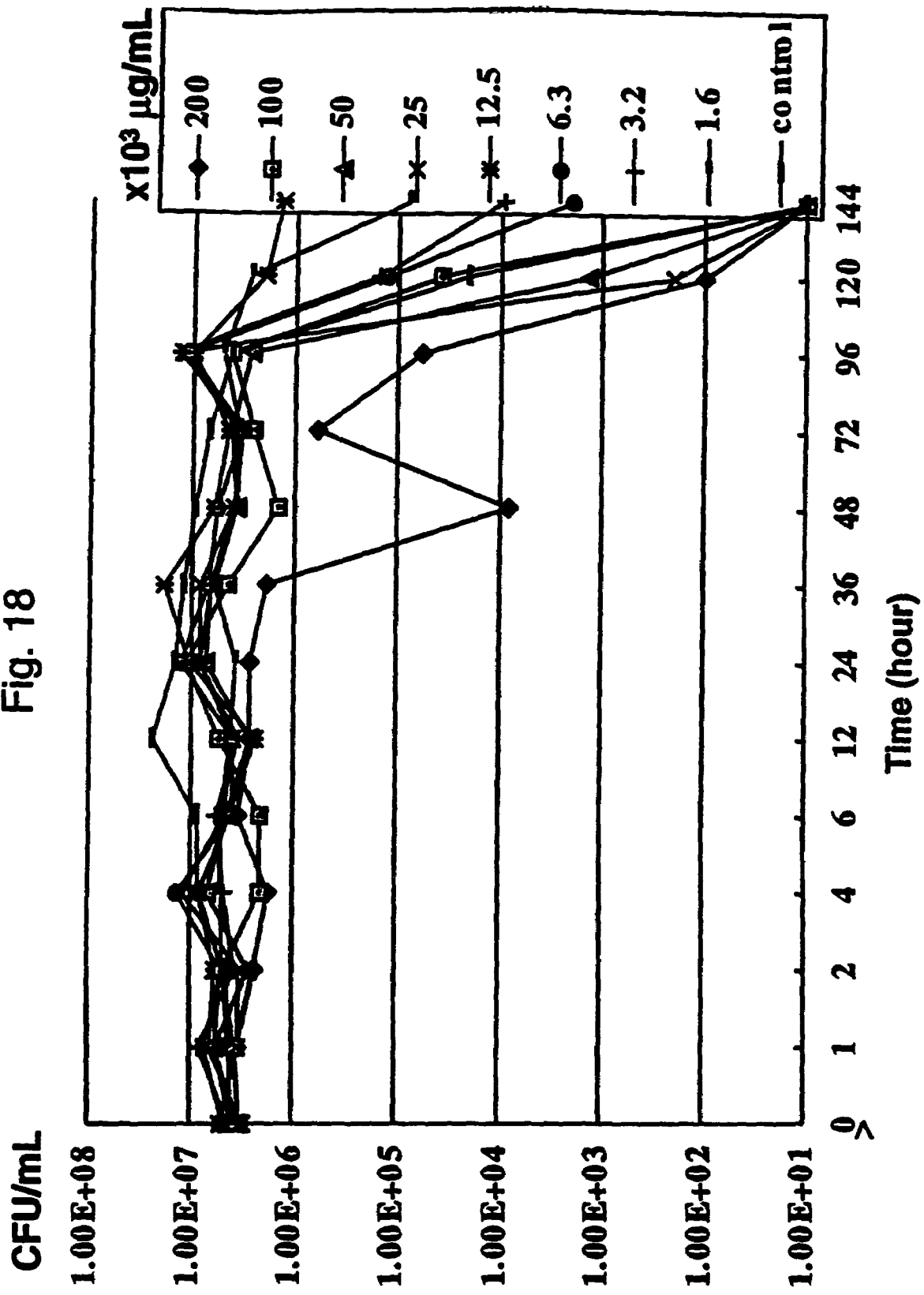
FIG. 18 is a graph of a time-kill study of vancomycin against vancomycin-resistant *enterococcus faecium*.
Figure 19:
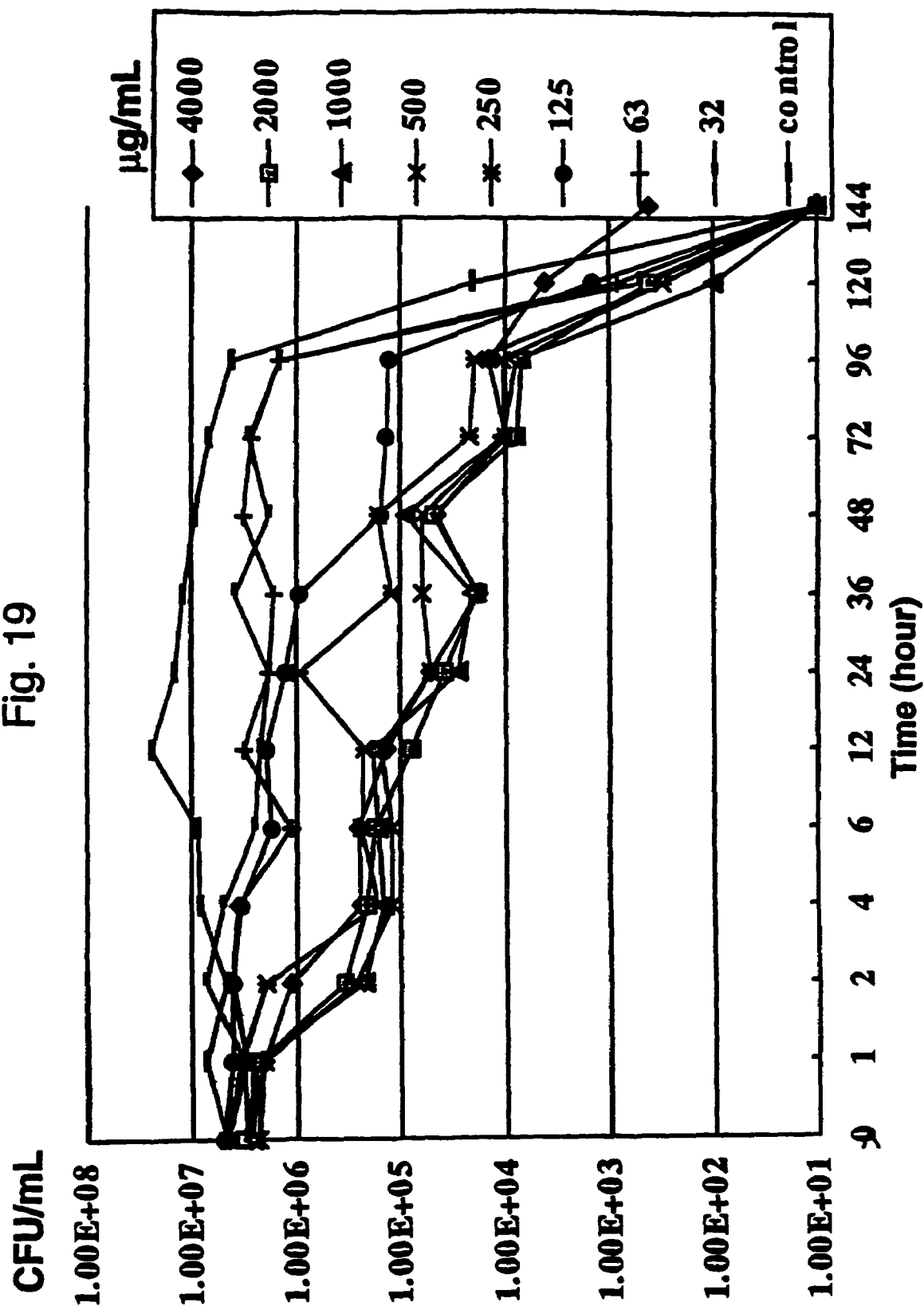
FIG. 19 is a graph of a time-kill study of N (4-chlorophenyl)benzyl vancomycin against vancomycin-resistant *enterococcus faecium*.

An alternative method for construction of a library of glycopeptide compounds starts with the synthesis of a suitably protected pseudoaglycone. A protected glycopeptide antibiotic having a disaccharide at residue $A_4$, i.e., a pseudoaglycone bearing an additional sugar residue, is treated with a Lewis acid in an organic solvent to remove the additional sugar residue, as illustrated in FIGS. 15a and 15b, and in the Examples. In a preferred embodiment of the invention, the Lewis acid is boron trifluoride, preferably as the complex with diethyl ether. When the glycopeptide antibiotic is vancomycin, it is preferred that allyloxycarbonyl (aloc) groups are present on the amines of $A_1$ and the vancosamine residue, acetates on the aliphatic hydroxyl groups, allyl phenyl ethers on the phenolic hydroxyls, and an allyl or o-nitrobenzyl ester on the $A_7$ terminal carboxyl; when solid-phase synthesis is employed, the o-nitrobenzyl ester is preferred. A degradation reaction proceeds which removes the additional sugar residue, leaving a pseudoaglycone in which all reactive functional groups (amine, carboxylic acid, phenols, and benzylic alcohols) are suitably protected except for a hydroxyl group on the remaining residue $A_4$ sugar, which is where an additional sugar is to be attached.

This pseudoaglycone is glycosylated via a non-enzymatic reaction in an organic solvent, as described hereinabove for glycosylation of an aglycone to which one sugar residue has already been attached.

In solid-phase synthesis of glycopeptide compounds from pseudoaglycones, the molecule is preferably attached to the resin after removal of the o-nitrobenzyl group from the protected pseudoaglycone.

The following examples are presented in order to illustrate various aspects of the present invention, but are not intended to limit it.

EXAMPLES

General Procedures

Unless specified otherwise, product purification by preparative reversed-phase HPLC is performed using a PHENOMENEX LUNA $C_{18}$ column (21.2×250 mm), 5 μm particle size; and semi-preparative reversed-phase HPLC is performed using a Vydac $C_{18}$ column (10×250 mm), 5 μm particle size. Detection is by UV absorption measurement at 285 nm.

Method A: Compounds are dissolved in DMF-water or DMF-methanol then diluted with water and filtered (0.45 μm). Multiple injections of 0.1 to 1 mL samples are required for most separations to avoid precipitation and overloading of the column. A gradient of acetonitrile in water containing 0.1% acetic acid at a flow rate of 7 to 8 mL/min. is used. Products purified by this method are treated with 1-butanol (approximately 1 to 1 with the anticipated water content) and evaporated to dryness under reduced pressure). The solid is then dissolved in methanol, diluted with toluene and evaporated under reduced pressure.

Method B: Compounds are dissolved in water or a water-methanol or water-DMF mixture and filtered (0.45 μm). Multiple injections of 0.1 to 1 mL samples are required for most separations to avoid precipitation and overloading of the column. A gradient of acetonitrile in water containing 0.1% trifluoroacetic acid at a flow rate of 7 to 8 mL/min. is used. Products purified by this method are evaporated under reduced pressure to remove the acetonitrile (bath temperature maintained at or below 25° C. to avoid loss of the vancosamine residue) and the remaining water solution froze and lyophilized. Purity of each aqueous sample is confirmed by analytical HPLC prior to lyophilizing.

Method C: Compounds are dissolved in water or a water-methanol or water-DMF mixture and filtered (0.45 μm). Multiple injections of 0.1 to 1 mL samples are required for most separations to avoid precipitation and overloading of the column. A gradient of acetonitrile in water (0.5% triethylamine adjusted to pH=3 with phosphoric acid) is used. Products purified by this method are desalted by adsorption onto a polystyrene column (10 mm×600 mm), followed by washing with 5 column volumes of water, and eluted with 75% methanol in water containing 0.1% acetic acid. Fractions containing product are combined, the methanol removed under reduced pressure and the resulting water solution froze and lyophilized. Purity of each aqueous sample is confirmed by analytical HPLC prior to lyophilizing.

Example 1

N,N'-dialoc Vancomycin Allyl Ester (III)

a) N,N'-diallyloxycarbonyl Vancomycin (II)

To a solution of vancomycin-HCl (13 g, 8.7 mmol) in 105 mL water is slowly added 80 mL acetone. A 30 mL aqueous solution of $NaHCO_3$ (1.54 g, 18.3 mmol) is then added over 5 min. affording a thick white slurry. After stirring 10 min. the suspension is treated with a solution of N-(allyloxycarbonyloxy)succinimide (18 g, 90 mmol) in 70 mL acetone. Within a few h the reaction became clear and stirred at room temperature for 36 h. TLC (6:4:1, chloroform-methanol-water) shows no vancomycin (baseline) remaining and one predominant glycopeptide product (Rf=0.3). The crude reaction mixture is treated with 1-butanol (100 mL) and evaporated to dryness under reduced pressure. The solid is dissolved in 50 mL methanol and precipitated by addition to 300 mL diethyl ether. Any chunks are crushed and the white suspension allowed to settle for 1 h at 4° C. Approximately 200 mL of the clear supernatant is decanted and the remaining suspension centrifuged and the supernatant decanted. The white solid is mixed vigorously with 240 mL acetone, the suspension centrifuged and the supernatant decanted. The solid is dissolved in methanol, diluted with 300 mL toluene and evaporated under reduced pressure affording (II) (15.5 g, containing a trace of NHS impurity) which could be used without further purification. If desired removal of the NHS; The solid is dissolved in a minimum of methanol/DMF (1:1) and precipitated by addition to water. The suspension is mixed well, the suspension centrifuged and the supernatant decanted. The white solid is dissolved in methanol to combine fractions, diluted with excess toluene, evaporated under reduced pressure, and dried en vacuo.

Preparation of N-(allyloxycarbonyloxy)succinimide is reported in *Int. J. Peptide Protein Res.* 1991, 37, 556-564.

b) N,N'-dialoc Vancomycin Allyl Ester (III)

Compound (II) (5 g, 3 mmol) is dissolved in 28 mL DMSO under an argon atmosphere (1 h with stirring). Powdered $NaHCO_3$ (2.5 g, 30 mmol) is added and the suspension stirred 10 min. followed by addition of allyl bromide (1.3 mL, 15 mmol). Stirring is continued for 7 h, at which time TLC shows the disappearance of (II) and one predominant product. The reaction is slowly diluted with acetone (co 25 mL) until the precipitate formed upon addition is just redissolved. This solution is vacuum filtered (removing the insoluble $NaHCO_3$) into a flask containing 200 mL acetone and 450 mL diethyl ether. The flask is swirled occasionally during filtrate addition to disperse the mixture of white precipitate and oil that formed. The reaction flask and filter are rinsed with 10 mL acetone-methanol (1:1). The filtrate/suspension is stored at 4° C. for 16 h with occasional swirling. The precipitate and oil coated the flask leaving a clear supernatant that is decanted. The solid mass is rinsed with acetone, dried under high vacuum, and dissolved in 10 mL DMF-methanol (1:1). This solution is precipitated by addition to 180 mL water (6×30 mL in 6 centrifuge tubes). The suspension is mixed, chunks crushed, centrifuged, and the supernatant decanted. The solids are combined in methanol-acetone, diluted with toluene, evaporated under reduced pressure, and dried en vacuo affording (III) (4.5 g). TLC: Rf=0.67; (chloroform-methanol-water; 6:4:1). An analytical sample is prepared by separation on HPLC; (Method A; 30 min. linear gradient of 25% to 60% acetonitrile; flow rate=7.5 mL/min.) affording (I), Ret. Time=24 min.; LRESI-MS calc for $C_{77}H_{87}N_9O_{28}Cl_2$: 1655.5; $[M+H]^+=1657$; $[M\text{-vancosamine}+H]^+=1431$ Example 2

Allyl-dialoc-tri-O All Peracetate Vancomycin Pseudoaglycone (VI)

a) Allyl dialoc-tri-O-allyl vancomycin (IV).

All-dialoc vancomycin (753 mg, 0.455 mmol) is taken in 5 mL DMF. Ground $Cs_2CO_3$ (750 mg, 2.30 mmol) is added to the reaction solution. The suspension is stirred under high vacuum for 30 minutes. Then allyl bromide (400 μL, 2.36 mmol) is added. TLC at 6 hours shows completed reaction. The suspension is precipitated in 100 mL water, centrifuged. The white solid is collected and loaded to a silica gel column (30 mm×12 cm) and eluted with gradient from $CHCl_3$ to 5% MeOH/$CHCl_3$ to give 660 mg (82%) of compound (IV) as white solid. $R_f$=0.6 (20% MeOH/$CHCl_3$). Mass Spec. $[M+Na]^+$, 1776; $[M-V]^+$, 1550, $[M-V-G]$, 1387.

b) Allyl-dialoc-tri-O-allyl peracetate vancomycin (V).

Allyl dialoc-tri-O-allyl vancomycin (IV) (100 mg, 0.0563 mmol) is dissolved in 5 mL $CH_2Cl_2$. Pyridine (164 βL, 2.027 mmol) is added followed by 2 mg DMAP. The reaction solution turns clear. $Ac_2O$ (96 mL, 1.013 mmol) is added. After 5 hours, TLC shows completed reaction. The reaction is quenched with 1 mL methanol and then all solvents are removed. The residue is loaded to a silica gel column (30 mm×12 cm) and eluted with a gradient of 0% to 5% MeOH/$CHCl_3$ to give 104 mg (91%) of compound (V) as white solid. $R_f$=0.3 (5% MeOH/$CHCl_3$). Mass Spec. $[M+Na]^+$2028.

c) Allyl-dialoc-tri-OAll peracetate vancomycin pseudoaglycone (VI).

Allyl-dialoc-tri-OAll peracetate vancomycin (V) (238 mg, 0.117 mmol) is azeotroped with toluene 3 times and then dissolved in 8 mL $CH_2Cl_2$. PhSH (120 μL, 1.173 mmol) is added followed by $BF_3.Et_2O$(431 μL, 3.51 mmol). TLC at 2 hours shows completed reaction. The reaction is quenched by 1 mL of DEBA and all solvents are removed. The residue is loaded to a silica gel column (30 mm×12 cm) and eluted with a gradient of 0 to 5% MeOH/CHCl$_3$ to give 144 mg (70%) of compound (VI) as white solid. R$_f$=0.3 (5% MeOH/CHCl$_3$). Mass Spec. [M+Na]$^+$2028.

Example 3

Vancosamine N-CBz-C-6-O-acetyl Sulfoxide (XI)

a) N,N'-bis-Cbz, Vancomycin (VII).

To a solution of vancomycin.HCl (1.76 g, 1.19 mmol) dissolved in 8.5 mL water and diluted with 10 mL acetone is added 3 mL water containing NaHCO$_3$ (210 mg, 2.5 mmol). To the stirred suspension is added 20 mL acetone, 15 mL water and N-(benzyloxycarbonyloxy)succinimide (1.2 g, 4.8 mmol) as a solution in 3 mL acetone. After 15 h. the clear solution is evaporated to dryness under reduced pressure with toluene azeotrope. The solid is dissolved in 15 mL DMF and precipitated by addition to 120 mL tetrahydrofuran. The suspension is centrifuged and the supernatant containing reagents decanted. The solid is then suspended in 120 mL acetone, mixed vigorously, centrifuged, and the supernatant decanted. This acetone wash of the solid is performed 3 times to remove all reagents. The white solid is dried under reduced pressure affording (VII) (1.9 g, 95%) that is used without further manipulation. TLC: Rf=0.33 (chloroform-methanol-water; 6:4:1). LRESI-MS calc for C$_{82}$H$_{87}$N$_9$O$_8$Cl$_2$ 1715.5; [M+Na]$^+$=1739; [M-vancosamine+H]$^+$=1440; [M-disaccharide+H]$^+$=1277 b) Vancosamine N-CBz methoxide (VIII).

Crude vancomycin BisCBz (VII) (3.414 g, 1.99 mmol) is dissolved in 18 mL methanol and 2.7 mL 10N HCl aqueous solution is added. A white precipitate is formed during reaction. After 2 hours, TLC shows completed reaction. All the solvents are removed and the residue is precipitated in 300 mL acetone. The acetone layer is collected and concentrated to give a thick oil. This oil is loaded onto a silica gel column (40 mm×14 cm) and eluted with 60% ETOAc/PE to give 303 mg(75%) of compound (VIII) as clear oil. (α:β=2:1) R$_f$=0.2 (40% ETOAc/PE)

c) Vancosamine N-CBz C4O-acetyl methoxide (IX).

The compound (VIII) (49 mg, 0.159 mmol) is dissolved in 2 mL CH$_2$Cl$_2$. DMAP (0.2 mg) is added to the reaction followed by pyridine (13 μL, 12.6 mmol) and acetic anhydride (15 μL, 16.23 mmol). After 12 hours, TLC shows completed reaction. The reaction is quenched by 0.5 mL methanol and all the solvents are removed. The residue is loaded to a silica gel column (20 mm×14 cm) and eluted with 30% ETOAc/PE to give 53 mg (95%) of compound (IX) as clear oil. (α:β=2:1). α anomer: R$_f$=0.4 (40% EtOAc/PE); $^1$H NMR (CDCl$_3$, 300 MHz) δ 7.35 (m, 5 H), 5.25-4.90 (m1, 3 H), 4.79 (d, J=6.5 Hz, H-1, 1 H), 4.74 (bs, H4, 1 H), 4.10 (m, H-5, 1 H), 3.34 (s, OCH$_3$, 3 H), 2.10 (s, COCH$_3$, 3 H), 2.00-1.88 (m, H-2, H-2', 2 H), 1.73 (s, CH$_3$, 3 H), 1.14 (d, J=6.4 Hz, CH$_3$, 3 H). βanomer: R$_f$=0.3 (40% EtOAc/PE); $^1$H NMR (CDCl$_3$, 300 MHz) δ 7.35 (m, 5 H), 5.10 (d, J=12.0 Hz, 1 H), 5.09 (s, 1 H), 4.95 (d, J=12.0 Hz, 1 H), 4.73 (bs, H-4, 1 H), 4.55 (d, J=12.0 Hz, H-1, 1 H), 3.84 (m, H-5, 1 H), 3.50 (s, OCH$_3$, 3 H), 2.07 (s, COCH$_3$, 3 H), 2.00-1.70(m, H-2, H-2', 2 H), 1.64 (s, CH$_3$, 3 H), 1.20 (d, J=6.4 Hz, CH$_3$, 3 H).

d) Vancosamine N-CBz C4-O-acetyl sulfide (X).

The compound (IX) (144 mg, 0.410 mmol) is azeotroped with toluene 3 times and then dissolved in 4 mL CH$_2$Cl$_2$. PhSH (84 μL, 0.82 mmol) is added followed by BF$_3$OEt$_2$ (100 μL, 0.82 mmol). TLC at 15 minutes shows completed reaction. The reaction is quenched by 20 mL saturated NaHCO$_3$ aqueous solution. The CH$_2$Cl$_2$ layer is separated and the aqueous layer is further extracted with CH$_2$Cl$_2$ (20 mL×3). The CH$_2$Cl$_2$ layers are combined and dried over anhydrous sodium sulfate, filtered, concentrated to give a clear oil. This oil is loaded to a silica gel column (30 mm×14 cm) and eluted with 20% ETOAc/PE to give 125 mg (71%) compound (X) as white solid. Rf=0.7 (40% EtOAc/PE) (α:β=3:1) βanomer: $^1$H NMR (CDCl$_3$, 500 Mhz) δ 7.47-7.24 (m, 10 H), 5.58 (dd, J=2.8, 6.7 Hz, H-1, 1 H), 5.10 (d, J=12.2 Hz, 1 H), 5.00-4.97 (m, 3 H), 4.90 (s, H-4, 1 H), 4.51 (m, H-5, 1 H), 2.55 (dd, J=6.7, 14.0 Hz, H-2, 1 H), 2.23 (d, J=14.0 Hz, H-2', 1 H), 2.09 (s, COCH$_3$, 3 H), 1.77 (s, CH$_3$, 3 H), 1.16 (d, J=6.4 Hz, CH$_3$, 3 H); $^{13}$C NMR (CDCl$_3$, 500 MHz) δ 170.94, 154.69, 136.60, 136.02, 131.20, 129.06, 128.71, 128.46, 128.35, 127.31, 83.12, 74.01, 66.61, 64.44, 53.66, 37.35, 24.11, 20.87, 17.13; α anomer: $^1$H NMR (CDCl$_3$, 500 MHz) δ 7.47-7.24 (m, 10 H), 5.58 (dd, J=2.8, 6.7 Hz, H-1, 1 H), 5.10 (d, J=12.2 Hz, 1 H), 5.00-4.97 (m, 3 H), 4.90 (s, H-4, 1 H), 4.51 (m, H-5, 1 H), 2.55 (dd, J=6.7, 14.0 Hz, H-2, 1 H), 2.23 (d, J=14.0 Hz, H-2', 1 H), 2.09 (s, COCH$_3$, 3 H), 1.77 (s, CH$_3$, 3 H), 1.16 (d, J=6.4 Hz, CH$_3$, 3 H); $^{13}$C NMR (CDCl$_3$, 500 MHz) δ 170.94, 154.69, 136.60, 136.02, 131.20, 129.06, 128.71, 128.46, 128.35, 127.31, 83.12, 74.01, 66.61, 64.44, 53.66, 37.35, 24.11, 20.87, 17.13.

e) Vancosamine N-CBz C4-O-acetyl sulfoxide (XI).

The vancosamine sulfide (X) (18 mg, 0.0433 mmol) is dissolved in 1.5 mL CH$_2$Cl$_2$ and cooled to −78° C. mCPBA is added and the reaction is slowly warmed up to −20° C. in 1 hour. TLC shows completed reaction. The reaction is quenched by 100 mL dimethyl sulfide. The reaction is extracted with 5 mL saturated NaHCO$_3$ aqueous solution. The aqueous layer is further extracted with CH$_2$Cl$_2$ (5 mL×3). The CH$_2$Cl$_2$ layers are combined and dried over anhydrous sodium sulfate, filtered, concentrated to a clear oil. This oil is loaded onto a silica gel column (20 mm×8 cm) and eluted with 60% ETOAc/PE to give 19 mg (95%) compound (XI) as white solid. R$_f$=0.15 (40% EtOAc/PE).

Example 4

Regeneration of Vancomycin from (VI)

a) Glycosylation of (VI) with (XI) to give (V).

The compound (VI) (22.7 mg, 0.0127 mmol) is azeotroped and dissolved in 1 mL CH$_2$Cl$_2$ and cooled to −78° C. BF$_3$.Et$_2$O (2 μL, 0.0168 mmol) is added followed by triflic anhydride (4 μL, 0.0247 mmol). Then the sulfoxide (XI) (22 mg, 0.0494 mmol) in 0.5 mL CH$_2$Cl$_2$ is added to the reaction vessel dropwise over 1 minute. TLC shows all sulfoxide is activated after addition. The reaction is slowly warmed up to −25° C. in 1.5 hour and then quenched with 100 mL methanol and 100 mL DIEA. All the solvents are removed and the residue is loaded to a silica gel column (10 mm×5 cm) and eluted with a gradient of 0 to 5% MeOH/CHCl$_3$ to give 17 mg of white solid. This white solid is purified by reverse-phase HPLC using a PHENOMENEX LUNA C$_{18}$ column (21.2× 250 mm), 5 μm particle, eluting with a 30 min. linear gradient of 80% acetonitrile/0.1% acetic acid in water to 100% acetonitrile/0.1% acetic acid ; flow rate of 8 mL/min. and UV detection at 285 nm. The fractions containing the pure products are combined and evaporated to give 11 mg (41%) of compound (V) as white solid. R$_f$=0.3 (5% MeOH/CHCl$_3$). Mass Spec. [M+Na]$^+$2028.

b) Deprotection of compound (V) to give compound (IV).

The glycosylation product (V) (9 mg, 0.00443 mmol) is dissolved in 0.4 mL methanol and 0.2 mL THF. Hydrazine (30 μL) is added. The reaction is quenched with 0.2 mL of acetic acid after 4 hours. All solvents are removed and the residue is purified by reverse-phase HPLC using a PHENOMENEX LUNA $C_{18}$ column (21.2×250 mm), 5 μm particle, eluting with a 30 min. linear gradient of 80% acetonitrile/0.1% acetic acid in water to 100% acetonitrile/0.1% acetic acid; flow rate of 8 mL/min. and UV detection at 285 nm. The fractions containing the pure products are combined and evaporated to give 5 mg (63%) of compound (IV) as white solid. $R_f$=0.3 (5% MeOH/CHCl$_3$). Mass Spec. [M+Na]$^+$ 2028.

c) Deprotection of Compound (IV) to give Vancomycin.

Compound (IV) (5 mg, 0.00281 mmol) is dissolved in 0.5 mL DMF/0.5 mL acetic acid. A catalytic amount of palladium dichloride-bis-triphenylphosphine is added and the reaction vessel is filled with nitrogen. To this mixture is added, with vigorous stirring, tributyltin hydride in 5 μL portions every 5 minutes until all starting materials and intermediates have disappeared by TLC. The crude reaction mixture is precipitated with 20 mL diethyl ether in a 50 mL centrifuge tube. The mixture is centrifuged and decanted to give a white solid that is vortexed with 20 mL diethyl ether, centrifuged, decanted and dried. The resulting white solid is purified by reverse-phase HPLC using a PHENOMENEX LUNA C18 column (21.2×250 mm), 5 μm particle, eluting with a 40 min. linear gradient of 0.1% trifluoroacetic acid in water to 20% acetonitrile/0.1% trifluoroacetic acid in water; flow rate of 7 mL/min. and ultraviolet (UV) detection at 285 nm. The fractions containing the product are combined, diluted with 10 mL water, organic solvents are evaporated and then the residue is lyophilized to give 3 mg (75%) of vancomycin TFA salt as white solid. $R_f$=0.05 (CHCl$_3$:MeOH:H$_2$O=3:4:2). Mass Spec. [M+Na$^+$] 1471.

Example 5

Benzyl N,N'-bis-Cbz Vancomycin (XII)

To a solution of (VII) (1.49 g, 0.87 mmol) in 15 mL DMSO under an argon atmosphere is added NaHCO$_3$ (35 mg, 0.4 mmol), then benzyl bromide (0.3 mL, 2.5 mmol) and the mixture stirred for 3 h at room temperature. The reaction is precipitated by addition to 400 mL 10% acetone in diethyl ether. The suspension is centrifuged, affording a thick sticky solid upon sitting, and the supernatant decanted. Combined supernatants are evaporated under reduced pressure to 10 mL volume and precipitated by addition to 200 mL diethyl ether. The suspension is centrifuged and the supernatant decanted. Solids are dissolved in methanol, combined, and evaporated under reduced pressure. Purification by HPLC (Method A: 3 min. at 38% acetonitrile followed by a 40 min. linear gradient of 38% to 75% acetonitrile; flow rate=8 mL/min.) affords (XII) (0.97 g, 61% from I). Ret. Time=26 min.; TLC: Rf=0.5 (chloroform-methanol-water, 50:21:4). LRESI-MS calc for $C_{89}H_{93}N_9O_{28}Cl_2$ 1805.6; [M+Na]$^+$=1829; [M-vancosamine+H]$^+$=1530; [M-disaccharide+H]$^+$=1368

Example 6

Benzyl CBZ-tri-O-methylvdiacetate Vancomycin Aglycone (XV)

a) Benzyl CBZ-tri-O-methyl vancomycin (XIII).

To a stirring solution of crude benzyl bis-CBZ-vancomycin (XII) (1.0262 g, 0.5677 mmol, 100% from vancomycin) in 20 mL of DMF is added Cs$_2$CO$_3$ (830 mg, 2.55 mmol) and MeI (530 μL, 8.52 mmol). The reaction is stirred for 3 hours and then 1 mL of acetic acid is added. The solution is filtered through a plug of silica gel with 15% MeOH/CH$_2$Cl$_2$ and concentrated. The residue is purified by flash chromatography (10-12.5% MeOH/CH$_2$Cl$_2$) to give 655.2 mg of semipure product. R$_f$0.53 (15% MeOH/CH$_2$Cl$_2$).

655.2 mg of the semipure product (0.354 mmol) is dissolved in 10.6 mL of acetic acid. Thiophenol (215 μL, 2.09 mmol) and 5.7 mL of 3% HBr in acetic acid are added. After 15 minutes, the reaction is poured into 150 mL of H$_2$O and the white precipitate is isolated by centrifuge. Purification of the precipitate by flash chromatography (5-7.5% MeOH/CH$_2$Cl$_2$) gives 313.5 mg (40% over 4 steps from vancomycin) of (XIII). $R_f$: 0.26 (7.5% MeOH/CH$_2$Cl$_2$); MS (ESI) calc 1410.2 ($C_{71}H_{70}N_8O_{19}Cl_2$) found 1433.2 M$^+$Na.

b) Benzyl CBZ-tri-O-methyl p-methoxybenzyl diacetate vancomycin aglycone (XIV).

To a solution of C (290.2 mg, 0.2058 mmol) in 10 mL of DMF is added Cs$_2$CO$_3$ (162 mg, 0.497 mmol) and p-methoxybenzyl chloride (PMBCl) (84 μL, 0.617 mmol). The reaction is stirred for 3.5 hours and then filtered through a plug of silica gel with 10% MeOH/CH$_2$Cl$_2$ and concentrated. The residue is purified by radial chromatography (0-6% MeOH/CH$_2$Cl$_2$) to give 222.3 mg (71%) of purified intermediate product. R$_f$0.33 (7.5% MeOH(CH$_2$Cl$_2$); MS (ESI) calc 1530.3 ($C_{79}H_{78}N_8O_{20}Cl_2$) found 1530.3.

To a solution of the purified intermediate product (222.3 mg, 0.144 mmol) in 5 mL of pyridine is added 1.25 mL of acetic anhydride. The reaction is stirred for three hours and then concentrated in vacuo. The residue is purified by flash chromatography (0-4% MeOH/CH$_2$Cl$_2$) to give 228.3 mg (97%) of (XIV). R$_f$0.29 (5% MeOH/CH$_2$Cl$_2$); MS (ESI) calc 1614.4 ($C_{83}H_{82}N_8O_{22}Cl_2$) found 1614.4.

c) Benzyl CBZ-tri-O-methyl diacetate vancomycin aglycone (XV).

To a solution of (XIV) (241.8 mg, 0.150 mmol) in 10 mL of CH$_2$Cl$_2$ is added 1 mL of trifluoroacetic acid (TFA). After 5 minutes, 25 mL of toluene is added and the reaction is concentrated in vacuo. Purification by radial chromatography (0-6% MeOH/CH$_2$Cl$_2$) gives 206.5 mg (92%) of (XV). $R_f$=0.25 (5% MeOH/CH$_2$Cl$_2$); MS (ESI) calc 1494.2 ($C_{75}H_{74}N_8O_{21}Cl_2$) found 1517.2 M$^+$Na.

Example 7

N,N'-dialoc-glucose-C6-Amine-Vancomycin Allyl Ester (XVIII)

a) N,N'-dialoc-glucose-C6-mesitylenesulfonyl-Vancomycin Allyl Ester (XVI).

To a stirred solution of compound (III) (370 mg, 0.22 mmol) in 2.5 mL anhydrous pyridine under an argon atmosphere at 4° C. is added 0.5 mL of a 1.4 M solution of mesitylenesulfonyl chloride in pyridine. The temperature is maintained at 4° C. for 24 h at which time the reaction is precipitated by addition to 50 mL diethyl ether (2×25 mL in two 50 mL centrifuge tubes). The suspension is centrifuged and the supernatant decanted. The solids are combined by dissolving in methanol and evaporated under reduced pressure. Separation by HPLC (Method A; 40 min. linear gradient of 30% to 75% acetonitrile; flow rate=7.5 mL/min.) affords starting material (III) (64 mg) and (XVI) (202 mg, 50%, 60% based on recovered III). Ret. Time=28 min.; TLC: Rf=0.7 (chloroform-methanol-water, 50:21:4). LRESI-MS calc for $C_{86}H_{97}N_9O_{30}S_1Cl_2$: 1837.5; [M+H]$^+$=1839; [M-vancosamine+H]$^+$=1614; [M-disaccharide+H]$^+$=1267.

b) N,N'-dialoc-glucose-C6-Azide-Vancomycin Allyl Ester (XVII).

To a stirred solution of compound (XVI) (310 mg, 0.17 mmol) in 8 mL anhydrous DMF under an argon atmosphere is added sodium azide (112 mg, 1.72 mmol) and the suspension stirred at 85° C. for 8 h. The mixture is cooled to room temperature and precipitated by addition to 80 mL diethyl ether. The white solid is centrifuged and the supernatant decanted. The solid is dissolved in a minimum of methanol and precipitated by addition to 80 mL water. The suspension is mixed vigorously then stored at 4° C. for 12 h. The suspension is centrifuged and the supernatant decanted. Separation by HPLC (Method A; 40 min. linear gradient of 25% to 50% acetonitrile; flow rate=7.5 mL/min. affords (XVII) (172 mg, 60%). Ret. Time=27 min.; TLC: Rf=0.55 (chloroform-methanol-water; 50:21:4). LRESI-MS calc for $C_{77}H_{86}N_{12}O_2Cl_2$ 1680.5; $[M+H]^+=1682$; [M-vancosamine+H]$^+$=1456; [M-disaccharide+H]$^+$=1267.

c) N,N'-dialoc-glucose-C6-Amine-Vancomycin Allyl Ester (XVIII).

A solution of azide (XVII) (172 mg, 0.1 mmol) and triphenylphosphine (180 mg, 0.7 mmol) in 25 mL THF containing 5 mL water is heated at 60° C. for 16 h. The reaction is cooled to room temperature, diluted with 200 mL toluene and evaporated to dryness under reduced pressure. The white solid is dissolved in 5.5 mL methanol-DMIF (10:1) and precipitated by addition to 75 mL diethyl ether (3×25 mL). The suspension is centrifuged and the supernatant containing triphenylphosphine decanted. The solid is dissolved in methanol, combined, and evaporated under reduced pressure. Separation by HPLC (Method A; 40 min. linear gradient of 15% to 50% acetonitrile; flow rate=7.5 mL/min.) affords (XVIII) (140 mg, 82%). Ret. Time=24 min.; TLC: Rf=0.3 (chloroform-methanol-water; 6:4:1). LRESI-MS calc for $C_{77}H_{88}N_{10}O_{27}Cl_2$: 1654.5; $[M+H]^+=1656$; [M-vancosamine+H]$^+$=1429; [M-disaccharide+H]$^+$=1267.

Example 8

Allyl N,N'-Dialoc-Glucose-C6-N-4-(4-chlorophenyl) benzyl Vancomycin (XIX)

To a stirred solution of (XVIII) (26 mg, 0.016 mmol) in 0.5 mL anhydrous DMF under an argon atmosphere is added 44-(4-chlorophenyl)benzylcarboxaldehyde (1.7 mg, 0.008 mmol). After 10 min. sodium cyanoborohydride (2 mg, 0.03 mmol) is added and the mixture stirred an additional 4 h. The reaction mixture is precipitated by addition to 8 mL diethyl ether. The suspension is centrifuged, the supernatant decanted, and the white solid then dried under reduced pressure to remove residual diethyl ether. Separation by HPLC (Method A; 30 min. linear gradient of 20% to 45% acetonitrile; flow rate=7.5 mL/min.) affords (XIX) (9 mg, 61%, based on aldehyde) Retention time=27 min., and 8 mg recovered (XVIII). TLC: Rf=0.66 (chloroform-methanol-water; 6:4:1). LRESI-MS calc for $C_{90}H_{97}N_{10}O_{27}Cl_3$ 1854.6; $[M+H]^+=1856$; [M-disaccharide+H]$^+$=1267 The preparation of 4-(4-chlorophenyl)benzylcarboxaldehyde is given in 3. Heterocyclic Chem. Vol. 22, 1985, pp. 873-878.

Example 9

Allyl N,N'-Dialoc-Glucose-C6-N-5-(4-chlorophenyl) furan-1-methylene Vancomycin (XX)

To a stirred solution of (XVIII) (63 mg, 0.036 mmol) in 0.9 mL anhydrous DMF under an argon atmosphere is added DIEA (7.4 μL, 0.04 mmol). After 5 min. 5-(4-chlorophenyl) furfal (7.3 mg, 0.035 mmol) is added and the solution heated at 70° C. for 100 min. Sodium cyanoborohydride (5 mg, 0.08 mmol) is then added and the mixture stirred an additional 2 h at 70° C. The reaction mixture is cooled to room temperature and precipitated by addition to 25 mL diethyl ether. The suspension is centrifuged and the supernatant decanted. Residual diethyl ether is removed under a flow of argon. Separation by HPLC (Method A; 40 min. linear gradient of 20% to 60% acetonitrile; flow rate=7.5 mL/min.) affords (XX) (42 mg, 64%) Retention time=23 min. TLC: Rf=0.6 (chloroform-methanol-water, 6:4:1). LRESI-MS calc for $C_{88}H_{95}N_{10}O_{28}Cl_3$:1844.5; $[M+H]^+=1846$; [M-vancosamine+H]$^+$=1656; [M-disaccharide+H]$^+$=1268.

Example 10

Allyl N,N'-Dialoc-Glucose-C6-N-decyl Vancomycin (XXI)

To a stirred solution of (XVIII) (11 mg, 0.007 mmol) in 0.45 mL anhydrous DMF under an argon atmosphere is added DIEA (1.3 μL, 0.0073 mmol). After 10 min. decylaldehyde (1.3 μL, 0.007 mmol) is added and the solution stirred at room temperature for 45 min. Sodium cyanoborohydride (2 mg, 0.03 mmol) is then added and the mixture stirred an additional 5 h. The reaction mixture is precipitated by addition to 6 mL diethyl ether, the suspension centrifuged and the supernatant decanted. Residual diethyl ether is removed under a flow of argon. Separation by HPLC (Method A; 40 min. linear gradient of 20% to 75% acetonitrile; flow rate=7.5 mL/min.) affords (XXI) (2 mg, 17%). Retention time=21 min. TLC: Rf=0.68 (chloroform-methanol-water; 6:4:1). LRESI-MS calc for $C_{87}H_{108}N_{10}O_{27}Cl_2$: 1794.7; $[M+H]^+=1796$; [M-disaccharide+H]$^+$=1267.

Example 11

Allyl N,N'-Dialoc-(6-N-thiocarbonyl Methylamino Glucose) Vancomycin (XXII)

A solution of amine (XVIII) (6 mg, 0.0036 mmol) in 0.2 mL anhydrous pyridine under an argon atmosphere is treated with methylisothiocyanate (0.8 mg, 0.01 mmol). After 10 min. TLC shows complete disappearance of starting material. The reaction mixture is added to 8 mL diethyl ether, the resulting suspension centrifuged and the supernatant decanted. The white solid is mixed vigorously with 10 mL diethyl ether, centrifuged, supernatant decanted and solid dried under reduced pressure affording (XXII) (6 mg, 96%) TLC shows one compound; Rf=0.8 (chloroform-methanol-water; 6:4:1). This product is subjected to deprotection without further manipulation. LRESI-MS calc for $C_{79}H_{91}N_{11}O_{27}S_1Cl_2$: 1727.5; $[M+H]^+=1729$; [M-vancosamine+H]$^+$=1502.

Example 12

Allyl N,N'-Dialoc-glucose-C6-N-(thiophene-2-carboxamide) Vancomycin (XXIII)

To a stirred solution of N-hydroxysuccinimide (NHS) (84 mg, 0.73 mmol) and triethylamine (92.5 μL, 0.66 mmol) in 1.3 mL acetonitrile-0.5 mL dichloromethane under an argon atmosphere at 4° C. is added a solution of thiophene-2-carbonyl chloride (71 μL, 0.66 mmol) in 0.3 mL acetonitrile. After.30 min. cooling is removed and the mixture stirred at room temperature for an additional 30 min. Stirring is stopped and triethylammonium chloride allowed to settle affording a 0.3 M solution of the NHS activated ester.

To a stirred solution of amine (XVIII) (9 mg, 0.005 mmol) in 0.5 mL anhydrous DMF under an argon atmosphere is added 50 µL of the 0.3 M NHS activated ester solution prepared above (0.015 mmol). After 48 h. the reaction mixture is precipitated by addition to 10 mL diethyl ether, the resulting suspension centrifuged and the supernatant decanted. Separation by HPLC (Method A; 40 min. linear gradient of 30% to 70% acetonitrile; flow rate=7.5 mL/min.) affords (XXIII) (6.7 mg, 70%). Retention time=19 min. TLC: Rf=0.75 (chloroform-methanol-water; 6:4:1). LRESI-MS calc for $C_{82}H_{90}N_{10}O_{28}S_1Cl_2$: 1764.5; [M+Na]$^+$=1788; [M-vancosamine+Na]$^+$=1562; [M-disaccharide+H]$^+$=1268.

Example 13

Allyl N,N'-Dialoc-glucose-6-N-(glycine-carboxamide) Vancomycin (XXIV)

To a stirred solution of amine (XVIII) (20 mg, 0.012 mmol) in 1 mL anhydrous DMF under an argon atmosphere is added N-Fmoc-glycine pentafluorophenyl ester (13 mg, 0.028 mmol). After 1 h. the mixture is precipitated by addition to 15 mL diethyl ether, centrifuged and the supernatant containing excess reagents decanted. The white solid is taken up in methanol, diluted with 50 mL toluene and evaporated under reduced pressure affording the Fmoc protected glycinamide product, one product by TLC: Rf=0.73 (chloroform-methanol-water, 6:4:1). The dry solid is dissolved in 1 mL anhydrous DMF under an argon atmosphere and treated with 0.15 mL piperidine. After 30 min. the mixture is precipitated by addition to 25 mL diethyl ether, the suspension centrifuged and the supernatant decanted. Separation by HPLC (Method A; 40 min. linear gradient of 10% to 45% acetonitrile; flow rate=8 mL/min.) affords (XXIV) (5 mg, 25%), Retention time=25 min. which is used for analytical purposes and 14 mg of (XXIV) contaminated with an impurity. This material is subjected to deprotection without further manipulation. TLC: Rf=0.4 (chloroform-methanol-water; 6:4:1). LRESI-MS calc for $C_{79}H_{91}N_{11}O_{28}Cl_2$: 1711.5; [M+H]$^+$=1713; [M-vancosamine+H]$^+$=1488; [M-disaccharide+H]$^+$=1268.

Example 14

Allyl N,N'-Dialoc-glucose-C6-N-myristoyl Vancomycin (XXV)

To a stirred solution of N-hydroxysuccinimide (NHS) (63 mg, 0.55 mmol) and triethylamine (69 µL, 0.5 mmol) in 1 mL acetonitrile under an argon atmosphere at 4° C. is added a solution of myristoyl chloride (135 µL, 0.5 mmol) in 1 mL acetonitrile-dichloromethane (1:1). After 30 min. cooling is removed and the mixture stirred at room temperature for an additional 2 h. Stirring is stopped and the triethylammonium chloride precipitate allowed to settle affording a 0.23 M solution of the NHS activated ester.

To a stirred solution of amine (XVIII) (15 mg, 0.009 mmol) in 0.6 mL anhydrous DMF under an argon atmosphere is added 50 µL of the 0.23 M NHS activated ester solution prepared above (0.01 mmol). After 8 h the reaction mixture is precipitated by addition to 10 mL diethyl ether. The resulting suspension is centrifuged and the supernatant decanted. Separation by HPLC (Method A; 40 min. linear gradient of 50% to 100% acetonitrile; flow rate=7.5 mL/min.) affords (XXV) (10 mg, 60%). Retention time=26 min. TLC: Rf=0.75 (chloroform-methanol-water, 6:4:1). LRESI-MS calc for $C_{91}H_{114}N_{10}O_{28}Cl_2$: 1864.7; [M+Na]$^+$=1888; [M-vancosamine+H]$^+$=1640; [M-disaccharide+H]$^+$=1268.

Example 15

Allyl N,N'-Dialoc-glucose-C6-N-2-iodo-benzoyl Vancomycin (XXVI)

To a stirred solution of N-hydroxysuccinimide (84 mg, 0.73 mmol) and triethylamine (92.5 µL, 0.66 mmol) in 1.5 mL acetonitrile under an argon atmosphere at 4° C. is added a solution of 2-iodobenzoyl chloride (177 mg, 0.66 mmol) in 0.8 mL acetonitrile. After 30 minutes cooling is removed and the mixture stirred at room temperature for an additional 1 h. Stirring is stopped and the triethylammonium chloride allowed to settle affording a 0.28 M solution of the NHS activated ester.

To a stirred solution of amine (XVIII) (7 mg, 0.004 mmol) in 0.6 mL anhydrous DMF under an argon atmosphere is added 22 µL of the 0.28 M NHS activated ester solution prepared above (0.006 mmol). After 1 h an additional 30 µL of the 0.28 M NHS activated ester solution is added and the solution stirred an additional 14 h. The reaction mixture is precipitated by addition to 14 mL diethyl ether. The suspension is centrifuged and the supernatant decanted. Separation by HPLC (Method A; 40 min. linear gradient of 20% to 70% acetonitrile; flow rate=7.5 mL/min.) affords (XXVI (5 mg, 66%) Retention time=26 min. TLC: Rf=0.6 (chloroform-methanol-water; 50:21:4). LRESI-MS calc for $C_{84}H_{91}N_{10}O_{28}I_1Cl_2$: 1884.4; [M+Na]$^+$=1907; [M-vancosamine+Na]$^+$=1681; [M-disaccharide+H]$^+$=1268.

Example 16

Allyl N,N'-Dialoc-glucose-C6-N-2-quinoxaloyl Vancomycin (XXVII)

To a stirred solution of N-hydroxysuccinimide (NHS) (27 mg, 0.23 mmol) and triethylamine (29.7 µL, 0.21 mmol) in 0.6 mL acetonitrile under an argon atmosphere at 4° C. is added a solution of 2-quinoxaloyl chloride (41 mg, 0.21 mmol) in 1.0 mL acetonitrile. After 10 minutes cooling is removed and the mixture stirred at room temperature for 30 min. The mixture is cooled to 4° C., stirring stopped, and the triethylammonium chloride allowed to settle affording a 0.12 M solution of the NHS activated ester.

To a stirred solution of amine (XVIII) (46 mg, 0.026 mmol) in 0.5 mL anhydrous DMF under an argon atmosphere is added 325 µL of the 0.12 M NHS activated ester solution prepared above (0.04 mmol). After 45 minutes the reaction mixture is precipitated by addition to 25 mL diethyl ether, the suspension centrifuged and the supernatant decanted. Separation by HPLC (Method A; 40 min. linear gradient of 30% to 80% acetonitrile; flow rate=7.5 mL/min.) affords (XXVII) (35 mg, 74%) Retention time=24 min. TLC: Rf=0.63 (50:21: 4, chloroform-methanol-water). LRESI-MS calc for $C_{86}H_{92}N_{12}O_{28}Cl_2$: 1810.6; [M+Na]$^+$=1834; [M-vancosamine+H]$^+$=1586; [M-disaccharide+H]$^+$=1268.

Example 17

Allyl N,N'-Dialoc-Glucose-C6-N-4-(4-chlorophenyl) benzoyl Vancomycin (XXIII)

4-(4-chlorophenyl)benzoic acid
To a stirred solution of 4-(4-chlorophenyl)benzaldehyde (0.84 g, 3.9 mmol) in 30 mL acetonitrile-acetone (2:1) is added 15 mL water and solid sodium bicarbonate (3.5 g, 41.7 mmol). After 5 min. a 25 mL solution of oxidation reagent (Oxone: 4.8 g, 7.8 mmol in 25 mL water containing $4\times10^{-4}$ M EDTA) is added dropwise over 15 min. then stirred for an additional 3.5 h. The reaction mixture is then treated with 18 mL aq. sodium bisulfite (9.5 g), stirred 2 h, then acidified with 10 mL 6 M HCl. The mixture is transferred to a separatory funnel and diluted with 300 mL dichloromethane and 400 mL water. The water layer is washed with dichloromethane (3×120 mL), organic layers combined, then washed with 500 mL water. The organic layer is dried over sodium sulfate, filtered, and evaporated under reduced pressure. The desired acid is crystallized from acetone-water (5:2), filtered, washed with water, and evaporated under reduced pressure from toluene affording 0.6 g product. Remaining product could be isolated by chromatography but the amount obtained is satisfactory. TLC: Rf=0.3 (chloroform-methanol; 10:1).

The foregoing procedure is adapted from Webb et. al. Tetrahedron, 1998, 54, 401-410.

To a stirred solution of 4-(4-chlorophenyl)benzoic acid (5.3 mg, 0.023 mmol) in 0.4 mL anhydrous DMF under an argon atmosphere is added 1-hydroxybenzotriazole (HOBt) (4 mg, 0.03 mmol) then DIEA (10 μL, 0.06 mmol). After 10 min. the solution is treated with PyBOP (10 mg, 0.02 mmol) and stirred an additional 30 min. TLC shows a trace of starting acid and one new product (expected to be the HOBt activated ester) affording a reagent stock solution (ca. 57 mM in activated acid).

To a stirred solution of amine (XVIII) (21 mg, 0.012 mmol) in 0.25 mL anhydrous DMF under an argon atmosphere is added DIEA (2 μL, 0.012 mmol). The solution is stirred 5 min. then treated with 0.3 mL of the 57 mM activated acid solution. After 20 min. the reaction is precipitated by addition to 20 mL diethyl ether, the resulting suspension is centrifuged, the supernatant decanted, and the residual solvent removed under a flow of argon. Separation by HPLC (Method A; 40 min. linear gradient of 35% to 80% acetonitrile; flow rate=7.5 mL/min.) affords (XXVIII) (18 mg, 82%); Retention time=26 min. TLC: Rf=0.7 (chloroform-methanol-water; 50:21:4). LRESI-MS calc for $C_{90}H_{95}N_{10}O_{28}Cl_3$: 1868.5; $[M+Na]^+$=1892; [M-vancosamine+H]$^+$=1669; [M-disaccharide+H]$^+$=1268.

Example 18

Deprotection of Compounds XIX-XXVII

General Procedure for Allyl/Aloc Removal.

To a solution of glycopeptide in DMF-acetic acid (4:3 or 1:1) is added $(Ph_3P)_2Pd(II)Cl_2$ (catalytic). With vigorous stirring, $Bu_3SnH$ is added in 5 to 10 molar equivalent portions every 2 to 10 min. until TLC (chloroform-methanol-water; 6:4:1) shows all glycopeptide product is baseline. The biphasic mixture is precipitated by addition to diethyl ether, the suspension centrifuged and the supernatant decanted. The white solid is dried under reduced pressure or by a steam of argon to remove residual diethyl ether, dissolved in water and then filtered to remove any remaining catalyst or hydrophobic salts. Separation by HPLC is performed as described for individual compounds.

a) Glucose-C6-N-4-(4-chlorophenyl)benzyl Vancomycin (XXIX).

Deprotection of compound (XIX) (8.5 mg, 0.0046 mmol) is performed as described in the general procedure for allyl/aloc removal. Separation by HPLC (Method B; 40 min. linear gradient of 5% to 50% acetonitrile; flow rate=7.5 mL/min.) affords (XXIX) (7 mg, 95%). Retention time=27 min. LRESI-MS calc for $C_{79}H_{85}N_{10}O_{23}Cl_3$: 1646.5; $[M+H]^+$=1648; [M-disaccharide+H]$^+$=1143.

Note: see also preparation of (XLVIII) for formation of (XXIX).

b) Glucose-C6-N-5-(4-chlorophenyl)furan-1-methylene Vancomycin (XXX).

Deprotection of compound (XX) (31 mg, 0.017 mmol) is performed as described in the general procedure for allyl/aloc removal. Separation by HPLC (Method B; 40 min. linear gradient of 5% to 60% acetonitrile; flow rate=7.5 mL/min.) affords (XXX) (27 mg, 92%) Retention time=26 min. LRESI-MS calc for $C_{77}H_{83}N_{10}O_{24}Cl_3$:1636.5; $[M+H]^+$=1638; [M-disaccharide+H]$^+$=1143.

c) Glucose-C6-N-decyl Vancomycin (XXXI)

Deprotection of compound (XXI) (2 mg, 0.001 mmol) is performed as described in the general procedure for allyl/aloc removal. Separation by HPLC (Method B; 40 min. linear gradient of 0% to 60% acetonitrile; flow rate=8 mL/min.) affords (XXXI) (2 mg, 95+%). Retention time=25 min. LRESI-MS calc for $C_{76}H_{96}N_{10}O_{23}Cl_2$: 1586.6; $[M+H]^+$=1588; [M-disaccharide+H]$^+$=1143.

d) Glucose-C6-N-thiocarbonyl Methylamino Vancomycin (X).

Deprotection of compound (XXII) (6 mg, 0.003 mmol) is performed as described in the general procedure for allyl/aloc removal. Separation by HPLC (Method B; 40 min. linear gradient of 0% to 50% acetonitrile; flow rate=7.5 mL/min.) affords (XXXII) (1 mg, 17%). Retention time=21 min. LRESI-MS calc for $C_{68}H_{79}N_{11}O_{23}S_1Cl_2$: 1519.5; $[M+H]^+$=1521; [M-vancosamine+H]$^+$=1379; [M-disaccharide+H]$^+$=1143.

e) Glucose-C6-N-(thiophene-2-carboxamide) Vancomycin (XXXIII).

Deprotection of compound (XXIII) (6.3 mg, 0.0034 mmol) is performed as described in the general procedure for allyl/aloc removal. Separation by HPLC (Method B; 40 min. linear gradient of 0% to 50% acetonitrile; flow rate=7.5 mL/min.) affords (XXXIII) (5 mg, 97%). Retention time=23 min. LRESI-MS calc for $C_{71}H_{78}N_{10}O_{24}S_1Cl_2$: 1556.5; $[M+H]^+$=1558; [M-vancosamine+H]$^+$=1415; [M-disaccharide+H]$^+$=1143.

f) Glucose-C6-N-(glycine-carboxamide) Vancomycin (XXXIV).

Deprotection of compound (XXIV) (14 mg, containing impurity as described) is performed as described in the general procedure for allyl/aloc removal. Separation by HPLC (Method B; 40 min. linear gradient of 0% to 35% acetonitrile; flow rate=7.5 mL/min.) affords (XXXIV) (8 mg, 57%). Retention time=22 min. LRESI-MS calc for $C_{68}H_{79}N_{11}O_{24}Cl_2$: 1503.5; $[M+H]^+$=1505; [M-vancosamine+H]$^+$=1362; [M-disaccharide+H]$^+$=1143.

g) Glucose-C6-N-myristoyl Vancomycin (XXXV).

Deprotection of compound (XXV) (10 mg, 0.005 mmol) is performed as described in the general procedure for allyl/aloc removal. Separation by HPLC (Method B; 40 min. linear gradient of 15% to 75% acetonitrile; flow rate=7.5 mL/min.) affords (XXXV) (8 mg, 89%). Retention time=27 min. LRESI-MS calc for $C_{80}H_{102}N_{10}O_{24}Cl_2$: 1656.6; $[M+H]^+$=1658; [M-vancosamine+H]$^+$=1517; [M-disaccharide+H]$^+$=1143.

h) Glucose-C6-N-2-iodobenzoyl Vancomycin (XXXVI).

Deprotection of compound XXVI (4 mg, 0.002 mmol) is performed as described in the general procedure for allyl/aloc removal. Separation by HPLC (Method B; 40 min. linear gradient of 0% to 50% acetonitrile; flow rate=7.5 mL/min.) affords (XXXVI) (3 mg, 89%). Retention time=23 min.

LRESI-MS calc for $C_{73}H_{79}N_{10}O_{24}I_1Cl_2$: 1676.4; $[M+H]^+$ =1678; $[M\text{-vancosamine}+H]^+$=1535; $[M\text{-disaccharide}+H]^+$=1143.

i) Glucose-C6-N-2-quinoxaloyl Vancomycin (XXXVII).

Deprotection of compound (XXVII) (30 mg, 0.017 mmol) is performed as described in the general procedure for allyl/aloc removal. Separation by HPLC (Method B; 40 min. linear gradient of 5% to 60% acetonitrile; flow rate=7.5 mL/min.) affords (XXXVII) (28 mg, 98%). Retention time=22 min. LRESI-MS calc for $C_{75}H_{80}N_{12}O_{24}Cl_2$: 1602.5; $[M+H]^+$=1605; $[M\text{-vancosamine}+H]^+$=1460; $[M\text{-disaccharide}+H]^+$=1143.

j) Glucose-C6-N-4-(4-chlorophenyl)benzoyl Vancomycin (XXXVIII).

Deprotection of compound (XXVIII) (10 mg, 0.005 mmol) is performed as described in the general procedure for allyl/aloc removal. Separation by HPLC (Method B; 40 min. linear gradient of 10% to 60% acetonitrile; flow rate=7.5 mL/min.) affords (XXXVIII) (8 mg, 90%). Retention time=24 min. LRESI-MS calc for $C_{79}H_{83}N_{10}O_{24}Cl_3$: 1660.5; $[M+H]^+$=1663; $[M\text{-vancosamine}+H]^+$=1520; $[M\text{-disaccharide}+H]^+$=1143.

Example 19

Glucose-C6-5-chloro-2-hydroxy-benzylamine Vancomycin (XXXIX)

a) N,N'-Dialoc-allyl-glucose-C6-5-chloro-2-hydroxy-benzylamine vancomycin.

N,N'-Dialoc-allyl-glucose-C6-amine vancomycin AcOH salt (XVIII, 193.7 mg, 0.113 mmol) is dissolved in dry DMF (5 mL) and DIEA (10.7 mL, 0.117 mmol) is added. The mixture is stirred at 70° C. under Ar. After 1.5 h 5-chlorosalicylaldehyde (11 mg, 0.0703 mmol) is added then the solution turns yellow. The mixture is stirred for 1 h then $NaBH_3CN$ (0.117 mL, 1M-THF, 0.117 mmol) is added. The mixture is stirred for an additional 2 h then cooled down to room temperature. The mixture is evaporated and the residue is purified by ODS-HPLC (LUNA 5 μm C18(2), 21.2×250 mm, UV=285 nm, A: 0.1% $AcOH/H_2O$, B: 0.1% AcOH/MeCN, 20-60% B 0-30 min., 8 mL/min, $t_r$=25 min.) to give the title compound as a white amorphous as AcOH salt (64.3 mg, 0.0346 mmol, 31%). LRESI-MS 1796 (M+2H, for $C_{84}H_{95}{}^{35}Cl_3N_{10}O_{28})^+$, 1569 $(M\text{-alocvancosamine}+2H)^+$. 1267 $(M\text{-alocvancosamine-glucose}+H)^+$.

(XXXIXa)

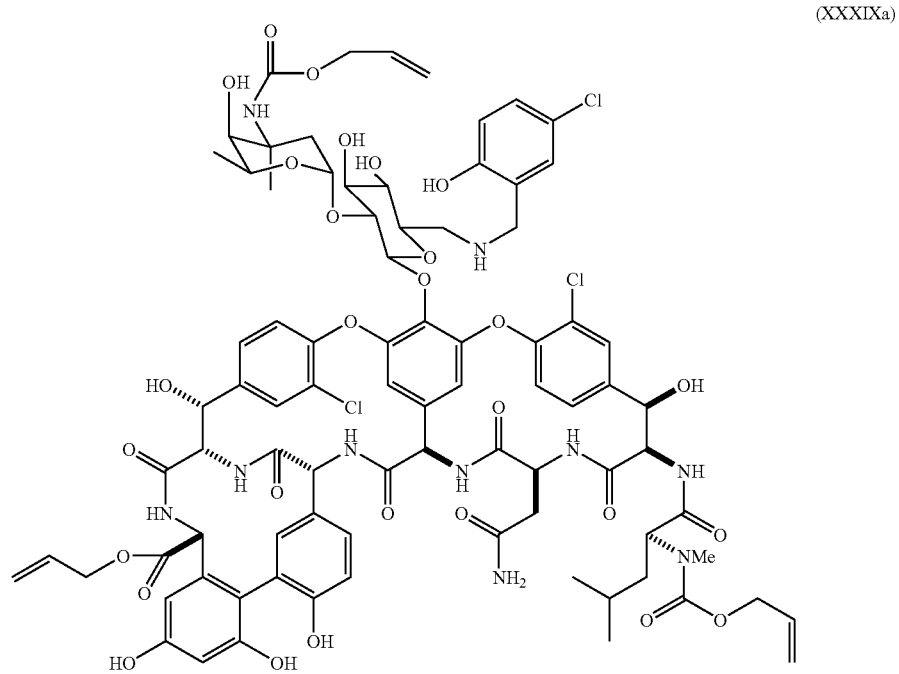

$C_{84}H_{93}Cl_3N_{10}O_{28}$
Exact Mass: 1794.52
Mol. Wt.: 1797.05
C, 56.14; H, 5.22; Cl, 5.92; N, 7.79; O, 24.93 b) Glucose-C6-5-chloro-2-hydroxy-benzylamine vancomycin (XXXIX).

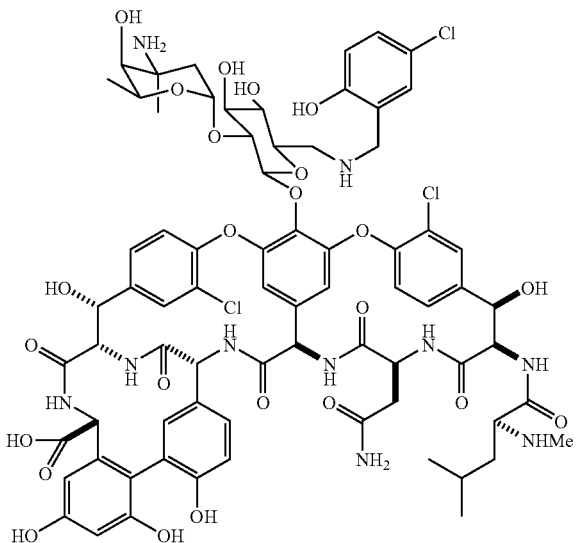

(XXXIX)

$C_{73}H_{81}Cl_3N_{10}O_{24}$
Exact Mass: 1586.45
Mol. Wt.: 1588.85
C, 55.18; H, 5.14; Cl, 6.69; N, 8.82; O, 24.17

N,N'-Dialoc-allyl-glucose-C6-5-chloro-2-hydroxy-benzylamine vancomycin (64.3 mg, 0.0346 mmol) is dissolved with dry DMF/AcOH (1/1) (2 mL). Pd(PPh$_3$)$_2$Cl$_2$ (1.2 mg, 0.00171 mmol) is added, then the mixture is stirred at room temperature under Ar. Bu$_3$SnH (10 mL) is added about every 5-20 min. After 5 h the reaction is done. Added ether then centrifuged three times. The residue is purified by ODS-HPLC (LUNA 5 μm C18(2), 21.2×250 mm, UV=285 nm, A: 0.1% TFA/H$_2$O, B: MeCN, 0-50% B over 50 min., 8 mL/min, t$_r$=14 min.) to give a white amorphous as TFA salt (XXXIX, 15.2 mg, 0.00893 mmol, 26%). LRESI-MS 1588 (M+2H, for $C_{73}H_{83}{}^{35}Cl_3N_{10}O_{24})^+$, 1143 (M-vancosamine-glucose+H)$^+$.

Example 20

Glucose-C6-trifluoroacetamide Vancomycin (XL)

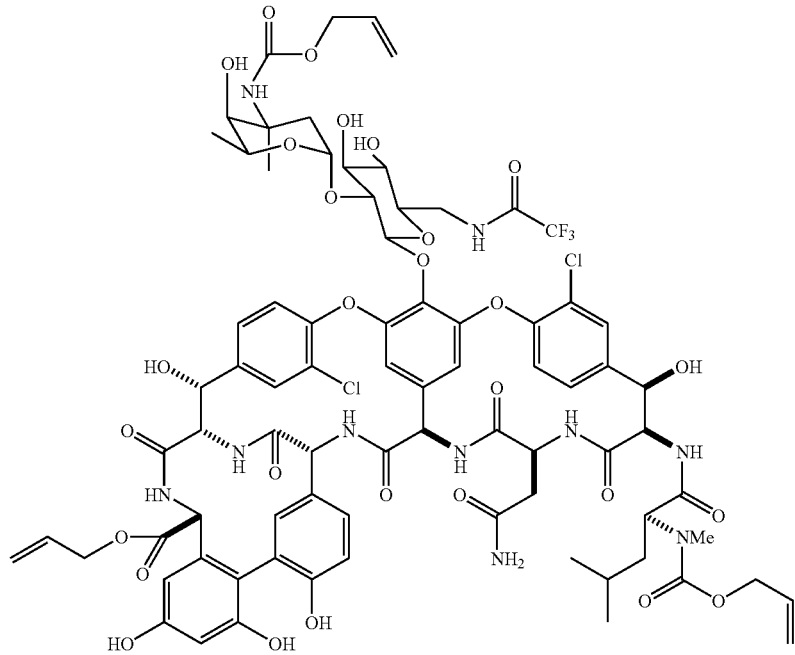

(XLa)

$C_{79}H_{87}Cl_2F_3N_{10}O_{28}$
Exact Mass: 1750.50
Mol. Wt.: 1752.49
C, 54.14; H, 5.00; Cl, 4.05; F, 3.25; N, 7.99; O, 25.56 a) N, N'-Dialoc-allyl-glucose-C6-trifluoroacetamide vancomycin.

N,N'-Dialoc-allyl-glucose-C6-amine vancomycin (AcOH salt of XVIII) (13.1 mg, 0.00768 mmol) is dissolved with dry pyridine (0.5 mL). The mixture is stirred at 0° C. Trifluoroacetic anhydride (1.7 mL, 0.012 mmol) is added. After 6 h an additional 10 mL of trifluoroacetic anhydride is added, and then the reaction is done. The mixture is passed through an ODS short column, then purified by ODS-HPLC (LUNA 5 μm C18(2), 21.2×250 mm, UV=285 nm, A: 0.1% TFA/H$_2$O, B: MeCN, 20-50-100% B 0-30-40 min., 8 mL/min, t$_r$=34 min.) to give the tide compound as a white amorphous solid (5.6 mg, 0.00302 mmol, 39%). LRESI-MS 1756 (M+6H, for $C_{79}H_{93}{}^{35}Cl_2F_3N_{10}O_{28}$)$^+$, 1507 (M-alocvancosamine-O+H)$^+$.

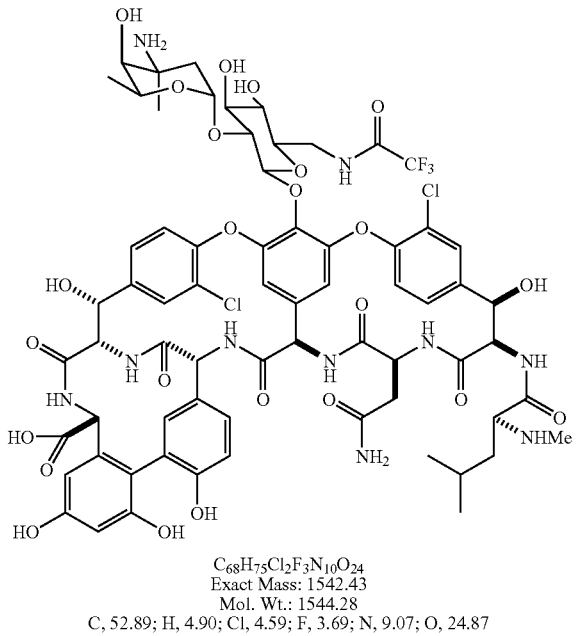

(XL)

$C_{68}H_{75}Cl_2F_3N_{10}O_{24}$
Exact Mass: 1542.43
Mol. Wt.: 1544.28
C, 52.89; H, 4.90; Cl, 4.59; F, 3.69; N, 9.07; O, 24.87 b) Glucose-C6-trifluoroacetamide Vancomycin (XL).

N,N'-Dialoc-allyl-glucose-C6-trifluoroacetamide vancomycin (5.3 mg, 0.00302 mmol) is dissolved with dry DMF/AcOH (1/1) (1 mL). Pd(PPh$_3$)$_2$Cl$_2$ (1.0 mg, 0.00142 mmol) is added, then the mixture is stirred at room temperature under Ar. Bu$_3$SnH (0.1 mL) is added about every 20 min. After 4 h the reaction is done. Diethyl ether is added, then the mixture is centrifuged twice. The residue is purified by ODS-HPLC (LUNA 5 μm C18(2), 21.2×250 mm, UV=285 nm, A: 0.1% TFA/H$_2$O, B: MeCN, 0-30% B over 30 min., 8 mL/min, t$_r$=14 min.) to give (XL) as a white amorphous TFA salt (13, 0.2 mg, 0.000121 mmol, 4%). LRESI-MS 1543 (M+H, for $C_{68}H_{76}{}^{35}Cl_2F_3N_{10}O_{24}$)$^+$, 1400 (M-vancosamine+H)$^+$, 1143 (M-vancosamine-glucose+H)$^+$.

Example 21

Glucose-C6-mesitylenesulfonyl Vancomycin (XLI)

To a stirred solution of mesitylenesulfonyl derivative (XVI) (52 mg, 0.028 mmol) in 3 mL anhydrous DMF is added 2 mL acetic acid then (Ph$_3$P)$_2$Pd(II)Cl$_2$ (catalytic). This solution is treated with tributyltin hydride (20 μL additions at 5 minute intervals for 20 min.) at which time TLC shows nearly so reaction. Five minutes after the last addition, 0.45 mL of Bu$_3$SnH is added at once. The reaction turns dark and TLC (Chloroform-methanol-water; 6:4:1) shows all glycopeptide baseline. The biphasic mixture is diluted with 0.5 mL methanol and 5 mL diethyl ether and stirred 5 min. The solution is precipitated by addition to 90 mL diethyl ether (3×30 mL in three centrifuge tubes). The resulting suspension is centrifuged, the supernatant decanted and the residual diethyl ether removed under a stream of argon. The solid is dissolved in water (ca. 5 mL per tube), stored at 4° C. for 5 h and filtered to remove remaining catalyst or hydrophobic salts. The aqueous solutions are combined, volume reduced under reduced pressure and separated by HPLC (Method B; 40 min. linear gradient of 0% to 60% acetonitrile; flow rate=7.5 mL/min.) affords (XLI) (44 mg, 90%) Retention time=24 min. LRESI-MS calc for $C_{75}H_{85}N_9O_{26}S_1Cl_2$: 1629.5; [M+H]$^+$=1631; [M-vancosamine+H]$^+$=1488; [M-disaccharide+H]$^+$=1143.

Example 22

N-4-(4-chlorophenyl)benzylvancosamine-glucose-C6-2-mesitylenesulfonated Vancomycin (XLII)

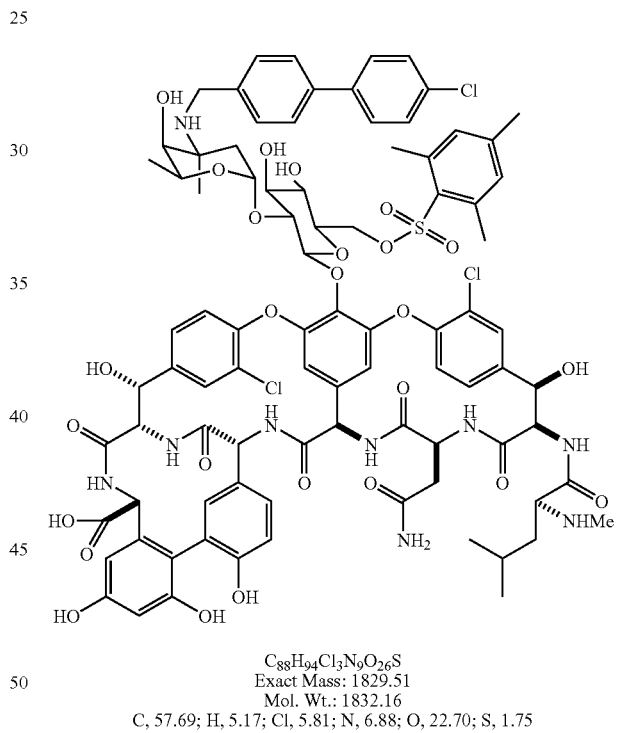

$C_{88}H_{94}Cl_3N_9O_{26}S$
Exact Mass: 1829.51
Mol. Wt.: 1832.16
C, 57.69; H, 5.17; Cl, 5.81; N, 6.88; O, 22.70; S, 1.75

Glucose-C6-2-mesitylenesulfonated vancomycin TFA salt (XLI) (100.0 mg, 0.0573 mmol) is dissolved with dry DMF (2 mL) and wet DIEA (50 mL 0.547 mmol) is added and the mixture is stabilized at 75° C. for 0.5 h. 4-(4-chlorophenyl)benzylcarboxylaldehyde (10.6 mg, 0.0490 mmol) is added and the reaction mixture is stirred at 75° C. for 2 h then NaBH$_3$CN (0.3 mL, 1M-THF, 0.3 mmol) is added. The mixture is stirred for additional 2 h, cooled down to room temperature, filtered and purified by ODS-HPLC (LUNA 5 μm C18(2), 21.2×250 mm, UV=285 nm, A: 0.1% TFA/H$_2$O, B: MeCN, 10-60% B 0-30 min., 8 mL/min, t$_r$=27 min.) to give (XLI) as a white amorphous solid (37.7 mg, 0.0194 mmol, 35%) and starting material (26.7 mg, 0.0153 mmol, 27%) as TFA salts. LRESI-MS 1831 (M+2H, for $C_{88}H_{96}{}^{35}Cl_3N_9O_{26}S)^+$, 1488 (M-N-4-(4-chlorophenyl)benzylvancosamine+2H)$^+$. 1143 (M-N-4-(4-chlorophenyl)benzylvancosamine -glucose+H)$^+$.

Example 23

N-decylvancosamine-glucose-C6-2-mesitylenesulfonated Vancomycin (XLIII)

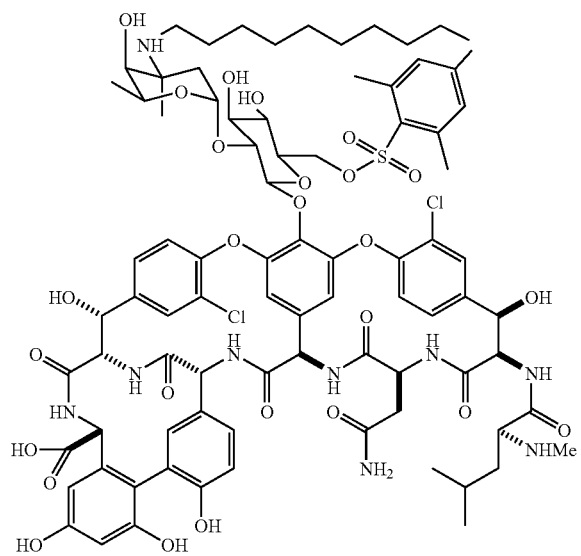

$C_{85}H_{105}Cl_2N_9O_{26}S$
Exact Mass: 1769.63
Mol. Wt.: 1771.76
C, 57.62; H, 5.97; Cl, 4.00; N, 7.11; O, 23.48; S, 1.81

$C_{85}H_{107}{}^{35}Cl_2N_9O_{26}S)^+$, 1488 (M-vancosamine+2H)$^+$, 1144 (M-N-decylvancosamine-glucose+2H)$^+$.

Example 24

Glucose-C6-hydrazine Vancomycin (XLIV)

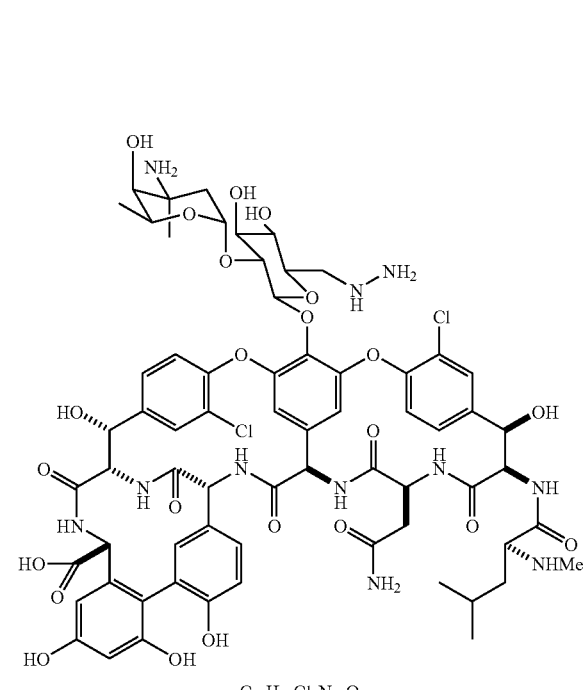

$C_{66}H_{77}Cl_2N_{11}O_{23}$
Exact Mass: 1461.46
Mol. Wt.: 1463.30
C, 54.17; H, 5.30; Cl, 4.85; N, 10.53; O, 25.15

Glucose-C6-2-mesitylenesulfonated vancomycin TFA salt (XLI) (101.5 mg, 0.0528 mmol) is dissolved with wet DMF (5 mL) and DIEA (28 mL, 0.306 mmol) is added and the mixture is stabilized at 70° C. for 0.5 h. Decylaldehyde (9.30 mL, 0.0494 mmol) is added and the reaction mixture is stirred at 70° C. for 1.5 h then NaBH$_3$CN (0.3 mL, 1M-THF, 0.3 mmol) is added. The mixture is stirred for additional 2 h then cooled down to room temperature. The mixture is evaporated and the residue is purified by ODS-HPLC (LUNA 5 µm C18(2), 21.2×250 mm, UV=285 nm, A: 0.1% TFA/H$_2$O, B: MeCN, 10-10-60-100% B 0-5-3040 min., 8 mL/min, $t_{rit.}$=29 min.) to give white amorphous (XLIII) (18.9 mg, 0.010 mmol, 17%) and the starting material (17.2 mg, 0.00985 mmol, 10%) as TFA salts. LRESI-MS 1771 (M+2H, for Glucose-C6-2-mesitylenesulfonated vancomycin (XLI) (10.0 mg, 0.00527 mmol ) and hydrazine (50 mL, 0.00159 mmol), are dissolved with dry DMF (0.5 mL). The mixture is stirred at 45° C. After 2.5 h. the solvent is removed in vacuo. Longer reaction time decomposes the compound The residue is purified by ODS-HPLC (LUNA 5 µm C18(2), 21.2×250 mm, UV=285 nm, A: 0.1% TFA/H$_2$O, B: MeCN, 0-30% B over 30 min., 8 mL/min, $t_r$=18 min.) to give a white amorphous TFA salt (XLIV) (1.2 mg, 0.000761 mmol, 14%).

LRESI-MS 1462 (M+H, for $C_{66}H_{78}{}^{35}Cl_2N_{11}O_{23}$)$^+$, 1321 (M-vancosamine+3H)$^+$, 1143 (M-vancosamine-glucose+H)$^+$.

Example 25

Glucose-C6-1-pyrenesulfonated Vancomycin (XLV)

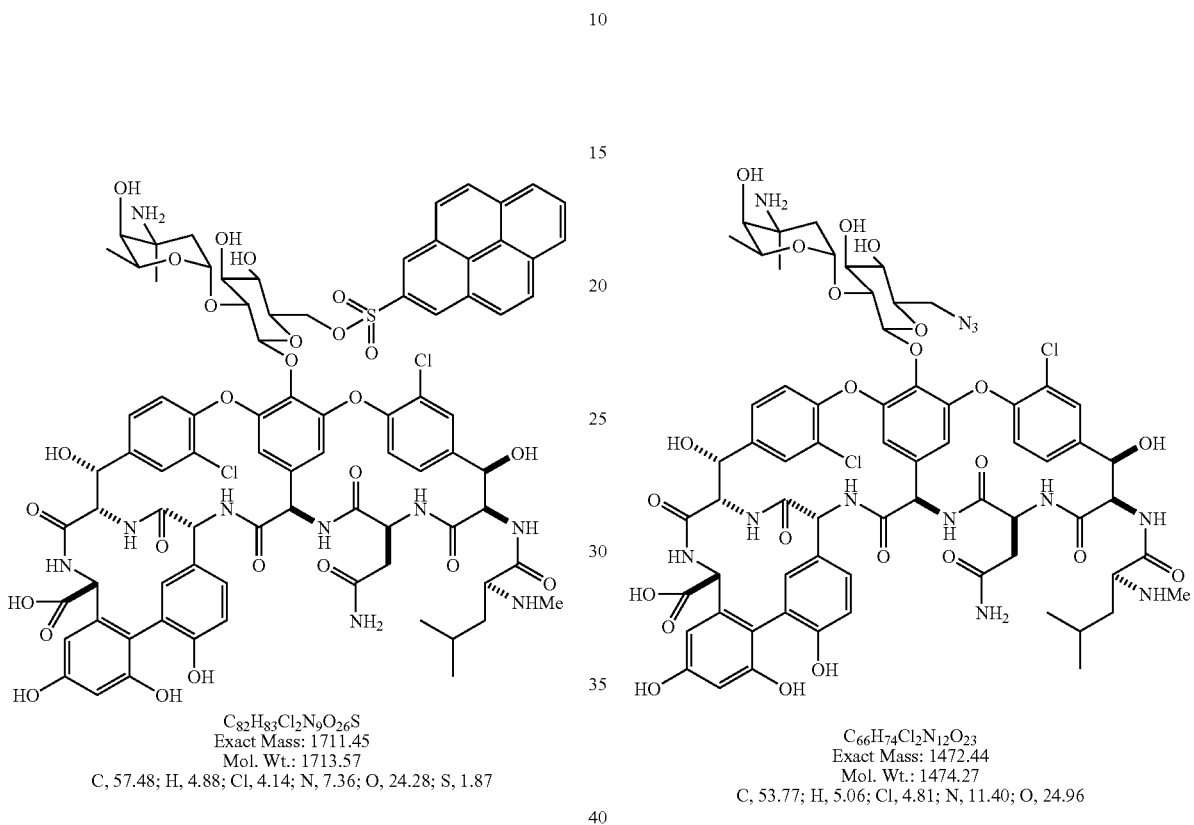

$C_{82}H_{83}Cl_2N_9O_{26}S$
Exact Mass: 1711.45
Mol. Wt.: 1713.57
C, 57.48; H, 4.88; Cl, 4.14; N, 7.36; O, 24.28; S, 1.87

$C_{66}H_{74}Cl_2N_{12}O_{23}$
Exact Mass: 1472.44
Mol. Wt.: 1474.27
C, 53.77; H, 5.06; Cl, 4.81; N, 11.40; O, 24.96

N,N'-Dialoc-allyl-vancomycin (III) (25.0 mg, 0.0151 mmol) is dissolved dry pyridine (1 mL). The mixture is stirred at 4° C. in the refrigerator and 1-pyrenesulfonyl chloride (13.6 mg, 0.0452 mmol) with pyridine (0.5 mL) is added. Stirred at 4° C. in the dark. After 57 h additional 3 eq. of 2-mesitylenesulfonyl chloride with pyridine (5 mL) is added. After total 70 h quenched the reaction with MeOH (0.5 mL) then added ether (10 mL). Centrifuged and the layer is removed (×2). The residue purified by ODS-HPLC (LUNA 5 μm C18(2), 21.2×250 mm, UV=285 nm, A: 0.1% AcOH/H$_2$O, B: 0.1% AcOH/MeCN, 40-80% B 0-30 min., 8 mL/min, $t_r$=22 min.) to give a white amorphous. The product is dissolved with dry DMF/AcOH (1/1)-(1 mL). Pd(PPh$_3$)$_2$Cl$_2$ (cat.) is added, then the mixture is stirred at room temperature under Ar. Added Bu$_3$SnH (0.2 mL) every about 5 min. After 3 h the reaction is done. Added ether then centrifuged twice. The mixture is filtered and purified by ODS-HPLC (LUNA 5 μm C18(2),21.2×250 mm, UV=285 nm, A: 0.1% TFA/H$_2$O, B: MeCN, 0-50-100% B 0-30-50 min., 8 mL/min, $t_{rit.}$=31 min.) to give white amorphous (XLV) as a TFA salt (4.5 mg, 0.00246 mmol, 5.4%, 2 step). LRESI-MS 1713 (M+2H, for $C_{82}H_{85}{}^{35}Cl_2N_9O_{26}S$)$^+$, 1570 (M-vancosamine+2H)$^+$, 1144 (M-vancosamine-glucose+2H)$^+$.

Example 26

Glucose-C6-azide Vancomycin (XLVI)

N,N'-Dialoc-allyl-glucose-C6-azide vancomycin (XVII) (19.5 mg, 0.0116 mmol) is dissolved with dry DMF/AcOH (1/1) (1 mL). Pd(PPh$_3$)$_2$Cl$_2$ (1.0 mg, 0.00142 mmol) is added, then the mixture is stirred at room temperature under Ar. Bu$_3$SnH (0.1 mL) is added about every 20 min. After 4 h the reaction is done. Ether is added and the mixture is centrifuged twice. The residue is purified by ODS-HPLC (LUNA 5 μm C18(2), 21.2×250 mm, UV=285 nm, A: 0.1% TFA/H$_2$O, B: MeCN, 0-30% B over 30 min., 8 mL/min, $t_r$=13 min.) to give a white amorphous (XLVI) as a TFA salt (6.3 mg, 0.0040 mmol, 34%). LRESI-MS 1473 (M+H, for $C_{66}H_{75}{}^{35}Cl_2N_{12}O_{23}$)$^+$, 1331 (M-vancosamine+2H)$^+$, 1143 (M-vancosamine-glucose+H)$^+$.

Example 27

Glucose-C6-amine Vancomycin (XLVII)

To a solution of amine (XVIII) (18 mg, 0.01 mmol) in 1 mL anhydrous DMF containing 0.8 mL acetic acid is added ($Ph_3P)_2Pd(II)Cl_2$ (catalytic). To the stirred solution $Bu_3SnH$ is added in 20 μL aliquots every 2 min. for 8 min. then 40 μL aliquots every 2 min. for 6 min., at which time addition of the $Bu_3SnH$ affords a dark reaction mixture and TLC (chloroform-methanol-water; 6:4:1) shows all glycopeptide is baseline. The crude mixture is precipitated by addition to 20 mL diethyl ether, the suspension centrifuged and the supernatant decanted. The white solid is dried under reduced pressure to remove residual diethyl ether, dissolved in water (ca. 5 mL) and filtered to remove any remaining catalyst or hydrophobic salts. Separation by HPLC (Method B; 40 min. linear gradient of 0% to 40% acetonitrile; flow rate=7.5 mL/min.) affords (XLVII) (15 mg, 96%) Retention time=23 min. LRESI-MS calc for $C_{66}H_{76}N_{10}O_{23}Cl_2$: 1446.5; $[M+H]^+=1448$; [M-vancosamine+H]$^+$=1305; [M-disaccharide+H]$^+$=1143.

Example 28

Glucose-C6-N-4-(4-chlorophenyl)benzyl Vancosamine-N4-4-(4-chlorophenyl)benzyl Vancomycin (XLVIII)

To a stirred solution of (XVIII) (10 mg, 0.007 mmol) in 0.4 mL anhydrous DMF under an argon atmosphere is added DIEA (6 μL, 0.035 mmol). After 5 min, 4-4-(4-chlorophenyl)benzylcarboxaldehyde (1.5 mg, 0.007 mmol) is added and the mixture stirred at 65° C. for 1 h. Sodium cyanoborohydride (3 mg, 0.05 mmol) is then added and the mixture stirred an additional 5 h. at 65° C. The reaction is cooled to room temperature and precipitated by addition to 15 mL diethyl ether The resulting suspension is centrifuged and the supernatant decanted. Residual diethyl ether is removed under a stream of argon. Separation by HPLC (Method B; 40 min. linear gradient of 10% to 65% acetonitrile; flow rate=7.5 mL/min.) affords (XLVIII) (2 mg, 15%); Retention time=27 min. and (XXIX) (3 mg, 26%) which is identical to that prepared previously. LRESI-MS calc for $C_{92}H_{94}N_{10}O_{23}Cl_4$: 1846.5; $[M+H]^+=1848$; [M-disaccharide+H]$^+$=1143.

Example 29

Glucose-C6-N-5-(4-chlorophenyl)furan-1-methylene-Vancosamine-N-decyl Vancomycin (XLIX)

To a stirred solution of glucose-C6-N-5-(4-chlorophenyl)furan-1-methylene derivative (XXX) (8.8 mg, 0.005 mmol) in 0.5 mL anhydrous DMF under an argon atmosphere is added DIEA (4.4 μL, 0.025 mmol) then decylaldehyde (0.85 μL 0.0045 mmol) and the solution stirred at 70° C. for 2 h. Sodium cyanoborohydride (2 mg, 0.03 mmol) is then added and the mixture stirred an additional 2 h. at 70° C. The mixture is cooled to room temperature and precipitated by addition to 8 mL diethyl ether. The resulting suspension is centrifuged, the supernatant decanted and residual diethyl ether removed under a stream of argon. Separation by HPLC (Method B; 35 min. linear gradient of 20% to 80% acetonitrile; flow rate=7.5 mL/min.) affords (XLIX) (1 mg, 12%). Retention time=19 min. LRESI-MS calc for $C_{87}H_{103}N_{10}O_{24}Cl_3$: 1776.6; $[M+H]^+=1778$; [M-disaccharide+H]$^+$=1143.

Example 30

Glucose-C6-N-5-(4-chlorophenyl)furan-1-methylene-Vancosamine-N-4-(4-chlorophenyl)benzyl Vancomycin (L)

To a stirred solution of glucose-C6-N-5-(4-chlorophenyl)furan-1-methylene derivative (XXX) (8.4 mg, 0.005 mmol) in 0.5 mL anhydrous DMF under an argon atmosphere is added DIEA (4.2 μL, 0.024 mmol) then 4-4-(4-chlorophenyl)benzyl-carboxaldehyde (0.9 mg, 0.004 mmol) and the solution stirred at 70° C. for 2 h. Sodium cyanoborohydride (2.5 mg, 0.04 mmol) is then added and the mixture stirred an additional 2 h at 70° C. The mixture is cooled to room temperature and precipitated by addition to 8 mL diethyl ether. The resulting suspension is centrifuged, the supernatant decanted, and residual diethyl ether removed under a stream of argon. Separation by HPLC (Method B; 40 min. linear gradient of 12% to 60% acetonitrile; flow rate=7.5 mL/min.) affords (L) (2.5 mg, 28%) Retention time=29 min. and 3.5 mg recovered starting material. LRESI-MS calc for $C_{90}H_{92}N_{10}O_{24}Cl_4$: 1836.5; $[M+H]^+=1838$; [M-disaccharide+H]$^+$=1143.

Example 31

Glucose-C6-N-2quinoxaloyl-Vancosamine-N-decyl Vancomycin (LI)

To a stirred solution of glucose-C6-N-2quinoxaloyl derivative (XXXVII) (11 mg, 0.007 mmol) in 0.5 mL anhydrous DMF under an argon atmosphere is added DIEA (6 μL, 0.035 mmol) then decylaldehyde (1.1 μL. 0.006 mmol) and the solution stirred at 70° C. for 2 h. Sodium cyanoborohydride (3 mg, 0.05 mmol) is then added and the solution stirred an additional 2 h at 70° C. The mixture is then cooled to room temperature and precipitated by addition to 15 mL diethyl ether. The resulting suspension is centrifuged, the supernatant decanted, and the residual diethyl ether removed under a stream of argon. Separation by HPLC (Method B; 40 min. linear gradient of 5% to 70% acetonitrile; flow rate=7.5 mL/min.) affords (LI) (5 mg, 40%) Retention time=32 min. LRESI-MS calc for $C_{85}H_{100}N_{12}O_{24}Cl_2$: 1742.6; $[M+H]^+=1744$; [M-disaccharide+H]$^+$=1143.

Example 32

Glucose-C6-N-2-quinoxaloyl-Vancosamine-N-4-(4-chlorophenyl)benzyl Vancomycin (LII)

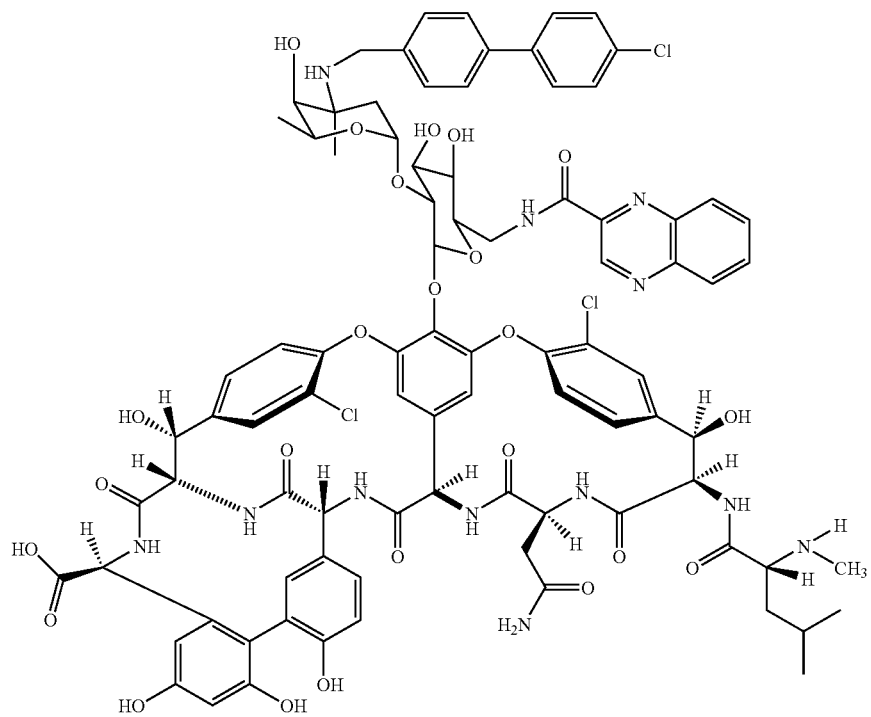

To a stirred solution of glucose-C6-N-2quinoxaloyl derivative (XXXVII) (10.3 mg, 0.006 mmol) in 0.4 mL anhydrous DMF under an argon atmosphere is added DIEA (5.2 μL, 0.03 mmol) then 4-4-(4-chlorophenyl)benzylcarboxaldehyde (1.2 mg, 0.0055 mmol) and the solution stirred at 70° C. for 100 min. Sodium cyanoborohydride (2.5 mg, 0.04 mmol) is then added and the mixture stirred an additional 2.5 h at 70° C. The mixture is cooled to room temperature and precipitated by addition to 15 mL diethyl ether. The resulting suspension is centrifuged, the supernatant decanted, and residual diethyl ether removed under a stream of argon. Separation by HPLC (Method B; 40 min. linear gradient of 5% to 70% acetonitrile; flow rate=7.5 mL/min.) affords (LII) (3.3 mg, 30%, 60% based on 3 mg recovered starting material). Retention time=29 min. LRESI-MS calc for $C_{88}H_{89}N_{12}O_{24}Cl_3$: 1802.5; $[M+H]^+$=1804; $[M-disaccharide+H]^+$=1143.

Example 33

Glucose-C6-thiopropianato Vancomycin (LIII)

General Procedure for Thiolate Displacements on Mesitylene Sulfonyl Derivative (XLI).

To a stirred solution of mesitylenesulfonyl derivative (XLI) (10 to 100 mg) in 0.5 to 4 mL anhydrous DMF under an argon atmosphere is added powdered potassium carbonate (20 to 30 molar equivalents). To the resulting suspension is added the thiol (10 to 20 molar equivalents) and the mixture is stirred at 60 to 65° C. until analytical HPLC shows disappearance of 9. The suspension is cooled to room temperature, diluted with 0.5 to 1 mL methanol, filtered (0.45 μm) to remove carbonate, and the filtrate is then evaporated under reduced pressure. Separation by HPLC is then performed.

Mesitylenesulfonyl derivative (XLI) (13 mg, 0.008 mmol) is subjected to thiolate displacement with 2-propanethiol (30 μL, 0.32 mmol) as described in the general method. Separation by HPLC (Method B; 5 min. at 0% acetonitrile then 40 min. linear gradient of 0% to 45% acetonitrile; flow rate=7.5 mL/min.) affords (LEI[) (8 mg, 66%). Retention time=37 min. LRESI-MS calc for $C_{69}H_{81}N_9O_{23}S_1Cl_2$: 1505.5; $[M+H]^+$=1507; $[M-vancosamine+H]^+$=1364; $[M-disaccharide+H]^+$=1143.

Example 34

Glucose-C6-thiophenyl Vancomycin (LIV)

Mesitylenesulfonyl derivative (XLI) (5 mg, 0.003 mmol) is subjected to thiolate displacement with thiophenol (5 μL, 0.05 mmol) as described in the general method. Separation by HPLC (Method B; 40 min. linear gradient of 5% to 60% acetonitrile; flow rate=7.5 mL/min.) affords (LIV) (3 mg, 67%). Retention time=19 min. LRESI-MS calc for $C_{72}H_{79}N_9O_{23}S_1Cl_2$: 1539.4; $[M+H]^+$=1540; $[M-vancosamine+H]^+$=1397; $[M-disaccharide+H]^+$=1143.

Example 35

Glucose-C6-3-chlorothiophenyl Vancomycin (LV)

Mesitylenesulfonyl derivative (XLI) (8 mg, 0.005 mmol) is subjected to thiolate displacement with 3-chlorothiophenol (6 μL, 0.05 mmol) as described in the general method. Separation by HPLC (Method B; 40 min. linear gradient of 8% to 50% acetonitrile; flow rate=7.5 mL/min.) affords (LV) (4 mg, 51%). Retention time=30 min. LRESI-MS calc for $C_{72}H_{78}N_9O_{23}S_1Cl_3$: 1573.4; $[M+H]^+=1574$; [M-vancosamine+H]$^+$=1433; [M-disaccharide+H]$^+$=1143.

Example 36

Glucose-C6-3-amino-5-mercapto-1,2,4-triazole Vancomycin (LVI)

Mesitylenesulfonyl derivative (XLI) (7 mg, 0.004 mmol) is subjected to thiolate displacement with 3-amino-5-mercapto-1,2,4-triazole (5 mg, 0.04 mmol) as described in the general method. Separation by HPLC (Method B; 40 min. linear gradient of 0% to 40% acetonitrile; flow rate=7.5 mL/min.) affords (LVI) (4 mg, 65%). Retention time=23 min. LRESI-MS calc for $C_{68}H_{77}N_{13}O_{23}S_1Cl_2$: 1545.4; $[M+H]^+=1547$; [M-vancosamine+H]$^+$=1404; [M-disaccharide+H]$^+$=1143.

Example 37

Glucose-C6-Imidazole Vancomycin (LVII)

Mesitylenesulfonyl derivative (XLI) (6 mg, 0.0034 mmol) and imidazole (18 mg, 0.26 mmol) are stirred in 0.7 mL anhydrous DMF under an argon atmosphere at 80° C. for 8 h. The mixture is cooled to room temperature, diluted with water and separation by HPLC (Method B; 40 min. linear gradient of 0% to 50% acetonitrile; flow rate=7.5 mL/min.) affords (LVII) (2.5 mg, 46%). Retention time=24 min. LRESI-MS calc for $C_{69}H_{77}N_{11}O_{23}Cl_2$: 1497.5; $[M+H]^+$ =1498; [M-vancosamine+H]$^+$=1357; [M-disaccharide+H]$^+$=1143.

Example 38

Glucose-C6-5-thio-1-methyl-tetrazole Vancomycin (LVIII)

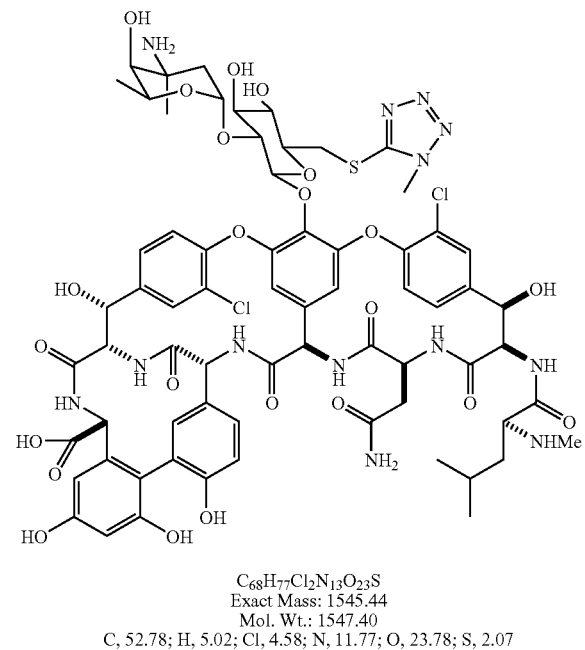

$C_{68}H_{77}Cl_2N_{13}O_{23}S$
Exact Mass: 1545.44
Mol. Wt.: 1547.40
C, 52.78; H, 5.02; Cl, 4.58; N, 11.77; O, 23.78; S, 2.07

Glucose-C6-2-mesitylenesulfonated vancomycin TFA salt (XLI) (10 mg, 0.00573 mmol), 5-mercapto-1-methyl-tetrazole (14 mg 0.121 mmol), and $K_2CO_3$ (17 mg 0.123 mmol), are dissolved with dry DMF (0.5 mL). The mixture is stirred at 70° C. After 4 h. analytical HPLC indicates that the reaction is done. The mixture is filtered and purified by ODS-HPLC (LUNA 5 μm C18(2), 21.2×250 mm, UV=285 nm, A: 0.1% TFA/$H_2O$, B: MeCN, 0-50% B 0-30 min., 8 mL/min, $t_r$=22 min.) to give (LVIII) as a white amorphous TFA salt (3.4 mg, 0.00205 mmol, 36%). LRESI-MS 1547 (M+2H, for $C_{68}H_{79}{}^{35}Cl_2N_{13}O_{23}S)^+$, 1404 (M-vancosamine+2H)$^+$, 1144 (M-vancosamine-glucose+2H)$^+$.

Example 39

Glucose-C6-1-thio-4-bromobenzene Vancomycin (LIX)

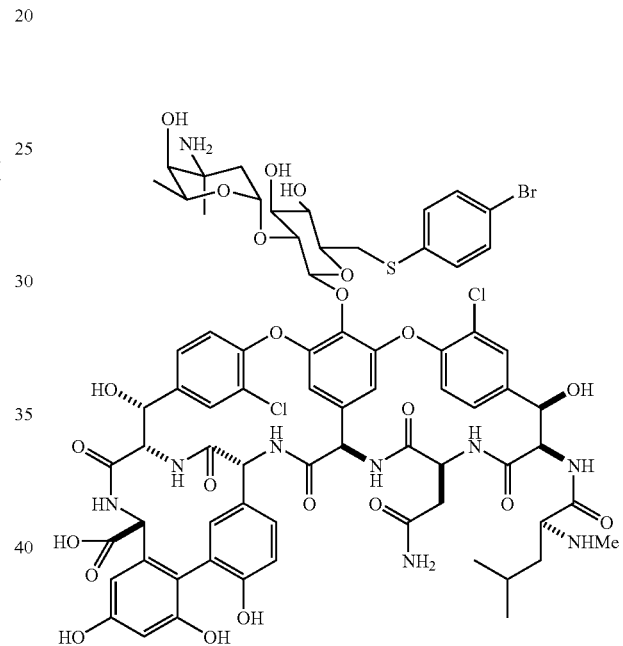

$C_{72}H_{78}BrCl_2N_9O_{23}S$
Exact Mass: 1617.35
Mol. Wt.: 1620.32
C, 53.37; H, 4.85; Br, 4.93; Cl, 4.38; N, 7.78; O, 22.71; S, 1.98

Glucose-C6-2-mesitylenesulfonated vancomycin TFA salt (XLI) (10 mg, 0.00573 mmol), 4-bromothiophenol (22.7 mg 0.12 mmol), and $K_2CO_3$ (17 mg 0.123 mmol), are dissolved with dry DMF (0.5 mL). The mixture is stirred at 70° C. After 1 h. analytical HPLC indicates that the reaction is done. The mixture is filtered and purified by ODS-HPLC (LUNA 5 μm C18(2), 21.2×250 mm, UV=285 nm, A: 0.1% TFA/$H_2O$, B: MeCN, 0-50% B 0-30 min., 8 mL/min, $t_r$=27 min.) to give (LIX) as a white amorphous TFA salt (3.2 mg, 0.00185 mmol, 32%). LRESI-MS 1618 (M+H, for $C_{72}H_{79}{}^{79}Br^{35}Cl_2N_9O_{23}S)^+$, 1475 (M-vancosamine+H)$^+$, 1143 (M-vancosamine-glucose+H)$^+$.

Example 40

Glucose-C6-2-thio-4-trifluoromethylpyridine Vancomycin (LX)

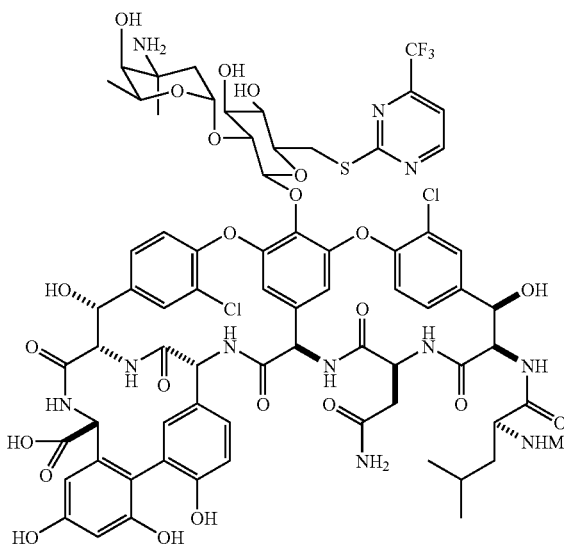

$C_{71}H_{76}Cl_2F_3N_{11}O_{23}S$
Exact Mass: 1609.42
Mol. Wt.: 1611.40
C, 52.92; H, 4.75; Cl, 4.40; F, 3.54; N, 9.56; O, 22.84; S, 1.99

Glucose-C6-2-mesitylenesulfonated vancomycin TFA salt (XLI) (10 mg, 0.00573 mmol), 4-(trifluoromethyl)-2-pyridinethiol (21.6 mg 0.12 mmol), and $K_2CO_3$ (17 mg 0.123 mmol), are dissolved with dry DMF (0.5 mL). The mixture is stirred at 65° C. After 2 h. analytical HPLC indicates the reaction is done. The mixture is filtered and purified by ODS-HPLC (LUNA 5 μm C18(2), 21.2×250 mm, UV=285 nm, A: 0.1% TFA/$H_2O$, B: MeCN, 0-50-100% B 0-30-40 min., 8 mL/min, $t_r$=35 min.) to give (LX) as a white amorphous TFA salt (2.3 mg, 0.00133 mmol, 23%). LRESI-MS 1613 (M+4H, for $C_{71}H_{80}{}^{35}Cl_2F_3N_{11}O_{23}S)^+$, 1143 (M-vancosamine-glucose+H)$^+$.

Example 41

Glucose-C6-2-thio-4-aminopyrimidine Vancomycin (LXI)

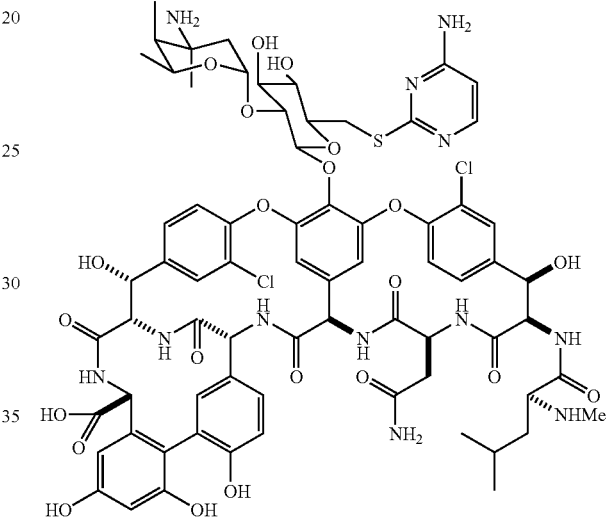

$C_{70}H_{78}Cl_2N_{12}O_{23}S$
Exact Mass: 1556.44
Mol. Wt.: 1558.41
C, 53.95; H, 5.04; Cl, 4.55; N, 10.79; O, 23.61; S, 2.06

Glucose-C6-2-mesitylenesulfonated vancomycin TFA salt (XLI) (17.5 mg, 0.0100 mmol), 4-amino-2-mercaptopyrimidine (26.1 mg 0.12 mmol), and $K_2CO_3$ (17 mg 0.123 mmol), are dissolved with dry DMF (0.5 mL). The mixture is stirred at 80° C. After 1 h. analytical HPLC indicates the reaction is done. The mixture is filtered and purified by ODS-HPLC (COSMOSIL 5C18-AR, 20×250 mm, and LUNA 5 μm C18 (2), 21.2×250 mm, UV=285 nm, A: 0.1% TFA/$H_2O$, B: MeCN, 0-70% B 0-60 min., 8 mL/min, $t_r$=30 min.) to give (LXI) as a white amorphous TFA salt (7.3 mg, 0.00436 mmol, 44%). LRESI-MS 1557 (M+H, for $C_{70}H_{79}Cl_2N_{12}O_{23}S)^+$, 1414 (M-vancosamnine+H)$^+$, 1143 (M-vancosamine-glucose+H)$^+$.

78%). LRESI-MS 1573 (M+2H, for $C_{70}H_{81}{}^{35}Cl_2N_{13}O_{23}S)^+$, 1430 (M-vancosamine+2H)$^+$, 1143 (M-vancosamine-glucose+H)$^+$.

Example 42

Glucose-C6-6-thio-2,4-diaminopyrimidine vancomycin (LXII)

Example 43

Glucose-C6-2-thio-4-amino-6-hydroxypyrimidine Vancomycin (LXIII)

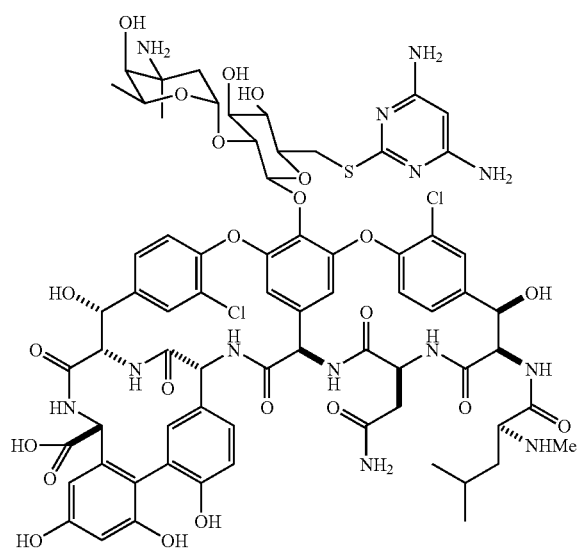

$C_{70}H_{79}Cl_2N_{13}O_{23}S$
Exact Mass: 1571.45
Mol. Wt.: 1573.42
C, 53.43; H, 5.06; Cl, 4.51; N, 11.57; O, 23.39; S, 2.04

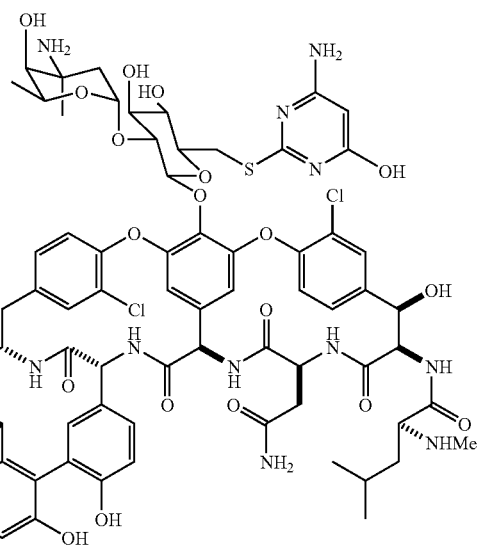

$C_{70}H_{78}Cl_2N_{12}O_{24}S$
Exact Mass: 1572.43
Mol. Wt.: 1574.41
C, 53.40; H, 4.99; Cl, 4.50; N, 10.68; O, 24.39; S, 2.04

Glucose-C6-2-mesitylenesulfonated vancomycin TFA salt (IXII) (13.3 mg, 0.00762 mmol), 4-amino-2-mercaptopyrimidine (31.2 mg 0.163 mmol), and $K_2CO_3$ (22.1 mg 0.160 mmol), are dissolved with dry DMF (0.5 mL). The mixture is stirred at 80° C. After 7 h. analytical HPLC indicates the reaction is done. The mixture is filtered and purified by ODS-HPLC (COSMOSIL 5C18-AR, 20×250 mn, and LUNA 5 μm C18(2), 21.2×250 mm, UV=285 nm, A: 0.1% TFA/H$_2$O, B: MeCN, 0-70% B 0-60 min., 8 mL/min, $t_r$=36 min.) to give (LXII) as a white amorphous TFA salt (10 mg, 0.00593 mmol, Glucose-C6-2-mesitylenesulfonated vancomycin TFA salt (XLI) (10 mg, 0.00573 mmol), 4,5-diamino-6-hydroxy-2-mercaptopyrimidine (19.4 mg 0.122 mmol), and $K_2CO_3$ (17 mg 0.123 mmol), are dissolved with dry DMF (0.5 mL). The mixture is stirred at 65° C. After 5 h the mixture is filtered and purified by ODS-HPLC (LUNA 5 μm C18(2), 21.2×250 mm, UV=285 nm, A: 0.1% TFA/H$_2$O, B: MeCN, 0-50-100% B 0-30-40 min., 8 mL/min, $t_r$=29 min.) to give (LXIII) as a white amorphous TFA salt (1.0 mg, 0.000592 mmol, 10%).

LRESI-MS 1574 (M+2H, for $C_{70}H_{80}{}^{35}Cl_2N_{12}O_{24}S)^+$, 1431 (M-vancosamine+2H)$^+$, 1143 (M-vancosamine-glucose+H)$^+$.

Example 44

Glucose-C6-2-thio-6-azathymine Vancomycin (LXIV)

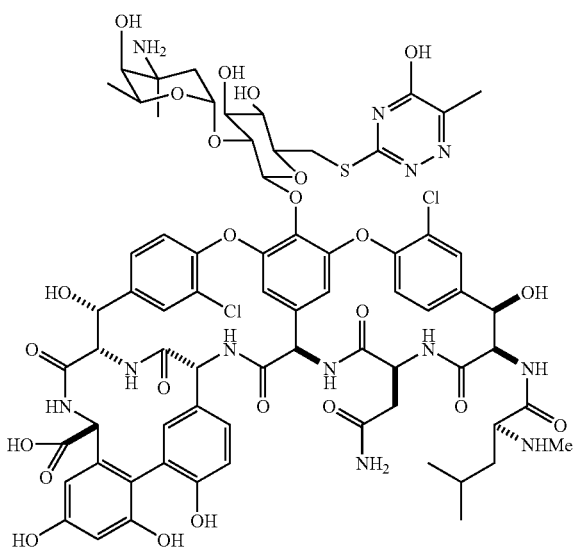

$C_{70}H_{78}Cl_2N_{12}O_{24}S$
Exact Mass: 1572.43
Mol. Wt.: 1574.42
C, 53.40; H, 4.99; Cl, 4.50; N, 10.68; O, 24.39; S, 2.04

Glucose-C6-2-mesitylenesulfonated vancomycin (XLI) (175 mg, 0.1 mmol), 6-aza-2-thiothymine (307 mg 2.1 mmol), and $K_2CO_3$ (304 mg 2.2 mmol), are dissolved with dry DMF (5 mL). The mixture is stirred at 80° C. After 5 h analytical HPLC indicates the reaction is done. The solvent is removed in vacuo. Water is added and the mixture is centrifuged. The residue is purified by ODS-HPLC (COSMOSIL 5C18-AR, 20×250 mm, and LUNA 5 μm C18(2), 21.2×250 mm, UV=285 nm, A: 0.1% TFA/$H_2O$, B: MeCN, 0-70% B 0-60 min., 8 mL/min, $t_r$=36 min.) to give (LXIV) as a white amorphous TFA salt (79 mg, 0.047 mmol, 47%). LRESI-MS 1573 (M+H, for $C_{70}H_{79}C_{12}N_{12}O_{24}S)^+$, 1430 (M-vancosamine+H)$^+$, 1143 (M-vancosamnine-glucose+H)$^+$.

$^1$H-NMR data in DMSO-$d_6$ at 298 K: δ 0.84 (3H, d, J=6.5 Hz, 1d), 0.90 (3H, d, J=6.5 Hz, 1c), 1.09 (3H, d, J=6.0 Hz, V6), 1.30 (3H, s, V7), 1.52 (2H, m, 1a), 1.70 (1H, br d, J=8.5 Hz, V2e), 1.72 (1H, m, 1b), 1.90 (1H, br d, J=8.5 Hz, V2a), 2.08 (3H, s, azathymine-6), 2.15 (1H, m, 3a), 2.41 (1H, m, 3a), 2.42 (3H, s, 1e), 3.17 (1H, br s, V4), 3.50-3.56 (5H, m, G2-6), 3.63 (1H, m, x1), 4.20 (1H, br s, x6), 4.37 (1H, m, x3), 4.44 (2H, br s, x5 and x7), 4.65 (1H, br d, J=5.0 Hz, V5), 4.92 (1H, br s, x2), 5.10 (1H, s, z6), 5.18 (1H, s, z2), 5.19 (1H, s, 4f), 5.24 (2H, s, V1 and G1), 5.40 (2H, br s, G3OH and G4OH), 5.55 (1H, s, 4b), 5.73 (1H, br s, x4), 5.80 (1H, br s, Z2OH), 5.94 (1H, br s, Z6OH), 6.25 (1H, s, 7f), 6.40 (1H, s, 7d), 6.90 (1H, m, w3 and w6), 6.72 (1H, d, J=9.0 Hz, 5e), 6.78 (1H, d, J=9.0 Hz, 5f), 7.19 (1H, s, 5b), 7.32 (1H, m, 2e), 7.39 (1H, m, 2b), 7.46 (1H, d, J=8.5 Hz, 6e), 7.51 (1H, d, J=8.5 Hz, 6f), 7.60 (1H, m, 2f), 7.85 (1H, s, 6b), 8.49 (2H, br s, w5 and w7), 8.66 (1H, br s, w4), 9.10 (1H, br s, 7cOH), 9.17 (1H, br s, 5dOH), 9.44 (1H, br s, 7eOH).

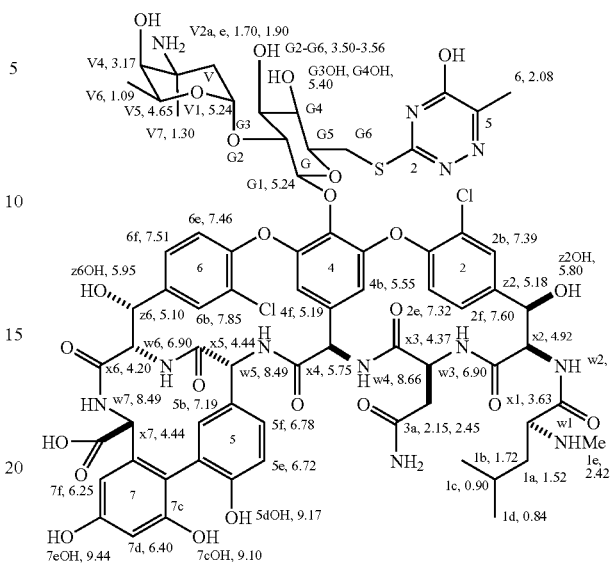

Example 45

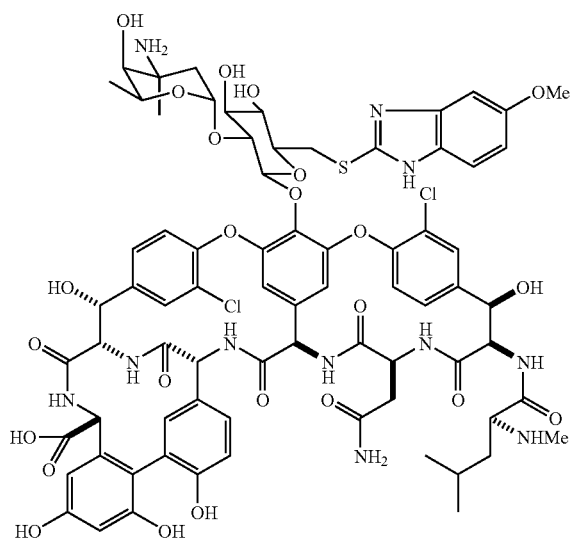

$C_{74}H_{81}Cl_2N_{11}O_{24}S$
Exact Mass: 1609.46
Mol. Wt.: 1611.47
C, 55.15; H, 5.07; Cl, 4.40; N, 9.56; O, 23.83; S, 1.99

Glucose-C6-2-mesitylenesulfonated vancomycin TFA salt (XLI) (5 mg, 0.00287 mmol), 5-methoxy-2-benzimidazolethiol (11.0 mg 0.0610 mmol), and $K_2CO_3$ (8.6 mg 0.0622 mmol), are dissolved with dry DMF (0.5 mL). The mixture is stirred at 65° C. After 4 h. analytical HPLC indicates the reaction is done. The mixture is filtered and purified by ODS-HPLC (LUNA 5 μm C18(2), 21.2×250 mm, UV=285 nm, A: 0.1% AcOH/$H_2O$, B: 0.1% AcOH/MeCN, 0-50% B 0-30 min., 8 mL/min, $t_r$=27 min.) to give (LXV) as a white amorphous TFA salt (1.2 mg, 0.000700 mmol, 24%). LRESI-MS 1611 (M+2H, for $C_{74}H_{83}{}^{35}Cl_2N_{11}O_{24}S)^+$, 1467 (M-vancosamine+2H)$^+$, 1143 (M-vancosamine-glucose+H)$^+$.

Example 46

Glucose-C6-2-thio-5-chlorobenzothiazole Vancomycin (LXVI)

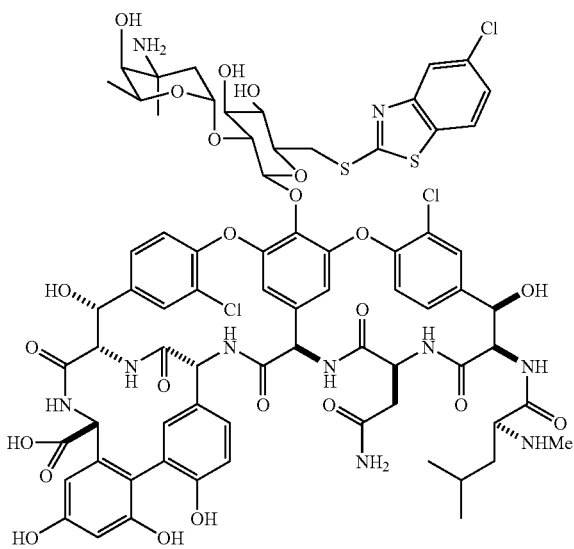

$C_{73}H_{77}Cl_3N_{10}O_{23}S_2$
Exact Mass: 1630.37
Mol. Wt.: 1632.94
C, 53.69; H, 4.75; Cl, 6.51; N, 8.58; O, 22.54; S, 3.9

Glucose-C6-2-mesitylenesulfonated vancomycin TFA salt (XLI) (103.9 mg, 0.0595 mmol), 5-chloro-2-mercapto-benzothiazole (256.9 mg 1.27 mmol), and $K_2CO_3$ (176.1 mg 1.27 mmol), are dissolved with dry DMF (5 mL). The mixture is stirred at 75-80° C. After 2 h. analytical HPLC indicates the reaction is done. The mixture is filtered and purified by ODS-HPLC (LUNA 5 μm C18(2), 50×250 mm, UV=285 nm, A: 0.1% TFA/H$_2$O, B: MeCN, 20-100% B over 60 min., 20 mL/min, t$_r$=36 min.) to give (LXVI) as a white amorphous TFA salt (75.8 mg, 0.0434 mmol, 73%). LRESI-MS 1632 (M+2H, for $C_{73}H_{79}{}^{35}Cl_3N_{10}O_{23}S_2)^+$, 1488 (M-vancosamine+H)$^+$, 1143 (M-vancosamine-glucose+H)$^+$.
$^1$H-NMR data in DMSO-d$_6$ at 298 K: δ 0.87 (3H, d, J=5.5 Hz, 1d), 0.92 (3H, d, J=6.0 Hz, 1c), 1.08 (3H, d, J=6.0 Hz, V6), 1.24 (3H, s, V7), 1.56 (1H, m, 1a), 1.65 (1H, m, 1b), 1.66 (1H, m, 1a), 1.72 (1H, br d, J=13 Hz, V2e), 1.90 (1H, br d, J=12 Hz, V2a), 2.19 (1H, m, 3a), 2.62 (3H, s, 1e), 2.63 (1H, m, 3a), 3.15 (1H, br s, V4), 3.47-3.57 (3H, m, G2, G3, and G4), 3.59 (1H, br d, J=11.0 Hz, G6), 3.73 (1H, m, G5), 3.83 (1H, br d, J=11.0 Hz, G6), 3.96 (1H, m, x1), 4.20 (1H, br s, x6), 4.43 (1H, d, J=5.5 Hz, x3), 4.45 (1H, br s, x7), 4.46 (1H, br s, x5), 4.67 (1H, br d, J=6.5 Hz, V5), 4.90 (1H, br s, x2), 5.10 (1H, s, z2), 5.16 (1H, s, z6), 5.21 (2H, br s, G1 and V1), 5.26 (1H, d, J=5.5 Hz, 4f), 5.45-5.55 (2H, m, G3OH and G4OH), 5.67 (1H, s, 4b), 5.80 (1H, d, J=7.5, x4), 5.90 (1H, br s, Z2OH), 5.95 (1H, d, J=5.0, Z6OH), 6.25 (1H, s, 7f), 6.40 (1H, s, 7d), 6.57 (1H, m, w3), 6.74 (1H, s, Chlorobenzothiazole-4), 6.74 (1H, d, J=8.5 Hz, 5e), 6.78 (1H, d, J=8.5 Hz, 5f), 7.14 (1H, d, J=9.0 Hz, 2e), 7.16 (1H, s, 5b), 7.30 (1H, d, J=8.0 Hz, 6e), 7.45 (1H, d, J=9.0 Hz, Chlorobenzothiazole-7), 7.46 (1H, s, 2b), 7.46 (1H, d, J=8.0 Hz, 6f), 7.53 (1H, d, J=9.0 Hz, 2f), 7.83 (1H, s, 6b), 8.05 (1H, d, J=9.0 Hz, Chlorobenzothiazole-4), 8.51 (2H, br s, w5 and w7), 8.78 (1H, br s, w4), 9.08 (1H, br s, 7cOH), 9.17 (1H, br s, 5dOH), 9.44 (1H, br s, 7eOH).

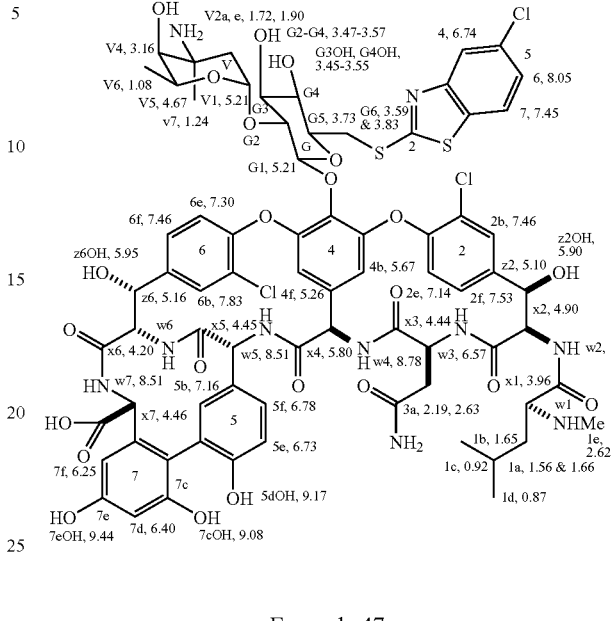

Example 47

Glucose-C6-2-thio-5-phenyl-1,3,4-oxadiazole Vancomycin (LXVII)

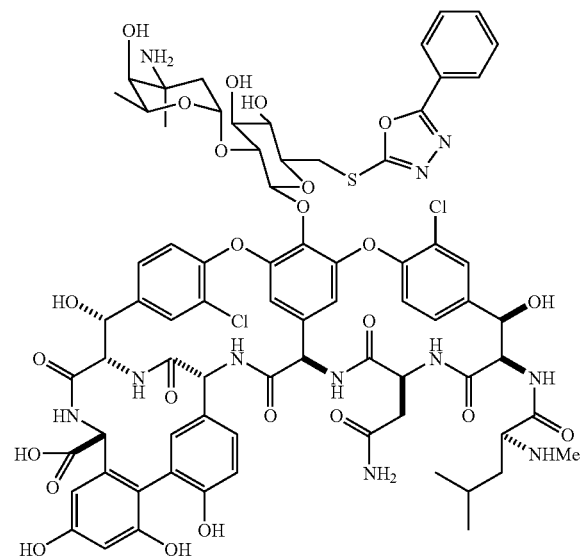

$C_{74}H_{79}Cl_2N_{11}O_{24}S$
Exact Mass: 1607.44
Mol. Wt.: 1609.45
C, 55.22; H, 4.95; Cl, 4.41; N, 9.57; O, 23.86; S, 1.99

Glucose-C6-2-mesitylenesulfonated vancomycin TFA salt (XLI) (78.0 mg, 0.0447 mmol), 5-phenyl-1,3,4-oxadiazole-2-thiol (170.4 mg 0.956 mmol), and $K_2CO_3$ (132.7 mg 0.960 mmol), are dissolved with dry DMF (2 mL). The mixture is stirred at 65° C. After 2 h. analytical HPLC indicates the reaction is done. The mixture is filtered and purified by ODS-HPLC (LUNA 5 μm C18(2), 21.2×250 mm, UV=285 nm, A:

0.1% TFA/H$_2$O, B: MeCN, 10-60% B 0-30 min., 8 mL/min, t$_r$=21 min.) to give (LXVII) as a white amorphous TFA salt (60.3 mg, 0.0350 mmol, 78%). LRESI-MS 1608 (M+H, for C$_{74}$H$_{80}$$^{35}$Cl$_2$N$_{11}$O$_{24}$S)$^+$, 1466 (M-vancosamine+2H)$^+$. 1143 (M-vancosamnine-glucose+H)$^+$.

(M+2H, for C$_{73}$H$_{81}$$^{35}$Cl$_2$N$_{13}$O$_{24}$S)$^+$, 1480 (M-vancosamine +2H)$^+$, 1143 (M-vancosamine-glucose+H)$^+$.

Example 49

Glucose-C6-2-thio-4,5-diphenyloxazole Vancomycin (LXIX)

Example 48

Glucose-C6-5-thio-1-(4-hydroxyphenyl)-1H-tetrazole Vancomycin (LXVIII)

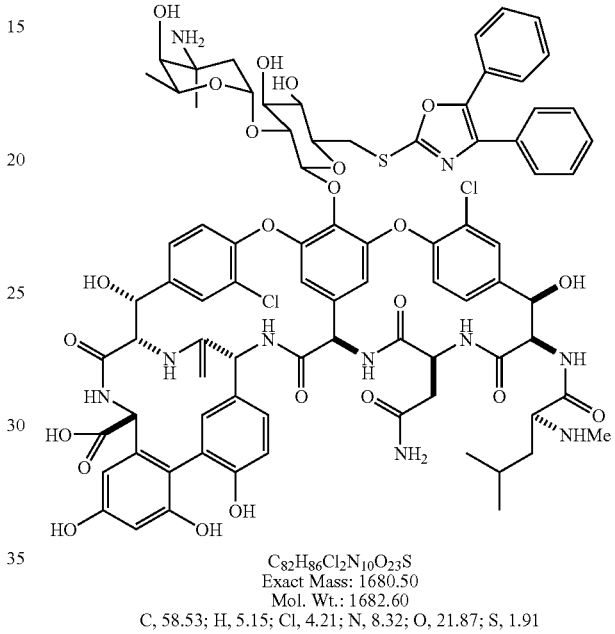

C$_{82}$H$_{86}$Cl$_2$N$_{10}$O$_{23}$S
Exact Mass: 1680.50
Mol. Wt.: 1682.60
C, 58.53; H, 5.15; Cl, 4.21; N, 8.32; O, 21.87; S, 1.91

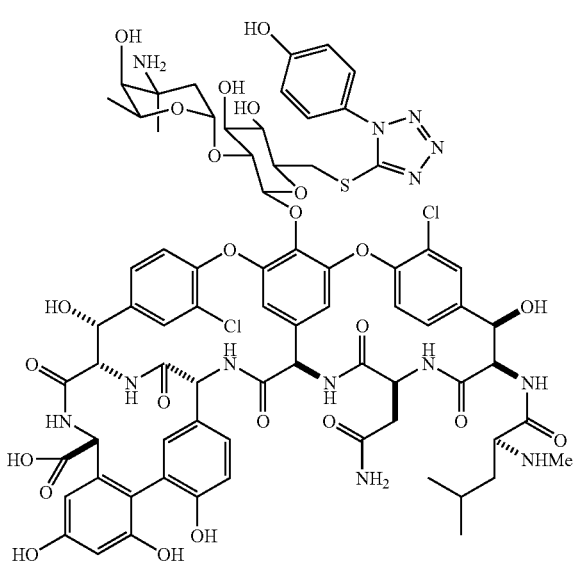

C$_{73}$H$_{79}$Cl$_2$N$_{13}$O$_{24}$S
Exact Mass: 1623.45
Mol. Wt.: 1625.47
C, 53.94; H, 4.90; Cl, 4.36; N, 11.20; O, 23.62; S, 1.97

Glucose-C6-2-mesitylenesulfonated vancomycin TFA salt (XLI) (10 mg, 0.00573 mmol), 4,5-diphenyl-2-oxazole thiol (30.4 mg 0.12 mmol), and K$_2$CO$_3$ (17 mg 0.123 mmol), are dissolved with dry DMF (0.5 mL). The mixture is stirred at 65° C. After 2 h. analytical HPLC indicates the reaction is done. The mixture is filtered and purified by ODS-HPLC (LUNA 5 μm C18(2), 21.2×250 mm, UV=285 nm, A: 0.1% TFA/H$_2$O, B: MeCN, 10-10-60% B 0-5-30 min., 8 mL/min, t$_r$=28 min.) to give (LXIX) as a white amorphous TFA salt (3.4 mg, 0.00133 mmol, 33%). LRESI-MS 1683 (M+3H, for C$_{82}$H$_{89}$$^{35}$Cl$_2$N$_{10}$O$_{23}$S)$^+$, 1540 (M-vancosamine +3H)$^+$, 1143 (M-vancosamine-glucose+H)$^+$.

Example 50

Glucose-C6-Iodo Vancomycin (LXX)

a) N,N'-dialoc-glucose-C6-Iodo-Vancomycin Allyl Ester.

Glucose-C6-2-mesitylenesulfonated vancomycin TFA salt (XLI) (10 mg, 0.00573 mmol), 1-(4-hydroxyphenyl)-1H-tetrazole-5-thiol (23.3 mg 0.12 mmol), and K$_2$CO$_3$ (17 mg 0.123 mmol), are dissolved with dry DMF (0.5 mL). The mixture is stirred at 65° C. After 14 h. analytical HPLC indicates the reaction is done. The mixture is filtered and purified by ODS-HPLC (LUNA 5 μm C18(2), 21.2×250 mm, UV=285 nm, A: 0.1% TFA/H$_2$O, B: MeCN, 0-50-100% B 0-30-40 min., 8 mL/min, t$_r$=35 min.) to give (LXVIII) as a white amorphous TFA salt (1.8 mg, 0.00103 mmol, 18%). LRESI-MS 1625

To a stirred solution of mesitylenesulfonyl derivative (XVI) (500 mg, 0.27 mmol) in 12 mL anhydrous dimethylacetamide (DMA) under an argon atmosphere is added powdered potassium iodide (0.9 g, 5.4 mmol) and the mixture stirred at 85° C. for 12 h. The reaction is cooled to room temperature and precipitated by addition to 120 mL diethyl ether (4×30 mL), the suspension centrifuged, the supernatant decanted, and the remaining diethyl ether removed under argon flow. The white solid in each tube is dissolved in 3 mL methanol/0.8 mL DMF, precipitated by the addition of 30 mL water, and the suspension stored at 4° C. for 12 h. Each suspension is then centrifuged and the supernatant is decanted. The solids are dissolved in methanol, combined, diluted with 250 mL toluene and evaporated to dryness under reduced pressure. The solid is dissolved in a minimum of methanol and diluted with as much dichloromethane as possible without precipitating, loaded onto a silica column packed in dichloromethane and eluted; first with 2 column volumes of dichloromethane-methanol-water (100:15:1), then dichloromethane-methanol-water (100:16:11). Fractions containing pure product are combined and evaporated affording (350 mg, 73%). Fractions containing impure product are combined, evaporated and separated by HPLC (Method A; 40 min. linear gradient of 25% to 70% acetonitrile; flow rate=7.5 mL/min.) affording additional pure product (30 mg). Ret. Time=25 min. Combined yield of title compound=380 mg, 80%. TLC: Rf=0.6 (chloroform-methanol-water, 50:21:4). LRESI-MS calc for $C_{77}H_{86}N_9O_{27}I_1Cl_2$: 1765.4; $[M+Na]^+$=1788; $[M-vancosamine+Na]^+$=1562; $[M-disaccharide+H]^+$=1289.

b) Glucose-C6-Iodo Vancomycin (LXX).

The iodo derivative from step (a) (109 mg, 0.062 mmol) is dissolved in 8 mL anhydrous DMF and divided into two separate 4 mL reactions. Acetic acid (3 mL) is then added to each flask followed by $(Ph_3P)_2Pd(II)Cl_2$ (catalytic). $Bu_3SnH$ is added to the vigorously stirred solution in 30 μL portions every min. for 4 min. After the forth addition, waited 5 min., then added 60 μL $Bu_3SnH$. The mixture turns dark and TLC (chloroform-methanol-water; 6:4:1) shows all glycopeptide is baseline. The crude mixture is diluted with 0.5 mL methanol and precipitated by addition to 80 mL diethyl ether. The suspension is centrifuged and the supernatant decanted. The white solid is suspended in diethyl ether and mixed vigorously. The suspension is centrifuged and the supernatant decanted. The white solid is dried under reduced pressure to remove residual diethyl ether, dissolved in water (ca. 10 mL) stored at 4° C. for 12 h then filtered to remove any remaining catalyst or hydrophobic salts. Separation by HPLC (Method B; 40 min. linear gradient of 5% to 60% acetonitrile; flow rate=7.5 mL/min.) affords (LXX) (89 mg, 86%). Retention time=22 min. LRESI-MS calc for $C_{66}H_{74}N_9O_{23}I_1Cl_2$: 1557.3; $[M+H]^+$=1558; $[M-vancosamine+H]^+$=1415; $[M-disaccharide+H]^+$=1143.

Example 51

Glucose-C6-thioacetato Vancomycin (LXXI)

To a stirred solution of iodide (LXX) (2.5 mg, 0.0016 mmol) in 0.2 mL anhydrous DMF under an argon atmosphere is added powdered potassium carbonate (10 mg, 0.07 mmol). To the resulting suspension is added mercaptoacetic acid, monosodium salt, (8 mg, 0.07 mmol) and the mixture stirred at 60° C. for 40 min. The suspension is cooled to room temperature, diluted with 1 mL methanol and filtered (0.45 μm) to remove carbonate. The filtrate is evaporated under reduced pressure to remove methanol then diluted with water (0.3 mL) and separation by HPLC (Method B; 40 min. linear gradient of 0% to 45% acetonitrile; flow rate=7.5 mL/min.) affords (LXXI) (1.5 mg, 62%). Retention time=22 min. LRESI-MS calc for $C_{68}H_{77}N_9O_{25}S_1Cl_2$: 1521.4; $[M+H]^+$=1523; $[M-vancosamine+H]^+$=1380; $[M-disaccharide+H]^+$=1143.

Example 52

Vancosamine-N-decyl-Glucose-C6-S-3-amino-5-mercapto-1,2,4-triazole Vancomycin (LXXII)

a) Vancosamine-N-decyl-Glucose-C6-Iodo-Vancomycin (LXXIIa).

To a stirred solution of (LXX) (32 mg, 0.019 mmol) in 0.6 mL anhydrous DMF under an argon atmosphere is added DIEA (17 μL, 0.1 mmol). After 10 min., decyl aldehyde (2.86 μL, 0.015 mmol) is added and the solution heated at 70° C. for 2 h. Sodium cyanoborohydride (3 mg, 0.05 mmol) is then added and heating continued for an additional 2 h. The reaction mixture is cooled to room temperature and precipitated by addition to 20 mL diethyl ether. The suspension is centrifuged and the supernatant decanted. The white solid is dried under reduced pressure to remove residual diethyl ether. Separation by HPLC (Method B; 40 min. linear gradient of 5% to 80% acetonitrile; flow rate=8 mL/min.) affords the iodo product (LXXIIa) (10 mg, 30%). (Retention time=28 min.) and 6 mg recovered (LXX). LRESI-MS for (LXXIIa) calc for $C_{76}H_{94}N_9O_{23}I_1Cl_2$: 1697.5; $[M+H]^+$=1699; $[M-vancosamine+H]^+$=1415; $[M-disaccharide+H]^+$=1143.

b) Vancosamine-N-decyl-Glucose-C6-S-3-amino-5-mercapto-1,2,4-triazole Vancomycin (LXXII).

To a stirred solution of the iodo product from step (a) (5 mg, 0.003 mmol) in 0.5 mL anhydrous DMF under an argon atmosphere is added potassium carbonate (10 mg, 0.07 mmol). After 5 min. 3-amino-5-mercapto-1,2,4-triazole (4.2 mg, 0.036 mmol) is added and the mixture stirred at 55° C. for 30 min. The mixture is cooled to room temperature, filtered (0.45 μm) to remove carbonate, and diluted with 8 mL water. Separation by HPLC (Method B; 40 min. linear gradient of 5% to 70% acetonitrile; flow rate=7.5 mL/min.) affords (LXXII) (4.8 mg, 95%). Retention time=28 min. LRESI-MS calc for $C_{78}H_{97}N_{13}O_{23}S_1Cl_2$: 1685.6; $[M+H]^+$=1687; $[M-vancosamine+H]^+$=1404; $[M-disaccharide+H]^+$=1143.

Example 53

Vancosamine-N-4-(4-chlorophenyl)benzyl,Glucose-C6-S-3-amino-5-mercapto-1,2,4-triazole Vancomycin (LXXIII)

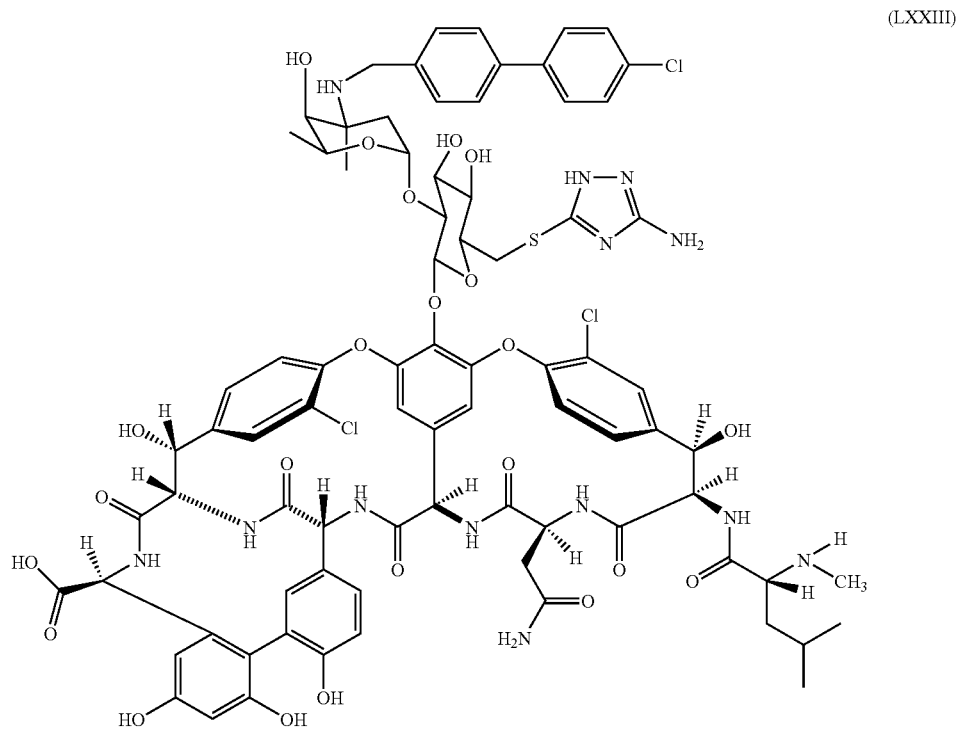

(LXXIII)

a) Vancosamine-N-4-(4-chlorophenyl)benzyl Glucose-C6-Iodo-Vancomycin (LXXIIIa).

To a stirred solution of (LXX) (21 mg, 0.013 mmol) in 0.5 mL anhydrous DMF under an argon atmosphere is added DEBA (11 μL, 0.06 mmol). After 10 min., 4-4-(4-chlorophenyl)benzyl-benzaldehyde (2.5 mg, 0.11 mmol) is added and the solution heated at 70° C. for 90 min.. Sodium cyanoborohydride (3 mg, 0.05 mmol) is then added and the mixture stirred at 70° C. for an additional 2 h. The reaction mixture is cooled to room temperature and precipitated by addition to 25 mL diethyl ether. The suspension is centrifuged and the supernatant decanted. The white solid is dried under reduced pressure to remove residual diethyl ether. Separation by HPLC (Method B; 40 min. linear gradient of 5% to 60% acetonitrile; flow rate=8 mL/min.) affords the iodo product (LXXIIIa) (11 mg, 46%); retention time=32 min.; and 3 mg recovered (LXX). LRESI-MS for (LXXIIIa) calc for $C_{79}H83N_9O_{23}I_1Cl_3$: 1757.4; $[M+H]^+=1759$; $[M-vancosamine+H]^+=1415$; $[M-disaccharide+H]^+=1143$.

b) Vancosamine-N-4-(4-chlorophenyl)benzyl,Glucose-C6-S-3-amino-5-mercapto-1,2,4-triazole Vancomycin (LXXIII).

To a stirred solution of the iodo product (LXXIIIa) (5.4 mg, 0.003 mmol) in 0.5 mL anhydrous DMF under an argon atmosphere is added potassium carbonate (10 mg, 0.07 mmol). After 5 min. 3-amino-5-mercapto-1,2,4-triazole (4.2 mg, 0.037 mmol) is added and the stirred mixture heated at 55° C. for 50 min. The mixture is cooled to room temperature, filtered (0.45 μm) to remove carbonate, and the filtrate diluted with 6 mL water. Separation by HPLC (Method B; 40 min. linear gradient of 10% to 65% acetonitrile; flow rate=8 mL/min.) affords (LXXIII) (4.5 mg, 90%). Retention time=28 min. LRESI-MS calc for $C_{81}H_{86}N_{13}O_{23}S_1Cl_3$: 1745.5; $[M+H]^+=1747$; $[M-vancosamine+H]^+=1405$; $[M-disaccharide+H]^+=1143$.

Example 54

N-4-(4-chlorophenyl)benzylvancosamine-glucose-C6-azide Vancomycin (LXXIV)

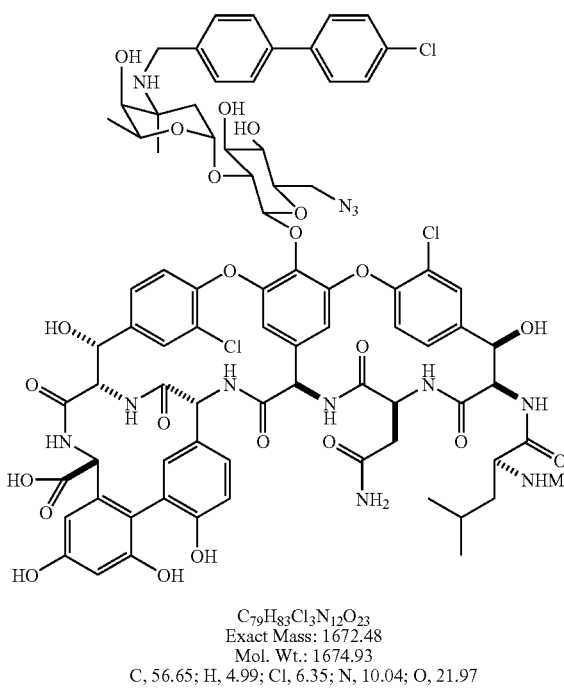

$C_{79}H_{83}Cl_3N_{12}O_{23}$
Exact Mass: 1672.48
Mol. Wt.: 1674.93
C, 56.65; H, 4.99; Cl, 6.35; N, 10.04; O, 21.97

N-4-(4-chlorophenyl)benzylvancosamine-glucose-C6-iodo vancomycin TFA salt (LXXIIIa) (10.9 mg, 0.00582 mmol) and NaN$_3$ (7.6 mg 0.116 mmol) are dissolved with dry DMF (1 mL). The mixture is stirred at 45° C. After 4 h. analytical HPLC indicates the reaction is done. the mixture is filtered then purified by ODS-HPLC (COSMOSIL 5C18-AR, 20×250 mm, and LUNA 5 μm C18(2), 21.2×250 mm, UV=285 nm, A: 0.1% TFA/H$_2$O, B: MeCN, 20-70% B 0-60 min., 8 mL/min, $t_r$=33 min.) to give the white amorphous title compound (8.2 mg, 0.00458 mmol, 79%) as TFA salt. LRESI-MS 1673 (M+H, for $C_{79}H_{84}{}^{35}Cl_3N_{12}O_{23}$)$^+$, 1330 (M-N-4-(4-chlorophenyl)benzylvancosamine-glucose+H)$^+$, 1143 (M-N-4-(4-chlorophenyl)benzylvancosamine-glucose+H)$^+$.

Example 55

N-4-(4-chlorophenyl)benzylvancosamine-glucose-C6-amine Vancomycin (LXXV)

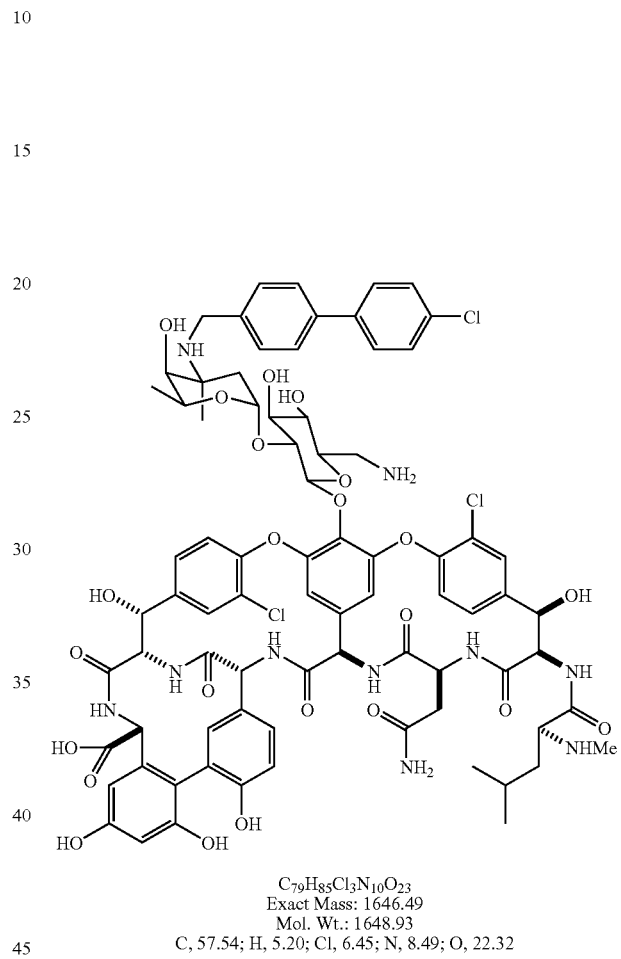

$C_{79}H_{85}Cl_3N_{10}O_{23}$
Exact Mass: 1646.49
Mol. Wt.: 1648.93
C, 57.54; H, 5.20; Cl, 6.45; N, 8.49; O, 22.32

N-4-(4-chlorophenyl)benzylvancosamine-glucose-6-azide vancomycin (LXXIV) (7.7 mg, 0.00430 mmol) and PPh$_3$ are suspended with THF (0.8 mL) and the mixture is stirred at room temperature under Ar for 0.5 h. Added H$_2$O (0.4 mL) and the mixture is stirred at 75° C. After 9 h the mixture is filtered then purified by ODS-HPLC (COSMOSIL 5C18-AR, 20×250 mm, and LUNA 5 μm C18(2), 21.2×250 mm, UV=285 nm, A: 0.1% TFA/H$_2$O, B: MeCN, 20-70% B 0-60 min., 8 mL/min, $t_r$=30 min.) to give the white amorphous title compound (3.2 mg, 0.00182 mmol, 42%) as TFA salt. LRESI-MS 1648 (M+2H, for $C_{79}H_{86}{}^{35}Cl_3N_{10}O_{23}$)$^+$, ? (M-N-

4-(4-chlorophenyl)benzylvancosamine-glucose+H)⁺. 1143 (M-N-4-(4-chlorophenyl)benzylvancosamine-glucose+H)⁺.

Example 56

Glucose-C6-2-thio-5-amino-1,3,4-thiadiazole Vancomycin (LXXVI)

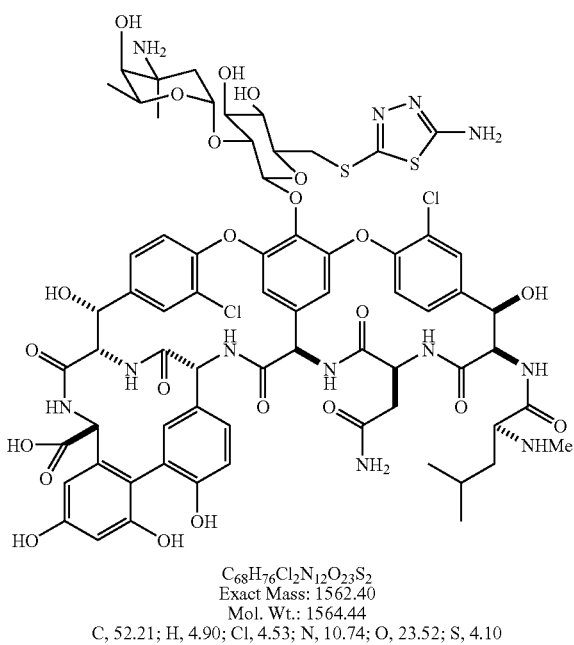

$C_{68}H_{76}Cl_2N_{12}O_{23}S_2$
Exact Mass: 1562.40
Mol. Wt.: 1564.44
C, 52.21; H, 4.90; Cl, 4.53; N, 10.74; O, 23.52; S, 4.10

Glucose-C6-iodo vancomycin TFA salt (LXX) (14 mg, 0.00837 mmol), 5-amino-1,3,4-thiadiazole-2-thiol (24 mg 0.18 mmol), and $K_2CO_3$ (25 mg 0.181 mmol), are dissolved with dry DMF (0.5 mL). The mixture is stirred at 40-50° C. After 0.5 h. analytical HPLC indicates the reaction is done. the mixture is filtered then purified by ODS-HPLC (COSMO-SIL 5C18-AR, 20×250 mm, and LUNA 5 μm C18(2), 21.2× 250 mm, UV=285 nm, A: 0.1% TFA/$H_2O$, B: MeCN, 10-70% B 0-60 min., 8 mL/min, $t_r$=27 min.) to give the white amorphous tide compound as the TFA salt (6.3 mg, 0.0375 mmol, 45%). LRESI-MS 1565 (M+H, for $C_{68}H_{77}{}^{35}Cl_2N_{12}O_{23}S_2$)⁺, 1143 (M-vancosamine-glucose+H)⁺.

Example 57

Glucose-C6-5-thio4-amino-3-hydrazino-1,2,4-triazole Vancomycin (LXXVII)

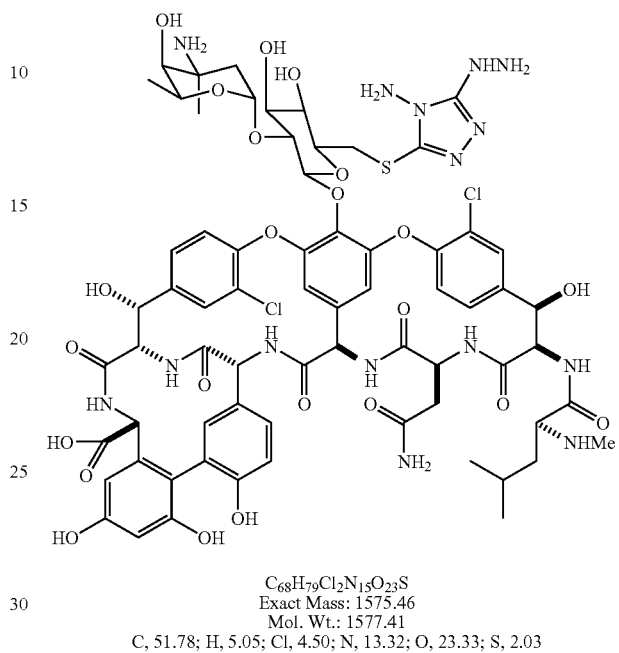

$C_{68}H_{79}Cl_2N_{15}O_{23}S$
Exact Mass: 1575.46
Mol. Wt.: 1577.41
C, 51.78; H, 5.05; Cl, 4.50; N, 13.32; O, 23.33; S, 2.03

Glucose-C6-iodo vancomycin TFA salt (LX) (20 mg, 0.0120 mmol), 4-amino-3-hydrazino-5-mercapto-1,2,4-triazole (Purpald®, 37.5 mg 0.257 mmol), and $K_2CO_3$ (35.4 mg 0.256 mmol), are dissolved with dry DMF (0.5 mL). The mixture is stirred at 45° C. After 2 h. analytical HPLC indicates the reaction is done. The mixture is filtered then purified by ODS-HPLC (COSMOSIL 5C18-AR, 20×250 mm, and LUNA 5 μm C18(2), 21.2×250 mm, UV=285 nm, A: 0.1% TFA/$H_2O$, B: MeCN, 0-70% B 0-60 min., 8 mL/min, $t_r$=32 min.) to give the white amorphous title compound as the TFA salt (8.3 mg, 0.0491 mmol, 41%). LRESI-MS 1569 (M-$NHNH_2$+H+Na, for $C_{68}H_{81}{}^{35}Cl_2N_{15}O_{23}SNa$)⁺, 1143 (M-vancosamine-glucose+H)⁺. ¹H-NMR data in DMSO-$d_6$ at 298 K: δ 0.86 (3H, d, J=6.0 Hz, Id), 0.90 (3H, d, J=6.0 Hz, 1c), 1.07 (3H, d, J=6.5 Hz, V6), 1.26 (3H, s, V7), 1.41 (1H, m, 1a), 1.48 (1H, m, 1a), 1.70 (1H, br d, J=12 Hz, V2e), 1.73 (1H, m, 1b), 1.89 (1H, brd, J=12 Hz, V2a), 2.14 (1H, m, 3a), 2.32 (3H, s, 1e), 2.36 (1H, m, 3a), 3.05 (1H, m, x1), 3.15 (1H, br s, V4), 3.46 (1H, br d, J=12.5 Hz, G6), 3.51 (1H, brd, J=12.5 Hz, G6), 3.52 (3H, m, G2, G3, and G4), 3.72 (1H, m, G5), 4.20 (1H, br s, x6), 4.37 (1H, m, x3), 4.43 (1H, s, x7), 4.44 (1H, br s, x5), 4.69 (1H, brd, J=6.5 Hz, V5), 4.88 (1H, brs, x2), 5.10 (1H, s, z6), 5.16 (1H, s, z2), 5.20 (1H, s, 4f), 5.20 (1H, br s, G4OH), 5.22 (1H, s, V1), 5.29 (1H, br s, G1), 5.43 (1H, br s, G3OH), 5.54 (1H, s, 4b), 5.74 (1H, br s, Z2OH), 5.75 (1H, br s, x4), 5.94 (1H, br s, Z6OH), 6.25 (1H, s, 7f), 6.40 (1H, s, 7d), 6.64 (1H, m, w3), 6.72 (1H, d, J=8.5 Hz, 5e), 6.77 (1H, d, J=8.5 Hz, 5f), 6.89 (1H, m, w6),7.19 (1H, s, 5b), 7.33 (1H, m, 2e), 7.34-7.57 (5H, m, $NH_2$ and $NHNH_2$ of 5-thioamino-3-hydrazino1, 2, 4-triazole), 7.37 (1H, m, 2b), 7.47 (1H, d, J=8.5 Hz, 6e), 7.51 (1H, d, J=8.5 Hz, 6f), 7.57 (1H, m, 2f), 7.85 (1H, s, 6b), 8.46 (2H, br s, w5 and w7), 8.66 (1H, br s, w4), 9.09 (1H, br s, 7cOH), 9.41 (1H, br s, 7eOH).

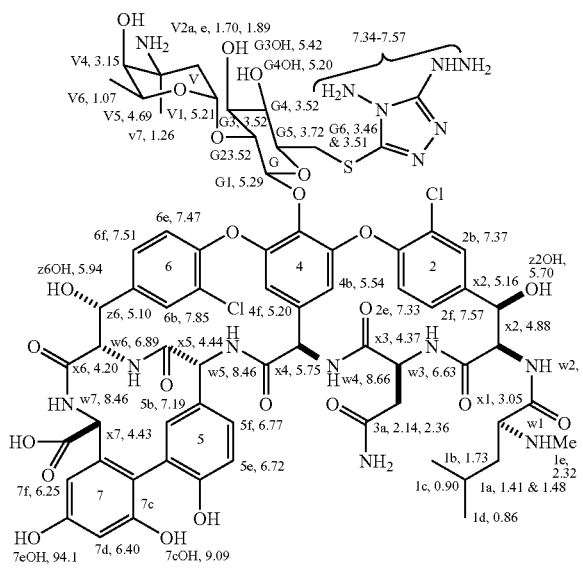

Example 58

Glucose-C6-2-thio-4-hydroxy-6-methylpyrimidine Vancomycin (LXXVIII)

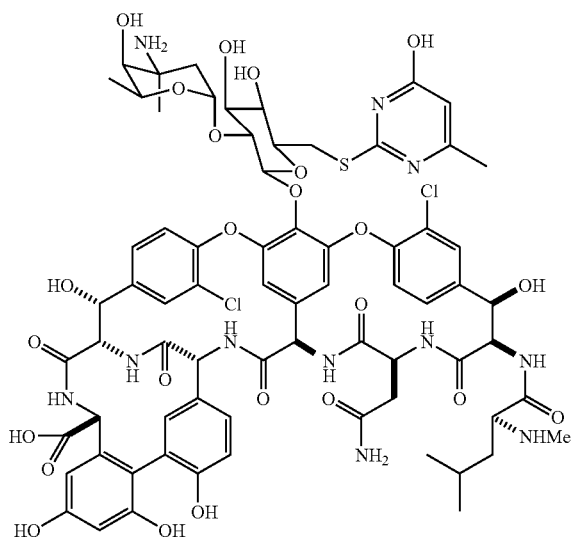

$C_{71}H_{79}Cl_2N_{11}O_{24}S$
Exact Mass: 1571.44
Mol. Wt.: 1573.42
C, 54.20; H, 5.06; Cl, 4.51; N, 9.79; O, 24.40; S, 2.04

Glucose-C6-iodo vancomycin TFA salt (LXX) (15 mg, 0.00897 mmol), 4-hydroxy-2-mercapto-6-methylpyrimidine (27.4 mg 0.193 mmol), and $K_2CO_3$ (26.5 mg 0.192 mmol), are dissolved with dry DMF (1 mL). The mixture is stirred at 45° C. After 0.5 h. analytical HPLC indicates the reaction is done, the mixture is filtered then purified by ODS-HPLC (COSMOSIL 5C18-AR, 20×250 mm, and LUNA 5 μm C18 (2), 21.2×250 mm, UV=285 nm, A: 0.1% TFA/$H_2O$, B: MeCN, 0-70% B 0-60 min., 8 mL/min, $t_r$=36 min.) to give the white amorphous title compound as the TFA salt (3.0 mg, 0.00178 mmol, 20%). LRESI-MS 1572 (M+H, for $C_{71}H_{80}{}^{35}Cl_2N_{11}O_{24}S)^+$, 1430 (M-vancosamine+2H)$^+$, 1143 (M-vancosamine-glucose+H)$^+$.

Example 59

N-decylvancosamine-glucose-C6-2-thio-6-azathymine Vancomycin (LXXIX)

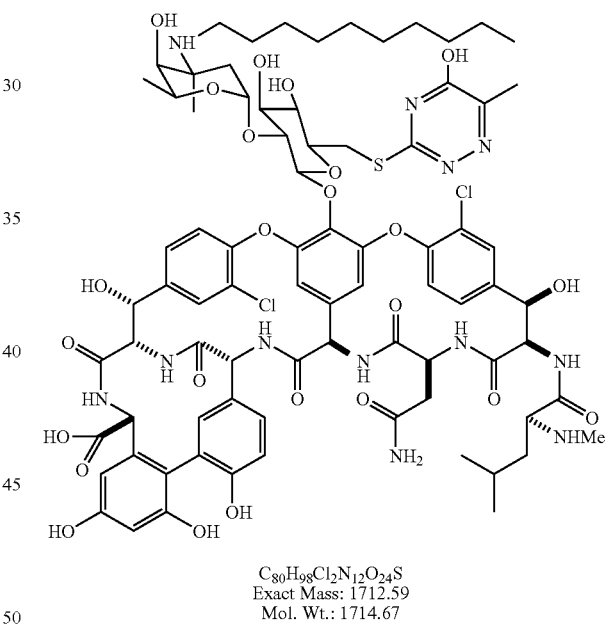

$C_{80}H_{98}Cl_2N_{12}O_{24}S$
Exact Mass: 1712.59
Mol. Wt.: 1714.67
C, 56.04; H, 5.76; Cl, 4.14; N, 9.80; O, 22.39; S, 1.87

N-decylvancosamine-glucose-C6-2-mesitylenesulfonated vancomycin TFA salt (Ex. 52 a) (10 mg, 0.00530 mmol), 6-aza-2-thiothymine (16.0 mg 0.112 mmol), and $K_2CO_3$ (31.0 mg 0.224 mmol), are dissolved with dry DMF (0.5 mL). The mixture is stirred at 75° C. After 8.5 h analytical HPLC indicates the reaction is done. The mixture is filtered and the residue is purified by ODS-HPLC (LUNA 5 μm C18(2), 21.2×250 mm, UV=285 nm, A: 0.1% TFA/$H_2O$, B: MeCN, 10-60% B 0-30 min., 8 mL/min, $t_r$=26 min.) to give the white amorphous title compound as a TFA salt (4.8 mg, 0.00262 mmol, 50%). LRESI-MS 1714 (M+2H, for $C_{80}H_{100}{}^{35}Cl_2N_{12}O_{24}S)^+$, 1143 (M-N-decylvancosamine-glucose+H)$^+$.

Example 60

N-decylvancosamnine-glucose-C6-2-thio-5-chlorobenzothiazole Vancomycin (LXXX)

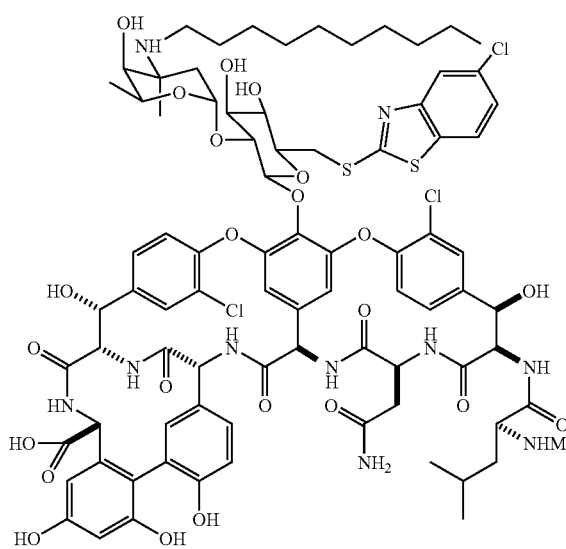

$C_{83}H_{97}Cl_3N_{10}O_{23}S$
Exact Mass: 1770.52
Mol. Wt.: 1773.20
C, 56.22; H, 5.51; Cl, 6.00; N, 7.90; O, 20.75; S, 3.62

N-decylvancosamine-glucose-C6-2-mesitylenesulfonated vancomycin TFA salt (Ex. 52 a) (6.5 mg, 0.00345 mmol), 5-chloro-2-mercapto-benzothiazole (14.8 mg 0.0734 mmol), and $K_2CO_3$ (10.1 mg 0.0731 mmol), are dissolved with dry DMF (0.5 mL). The mixture is stirred at 75° C. After 2.5 h. analytical HPLC indicates the reaction is done. The mixture is filtered and the residue is purified by ODS-HPLC (LUNA 5 μm C18(2), 21.2×250 mm, UV=285 nm, A: 0.1% TFA/H$_2$O, B: MeCN, 10-60% B 0-30 min., 8 mL/min, $t_r$=28 min.) to give the white amorphous title compound as a TFA salt (1.4 mg, 0.000742 mmol, 22%). LRESI-MS 1771 (M+H, for $C_{83}H_{98}{}^{35}Cl_3N_{10}O_{23}S_2)^+$.

Example 61

N-decylvancosamine-glucose-C6-2-thio-5-phenyl-1,3,4-oxadiazole Vancomycin (LXXXI)

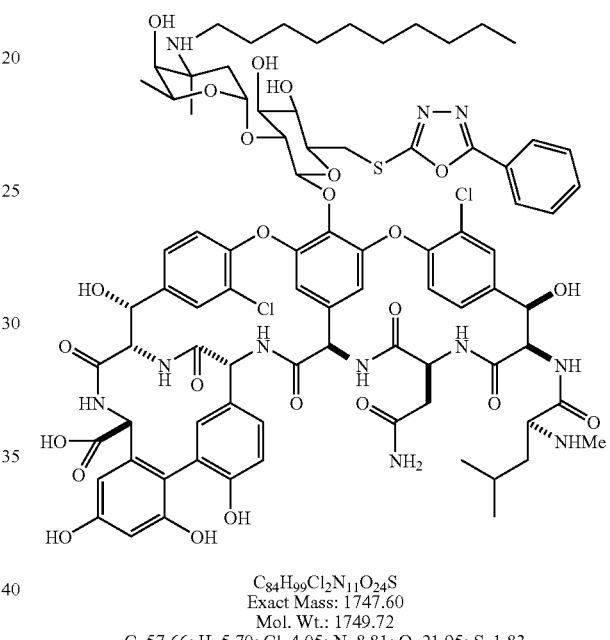

$C_{84}H_{99}Cl_2N_{11}O_{24}S$
Exact Mass: 1747.60
Mol. Wt.: 1749.72
C, 57.66; H, 5.70; Cl, 4.05; N, 8.81; O, 21.95; S, 1.83

Glucose-C6-2-thio-5-phenyl-1,3,4-oxadiazole vancomycin TFA salt (LXVII) (50.0 mg, 0.0290 mmol) is dissolved with wet DMF (2 mL) and DIEA (14.2 mL, 0.155 mmol) is added and the mixture is stabilized at 70° C. for 20 min. Decylaldehyde (4.70 mL, 0.0250 mmol) is added and the reaction mixture is stirred at 70° C. for 1.5 h then NaBH$_3$CN (0.1 mL, 1M-THF, 0.1 mmol) is added. The mixture is stirred for additional 2 h then cooled down to room temperature. The mixture is evaporated and the residue is purified by ODS-HPLC (LUNA 5 μm C18(2), 21.2×250 mm, UV=285 nm, A: 0.1% TFA/H$_2$O, B: MeCN, 10-60% B 0-30 min., 8 mL/min, $t_{rit.}$=22 min.) to give the white amorphous title compound (10.8 mg, 0.00579 mmol, 20%) and the starting material (12.1 mg, 0.00702 mmol, 24%) as TFA salts. LRESI-MS 1749 (M+2H, for $C_{84}H_{101}{}^{35}Cl_2N_{11}O_{24}S)^+$, 1144 (M-N-decyl-vancosamine-glucose+2H)$^+$.

Example 62

N-decylvancosamine-glucose-C6-2-thio-4,5-diphenyloxazole Vancomycin (LXXXII)

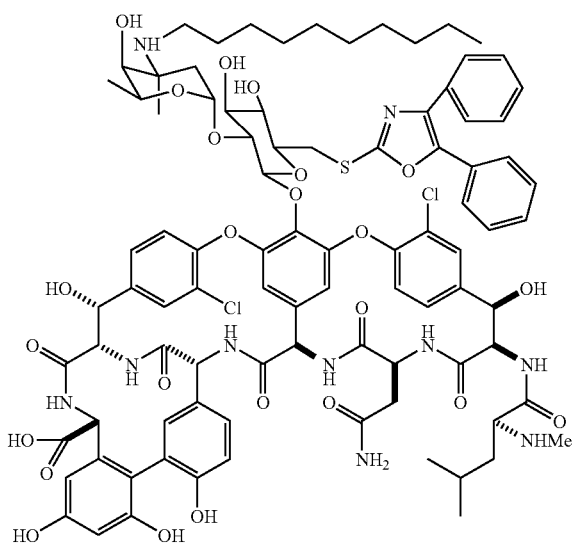

C$_{91}$H$_{104}$Cl$_2$N$_{10}$O$_{24}$S
Exact Mass: 1822.63
Mol. Wt.: 1824.82
C, 59.89; H, 5.74; Cl, 3.89; N, 7.68; O, 21.04; S, 1.76

N-decylvancosamine-glucose-C6-2-mesitylenesulfonated vancomycin TFA salt (XLIII) (5.6 mg, 0.00321 mmol), 4,5-diphenyl-2-oxazole thiol (16.0 mg 0.0632 mmol), and K$_2$CO$_3$ (8.8 mg 0.0637 mmol), are dissolved with dry DMF (0.5 mL). The mixture is stirred at 65° C. After 2 h. analytical HPLC indicates the reaction is done. The mixture is filtered and the residue is purified by ODS-HPLC (LUNA 5 μm C18(2), 21.2×250 mm, UV=285 nm, A: 0.1% TFA/H$_2$O, B: MeCN, 20-60% B 0-30 min., 8 mL/min, t$_r$=29 min.) to give the title compound as a white amorphous TFA salt (2.1 mg, 0.00108 mmol, 34%). LRESI-MS 1824 (M+H, for C$_{91}$H$_{106}$$^{35}$Cl$_2$N$_{10}$O$_{24}$S)$^+$, 1143 (M-N-decylvancosamine-glucose+H)$^+$.

Example 63

N-4-(4-chlorophenyl)benzylvancosamine-glucose-C6-2-thio-5-amino-1,3,4-thiadiazole Vancomycin (LXXXIII)

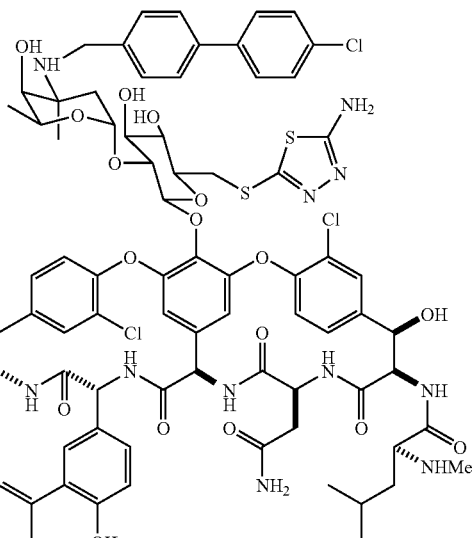

C$_{81}$H$_{85}$Cl$_3$N$_{12}$O$_{23}$S$_2$
Exact Mass: 1762.44
Mol. Wt.: 1765.10
C, 55.12; H, 4.85; Cl, 6.03; N, 9.52; O, 20.85; S, 3.63

N-4-(4-chlorophenyl)benzylvancosamine-glucose-C6-iodo vancomycin TFA salt (Ex. 53 a) (13.0 mg, 0.00694 mmol ), 5-amino1,3,4-thiadiazole-2-thiol (19.7 mg, 0.148 mmol), and K$_2$CO$_3$ (20.5 mg 0.148 mmol), are dissolved with dry DMF (0.5 mL). The mixture is stirred at 40-50° C. After 0.5 h analytical HPLC indicates the reaction is done. The mixture is filtered then purified by ODS-HPLC (COSMOSIL 5C18-AR, 20×250 mm, and LUNA 5 μm C18(2), 21.2×250 mm, UV=285 nm, A: 0.1% TFA/H$_2$O, B: MeCN, 20-70% B 0-60 min., 8 mL/min, t$_r$=33 min.) to give the white amorphous title compound (3.0 mg, 0.00160 mmol, 23%) as TFA salt. LRESI-MS 1763 (M+H, for C$_{81}$H$_{86}$$^{35}$Cl$_3$N$_{12}$O$_{23}$S$_2$)$^+$, 1420 (M-N-4-(4-chlorophenyl)benzylvancosamine-glucose+H)$^+$. 1143 (M-N-4-(4-chlorophenyl)benzylvancosamine-glucose+H)$^+$.

Example 64

N-4-4-chlorophenyl)benzylvancosamine-glucose-C6-5-thio-4-amino-3-hydrazino-1,2,4-triazole Vancomycin (LXXIV)

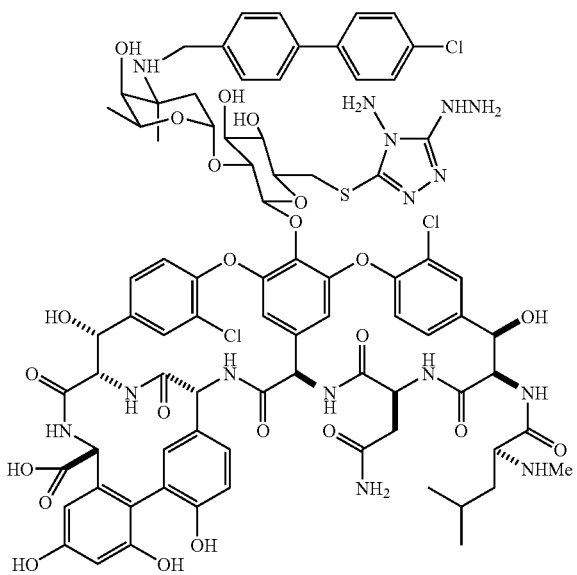

$C_{81}H_{88}Cl_3N_{15}O_{23}S$
Exact Mass: 1775.50
Mol. Wt.: 1778.08
C, 54.71; H, 4.99; Cl, 5.98; N, 11.82; O, 20.70; S, 1.80

N-4-(4-chlorophenyl)benzylvancosamine-glucose-C6-iodo vancomycin TFA salt (Ex. 53a) (12.0 mg, 0.0639 mmol), 4-amino-3-hydrazino-5-mercapto-1, 2, 4-triazole (20.0 mg 0.137 mmol), and $K_2CO_3$ (18.8 mg 0.136 mmol), are dissolved with dry DMF (1 mL). The mixture is stirred at 45° C. After 3 h analytical HPLC indicates the reaction is done. The mixture is filtered then purified by ODS-HPLC (COSMOSIL 5C18-AR, 20×250 mm, and LUNA 5 μm C18(2), 21.2×250 mm, UV=285 nm, A: 0.1% TFA/$H_2O$, B: MeCN, 0-70% B 0-60 min., 8 mL/min, $t_r$=43 min.) to give the title compound as a white amorphous TFA salt (43, 5.1 mg, 0.0491 mmol, 41%). LRESI-MS 1748 (M-$NHNH_2$+H, for $C_{81}H_{86}{}^{35}Cl_3N_{13}O_{23}S)^+$, 1403 (M-$NHNH_2$-N-4-(4-chlorophenyl)benzylvancosamine+H)$^+$. 1143 (M-N-4-(4-chlorophenyl)benzylvancosamine-glucose+H)$^+$.

Example 65

N-4-(4-chlorophenyl)benzylvancosamine-glucose-C6-2-thio-4-hydroxy-6-methylpyrimidine Vancomycin (LXXXV)

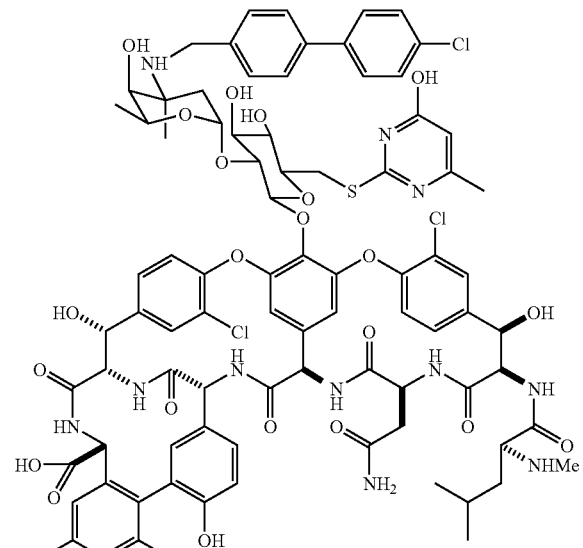

$C_{84}H_{88}Cl_3N_{11}O_{24}S$
Exact Mass: 1771.48
Mol. Wt.: 1774.08
C, 56.87; H, 5.00; Cl, 6.00; N, 8.68; O, 21.64; S, 1.81

N-4-(4-chlorophenyl)benzylvancosamine-glucose-C6-iodo vancomycin TFA salt (Ex. 53 a) (10.0 mg, 0.00534 mmol), 4-hydroxy-2-mercapto-6-methylpyrimidine (16.2 mg 0.114 mmol), and $K_2CO_3$ (15.8 mg 0.114 mmol), are dissolved with dry DMF (1 mL). The mixture is stirred at 45° C. After 1 h analytical HPLC indicates the reaction is done. The mixture is filtered then purified by ODS-HPLC (COSMOSIL 5C18-AR, 20×250 mm, and LUNA 5 μm C18(2), 21.2×250 mm, UV=285 nm, A: 0.1% TFA/$H_2O$, B: MeCN, 0-70% B 0-60 min., 8 mL/min, $t_r$=46 min.) to give the title compound as a white amorphous TFA salt (6.0 mg, 0.00318 mmol, 60%). LRESI-MS 1773 (M+2H, for $C_{84}H_{90}{}^{35}Cl_3N_{11}O_{24}S)^+$, 1429

(M-N-4-(4-chlorophenyl)benzylvancosamine+H)$^+$. 1143 (M-N-4-(4-chlorophenyl)benzylvancosamine-glucose+H)$^+$.

Example 66

N-4-(4chlorophenyl)benzylvancosamine-glucose-C6-2-thio-6-azathymine Vancomycin (LXXXVI)

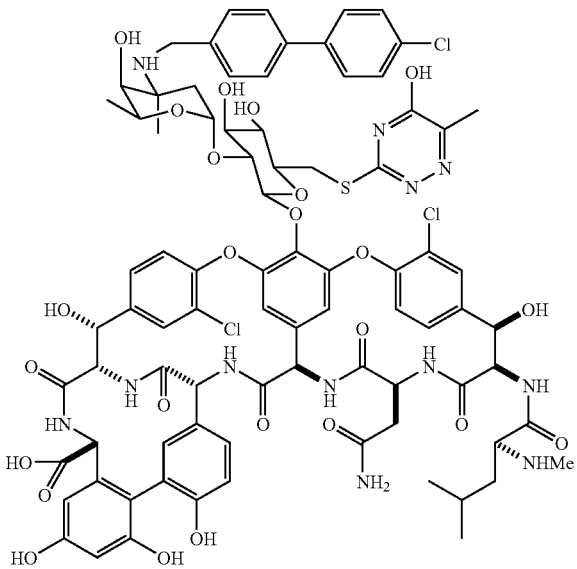

$C_{83}H_{87}Cl_3N_{12}O_{24}S$
Exact Mass: 1772.47
Mol. Wt.: 1775.07
C, 56.16; H, 4.94; Cl, 5.99; N, 9.47; O, 21.63; S, 1.81

N-4-(4-chlorophenyl)benzylvancosamine-glucose-C6-iodo vancomycin TFA salt (Ex. 53 a) (10.5 mg, 0.00560 mmol), 6-aza-2-thiothymine (18.0 mg 0.126 mmol), and $K_2CO_3$ (17.4 mg 0.126 mmol), are dissolved with dry DMF (1 mL). The mixture is stirred at 45° C. After 1 h. analytical HPLC indicates the reaction is done. The mixture is filtered and the residue is purified by ODS-HPLC (COSMOSIL 5C18-AR, 20×250 mm, and LUNA 5 μm C18(2), 21.2×250 mm, UV=285 nm, A: 0.1% TFA/H$_2$O, B: MeCN, 0-70% B 0-60 min., 8 mL/min, t$_r$=44 min.) to give the title compound as a white amorphous TFA salt (4.4 mg, 0.00233 mmol, 42%). LRESI-MS 1774 (M+2H, for $C_{83}H_{89}{}^{35}Cl_3N_{12}O_{24}S$)$^+$, 1432 (M-vancosamine+2H)$^+$, 1143 (M-vancosamine-glucose+H)$^+$.

Example 67

N-4-(4-chlorophenyl)benzylvancosamine-glucose-C6-2-thio-4,5-diphenyloxazole Vancomycin (LXXXVII)

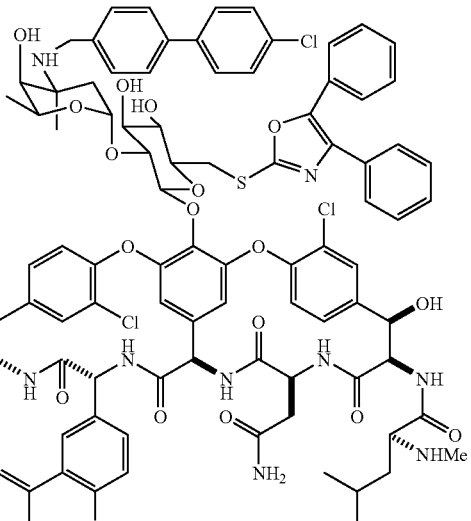

$C_{94}H_{93}Cl_3N_{10}O_{24}S$
Exact Mass: 1882.52
Mol. Wt.: 1885.22
C, 59.89; H, 4.97; Cl, 5.64; N, 7.43; O, 20.37; S, 1.70

N-4-(4-chlorophenyl)benzylvancosamine-glucose-6-2-mesitylenesulfonated vancomycin (Ex. 53 a) (11.6 mg, 0.0060 mmol), 4, 5diphenyl-2-oxazole thiol (31.9 mg 0.126 mmol), and $K_2CO_3$ (17.5 mg 0.127 mmol), are dissolved with dry DMF (0.5 mL). The mixture is stirred at 75° C. After 3 hours, analytical HPLC indicates the reaction is done. The mixture is filtered and purified by ODS-HPLC (LUNA 5 μm C18(2), 21.2×250 mm, UV=285 nm, A: 0.1% TFA/H$_2$O, B: MeCN, 20-60% B 0-30 min., 8 mL/min, t$_r$=19 min.) to give the white amorphous title compound as the TFA salt (3.5 mg, 0.00175 mmol, 29%). LRESI-MS 943 (M+4H, for $C_{94}H_{97}{}^{35}Cl_3N_{10}O_{24}S$)$^{2+}$.

Example 68

N,N'-Dialoc, Methyl Glycine Vancomycin (LXXXVIII)

a) Methyl Glycine Vancomycin.

To a stirred solution of vancomycin.HCl (3.16 g, 2.13 mmol) in 21 mL of DMSO-DMF (16:5) under an argon atmosphere is added glycine methyl ester.HCl (0.53 g, 4.26 mmol) and diisopropylethylamine (1.13 mL, 6.5 mmol). The solution is cooled with an ice bath and 7 mL of a 0.45 M solution of HOBT/HBTU in DMF is added. After 1 h the ice bath is removed and stirring continued for 6 h. The reaction mixture is precipitated by addition to 400 mL acetone-ethanol (3:1), stored at 4° C. for 16 h, clear supernatant decanted, and the remaining suspension centrifuged. The white solid is suspended in 100 mL ethanol, centrifuged, and supernatant decanted. The ethanol wash is repeated twice, at which time TLC shows complete removal of reagents. The white solid is dried en vacuo affording 3.6 g of crude product. This product is used in the next step without further purification.

b) N,N'-Dialoc, Methyl Glycine Vancomycin (LXXXVIII).

To a stirred solution of the crude product (2.1 g, 1.4 mmol) in 18 mL DMSO-DMF (5:4) under an argon atmosphere with ice bath cooling is added allyl 1-benzotriazolyl carbonate (0.76 g, 3.5 mmol) and triethylamine (0.4 mL, 2.83 mmol). After 1.5 h the reaction is warmed to room temperature and stirring continued for an additional 1.5 h. The reaction mixture is precipitated by addition to 200 mL of acetone-diethyl ether (1:1) affording a white precipitate that is centrifuged and the supernatant decanted. The solid is suspended in 200 mL diethyl ether, centrifuged and the supernatant decanted. The solid is dissolved in methanol and evaporated under reduced pressure affording a tan foam. Separation by HPLC (Method A; 25 min. linear gradient of 30% to 44% acetonitrile; flow rate=7 mL/min.) affords (LXXXVIII) (1 g, 48%) Ret. Time=21.5 min. TLC: Rf=0.7 (chloroform-methanol-water, 6:4:1). LRESI-MS calc for $C_{77}H_{88}N_{10}O_{29}Cl_2$: 1686.5; $[M+Na]^+=171$.

Example 69

Glucose-6-mesitylenesulfonyl-N,N'-Dialoc, Methyl Glycine Vancomycin (LXXXIX).

A solution of 2-mesitylenesulfonyl chloride (160 mg, 0.73 mmol) in 0.5 mL anhydrous pyridine is stirred at 4° C. for 30 min. This solution is added to compound (LXXXVIII) (310 mg, 0.18 mmol) and stirred in 2.5 mL anhydrous pyridine under an argon atmosphere at 4° C. The stirred mixture is maintained at 4° C. for 12 hours, precipitated by addition to 30 mL diethyl ether-acetone (3:2), centrifuged and the supernatant decanted. The white solid is taken up in methanol and evaporated under reduced pressure. Separation by HPLC (Method A; 40 min. linear gradient of 30% to 75% acetonitrile; flow rate=7.5 mL/min.) affords starting material (60 mg) and the title compound (225 mg, 65%, 81% based on recovered starting material) Ret. Time=30.7 min. TLC: Rf=0.7 (chloroform-methanol-water, 50:21:4). LRESI-MS calc for $C_{86}H_{98}N_{10}O_{31}S_1Cl_2$: 1868.6; $[M+H]^+=1870$; [M-vancosamine+H]$^+=1645$; [M-disaccharide+H]$^+=1299$.

Example 70

Glucose-C6-Azide-N,N'-Dialoc, Methyl Glycine Vancomycin (XC)

To a stirred solution of mesitylenesulfonyl derivative (LXXXIX) (54 mg, 0.03 mmol) in 2 mL anhydrous DMF under an argon atmosphere is added sodium azide (50 mg, 0.8 mmol). The suspension is stirred at 85° C. for 6 h then cooled to room temperature. The mixture is diluted with a minimum of methanol (ca 0.5 mL) to dissolve the sodium azide then diluted with chloroform until precipitate formed. Methanol is then added dropwise to dissolve the precipitate. The mixture is subjected to a short Silica gel column (3×15 cm) eluting with chloroform-methanol-water (50:21:4). Fractions containing product are combined and evaporated under reduced pressure. Separation by HPLC (Method A; 40 min. linear gradient of 25% to 50% acetonitrile; flow rate=7 mL/min.) affords (XC) (35 mg, 70%); Ret. Time=29.1 min. TLC: Rf=0.5 (chloroform-methanol-water, 50:21:4). LRESI-MS calc for $C_{77}H_{87}N_{13}O_{28}Cl_2$: 1711.5; $[M+Na]^+=1735$; [M-vancosamine+H]$^+=1486$; [M-disaccharide+H]$^+=1299$.

Example 71

Glucose-C6-Amine-N,N'-Dialoc, Methyl Glycine Vancomycin (XCI)

To a stirred solution of azide (XC) (59 mg, 0.035 mmol) in 1 mL DMF under an argon atmosphere is added trimethylphosphine (100 μL of 1 M THF solution). After 1.5 h, 0.2 mL water is added and the mixture stirred at room temperature for 17 h and then at 45° C. for an additional 6 h. The mixture is cooled to room temperature, evaporated to 0.5 mL and precipitated by addition to 16 mL diethyl ether. The resulting suspension is centrifuged, the supernatant is decanted, and the solid is dried under reduced pressure. Separation by HPLC (Method A; 40 min. linear gradient of 15% to 50% acetonitrile; flow rate=7 mL/min.) affords (XCI) (28 mg, 64%); Ret. Time=18.4 min. TLC: Rf=0.2 (chloroform-methanol-water, 6:4:1). LRESI-MS calc for $C_{77}H_{89}N_{11}O_{28}Cl_2$: 1685.5; $[M+H]^+=1687$; [M-vancosamine+H]$^+=1460$; [M-disaccharide+H]$^+=1298$.

Example 72

Glucose-C6-N,N-bis-Cbz-guanidinyl, N,N'-Dialoc, Methyl Glycine Vancomycin (XCII) and Glucose-C6-N,N-bis-Cbz-guanidinyl, Methyl Glycine Vancomycin (XCIII)

To a stirred solution of amine (XCI) (12 mg, 0.007 mmol) in 0.3 mL anhydrous DMF is added N,N'-bis-Cbz-methylpsuedothiourea (25 mg, 0.07 mmol) and stirring continued for 12 h. The reaction mixture is precipitated by addition to 10 mL diethyl ether, centrifuge and decanted. The white solid is suspended in 20 mL diethyl ether, suspension centrifuged, supernatant decanted and solid dried under reduced pressure affording (XCII) (13 mg, 93%). TLC: Rf=0.8 (chloroform-methanol-water, 6:4:1). This product is used in the next step without further purification. An analytical sample of (XCII) is similarly prepared followed by separation using HPLC (Method A; 40 min. linear gradient of 40% to 75% acetonitrile; flow rate=7 mL/min.) 7 Ret. Time=23.3 min. LRESI-MS calc for $C_{94}H_{103}N_{13}O_{32}Cl_2$: 1995.6; $[M+H]^+=1997$; [M-disaccharide+Na]$^+=1321$.

To a stirred solution of guanidine derivative (XCII) in 0.5 mL anhydrous DMF is added 0.15 mL acetic acid and a catalytic amount of $(Ph_3P)_2PdCl_2$. The mixture is treated with tributyltin hydride (5 μL every 10 min. for 2 h) until TLC shows all glycopeptide is baseline (chloroform-methanol-water, 6:4:1). The reaction mixture is precipitated by addition to 10 mL diethyl ether, suspension centrifuged, supernatant decanted and the solid dried under reduced pressure. Separation by HPLC (Method A; 40 min. linear gradient of 10% to 60% acetonitrile; flow rate=7 mL/min.) affords (XCC) (11 mg, 86% from XCI) Ret. Time=23.5 min. LRESI-MS calc for $C_{86}H_{95}N_{13}O_{28}Cl_2$: 1827.6; $[M+H]^+=1830$; [M-disaccharide+H]$^+=1216$.

The preparation of N,N'-bis-Cbz-methylpsuedothiourea is given in Int. J. Pep. Prot. Res. Vol.40, 1992, pp. 119-126.

Example 73

Glucose-C6-mesitylenesulfonyl, Methyl Glycine Vancomycin (XCIV)

To a stirred solution of mesitylenesulfonyl derivative (LXXXIX) (10 mg, 0.005 mmol) in 0.1 mL anhydrous DMF containing 2 μL formic acid is added triphenylphosphine (0.5 mg, 0.002 mmol) and a catalytic amount of tetrakis(triphenylphosphine)Pd(0). After 72 h the reaction mixture is precipitated by addition to 6 mL diethyl ether, suspension centrifuged, supernatant decanted, and the solid dried under reduced pressure. Separation by HPLC (Method C; semi-prep column; 40 min. linear gradient of 5% to 75% acetonitrile; flow rate=4 mL/min.) affords (XCIV) (4 mg, 40%) Ret. Time=17.4 min. LRESI-MS calc for $C_{78}H_{90}N_{10}O_{27}S_1Cl_2$: 1700.5; $[M+H]^+$=1703; $[M-vancosamine+H]^+$=1561; $[M-disaccharide+H]^+$=1215.

Example 74

Glucose-C6-amine, Methyl Glycine Vancomycin (XCV)

To a stirred solution of amine (XCI) (6 mg, 0.004 mmol) in 0.5 mL anhydrous DMF containing 0.35 mL acetic acid is added a catalytic amount of $(Ph_3P)_2PdCl_2$. This mixture is treated with tributyltin hydride (10 μL every 10 min. for 1 h) until TLC shows all glycopeptide is baseline (chloroform-methanol-water, 6:4:1). The reaction mixture is precipitated by addition to 20 mL diethyl ether, the suspension centrifuged, the supernatant decanted and the remaining diethyl ether removed under reduced pressure. The solid is separated by HPLC (Method B; 40 min. linear gradient of 0% to 40% acetonitrile; flow rate=7.5 mL/min.) affording (XCV) (5 mg, 92%) Ret. Time=19.7 min. LRESI-MS calc for $C_{69}H_{81}N_{11}O_{24}Cl_2$: 1517.5; $[M+H]^+$=1519; $[M-vancosamine+H]^+$=1378; $[M-disaccharide+H]^+$=1216.

Example 75

Glucose-C6-guanidine, Methyl Glycine Vancomycin (XCVI)

Guanidine derivative (XCIII) (6 mg, 0.003 mmol) is dissolved in 0.4 mL water-methanol (1:1) and hydrogenated under balloon pressure with catalytic 10% Pd/C for 3.5 h. The reaction mixture is filtered and the methanol removed under reduced pressure. Separation by HPLC (Method B, semi-prep column; 40 min. linear gradient of 5% to 25% acetonitrile; flow rate=4 mL/min.) affords (XCVI) (1 mg, 15%) Ret. Time=19.3 min. LRESI-MS calc for $C_{70}H_{83}N_{13}O_{24}Cl_2$: 1559.5; $[M+H]^+$=1561; $[M-vancosamine+H]^+$=1418; $[M-disaccharide+Na]^+$=1239.

Example 76

Glucose-C6-Iodo-N,N'-Dialoc, Methyl Glycine Vancomycin (XCVII)

To a stirred solution of mesitylenesulfonyl derivative (LXXXIX) (26 mg, 0.014 mmol) in 0.7 mL anhydrous dimethylacetamide (DMA) is added potassium iodide (50 mg, 0.3 mmol). The mixture is stirred at 85° C. for 16 hours then cooled to room temperature. The solution is diluted with water and separation by HPLC (Method A; 40 min. linear gradient of 30% to 60% acetonitrile; flow rate=7 mL/min.) affords (XCVII) (19 mg, 75%) Ret. Time=23.9 min. TLC: Rf=0.55 (chloroform-methanol-water; 50:21:4). LRESI-MS calc for $C_{77}H_{87}N_{10}O_{28}Cl_2$: 1796.4; $[M+H]^+$=1798; $[M-vancosamine+H]^+$=1571; $[M-disaccharide+Na]^+$=1323.

Example 77

Glucose-C6-Iodo, Methyl Glycine Vancomycin (XCVIII) and Glucose-C6-deoxy, Methyl Glycine Vancomycin (XCIX)

a) Preparation of (XCVIII) Only.

A catalytic amount of $(Ph_3P)_2PdCl_2$ is added to a stirred solution of (XCVII) (4 mg, 0.002 mmol) dissolved in 0.2 mL anhydrous DMF containing 0.1 mL acetic acid. This mixture is treated with tributyltin hydride (5 μL every 10 min. for 50 min.) until TLC shows all glycopeptide is baseline (chloroform-methanol-water; 6,4,1). The reaction mixture is precipitated by addition to 6 mL diethyl ether, the suspension centrifuged, the supernatant decanted and the remaining diethyl ether removed under reduced pressure. Separation by HPLC (Method C; 2% acetonitrile for 5 min. then 30 min. linear gradient of 2% to 30% acetonitrile; flow rate=4 mL/min.) affords (XCVIII) (3 mg, 75%) Ret. Time=23.1 min. LRESI-MS calc for $C_{69}H_{79}N_{10}O_{24}I_1Cl_2$: 1628.4; $(M+H]^+$=1630; $[M-vancosamine+H]^+$=1487; $[M-disaccharide+H]^+$=1215.

b) Preparation of (XCVIII) and (XCIX).

A catalytic amount of $(Ph_3P)_2PdCl_2$ is added to a stirred solution of (XCVII) (12 mg, 0.007 mmol) dissolved in 0.5 mL anhydrous DMF containing 0.35 mL acetic acid. This mixture is treated with tributyltin hydride (10 μL every 5 min. for 30 min.) at which time TLC shows all product is baseline (chloroform-methanol-water; 6:4:1). The reaction mixture is precipitated by addition to 25 mL diethyl ether, the suspension centrifuged, the supernatant decanted and the remaining diethyl ether removed under reduced pressure. Separation by HPLC (Method A; linear gradient of 0% to 40% acetonitrile at a flow rate of 7.5 mL/min.) affords (XCVIII) (4 mg, 33%) Ret. Time=26.7 min. and (XCIX) (2.5 mg, 21%) Ret. Time=22.3 min.

Example 78

Glucose-C6-deoxy, Methyl Glycine Vancomycin (XCIX)

A stirred solution of (XCVIII) (1 mg) and 10% Pd/C (catalytic) in 0.4 mL 50% aq. methanol is hydrogenated under balloon pressure for 3 h. The reaction mixture is filtered through a 0.2 μm syringe filter and separated by HPLC (Method B, semi-prep column; linear gradient of 2% to 30% acetonitrile; flow rate=4 mL/min.) affording (XCIX) (1 mg) Ret. Time=23.4 min. LRESI-MS calc for $C_{69}H_{80}N10O_{24}Cl_2$: 1502.5; $[M+H]^+$=1504; $[M-vancosamine+H]^+$=1360; $[M-disaccharide+H]^+$=1215.

Example 79

N,N'-bis-Cbz, Vancomycin (VII)

To a solution of vancomycin.HCl (1.76 g, 1.19 mmol) dissolved in 8.5 mL water and diluted with 10 mL acetone is added 3 mL water containing $NaHCO_3$ (210 mg, 2.5 mmol). To the stirred suspension is added 20 mL acetone, 15 mL water and N-(benzyloxycarbonyloxy)succinimide (1.2 g, 4.8 mmol) as a solution in 3 mL acetone. After 15 h the clear solution is evaporated to dryness under reduced pressure with toluene azeotrope. The solid is dissolved in 15 mL DMF and precipitated by addition to 120 mL tetrahydrofuran. The suspension is centrifuged and the supernatant containing reagents decanted. The solid is then suspended in 120 mL acetone, mixed vigorously, centrifuged, and the supernatant decanted. This acetone wash of the solid is performed 3 times to remove all reagents. The white solid is dried under reduced pressure affording the title compound (1.9 g, 95%) that is used without further manipulation. TLC: Rf=0.33 (chloroform-methanol-water, 6:4:1).

Example 80

N,N'-bis-Cbz Benzyl Vancomycin (XII)

To a solution of (C) (1.49 g, 0.87 mmol) in 15 mL DMSO under an argon atmosphere is added NaHCO$_3$ (35 mg, 0.4 mmol), then benzyl bromide (0.3 mL, 2.5 mmol) and the mixture stirred for 3 h at room temperature. The reaction is precipitated by addition to 400 mL 10% acetone in diethyl ether. The suspension is centrifuged, affording a thick sticky solid upon sitting, and the supernatant decanted. Combined supernatants are evaporated under reduced pressure to 10 mL volume and precipitated by addition to 200 µl diethyl ether. The suspension is centrifuged and the supernatant decanted. Solids are dissolved in methanol, combined, and evaporated under reduced pressure. Purification by HPLC (Method A; 3 min. at 38% acetonitrile followed by a 40 min. linear gradient of 38% to 75% acetonitrile; flow rate=8 mL/min.) affords (XII) (0.97 g, 61% from 1). Ret. Time=26 min.; TLC: Rf=0.5 (chloroform-methanol-water, 50:21:4).

Example 81

Glucose-C6-mesitylenesulfonyl-N,N'-bis-Cbz Benzyl Vancomycin (CII)

To a stirred solution of compound (CI) (250 mg, 0.138 mmol) in 1.8 mL anhydrous pyridine under an argon atmosphere at 4° C. is added 0.25 mL of a 1.12 M solution of mesitylenesulfonyl chloride in pyridine. The temperature is maintained at 4° C. for 18 h at which time 0.1 mL of 1.12 M mesitylenesulfonyl chloride in pyridine is added. After an additional 8 h the mixture is precipitated by addition to 50 mL diethyl ether, centrifuged, supernatant decanted and the white solid dried en vacuo. Separation by HPLC (Method A; 40 min. linear gradient of 35% to 95% acetonitrile; flow rate=7.8 mL/min.) affords starting material (33 mg) and (CII) (154 mg, 56%, 64% based on recovered 3). Ret. Time=27 min.; TLC: Rf=0.53 (chloroform-methanol-water, 45:10:1). LRESI-MS calc for C$_{98}$H$_{103}$N$_9$O$_{30}$S$_1$Cl$_2$: 1987.6; [M+H]$^+$=1989; [M-vancosamine+H]$^+$=1711; [M-disaccharide+Na]$^+$=1390.

Example 82

Glucose-C6-Azide-N,N'-bis-Cbz Benzyl Vancomycin (CIII)

To a stirred solution of mesitylenesulfonyl derivative (CII) (80 mg, 0.04 mmol) in 1 mL anhydrous DMF under an argon atmosphere is added sodium azide (26 mg, 0.4 mmol). The suspension is heated at 85° C. for 7.5 h then cooled to room temperature. The mixture is precipitated by addition to 20 mL diethyl ether, centrifuged, and the supernatant decanted. The tan solid is dissolve in methanol (ca 1 mL) and precipitated by addition to 20 µL water. The suspension is centrifuged and the supernatant decanted. Separation by HPLC (Method A; 40 min. linear gradient of 35% to 80% acetonitrile; flow rate=7.8 mL/min.) affords (CIII) (38 mg, 52%). Ret. Time=24 min.; TLC: Rf=0.45 (chloroform-methanol-water, 45:10:1). LRESI-MS calc for C$_{89}$H$_{92}$N$_{12}$O$_{27}$Cl$_2$: 1830.6; [M+Na]$^+$=1854; [M-vancosamine+H]$^+$=1556; [M-disaccharide+Na]$^+$=1389.

Example 83

Glucose-C6-Amine-N,N'-bis-Cbz, Benzyl Vancomycin (CIV)

A solution of triphenylphosphine (32 mg, 0.12 mmol) and azide (CIII) (25 mg, 0.014 mmol) in 3 mL THF containing 1 mL water is heated at 55° C. for 5 h. After cooling to room temperature, the mixture is diluted with 40 mL toluene and evaporated to dryness under reduced pressure. The solid is dissolved in methanol (ca 1 mL) and precipitated by addition to 25 mL diethyl ether. The resulting suspension is centrifuged, supernatant decanted, and solid dried under reduced pressure. Separation by HPLC (Method A; 40 min. linear gradient of 20% to 75% acetonitrile; flow rate=7.5 mL/min.) affords (CIV) (18 mg, 73%). Ret. Time=21 min.; TLC: Rf=0.15 (chloroform-methanol-water, 50:21:4). LRESI-MS calc for C$_{89}$H$_{94}$N$_{10}$O$_{27}$Cl$_2$: 1804.6; [M+H]$^+$=1806; [M-disaccharide+H]$^+$=1369.

Example 84

Glucose-C6-N-Acetyl-N,N'-bis-Cbz Benzyl Vancomycin (CV) and Glucose-C6N-Acetyl Vancomycin (CVI)

To a solution of amine (CIV) (15 mg, 0.008 mmol) in 0.3 mL anhydrous DMF under an argon atmosphere at 4° C. is added acetic anhydride (0.1 mL, 0.01 mmol). After 30 min. 8 mL toluene is added and the mixture evaporated to dryness under reduced pressure affording 15 mg (CV) (one spot by TLC: Rf=0.7 (chloroform-methanol-water, 50:21:4)). This product is subjected to deprotection without further purification.

N-acetyl derivative (CV) (11 mg) is dissolved in 0.8 mL DMF-methanol-water (1:2:1) and hydrogenated under balloon pressure with a catalytic 10% Pd/C. After 70 min. the reaction mixture is filtered to remove catalyst and diluted with 0.6 mL water. Separation by HPLC (Method B; 50 min. linear gradient of 0% to 30% acetonitrile; flow rate=7.5 mL/min.) affords (CVI) (6 mg, 67% from CIV). Ret. Time=24 min. LRESI-MS calc for C$_{68}$H$_{78}$N$_{10}$O$_{24}$Cl$_2$: 1488.5; [M+H]$^+$=1490; [M-vancosamine+H]$^+$=1346; [M-disaccharide+H]$^+$=1143.

Example 85 N,N'-Di-Fmoc Vancomycin (CVII)

To a solution of vancomycin.HCl (178 mg, 0.012 mmol) in 2 mL water is added 21 mg NaHCO$_3$. The resulting suspension is diluted with 3 mL acetone and stirred for 10 min. The clear solution is then treated with N-(9-fluorenylmethoxycarbonyloxy)succinimide (Fmoc-succinimide) (90 mg, 0.26 mmol) and 1 mL DMSO and stirred for 24 h. An additional 80 mg Fmoc-succinimide is then added and the mixture stirred for an additional 16 h. The mixture is precipitated by addition to 6 mL diethyl ether-acetone (5:2), the suspension centrifuged and the supernatant decanted. The white solid is suspended in diethyl ether, the suspension centrifuged, the supernatant decanted and the solid dried under reduced pressure. Purification by HPLC (Method A; 75 min. linear gradient of 20% to 100% acetonitrile; flow rate=7 mL/minute) affords (CVII) (167 mg) Ret. Time=73 min. TLC: Rf=0.6 (chloroform-methanol-water; 6:4:1). LRESI-MS calc for $C_{96}H_{95}N_9O_{28}Cl_2$: 1891.6; [M+H]$^+$=1893.

Example 86

N,N'-Di-Fmoc Allyl Vancomycin (CVIII)

To a solution of Fmoc protected derivative (CVII) (35 mg, 0.018 mmol) in 0.6 mL DMSO is added NaHCO$_3$ (13 mg, 0.15 mmol) and the mixture is stirred 10 min. Allyl bromide (10 µL, 0.12 mmol) is then added and stirring continued for 24 h. The reaction mixture is precipitated by addition to 10 mL THF-ethyl acetate (9:1), the suspension centrifuged, the supernatant decanted and the solid dried under reduced pressure. Separation by HPLC (Method A; 45 min. linear gradient of 30% to 80% acetonitrile; flow rate=7 mL/min.) affords (CVIII) (24 mg, 68%) Ret. Time=37 min. TLC: Rf=0.8 (chloroform-methanol-water; 6:4:1). LRESI-MS calc for $C_{99}H_{99}N_9O_{28}Cl_2$: 1931.6; [M+Na]$^+$=1955.

Example 87

N,N'-dialoc-glucose-C6-Bromo-Vancomycin Allyl Ester (CIX)

To a stirred solution of mesitylenesulfonyl derivative (XVI) (10 mg, 0.005 mmol) in 0.3 mL anhydrous DMF under an argon atmosphere is added lithium bromide (10 mg, 0.11 mmol) and the mixture stirred at 80° C. for 7.5 h. The reaction is cooled to room temperature and evaporated to dryness under reduced pressure. Separation by HPLC (Method A; 40 min. linear gradient of 30% to 55% acetonitrile; flow rate=7.5 mL/min.) affords (CIX) (10 mg, containing a small amount of apparent mesitylenesulfonate salt) Ret. Time=25 min.; TLC: Rf=0.6 (chloroform-methanol-water; 50:21:4). LRESI-MS calc for $C_{77}H_{86}N_9O_{27}{}^{79}Br_1Cl_2$: 1717.4; [M+Na]$^+$1741; [M-vancosamine+H]$^+$=1493; [M-disaccharide+Na]$^+$=1290.

This intermediate is subjected to deprotection without further purification.

Example 88

Glucose-C6-bromo Vancomycin (CX)

To a stirred solution of bromide (CIX) (10 mg, 0.005 mmol, containing impurity as described) in 0.4 mL anhydrous DMF containing 0.3 mL acetic acid is added (Ph3P)$_2$Pd(II)Cl$_2$ (catalytic). With vigorous stirring, Bu$_3$SnH is added in 10 µL aliquots every 10 to 20 min. for 2 h (110 µL total added), at which time TLC (chloroform-methanol-water; 6:4:1) showed all glycopeptide baseline. The biphasic mixture is diluted with 150 µL methanol and precipitated by addition to 15 mL diethyl ether. The suspension is centrifuged and the supernatant decanted. The white solid is dried under a stream of argon to remove residual diethyl ether, dissolved in DMF-water (1:2, ca 2 mL) and filtered to remove any remaining catalyst or hydrophobic salts. Separation by HPLC (Method B; 40 min. linear gradient of 0% to 45% acetonitrile; flow rate=7.5 mL/min.) affords (CX) (7 mg, 85% from 4). Retention time=24 min. LRESI-MS calc for $C_{66}H_{74}N_9O_{23}{}^{79}Br_1Cl_2$: 1509.3; [M+H]$^+$=1511; [M-vancosamine+H]$^+$=1369; [M-disaccharide+H]$^+$=1143.

Example 89

2-(2,2-dimethylacetoacetyl)-3,4,6tri-O-benzyl-β-D-glucose Phenyl Sulfoxide (CXVI)

Compound (CXI) (3,4,6-tri-O-benzyl-D-glucose) is prepared on a multi-gram scale from commercially available β-D-glucose pentaacetate in 5 steps with an overall yield of 50%. [V. Betaneli et al., Carbohydrate Research, 1982, Vol. 107, page 285]

a) 2-acetyl-3,4,6-tri-O-benzyl-D-glucose Phenyl Sulfide (CXII).

To a solution of (CXI) (5.1 g, 11.3 mmol) in 200 mL of dry $CH_2Cl_2$ is added pyridine (9.2 mL, 113 mmol), acetic anhydride ($Ac_2O$) (5.3mL, 56.7 mmol), and 4-dimethylaminopyridine (DMAP) (100 mg, 0.82 mmol). The reaction is stirred for 1.5 hours and then concentrated in vacuo. The residue is dissolved in 500 mL of EtOAc and washed with 1 N HCl (2×100 mL), saturated NaHCO$_3$ (2×100 mL), H$_2$O (100 mL) and saturated NaCl (100 mL). The organic layer is dried over Na$_2$SO$_4$ and concentrated in vacuo to give 6.1 grams of crude diacetate. This material is dissolved in 200 mL of dry $CH_2Cl_2$ and the solution is cooled to 40° C. Thiophenol (1.2 mL, 11.7 mmol) is added followed by BF3Et$_2$O (2.9 mL, 22.6 mmol). The reaction is allowed to warm slowly to room temperature and then stirred at room temperature for 1.5 hours. The reaction is then poured into 200 mL of saturated NaHCO$_3$ and stirred for 30 minutes. The product is extracted with $CH_2Cl_2$ (3×200 mL). The organic layers are combined, dried over Na$_2$SO$_4$ and concentrated. The residue is purified by flash chromatography (10-15% EtOAc/petroleum ether) to give 5.6 g (85%) of (CXII) as a white solid (14:1 ratio of β:α sulfides). R$_f$=0.41 (15% EtOAc/petroleum ether); $^1$H NMR (CDCl$_3$, 500 MHz) δ 7.22-7.54 (m, 20H), 5.05 (appt, J=9.0 Hz, 1H, H2), 4.80-4.83 (m, 2H), 4.55-4.70 (m, 5H), 3.68-3.82 (m, 4H), 3.55-3.58 (m, 1H), 2.02 (s, 3H, CH$_3$ on acetate); $^{13}$C NMR (CDCl$_3$, 500 MHz) δ 170.2, 138.9, 138.8, 138.6, 133.7, 133.0, 129.6, 129.2, 129.1, 128.7, 128.6, 128.5, 128.4, 128.3, 86.7, 85.2, 80.1, 78.5, 76.0, 75.8, 74.2, 72.6, 69.7, 21.8.

b) 3,4,6-tri-O-benzyl-D-glucose Phenyl Sulfide (CXIII).

To a solution of (CXII) (802 mg, 1.37 mmol) in 10 mL of THF is added MeOH (20 mL) and 12 drops of a saturated methanolic solution of NaOH. The reaction is stirred overnight then diluted with 150 mL of MeOH. Amberlite acidic resin is added and the reaction is stirred for 10 minutes. Litmus paper indicates that the pH is neutral and the resin is filtered off. The filtrate is concentrated in vacuo and the residue is purified by flash chromatography (20% EtOAc/ petroleum ether to give 654 mg (93%) of the β sulfide (CXIII), and 49 mg (7%) of the a sulfide as white solids. R$_f$(β)=0.20 (15% EtOAc/petroleum ether) R$_f$(α)=0.13 (15% EtOAc/petroleum ether); $^1$H NMR (β) (CDCl$_3$, 500 MHz) δ 7.25-7.63 (m, 20H), 4.87-4.98 (m, 3H), 4.55-4.68 (m, 4H), 3.85 (dd, J=11.0, 1.5 Hz, 1H), 3.79 (dd, J=10.5, 4.5 Hz, 1H), 3.63-3.68 (m, 2H), 3.54-3.60 (m, 2H), 2.50 (s, 1H, free OH); $^{13}$C NMR (β) (CDCl$_3$, 500 z) δ 139.2, 139.0, 138.8, 133.6, 132.6, 129.7, 129.3, 129.2, 129.1, 128.8, 128.7, 128.5, 128.4, 128.3.

c) 2-2-methyl)-acetoacetyl-3,4,6-tri-O-benzyl-β-D-glucose Phenyl Sulfide (CXIV).

To a 2-neck 100 mL round bottom flask outfitted with a condenser is added (CXIII) (1.06 g, 1.96 mmol), dry toluene (35 mL), DMAP (240 mg, 1.96 mmol), and ethyl-2-methyl acetoacetate (1.5 mL, 9.8 mmol). The reaction is heated at reflux for 48 hours then cooled and concentrated in vacuo. Purification of the residue by flash chromatography (15-20% EtOAc/petroleum ether) gives 1.07 g (86%) of (CXIV) as a white solid along with 95 mg (9%) of recovered (CXIII). $R_f$=0.20 (15% EtOAc/petroleum ether) (mixture of isomers).

d) 2-(2,2-dimethylacetoacetyl)-3,4,6-tri-O-benzyl-β-D-glucose Phenyl Sulfide (CXV).

A solution of (CXIV) (189.5 mg, 0.296 mmol) in 12 mL of THF is cooled to 0° C. and potassium-t-butoxide (66.5 mg, 0.592 mmol) is added. The solution is stirred at 0° C. for 10 minutes and then methyl iodide (37 μL, 0.592 mmol) is added. The reaction is stirred at 0° C. for 45 minutes and then poured into 20 mL of saturated NH₄Cl and extracted with CH₂Cl₂ (3×20 mL). The organic layers are combined, dried over Na₂SO₄ and concentrated in vacuo. Purification by flash chromatography (20% EtOAc/petroleum ether) gives 181 mg (94%) of (CXV) as an oil. $R_f$ 0.25 (15% EtOAc/petroleum ether); ¹H NMR (CDCl₃, 500 MHz) δ 7.17-7.54 (m, 20H), 5.15 (appt, J=10 Hz, 1H, H2), 4.86 (d, J=11 Hz, 1H), 4.74 (d, J=10.5 Hz), 4.56-4.69 (m, 5H), 3.70-3.82 (m, 1H), 3.551H), 2.22 (s, 3H), 1.44 (s, 3H), 1.37 (s, 3H); ¹³C NMR (CDCl₃, 500 MHz) δ 206.2, 172.6, 138.8, 138.6, 138.4, 133.6, 132.9, 129.7, 129.1, 128.7, 128.6, 128.4, 128.3, 127.6, 86.7, 84.8, 80.0, 78.6, 75.7, 75.5, 74.2, 73.0, 69.5, 56.5, 27.1, 22.8, 22.6.

e) 2-(2,2-dimethylacetoacetyl)3,4,6-tri-O-benzyl-β-D-glucose Phenyl Sulfoxide (CXVI).

A solution of (CXV) (189.5 mg, .290 mmol) in 15 mL of CH₂Cl₂ is cooled to –60° C. and m-chloroperoxybenzoic acid (mCPBA) (64% purity, 85 mg, 0.315 mmol) is added. The reaction is allowed to warm slowly to –5° C. and quenched with 50 μL of Me₂S. The reaction is poured into 20 mL of saturated NaHCO₃ and extracted with CH₂Cl₂ (3×20 mL). The organic layers are combined, dried over Na₂SO₄, and concentrated. The residue is purified by flash chromatography (40% EtOAc/petroleum ether) to give 186.1 mg (96%) of (CXVI) as a 1:1 mixture of sulfoxide isomers. $R_f$ (less polar isomer)=0.29 (40% EtOAc/petroleum ether); $R_f$ (more polar isomer)=0.23 (40% EtOAc/petroleum ether); ¹H NMR (less polar isomer) (CDCl₃, 500 MHz) δ 7.15-7.61 (m, 20H), 5.51 (appt, J=9.5 Hz, 1H, H2), 4.19-4.86 (m, 6H, 333 CH₂ on Bns), 4.17 (d, J=9.5 Hz, 1H, H1), 3.78 (appt J=8.5, 1H), 3.51-3.69 (m, 3H), 3.45-3.48 (m, 1H), 2.23 (s, 3H), 1.47 (s, 3H), 1.40 (s, 3H); ¹H NMR (more polar isomer) (CDCl₃, 500 MHz) δ 7.14-7.82 (m, 20H), 5.29 (appt, J=8.5 Hz, 1H, H2), 4.54-4.85 (m, 4H, 2×CH₂ on Bns), 4.30-4.37 (m, 3H), 3.78 (appt, J=8.5 Hz, 1H), 3.64-3.74 (m, 3H), 3.50-3.52 (m, 1H), 2.22 (s, 3H), 1.46 (s, 3H), 1.42 (s, 3H); ¹³C NMR Oess polar isomer) (CDCl₃, 500 MHz) δ 206.4, 172.1, 139.7, 138.7, 138.4, 138.2, 132.1, 129.6, 129.2, 129.1, 128.6, 128.4, 127.7, 126.3, 91.3, 84.5, 81.0, 75.6, 75.4, 74.2, 70.0, 69.2, 56.7, 26.9, 22.8, 22.6; ¹³C NMR (more polar isomer) (CDCl₃, 500 MHz) δ 206.2, 173.1, 139.8, 138.7, 138.3, 129.4, 129.1, 129.0, 128.6, 128.5, 128.4, 128.3, 128.0, 127.1, 93.7, 83.7, 80.2, 75.5, 75.4, 74.2, 71.4, 68.8, 56.6, 26.8, 22.8, 22.7.

Example 90

Glycosylation of a Model Phenol. Preparation of 3,4,6-tri-O-benzyl-β-D-glucopyranosyl 2,6-dimethoxy Phenol (CXVIII)

a) 2-(2,2-dimethylacetoacetyl)-3,4,6-tri-O-benzyl-β-D-glucopyranosyl-2,6-dimethoxy phenol (CXVII). 2,6-dimethoxyphenol (48.6 mg, 0.315 mmol) is dissolved in 5 mL of benzene and bis(tributyltin)oxide (88.3 μL, 0.173 mmol) is added. The solution is refluxed overnight with a Dean Stark trap which contains 4 angstrom molecular sieves in the side arm. The reaction is cooled and concentrated in vacuo to give tributyltin-2,6-dimethoxy phenoxide which is dissolved in 1 ml of dry methylene chloride to give a stock solution. In a separate flask, (CXVI) (62.4 mg, 0.0931 mmol) and 2,6 di-t-butyl-4-methyl pyridine (40.6 mg, 0.198 mmol) are azeotroped 3 times with toluene. Flame dried 4 angstrom sieves and a stir bar are added to the flask followed by 4 ml of EtOAc. The solution is stirred for 1 hour and cooled to –78°. 157 μL of a stock solution containing 100 μof Tf₂O and 900 μL of CH₂Cl₂ is added (0.093 mmol of Tf₂O). The reaction is allowed to warm to –60° C. The temperature is maintained at –60° C. for 10 minutes and then the reaction is cooled back to –78° C. 170.5 μL (0.0473 mmol) of the stock solution of tributyltin 2,6-dimethoxy phenoxide is added dropwise by syringe. After 5 minutes, 40 μL of pyridine is added and then the reaction is diluted with 50 ml of EtOAc and poured into 25 ml of saturated NaHCO₃. The EtOAc layer is washed with 25 mL of saturated NaCl, dried over Na₂SO₄ and concentrated. The residue is purified by flash chromatography (30% EtOAc/petroleum ether) to give 30.8 mg (93%) of (CXVII). $R_f$=0.30 (25% EtOAc/petroleum ether); ¹H NMR (CDCl₃, 270 MHz) δ 7.17-7.33 (m, 15H), 7.04 (t, J=8.6 Hz, 1H, $H_a$ of phenol), 6.565 (d, 2H, J=8.6 Hz, $H_b$ of phenol), 5.44 (appt, J=8.4 Hz, 1H, H-2), 5.075 (d, J=7.9 Hz, 1H, H-I), 4.46-4.88 (m, 6H, 3×CH₂ on Bns), 3.69-3.88 (m, 2H), 3.79 (s, 6H, 2×OMe on phenol), 3.39-3.46 (m, 1H), 2.12 (s, 3H), 1.37 (s, 3H), 1.32 (s, 3H); ¹³C NMR (CDCl₃, 270 MHz) δ 206.1, 172.4, 153.7, 138.6, 138.3, 138.0, 133.7, 128.5, 128.0, 127.6, 127.2, 124.8, 105.4, 100.5, 83.1, 78.1, 76.1, 75.0, 74.7, 74.1, 73.9, 68.7, 56.2, 55.9, 26.0, 22.3, 21.5; MS (ESI) calc 698.8 (C₄₁H₄₆O₁₀) found 721.8 M⁺Na.

b) 3,4,6-tri-O-benzyl-β-D-glucopyranosyl 2,6-dimethoxy Phenol (CXVIII).

To a solution of (CXVII) (53.2 mg, 0.0761 mmol) in 650 μL of THF is added 1.3 ml of MeOH followed by hydrazine (40 μL, 1.3 mmol). The reaction is stirred for 3 hours and then 1000 of acetic acid is added The reaction is poured into 40 mL of saturated aqueous ammonium chloride and extracted with methylene chloride (3×25 mL). The organic extracts are combined, dried over Na₂SO₄ and concentrated. Purification by flash chromatography (20% EtOAc/petroleum ether) gives 35.1 mg (79%) of (CXVIII). $R_f$=0.24 (25% EtOAc/petroleum ether); ¹H NMR (CDCl₃, 270 MHz) δ 7.17-7.44 (m, 15H), 7.06 (t, J=8.6 Hz, 1H, $H_a$ of phenol), 6.61 (d, J=8.6 Hz, 2H, $H_b$ of phenol), 5.07 (d, J=11.2 Hz, 1H), 4.84 (appt, J=11.7 Hz, 2H), 4.54-4.60 (m, 4H), 3.88-3.94 (m, 1H), 3.85 (s, 6H, 2×OCH₃ on phenol), 3.49-3.78 (m, 5H); ¹³C NMR (CDCl₃, 270 MHz) δ 153.2, 139.0, 138.6, 138.3, 136.0, 127.2-129.0 (multiplet, aromatics), 125.0, 106.5, 105.6, 85.0, 77.4, 76.1, 75.8, 75.2, 75.1, 73.8, 69.6, 56.5.

Example 91

CBz-tetra-O-benzyl Diacetate Vancomycin Aglycone (CXXIII)

a) CBZ-Bn-vancomycin Aglycone (CXIX).

Trifluoroacetic acid (6.4 mL) is added to bis-CBz-Bn-vancomycin (XII) (250.2 mg; 0.138 mmol; >80% pure by HPLC). The reaction mixture turns black and is stirred at room temperature for 11 hours and then precipitated in 80 mL of H₂O. The precipitate is collected by centrifugation and subjected to silica gel flash chromatography (15% MeOH/CH₂Cl₂). Fractions containing the desired product are combined and concentrated. This material is purified by reverse phase preparatory HPLC (C18, 40-80% CH₃CN/H₂O with 0.1% HOAc over 40 min) to give (CXIX) (60.1 mg; 32%) as a white solid. $R_f$=0.17 (15% MeOH(CH₂Cl₂); MS (ESI) calc 1368.1 (C₆₈H₆₄N₈O₁₉Cl₂) found 1369.1 M⁺H.

b) CBZ-Bn-O-allyl Vancomycin Aglycone (CXX).

4 Å molecular sieves are added to (CXIX) (171.2 mg; 0.125 mmol) and then DMF (7.5 mL) is added. The solution is stirred for 30 minutes and then $Cs_2CO_3$ (52.6 mg, 0.162 mmol) is added and the mixture is stirred for 30 minutes. The solution is cooled to 0° C. and allyl bromide (75.6 µL, 0.625 mmol) is added. After 50 minutes the reaction is quenched by the addition of HOAC (100 µL). The reaction mixture is filtered through a plug of silica gel with 15% $MeOH/CH_2Cl_2$ and the filtrate is concentrated. Purification by reverse phase preparatory HPLC (C18, 40-80% $CH_3CN/H_2O$ with 0.1% HOAc over 45 min) gives (CXX) (77.4 mg; 44%) as a white solid along with recovered (CXIX) (23.8 mg; 14%). $R_f$=0.28 (15% $MeOH/CH_2Cl_2$); MS (ESI) calc 1408.2 ($C_{71}H_{68}N_8O_{19}Cl_2$) found 1409.2 $M^+H$.

c) CBZ-tetra-O-benzyl-O-allyl Vancomycin Aglycone (CXXI).

4 Å molecular sieves are added to (CXX) (26.3 mg; 0.0187 mmol) and then DMF (1.5 mL) is added. The solution is stirred for 30 minutes and then $Cs_2CO_3$ (29.0 mg, 0.089 mmol) is added and the mixture is stirred for 30 minutes. The solution is cooled to 0° C. and benzyl bromide (44.4 µL, 0.3736 mmol) is added. The reaction is stirred for 2.5 hours at 0° C. and then warmed to room temperature and stirred at room temperature for 5 hours. The reaction is then quenched with HOAc (40 µL) and filtered through a plug of silica gel with 15% $MeOH/CH_2Cl_2$. The filtrate is concentrated and the residue is purified by radial chromatography (5% $MeOH/CH_2Cl_2$) to give (CXXI) (22.7 mg; 73%) as a white solid. $R_f$=0.125 (5% $MeOH/CH_2Cl_2$); MS (ESI) calc 1678.5 ($C_{92}H_{86}N_8O_{19}Cl_2$) found 1701.5 $M^+Na$.

d) CBZ-tetra-O-benzyl-O-allyl diacetate Vancomycin Aglycone (CXXII).

Compound (CXXI) (47.8 mg; 0.0285 mmol) is dissolved in pyridine (4mL) and $Ac_2O$ (1 mL) is added. The reaction is stirred at room temperature for 2.5 hours and then concentrated. The residue is filtered through a plug of silica gel with 10% $MeOH/CH_2Cl_2$ and the filtrate is concentrated. The residue is purified by radial chromatography (4% $MeOH/CH_2Cl_2$) to give (CXXII) (47.8 mg; 95%) as a white solid. $R_f$=0.30 (5% $MeOH/CH_2Cl_2$); MS (ESI) calc 1762.6 ($C_{96}H_{90}N_8O_{21}Cl_2$) found 1785.6 $M^+Na$.

e) CBZ-tetra-O-benzyl Diacetate Vancomycin Aglycone (CXXIII).

To (CXXII) (44.8 mg; 0.0254 mmol) is added $CHCl_3$ (4.5 mL), HOAc (0.59 mL), and N-methyl morpholine (0.29 mL). The solution is degassed for 5 minutes and then $Pd(PPh_3)_4$ (11.1 mg; 9.6×$10^{-3}$ mmol) is added. The reaction is stirred for 45 minutes and then an additional amount of $Pd(PPh_3)_4$ (3.5 mg; 3×$10^{-3}$ mmol) is added. The reaction is stirred for another 15 minutes and then filtered through a plug of silica gel with 10% $MeOH/CH_2Cl_2$. The filtrate is concentrated and the residue is purified by radial chromatography (5% $MeOH/CH_2Cl_2$) to give (CXXIII) (41.9 mg; 96%). $R_f$=0.25 (5% $MeOH/CH_2Cl_2$); MS (ESI) calc 1722.5 ($C_{93}H_{86}N_8O_{21}Cl_2$) found 1723.5 $M^+H$.

Example 92

[2-(2,2-dimethylacetoacetyl)-3,4,6-tri-O-benzyl-β-D-glucopyranoside]-N-CBZ-tetra-O-benzyl-diacetato Vancomycin Aglycone (CXXIV)

Sulfoxide (CXVI) (101.3 mg, 0.151 mmol) is combined with 2,6-di-t-butyl-4-methyl pyridine (62.7 mg, 0.303 mmol) and 5 mL of dry $CH_2Cl_2$ is added. The solution is cooled to −70° C. and $Tf_2O$ (25.5 µL, 0.151 mmol) is added. The reaction is warmed to −60° C. and maintained at this temperature for 30 minutes. Then (CXXIII) (39.6 mg; 0.023 mmol) is added dropwise in 1 mL of $CH_2Cl_2$. The reaction is allowed to warm slowly to −50° C. and then the temperature is maintained between −50° C. and −55° C. for 30 minutes. The reaction is quenched by the addition of thiophenol (15 µL) followed by DIEA (100 µL). The cold reaction mixture is filtered through silica gel with 10% $MeOH/CH_2Cl_2$ (100 mL). The filtrate is concentrated and subjected to radial chromatography (4% $MeOH/CH_2Cl_2$). Fractions containing the desired product are combined and repurified by radial chromatography (3.5% $MeOH/CH_2Cl_2$) to give (CXXIV) (8.7 mg; 17%). $R_f$=0.23 (3.5% $MeOH/CH_2Cl_2$); MS (FAB) calc 2,267.1 ($C_{126}H_{122}N_8O_{28}Cl_2$) found 2268.2 $M^+H$.

Example 93

N,N'-Diallyloxycarbonyl-methoxy-glycine-deleucine Aspartatic Acid Vancomycin (CXXVIII)

a) Deleucine-vancomycin (CXXV).

Vancomycin-HCl (497 mg, 0.335 mmol) is dissolved in 4 mL water to which is added 4 mL distilled pyridine with stirring in a 40° C. oil bath. To this solution is added phenyl isothiocyanate (50 mg, 0.368 mmol). After stirring for 30 minutes the clear solution is evaporated of organic solvent under reduced pressure and then added 100 mL water is added, which is frozen and lyophilized to dryness. To the powder is added 4 mL of $CH_2Cl_2$ and 4 mL of trifluoroacetic acid. This clear solution is stirred at room temperature for 3 minutes and then evaporated under reduced pressure to dryness. The brown oil is partitioned between 100 mL of ethyl acetate (EtOAc) and 100 mL $H_2O$. The aqueous layer is collected and the organic layer is extracted twice with water (40 mL each). The aqueous layers are combined and evaporated under reduced pressure to dryness. The white solid is dissolved in methanol, loaded to a C18 reverse phase column (50 mm×12 cm, particle size 40 µm, pore size 60 A (J. T. Baker) and eluted with 10% acetonitrile/0.1% acetic acid in water. The fractions containing the pure products are combined and evaporated to give 325 mg of (CXXV) as a white powder, 73.5%. Rf=0.1 ($CHCl_3$:MeOH:$H_2O$=3:5:1.5). Mass Spec. $[M+H]^+$, 1322; $[M-V]^+$, 1178.

b) Methoxy-glycine-deleucine Vancomycin (CXXVI).

Compound (CXXV) (162 mg, 0.117 mmol) and glycine methyl ester hydrochloride (74 mg, 0.585. mmol) are dissolved in 0.8 mL DMSO and 0.8 mL DMF and stirred at 0° C. Diisopropylethylamine (204 µl, 0.585 mmol) is added to the reaction vessel via syringe followed by HOBt/HBTU (1.17 mL 0.45M DMF solution, 0.526 mmol). The ice bath is removed after addition. After 10 minutes, the reaction is completed and the reaction solution is directly loaded to a poly(divinylbenzene) column (30 mm×8 cm, 50-100 micron particle size) and eluted with methanol/water (0, 10%, 20%, 30%, 40%, 50% of 100 mL each). The fractions containing the pure products are combined and evaporated to give 160 mg of (CXXVI) as a white powder, 95%. Rf=0.1 ($CHCl_3$:MeOH:$H_2O$=3:3:1). Mass Spec. $[M+H]^+$, 1393; $[M-V]^+$, 1249.

c) N-allyloxycarbonyl-methoxy-glycine-deleucine Vancomycin (CXXVII).

Compound (CXXVI) (647 mg, 0.465 mmol) is dissolved in 10 mL water and 10 mL dioxane mixture. Fmoc-succinimide (172 mg, 0.511 mmol) in 5 mL dioxane is added to the solution over 10 hours via syringe pump. The reaction mixture is stirred for an additional 5 hours after addition. Then the solution is rotary evaporated to dryness under reduced pressure. The crude oil obtained is dissolved in 10 mL DMF. To this clear solution is added diisopropylethylamine (406 µL, 2.32 mmol) followed by Aloc-OBt (102 mg, 0.465 mmol) in 1 mL DMF. The reaction is stirred at room temperature for 30 minutes. Piperidine (2 mL) is added to the reaction flask at this time. After stirring for another 5 minutes, the solution is suspended into 160 mL of acetone and stirred, centrifuged, and decanted. The white precipitate obtained is collected, loaded to a C18 reverse phase column (50 mm×12 cm, particle size 40 µm, pore size 60 A (J. T. Baker) and eluted with isopropanol/water (0, 10%, 20%, 30%, 40%, 50%, 60% of 100 mL each). The fractions containing the pure products are combined and evaporated to give 309 mg of (CXXVII) as a white powder, 58% over 3 steps. Rf=0.4 (CHCl$_3$:MeOH:H$_2$O=3:2:0.5). Mass Spec. [M+2H]$^+$, 1478; [M−V+H]$^+$, 1250.

d) N,N'-diallyloxycarbonyl-methoxy-glycine-deleucine aspartatic acid vancomycin (CXXVIII).

Compound (CXXVII) (102 mg, 0.0691 mmol) and Aloc-Asp(OFm)-OH (55 mg, 0.138 mmol) are premixed and azeotroped with toluene three times, dissolved in 1.5 mL DMF and then cooled to 0° C. Diisopropylethylamine (48 µL, 0.276 mmol) is added to the reaction vessel followed by HOBt (19 mg, 0.138 mmol) and PyBOP (72 mg, 0.138 mmol). After stirring for 15 minutes, 200 µL piperidine is added to the reaction. The ice bath is removed and the reaction is stirred at room temperature for 5 minutes. The clear solution is suspended in 45 mL acetone and stirred, centrifuged, and decanted. The solid is dried under reduced pressure and purified by reverse-phase HPLC using a PHENOMENEX LUNA C18 column (21.2×250 mm), 5 micron particle, eluting with a 30 min. linear gradient of 0.1% acetic acid in water to 70% acetonitrile/0.1% acetic acid in water; flow rate of 7 mL/min. and ultraviolet (UV) detection at 285 nm. The fractions containing the product are combined and evaporated to give 71 mg of compound (CXXVIII), 62% over 2 steps. Rf=0.5 (CHCl$_3$:MeOH:H$_2$O=3:2:0.5). Mass Spec. [M+Na]$^+$, 1698; [M−V+Na]$^+$, 1472.

Example 94

N-Allyloxycarbonyl-N'-methoxyglycine [N-acetato-vancosamino] Vancomycin (CXXXI)

a) Methoxy-glycine Vancomycin (CXXIX).

Vancomycin hydrochloride (317 mg, 0.213 mmol) and glycine methyl ester hydrochloride (54 mg, 0.426 mmol) are dissolved in 2 mL DMSO and 2 mL DMF and stirred at 0° C. Diisopropylethylamine (186 µL, 0.3195 mmol) is added to the reaction vessel via syringe followed by HOBt/HBTU (710 µL 0.45M DMF solution, 0.319 mmol). The ice bath is removed after addition. After 10 minutes, the reaction is completed and the reaction solution is directly loaded to a poly(divinylbenzene) column (30 mm×8 cm, 50-100 micron particle size) and eluted with methanol/water (0, 10%, 20%, 30%, 40%, 50% of 100 mL each). The fractions containing the pure products are combined and evaporated to give 249 mg of (CXXIX) as a white powder, 77%. Rf=0.15 (CHCl$_3$:MeOH:H$_2$O=3:2:0.5). Mass Spec. [M+H]$^+$, 1521; [M−V]$^+$, 1377.

b) N-allyloxycarbonyl-N'-methoxyglycine Vancomycin (CXXX).

Compound (CXXIX) (110 mg,0.0723 mmol) is dissolved in 3 mL DMF. Aloc-OBt (17 mg, 0.0795 mmol) in 0.5 mL DMF is added to the solution over 10 hours via syringe pump. The reaction is stirred for additional 5 hours after addition. The solution is then suspended into 160 mL of acetone and stirred, centrifuged, and decanted. The white solid is directly loaded to a poly(divinylbenzene) column (30 mm×8 cm, 50-100 micron particle size) and eluted with methanol/water (0, 10%, 20%, 30%, 40%, 50% of 100 mL each). The fractions containing the pure product are combined and evaporated to give 115 mg of (CXXX) as a white powder, 62%. Rf=0.4 (CHCl$_3$:MeOH:H$_2$O=3:2:0.5).

Mass Spec. [M+H]$^+$, 1605; [M−V]$^+$, 1461.

c) N-allyloxycarbonyl-N'-methoxyglycine [N-acetato-vancosamino] vancomycin (CXXXI).

Compound (CXXX) (32 mg, 0.0202 mmol) and glyoxylic acid monohydrate (2 mg, 0.0222 mmol) are dissolved in 400 µL methanol and stirred at 40° C. for 2 hours. A white precipitate is generated and the suspension is cooled back to room temperature and 100 µL DMF is added followed by 61 µL of NaCNBH$_3$ in THF (1M solution). After 20 minutes, the resulting clear solution is directly purified by reverse-phase HPLC using a PHENOMENEX LUNA C18 column (21.2×250 mm), 5 µm particle, eluting with a 30 min. linear gradient of 20% acetonitrile/0.1% acetic acid in water to 70% acetonitrile/0.1% acetic acid in water; flow rate of 7 mL/min. and ultraviolet (UV) detection at 285 nm. The fractions containing the product are combined and evaporated to give 18 mg of product (CXXXI), 54%. Rf=0.4 (CHCl$_3$:MeOH:H$_2$O=3:2:0.5).

Mass Spec.: [M+H]$^+$, 1662; [M−V]$^+$, 1460.

Example 95

2-(4-Azidobutyryl)-3,4,6-triacetyl Glucose Sulfoxide (CXXXII)

a) 2-(4-azidobutyryl)-1,3,4,6-tetraacetyl-D-glucose.

1,3,4,6 tetraacetyl D-glucose (W. E. Dick, Carbohyd. Res., 21, 255-268 (1972)) is dissolved in CH$_2$Cl$_2$ to make a 0.1M solution. 6 eqivalents of pyridine and 3 equivalents of 4-azidobutyryl chloride (S. Kusumoto et. al., Bull. Chem. Soc. Jpn., 59, 1289-1298 (1986)) are added. After several hours, the reaction is poured into saturated NaHCO$_3$, extracted with CH$_2$Cl$_2$, dried over Na$_2$SO$_4$, and concentrated. The residue is purified by flash chromatography to give the title compound.

b) 2-(4-azidobutyryl)-3,4,6-triacetyl-D-glucose sulfide.

The product of step a) is dissolved in CH$_2$Cl$_2$ to make a 0.1M solution. 5 equivalents of BF$_3$Et$_2$O and 1.25 equivalents of thiophenol are added. After several hours, the reaction is poured into saturated NaHCO$_3$, extracted with CH$_2$Cl$_2$, dried over Na$_2$SO$_4$, and concentrated. The residue is purified by flash chromatography to give the title compound.

c) 2-(4-azidobutyryl)-3,4,6-triacetyl-D-glucose sulfoxide.

The product of step b) is dissolved in CH$_2$Cl$_2$ to make a 0.1M solution. The solution is cooled to −78° and 1.1 equivalents of mCPBA is added. The reaction is slowly warmed until conversion to sulfoxide is complete. The reaction is quenched with 1 equivalent of Me$_2$S, poured into saturated NaHCO$_3$, extracted with CH$_2$Cl$_2$, dried over Na$_2$SO$_4$, and concentrated. The residue is purified by flash chromatography to give the title compound (CXXXII).

Example 96

Modified Sulfoxide Glycosylation Procedure. CBZ-Bn-tri-O-Me Vancomycin Pseudoaglycone (CXXXIII)

a) CBZ-Bn-tri-O-Me-hexaacetyl Vancomycin pseudoaglycone.

Peracetylated glucose sulfoxide (47.3 mg, 0.1036 mmol) and 2,6-di-t-butyl-4-methyl pyridine (43.3 mg, 0.2108 mmol) are azeotroped 3 times with toluene. Flame dried 4 angstrom molecular sieves and a stir bar are added followed by 3 ml of $CH_2Cl_2$. The solution is stirred for 45 minutes and then cooled to −78°. 174 μL of a stock solution containing 100 μL of $Tf_2O$ and 900 μL of $CH_2Cl_2$ is added (0.1036 mmol of $Tf_2O$). The reaction is warmed to −60°, maintained at that temperature for 20 minutes, and then cooled back to −78°. CBZ-Bn-tri-O-Me-diacetyl vancomycin aglycone (XV) (49.0 mg, 0.0328 mmol) is dissolved in 1 ml of $CH_2Cl_2$ and $BF_3.Et_2O$ (83 μL, 0.656 mmol) is added. This solution is added to the activated sulfoxide and the reaction is warmed to −15° over 1.5 hours. The reaction is then filtered through a plug of silica gel with 7.5% $MeOH/CH_2Cl_2$ into a flask containing 200 μL of pyridine. The filtrate is concentrated. Purification by radial chromatography gave 28.3 mg (47%) of the title compound. $R_f$ 0.21 (50% EtOAc/petroleum ether then 5% $MeOH/CH_2Cl_2$); MS (SM) calc 1824.5 ($C_{89}H_{92}N_8O_{30}Cl_2$) found 1847.5 M$^+$Na.

b) CBZBn-tri-O-Me Vancomycin pseudoaglycone.

The product of step a) (7.2 mg, 0.0039 mmol) is dissolved in 250 μL of THF and 500 μL of MeOH are added. 20 μL of $H_2NNH_2$ are added and the reaction is allowed to stir for 10 hours. The reaction is then quenched with 60 μL of acetic acid (HOAc) and filtered through a plug of silica gel with 20% $MeOHWCH_2Cl_2$. The filtrate is concentrated and purified by reverse-phase HPLC using a PHENOMENEX LUNA $C_{18}$ column (21.2×250 mm), 5 μm particle, eluting with a 35 minute linear gradient of 35% -80% acetonitrile/0.1% acetic acid in water, flow rate 7ml/min. 2.0 mg (32%) of the title compound (CXXXIII) is isolated as a white solid. Retention time on HPLC is 24.8 minutes; MS (ESI) calc 1572.3 ($C_{77}H_{80}N_8O_{24}Cl_2$) found 1595.3 M$^+$Na.

Example 97

Modified Sulfoxide Glycosylation Procedure. Preparation of Aloc-tetra-O-allyl-pentaacetyl Vancomycin Pseudoaglycone (VI)

a) Aloc-tetra-O-allyl-pentaacetyl-2(4-azidobutyryl)-glucose vancomycin pseudoaglycone.

2-(4-azidobutyryl)-3,4,6-triacetyl-D-glucose sulfoxide (CXXXII) (3 equivalents) and 2,6-di-t-butyl-4-methyl pyridine (6 equivalents) are azeotroped 3 times with toluene. Flame dried 4 angstrom molecular sieves and a stir bar are added followed by 3 ml of $CH_2Cl_2$. The solution is stirred for 45 minutes and then cooled to −78°. $Tf_2O$ (3 equivalents) is added. The reaction is warmed to −60°, maintained at that temperature for 20 minutes, and then cooled back to −78°. Aloc-tetra-O-allyl diacetate vancomycin aglycone (1 equivalent, prepared analogously to the preparation of XV, using allyl bromide in place of benzyl bromide; and methyl iodide and aloc-succinimide in place of N-(benzyloxycarbonyloxy) succinimide) is dissolved in 1 ml of $CH_2Cl_2$ and $BF_3.Et_2O$ (20 equivalents) is added. This solution is added to the activated sulfoxide and the reaction is warmed to −15° over 1.5 hours. The reaction is then filtered through a plug of silica gel with 7.5% $MeOH/CH_2Cl_2$ into a flask containing 200 μL of pyridine. The filtrate is concentrated. Purification by radial chromatography gives alloc-tetra-O-allyl-pentaacetyl-2 (4-azidobutyryl)-glucose vancomycin pseudoaglycone.

b) Aloc-tetra-O-allyl-pentaacetyl vancomycin pseudoaglycone (VI).

Aloc-tetra-O-allyl-pentaacetyl-2-(4-azidobutyryl)-glucose vancomycin pseudoaglycone is dissolved in 5:1 THF/$H_2O$ to make a 0.1 M solution. 5 equivalents of $Ph_3P$ are added and the reaction is heated to 60°. The reaction is maintained at this temperature until TLC indicates that the reaction is complete. Then the reaction is cooled to room temperature and filtered through silica gel with 10% $MeOH/CH_2Cl_2$. Purification by radial chromatography gives (VI).

Example 98

Glycosylation of a Model Phenol. Preparation of 2,3,4,6-Tetra-O-benzyl-β-D-glucopyranosyl-2,6-dimethoxy Phenol Peracetylated glucose sulfoxide (50.1 mg, 0.1098 mmol) and 2,6-di-t-butyl-4-methyl pyridine (47.4 mg, 0.231 mmol) were azeotroped 3 times with toluene. Flame dried 4 angstrom sieves and a stir bar were added to the flask, followed by 3 ml of $CH_2Cl_2$. This solution is stirred for 45 minutes and then cooled to −78°. 185 μL of a stock solution containing 100 μL of $Tf_2O$ and 900 μL of $CH_2Cl_2$ is added (0.1098 mmol of $Tf_2O$). The reaction is warmed to −60°, maintained at this temperature for 20 minutes, and then cooled back to −78°. 2,6-dimethoxy phenol (8.4 mg, 0.0545 mmol) is dissolved in 1 ml of $CH_2Cl_2$ and $BF_3.Et_2O$ (140 μL, 1.098 mmol) is added. This solution is added to the activated sulfoxide by syringe. The reaction is allowed to warm to 0° and then filtered through a plug of silica gel with ethyl acetate into a flask containing 200 μL of pyridine. This filtrate is concentrated and purified by flash chromatography (45% EtOAc/petroleum ether) to give 14.9 mg (56%) of the title compound. $R_f$ 0.27 (50% EtOAc/petroleum ether); $^1$H NMR (CDCl$_3$, 500 MHz) δ 7.05 (t, J=8.5 Hz, 1H, H$_a$ of phenol), 6.59 (d, J=8 Hz, 2H, H$_b$ of phenol), 5.25-5.36 (m, 3H, H2, H3, and H4), 5.10 (d, J=7.5 Hz, 1H, H1), 4.28 (dd, J=12.3 Hz, 3=5 Hz, 1H, H6), 4.15 (dd, J=12 Hz, J=2.5 Hz, H6'), 3.86 (s, 6H, 2×Me on phenol), 3.70-3.73 (m, 1H, H5), 2.05-2.06 (m, 12H, 4 acetates).

Example 99

Di-{N,N'-diallyloxycarbonyl-O-allyl-6-glucosamino vancomycin}-C(O)CH$_2$—(O) (CXXXV)

a) Allyl N,N'-diailyloxycarbonyl [6-N-acetato-glucosamino] vancomycin (CXXXIV).

Compound (III) (17 mg, 0.0103 mmol) and glyoxylic acid monohydrate (0.95 mg, 0.103 mmol) are dissolved in 1 mL methanol and stirred at 40° C. for 2 hours to generate a white precipitate. The suspension is cooled back to room temperature and 250 μL DMF is added followed by 200 μL of NaC-NBH$_3$ in THF (1M solution). After 20 minutes, the resulting clear solution is directly purified by reverse-phase HPLC using a PHENOMENEX LUNA C18 column (21.2×250 mm), 5 μL particle, eluting with a 30 min. linear gradient of 20% acetonitrile/0.1% acetic acid in water to 70% acetonitrile/0.1% acetic acid in water; flow rate of 7 mL/min. and ultraviolet (UV) detection at 285 nm. The fractions containing the product were combined and evaporated to give 6 mg of product (CXXXIV), 33%. Rf=0.28 (CHCl$_3$:MeOH:H$_2$O=3: 2:0.5).

Mass Spec. [M+H]$^+$, 1716; [M−V]$^+$, 1488.

b) Di-{ N,N'-diallyloxycarbonyl-O-allyl-6-glucosamino vancomycin}-C(O)CH$_2$—(O) (CXXXV).

Figure 13A:
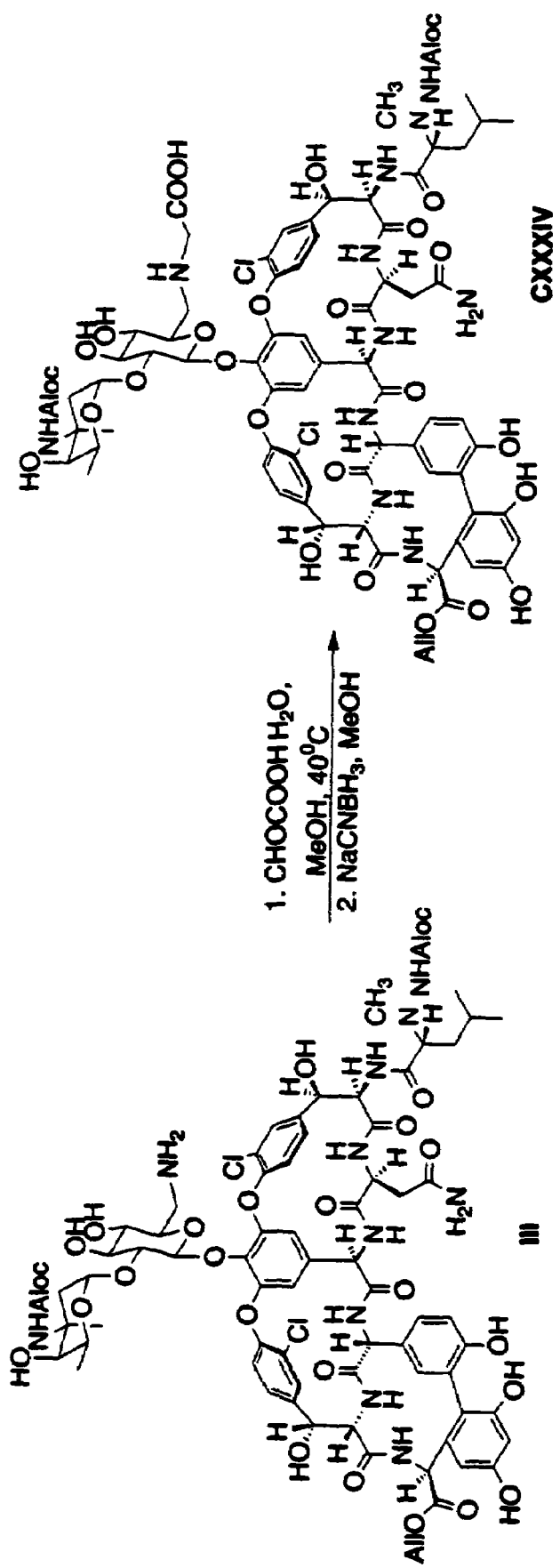
FIG. 13a illustrates a portion of a scheme for preparation of a vancomycin dimer through the glucose C-6 position.
Figure 13B:
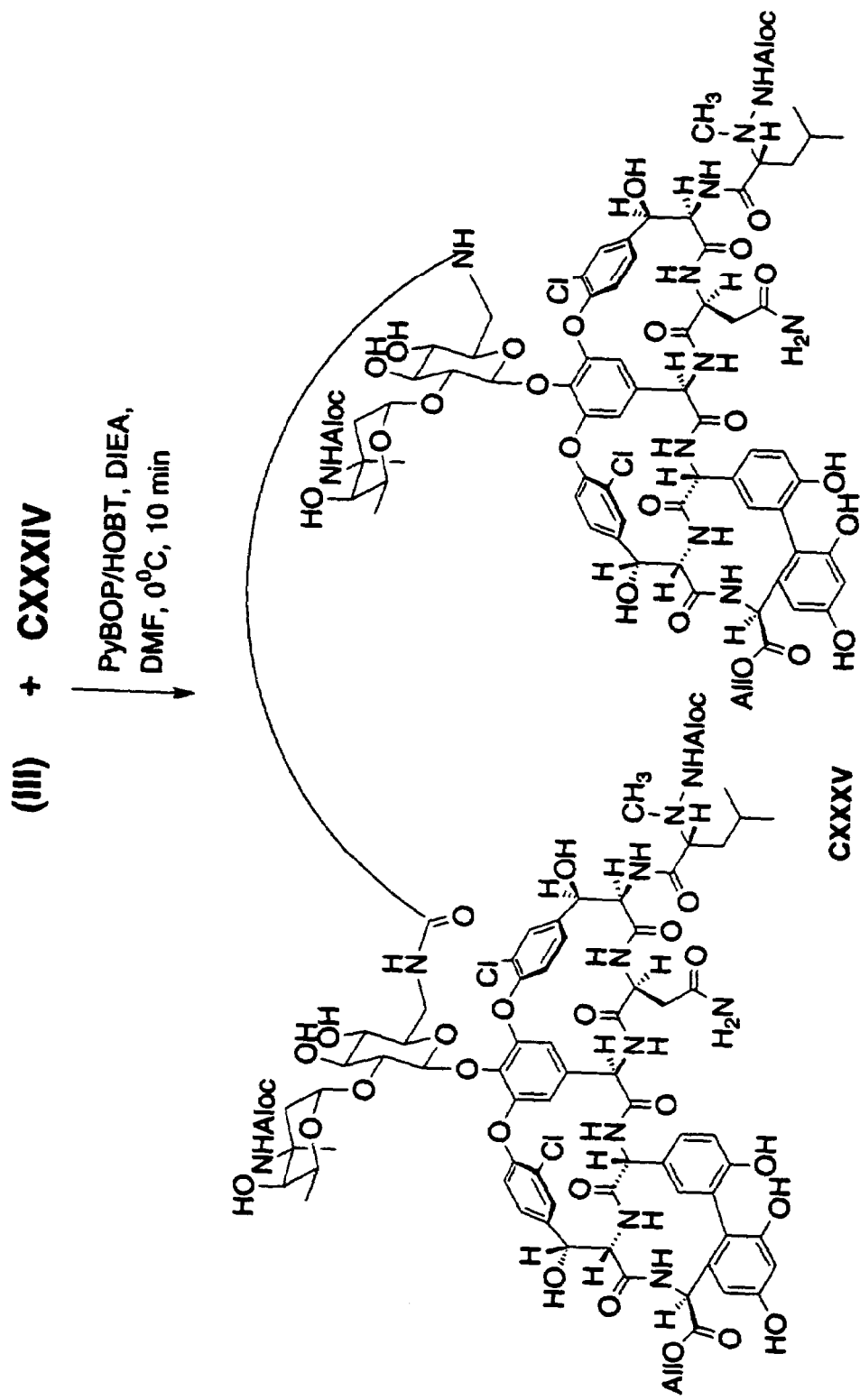
FIG. 13b illustrates a portion of a scheme for preparation of a vancomycin dimer through the glucose C-6 position.
Figure 14:
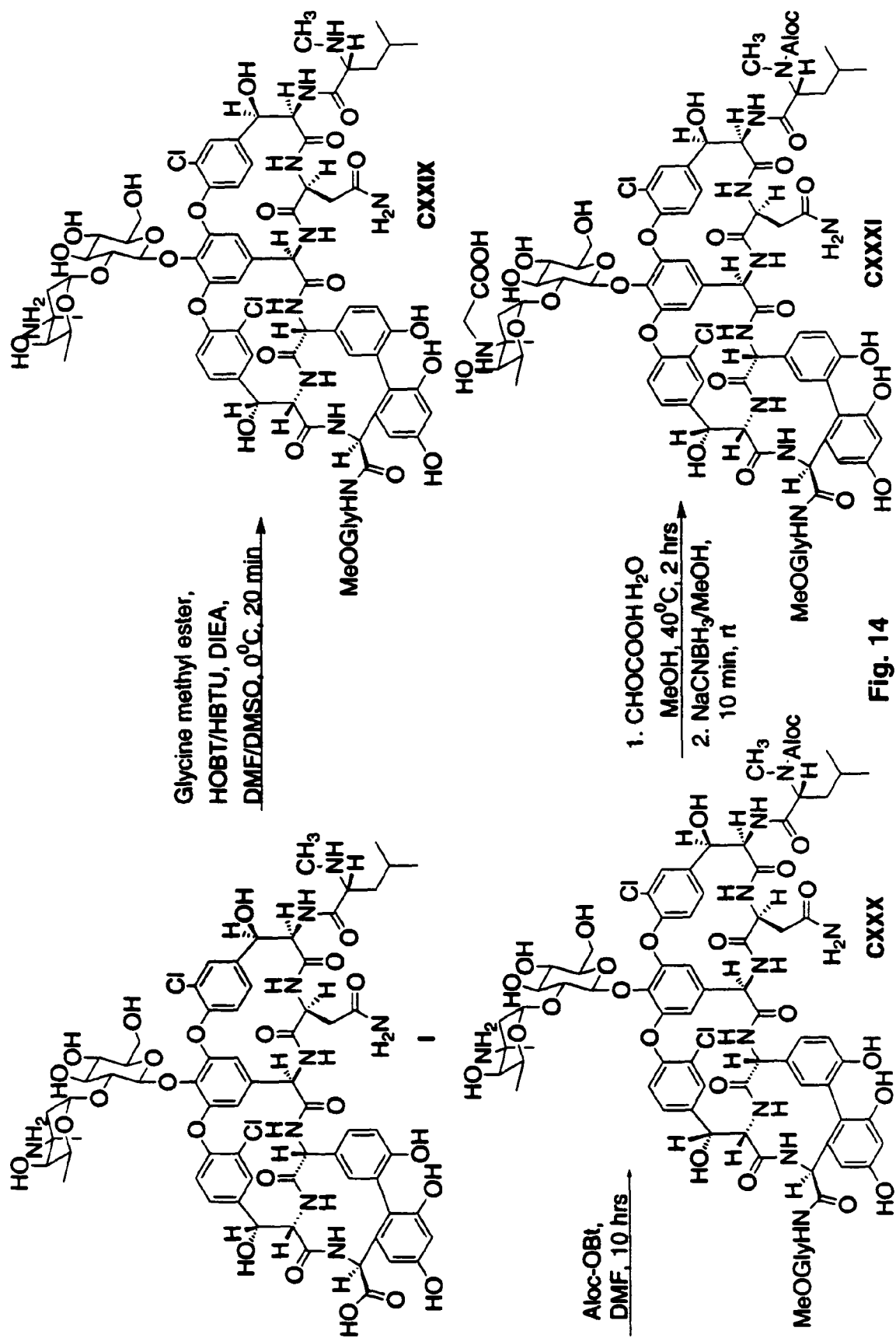
FIG. 14 illustrates the substitution of a linker group on the vancosamine nitrogen.

As shown in FIGS. 13a and 13b, compound (CXXXIV) (5 mg, 0.00292 mmol) is dissolved in 1 mL methanol and 300 μL DIEA is added. This solution is stirred for 10 minutes and then loaded to a 5 mm×30 mm polystyrene column and eluted with methanol/water/1% DIEA (0%, 10%, 20%, 30%, 40%, 50% of 10 mL each). The fractions containing compound (CXXXIV) are combined and concentrated to give a white solid. This white solid is mixed with C-6 amine (III) (10 mg, 0.00582 mmol, purified from silica gel column as free base), azeotroped with toluene 3 times and dissolved in 100 μL DMF. The reaction solution is stirred at 0° C. and DIEA (5 μL, 0.0283 mmol) is added followed by HOBt (2 mg, 0.0148 mmol) and pyBOP (5 mg, 0.00962 mmol). After 10 minutes, the reaction is directly loaded to a 10 mm×12 cm silica gel column and eluted with 30% methanol/CHCl₃ to give a crude product. The crude product is purified by reverse-phase HPLC using a PHENOMENEX LUNA C18 column (21.2× 250 mm), 5 micron particle, eluting with a 40 min. linear gradient of 20% acetonitrile/0.1% acetic acid in water to 70% acetonitrile/0.1% acetic acid in water; flow rate of 7 mL/min. and ultraviolet (UV) detection at 285 nm. The fractions containing the product are combined and evaporated to give 2 mg of dimer (CXXXV), 20%. Rf=0.7 (30% CHCL₃/MeOH). Mass Spec. [M+2Na]⁺, 3396.

Example 100

N-4-(4-Chlorophenyl)benzyl Vancosamine-glucose-C6-iminotriphenylphosphorane Vancomycin (CXXXVI)

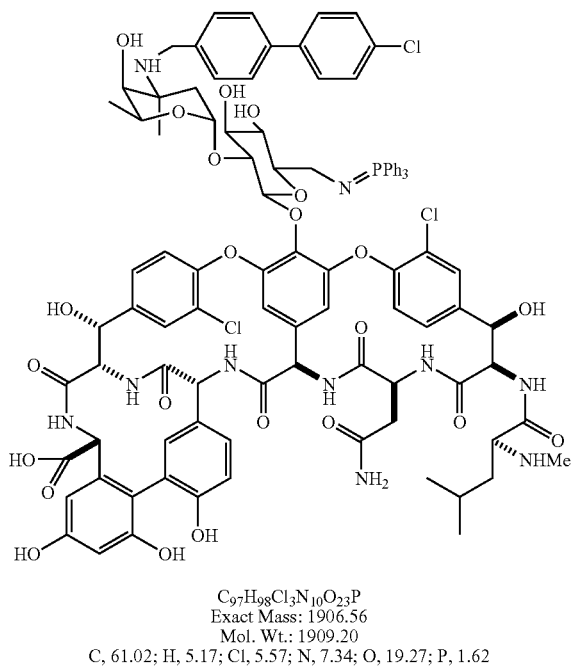

$C_{97}H_{98}Cl_3N_{10}O_{23}P$
Exact Mass: 1906.56
Mol. Wt.: 1909.20
C, 61.02; H, 5.17; Cl, 5.57; N, 7.34; O, 19.27; P, 1.62

N-chlorobiphenylvancosamine-glucose-C6-azide vancomycin (LXXIV) (15 mg, 0.00838 mmol) and PPh₃ (44.0 mg, 0.168 mmol) are suspended with THF/H₂O (1 mL, 4/1) and the mixture is stirred at 45° C. After 6 hours, 10 eq. of PPh₃ and 1 mL of THF are added. After 18 hours, the mixture is filtered then purified by ODS-HPLC (COSMOSIL 5C18-AR, 20×250 mm, and LUNA 5 μm C18(2), 21.2×250 mm, UV=285 nm, A: 0.1% TFA/H₂O, B: MeCN, 20-70% B 0-60 min., 8 mL/min, $t_r$=49 min.) to give the white amorphous solid product (CXXXVI) (5.5 mg, 0.00182 mmol, 42%) as a TFA salt. LRESI-MS 1908 (M+2H, for $C_{99}H_{98}{}^{35}Cl_3N_{10}O_{23}P)^+$, 1708 (M-N-4-(4-chlorophenyl)ben- zyl+2H)⁺, 1564 (M-N-4-(4-chlorophenyl)benzyl-vancosamine+2H)⁺. 1143 (M-N-4-(4-chlorophenyl)benzyl-vancosamine-glucose+H)⁺.

Example 101

Figure 12:
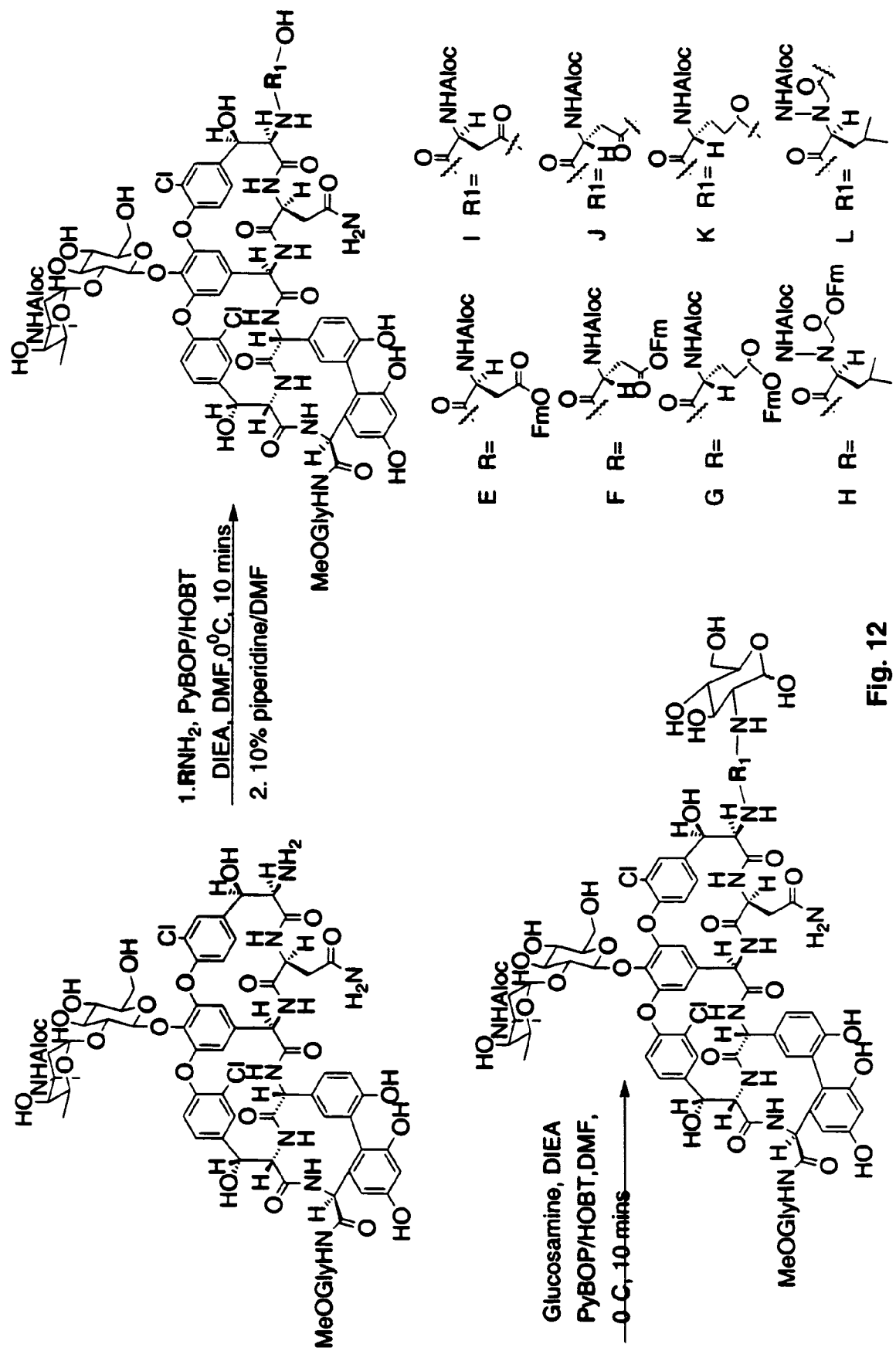
FIG. 12 illustrates reactions at the $A_2$ terminal amino group.

N,N'-diallyloxycarbonyl-methoxy-glycine-deleucine glucosamino-aspartate Vancomycin (FIG. 12, I)

As shown in FIG. 12, compound (CXXII) (20 mg, 0.0119 mmol) and glucosamine.HCl (8 mg, 0.0358 mmol) are premixed and azeotroped with toluene 3 times, dissolved in 240 μL DMF and then cooled to 0° C. Diisopropylethylamine (21 μL, 0.119 mmol) is added to the reaction vessel followed by HOBt (4.8 mg, 0.0357 mmol) and pyBOP (18 mg, 0.0358 mmol). After stirring 15 minutes, the clear solution is suspended in 45 mL acetone and stirred, centrifuged, and decanted. The solid is dried under reduced pressure and purified by reverse-phase HPLC-using a PHENOMENEX LUNA C18 column (21.2×250 mm), 5 μm particle, eluting with a 40 min. linear gradient of 0.1% acetic acid in water to 40% acetonitrile/0.1% acetic acid in water; flow rate of 7 mL/min. and ultraviolet (UV) detection at 285 nm. The fractions containing the product are combined and evaporated to give 13 mg of the title compound, 60% over 2 steps. Rf=0.15 (CHCl₃: MeOH:H₂O=3:2:0.5). Mass Spec. [M+Na]⁺,1859; [M−V+Na]⁺, 1632.

Example 102

Evaluation of Vancomycin Analogs for Anti-Microbial Activity

Evaluation of vancomycin analogs is performed using in vitro susceptibility tests and a time-kill assay. [NCCL Standard, 1993] In susceptibility tests, five strains of bacteria, two of the most important: *Staphylococcus aureus* and *Enterococcus faecalis* (both susceptible and resistant strains), and *Bacillus cereus* are chosen and bacteria viability remaining in each well is evaluated using a colorimetric assay based on the tetrazolium salt 3-(4,5-dimethyl-2-thiazolyl)-2,5-diphenyl-2H tetrazolium bromide (MIT) and minimum inhibitory concentration (MIC) values are determined as μg/mL. [Mosmann, T. (1983); Damour, O., et al. (1992); Mikami, Y., et al. (1994)] This assay gives susceptibility information quickly, efficiently, and clearly.

Promising analogs that pass this first screening are studied to evaluate their activity against resistant strains in greater detail using a time-kill assay. [Pankuch G., et al., (1994); Zelinitsky, S. et al. (1997); Mercier, R-C., et al. (1997)] This study gives the information regarding their bactericidal ability or mode of action.

Bacteria

All strains [*Bacillus cereus* (ATCC® 11778), *Staphylococcus aureus* (ATCC® 29213), Methicillin resistant *Staphylococcus aureus* (ATCC® 33591), *Enterococcus faecalis* (ATCC® 29212), and gentamicin, streptmycin, vancomycin resistant *Enterococcus faecalis* (ATCC® 51299), are purchased from REMEL (Lenexa, Kans.).

Suscelptibility Tests

MICs are determined by the microdilution method using 96-well microplates. Samples are suspended with Cation Adjusted (20 to 25 mg of Ca²⁺/mL and 10 to 12.5 mg/mL of Mg²⁺) Mueller-Hinton broth (Difco Laboratories, Detroit, Mich.) and are two-fold diluted from 5 μg/mL to 0.0025 mg/mL on microplates (12 step dilution). To each well, which contained 100 μL of cell suspension ($10^6$ CFU/mL), 100 μL of antibiotic solution is added and the plates are incubated at 37° C. for 24 h. 50 μL of MTT solution (1 mg/mL) is added to each well, then the plates are incubated under the same conditions (incubation time; 30 min for *Bacillus cereus, Staphylococcus aureus*, and Methicillin resistant *Staphylococcus aureus*; 2 hours for *Enterococcus faecalis* and Gentamicin, Streptmycin, Vancomycin *Enterococcus faecalis*). MTT is a yellow tetrazolium salt that is reduced by mitochondrial enzymes in viable cells to an insoluble blue formazan product. MIC values are evaluated by observing the lowest drug concentration to inhibit bacteria growth. Results for the anti-bacterial activities of the compounds tested are given in the Tables provided hereinbelow.

Time-kill Assays

For time-kill studies, a 24-well microplate containing 1 mL of Cation-Adjusted Mueller-Hinton broth plus 5% lysed horse blood with doubling antibiotic concentrations are used. Antibiotic concentrations are chosen to be 7 doubling dilutions above the microdilution MIC. A drug-free control well is included with each run. Lysed horse blood is prepared by freezing and thawing horse blood REMEL (Lenexa, Kans.) six times. Equal volumes of lysed blood and sterile deionized water are then mixed and centrifuged at 12000×g for 20 min. Appropriate amounts of 50% lysed blood are then added to the Cation Adjusted Mueller-Hinton broth to yield a final concentration of 5% lysed horse blood. To each well, which contained 0.5 mL of cell suspension ($10^6$ CFU/mL), 0.5 mL of antibiotic solution is added and the plates are incubated at 37° C. in a shaking incubator. Viability counts of antibiotic containing suspensions are performed at 0, 1, 2, 4, 6, 12, 24, 36, and 48 h by plating of 10-fold dilutions of 0.1 mL aliquots from each well in Cation Adjusted Mueller-Hinton broth onto Trypticase soy agar-5% sheep blood agar plates. Recovery plates are incubated for up to 48 h. The lower limit of sensitivity of colony counts is 300 CFU/mL. [Pankuch G., et al. (1994)] The results are illustrated in FIGS. 16-19, where the amount of antibiotic is given in μg/mL and is indicated by the respective symbol.

| X= | | BC | SA | MRSA | EF | VREF | CL5137 | CL5244 |
|---|---|---|---|---|---|---|---|---|
| | MIC values of glucose-C6 modified vancomycin derivatives (μg/mL) | | | | | | | |
| OH (vancomycin) | I | 1.0 | 1.0 | 1.3 | 1.3 | 5.0< | 1600 | 25 |
| I | LXX | 0.63 | 0.63 | 1.3 | 0.63 | 1.9 | 50< | 6.3 |
| N₃ | XLVI | 1.0 | 0.63 | 1.3 | 1.3 | 2.5 | 50< | 25 |
| NH₂ | XLVII | 1.0 | 0.63 | 0.32 | 1.9 | 1 | 50< | 25 |
| NHNH₂ | XLIV | 1.3 | 0.63 | 1.3 | 1.3 | 2.5 | 50< | 50 |
| HN-C(O)-CF₃ | XL | 1.3 | 0.48 | 1.0 | 1.3 | 5.0 | 50< | 25 |
| HN-C(O)-CH₂-NH₂ | XXXIV | 5.0 | 1.9 | 2.5 | 2.5 | 5.0< | nd | nd |
| HN-C(S)-NHMe | XXXII | 1.9 | 1.9 | 2.5 | 1.3 | 5.0 | nd | nd |
| S-CH(CH₃)₂ | LIII | 1.3 | 2.5 | 2.5 | 2.5 | 5.0< | nd | nd |
| S-CH₂-C(O)-OH | LXXI | 5.0< | 5.0 | 5.0< | 5.0< | 5.0< | nd | nd |
| HN-(CH₂)₉-CH₃ | XXXI | 1.3 | 1.3 | 1.3 | 0.32 | 2.5 | nd | nd |
| HN-C(O)-(CH₂)₁₀-CH₃ | XXXV | 3.8 | 2.5 | 1.3 | 0.015 | 0.16 | nd | nd |
| imidazole | LVII | 2.5 | 1.3 | 1.9 | 2.5 | 5.0 | 50< | 50 |

-continued

| X= | | BC | SA | MRSA | EF | VREF | CL5137 | CL5244 |
|---|---|---|---|---|---|---|---|---|
| tetrazole-NMe-S | LVIII | 1.3 | 1.9 | 2.5 | 2.5 | 5.0 | 50< | 50 |
| 3-amino-1H-1,2,4-triazole-5-thiol | LVI | 1.0 | 0.48 | 0.63 | 0.63 | 0.63 | 50< | 1.6 |
| 5-amino-1,3,4-thiadiazole-2-thiol | LXXVI | 0.63 | 0.63 | 0.63 | 1.3 | 5.0< | 50< | 19 |
| 4-amino-5-hydrazino-1,2,4-triazole-3-thiol | LXXVII | 0.63 | 1.3 | 1.3 | 0.63 | 1.3 | 63 | 3.2 |
| thiophene-2-carboxamide | XXXIII | 1.3 | 1.3 | 2.5 | 1.3 | 5.0 | nd | nd |
| phenylthio | LIV | 1.3 | 1.0 | 0.63 | 1.3 | 2.5 | 50< | 13 |
| 4-bromophenylthio | LIX | 1.3 | 0.63 | 1.0 | 1.0 | 0.32 | 50< | 6.3 |
| 3-chlorophenylthio | LV | 0.63 | 0.48 | 0.32 | 0.63 | 0.63 | 50< | 3.2 |
| 4-(trifluoromethyl)pyrimidin-2-ylthio | LX | 5.0 | 5.0 | 5.0 | 2.5 | 2.5 | 50< | 50< |
| 4-aminopyrimidin-2-ylthio | LXI | 0.63 | 0.63 | 1.3 | 0.63 | 0.63 | 50< | 3.2 |
| 4,6-diaminopyrimidin-2-ylthio | LXII | 0.63 | 1.9 | 2.5 | 1.3 | 1.3 | 50< | 6.3 |

-continued

| X= | | BC | SA | MRSA | EF | VREF | CL5137 | CL5244 |
|---|---|---|---|---|---|---|---|---|
| 2-mercapto-6-amino-pyrimidin-4-ol | LXIII | 5.0 | 5.0 | 5.0< | 2.5 | 5.0< | 50< | 6.3 |
| 2-mercapto-6-methyl-pyrimidin-4-ol | LXXVIII | 0.63 | 1.0 | 1.3 | 0.63 | 2.5 | 50< | 6.3 |
| 3-mercapto-6-methyl-1,2,4-triazin-5-ol | LXIV | 0.08 | 0.24 | 0.32 | 0.12 | 0.16 | 500< | 1.2 |
| 5-chloro-2-hydroxybenzylamine | XXXIX | 1.3 | 1.3 | 1.3 | 2.5 | 5.0< | 50< | 25 |
| 2-iodobenzamide | XXXVI | 1.3 | 1.3 | 2.5 | 1.3 | 2.5 | nd | nd |
| mesitylenesulfonyl | XLI | 1.3 | 0.63 | 1.3 | 1.3 | 1.3 | 50< | 6.3 |
| 2-mercapto-5-methoxybenzimidazole | LXV | 0.63 | 1.9 | 2.5 | 0.63 | 2.5 | 50< | 13 |
| 2-mercapto-5-chlorobenzothiazole | LXVI | 0.16 | 0.63 | 1.3 | 0.24 | 0.32 | 50 | 0.4 |
| quinoxaline-2-carboxamide | XXXVII | 0.32 | 0.32 | 0.63 | 0.32 | 0.32 | 50< | 1.6 |
| 4'-chlorobiphenyl-4-methylamine | XXIX | 0.63 | 0.63 | 0.63 | 0.63 | 0.63 | 50 | 0.6 |

-continued
| X= | | BC | SA | MRSA | EF | VREF | CL5137 | CL5244 |
|---|---|---|---|---|---|---|---|---|
| 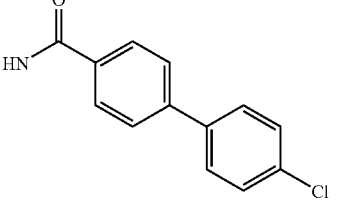 | XXXVIII | 0.32 | 1.0 | 0.63 | 0.32 | 0.16 | 50< | 0.4 |
| 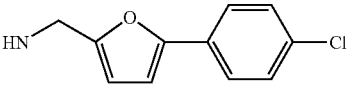 | XXX | 0.63 | 0.32 | 0.32 | 0.63 | 0.63 | 50< | 1.6 |
| 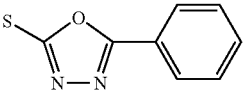 | LXVII | 0.32 | 0.48 | 1.3 | 0.63 | 0.63 | 50< | 3.2 |
| 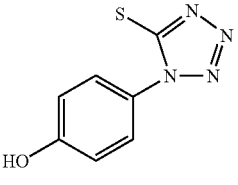 | LXVIII | 1.3 | 2.5 | 2.5 | 2.5 | 5.0< | 50< | 13 |
| 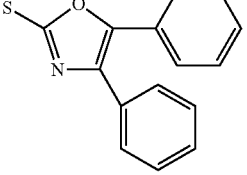 | LXIX | 1.3 | 1.9 | 2.5 | 0.24 | 0.32 | 50 | 0.6 |
| 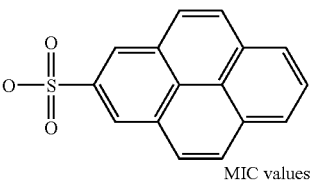 | XLV | 1.3 | 2.5 | 1.3 | 0.63 | 0.48 | 50< | 3.2 |
| MIC values of glucose-C6 modified N-4-(4-chlorophenyl)benzyl vancomycin derivatives (μg/mL) | | | | | | | | |
|---|---|---|---|---|---|---|---|---|
| OH | | 0.08 | 0.16 | 0.08 | 0.08 | 0.08 | 13 | 0.4 |
| I | LXXIIa | 0.32 | 0.48 | 0.63 | 0.16 | 0.32 | 13 | 0.3 |
| $N_3$ | LXXIV | 0.32 | 1.0 | 0.48 | 0.16 | 0.16 | 13 | 0.3 |
| $NH_2$ | LXXV | 0.16 | ≦.03 | ≦.03 | ≦.03 | 0.63 | 2 | ≦.03 |
| N=$PPh_3$ | CXXXVI | 1.3 | 1.3 | 0.32 | 0.32 | 0.16 | 5.0 | 0.32 |
| 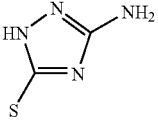 | LXXIII | 0.48 | 1.9 | 1.0 | 0.16 | 0.08 | 3.2 | 0.2 |
| 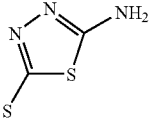 | LXXXIII | 0.32 | 0.48 | 0.48 | 0.16 | 0.32 | 3.2 | 0.2 |
| 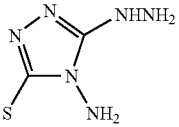 | LXXXIV | 0.08 | 0.63 | 0.48 | 0.12 | 0.16 | 6.3 | 0.2 |

-continued
| X= | | BC | SA | MRSA | EF | VREF | CL5137 | CL5244 |
|---|---|---|---|---|---|---|---|---|
| 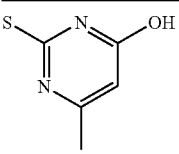 | LXXXV | 1.3 | 1.9 | 1.3 | 0.32 | 0.32 | 6.3 | 0.4 |
| 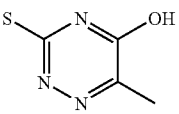 | LXXXVI | 0.32 | 1.0 | 1.0 | 0.12 | 0.16 | 3.2 | 0.4 |
| 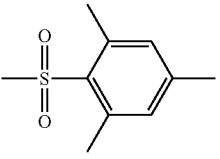 | XLII | 1.9 | 5.0< | 5.0< | 1.0 | 1.9 | 6.3 | 0.8 |
| 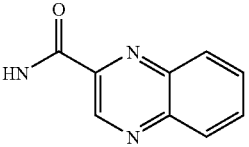 | LII | 1.9 | 5.0 | 5.0 | 0.08 | 0.16 | 3.2 | 0.2 |
| 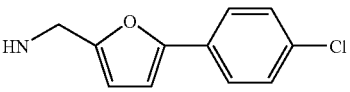 | L | 3.8 | 5.0 | 2.5 | 1.3 | 1.0 | 6.3 | 0.8 |
| 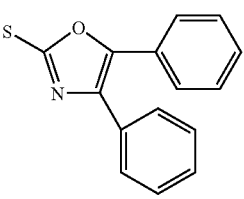 | LXXXVII | 5.0< | 5.0< | 5.0< | 5.0 | 5.0 | 50 | 10 |
MIC values of glucose-C6 modified N-decyl vancosamine vancomycin derivatives (µg/mL)
| X= | | BC | SA | MRSA | EF | VREF | CL5137 | CL5244 |
|---|---|---|---|---|---|---|---|---|
| OH | | 0.32 | 0.63 | 0.48 | 0.16 | 0.32 | 25 | 3.2 |
| I | | 1.0 | 1.3 | 0.32 | 0.08 | 0.12 | 6.3 | 0.4< |
| 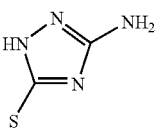 | LXXII | 2.5 | 3.8 | 1.9 | 0.32 | 0.32 | 6.3 | 0.3 |
| 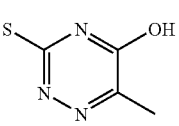 | LXXIX | 0.63 | 2.5 | 1.3 | 0.32 | 0.63 | 25 | 0.6 |
| 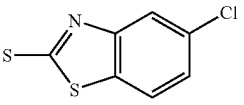 | LXXX | 5.0 | 5.0< | 5.0 | 1.3 | 2.5 | 50 | 2.4 |
| 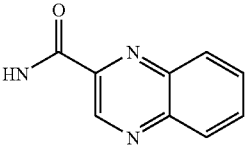 | LI | 2.5 | 5.0< | 5.0< | 0.63 | 1.3 | 6.3 | 0.2 |

-continued

| X= | | BC | SA | MRSA | EF | VREF | CL5137 | CL5244 |
|---|---|---|---|---|---|---|---|---|
| 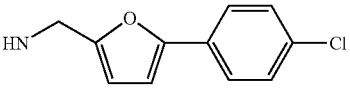 | XLIX | 3.8 | 5.0 | 2.5 | 1.9 | 1.3 | 13 | 0.8 |
| 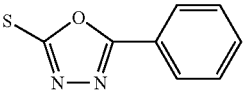 | LXXXI | 2.5 | 5.0< | 2.5 | 0.32 | 0.63 | 16 | 0.8 |
| 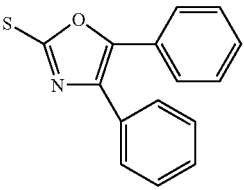 | LXXXII | 5.0< | 5.0< | 5.0< | 5.0< | 5.0< | 50< | 13 |

BC; *Bacillus ceres* ATCC11778
SA; *Staphylococcus aureus* ATCC29213
MRSA; *Staphylococcus aureus* ATCC3359, Methicillin resistance
EF; *Enterococcus faecalis* ATCC29212
VREF; *Enterococcus faecalis* ATCC51299, vancomycin resistance
CL5137; *Enterococcus faecium* CL5137, VanA
CL5244; *Enterococcus faecalis* CL5244, VanB It should be apparent from the instant teaching, including the biological data presented above, that in one embodiment of the invention replacement of one or more natural substituents of a hexose residue, preferably at the C6 position of a glucose residue, with an unnatural substituent enhances the antibiotic activity of the resulting modified glycopeptide derivative across a cross section of infectious microorganisms but especially against vancomycin resistant strains. In certain embodiments of the invention, further substitutions and/or modifications elsewhere in the core structure of the starting glycopeptide antibiotic modulate the antibiotic activity, providing even greater enhancements of the antibiotic activity in given strains of infections microorganisms. In preferred embodiments of the invention, changes at glucose-C6 are combined with further substitutions at the amino group of a vancosamine residue.

The preceding Examples are intended to describe certain preferred embodiments of the present invention. It should be appreciated, however, that obvious additions and modifications of the invention will be apparent to one skilled in the art. The invention is not limited except as set forth in the claims.

REFERENCES CITED

Cohen M. (1992), *Science*, 257:1050
Neu H. (1992), *Science*, 257:1064.
Axelsen, P. H. et al. (1997), *J. Am. Chem. Soc. (JACS)*, 119:1516.
Westwell et al. (1995), *J. Antibiotics*, 48:1292.
Walsh C. (1993), *Science*, 261:308.
Malabarba A., et al. (1997a), "Structural Modifications of Glycopeptide Antibiotics," *Med. Res. Rev.*, 17(1):69-137.
Nagarajan R., et al. (1988), "Selective cleavage of vancosamiune, glucose, and N-methyl-leucine from vancomycin and related antibiotics," *J.Chem.Soc.Chem.Comm.*, 1306-1307.
Nagarajan R. (1991), "Antibacterial Activities and Modes of Action of Vancomycin and Related Glycopeptides," *Antimicr. Agents Chemother.*, 35:605-609.
Nagarajan R. (1993), "Structure-activity relationships of vancomycin-type glycopeptide antibiotics," *J. Antibiotics*, 46:1181-1195.
Yan L., et al. (1994), *JACS*, 116: 6953.
Prowse W., et al. (1995), *Biochemistry*, 34:9632-9644.
Pierce C., et al. (1995), *J.Chem.Soc. Perkin Trans.*, 2:153-157.
Williams D., et al. (1988), "Molecular Basis of the Activity of Antibiotics of the Vancomycin Group," *Biochem. Pharm.*, 37:133-141.
Kannan R., et al. (1988), "Function of the Amino Sugar and N-terminal Amino Acid of the Antibiotic Vancomycin in its Complexation with Cell Wall Peptides," *JACS*, 110: 2946-2953.
Mackay J., et al. (1994), "Dissection of the contributions toward Dimerization of Glycopeptide Antibiotics," *JACS*, 116:4573.
Williams D. et al., (1993), "Toward an estimation of binding constants in aqueous solution: Studies of associations of vancomycin group antibiotics," *PNAS USA*, 90:1172-1178.
Gerhard U., et al. (1993), "The role of the sugar and chlorine substituents in the dimerization of vancomycin antibiotics," *JACS*, 115:232-237.
Beauregard D., et al. (1995), "Dimerization and Membrane Anchors in Extracellular Targeting of Vancomycin Group Antibiotics," *Antimicr.Agents & Chemo.*, 39: 781-785.
Loll P., et al. (1997), "Simultaneous Recognition of a Carboxylate-containing Ligand and an Intramolecular Surrogate Ligand in the Crystal Structure of an Asymmetric Vancomycin Dimer," *JACS*, 119:1516-1522.
Felmingham, D. (1993), "Towards the ideal glycopeptide." *J.Antimicrob. Chemother.*, 32, 663-666.
Cooper, R. et al. (1996), "Chapter 14. Semisynthetic Glycopeptide Antibiotics," in *Ann. Rept. In Med. Chem.*—31. Academic Press, Inc., 131-140.
Malabarba, A. et al. (1997b), "Glycopeptide resistance in multiple antibiotic-resistant Gram-positive bacteria: a current challenge for novel semi-synthetic glycopeptide derivatives," *Eur. J. Med Chem.*, 32:459-478.

Allen N. et al., (1997), "The Role of Hydrophobic Side Chains as Determinants of Antibacterial Activity of Semisynthetic Glycopeptide Antibiotics," *J.Antibiot.,* 50: 677-684.

Pavlov A., et al. (1993), "Synthesis and Biological Activity of Derivatives of Glycopeptide Antibiotics Eremomycin and Vancomycin Nitrosated, Acylated or Carbamoylated at the N-terminal," *J.Antibiot.,* 46:1731-1739.

National Committee for Clinical Laboratory (NCCL) Standard. 1993. Methods for Dilution Antimicrobial Susceptibility Tests for Bacteria that grow Aerobically-Third Edition; Approved Standard. NCCLS document M7-A3. National Committee for Clinical Laboratory Standard, Villanova, Pa.

Mosmann, T. (1983), "Rapid colorimetric assay for cellular growth and survival; application to proliferation and cytotoxicity assays," *J. Immunol. Methods.* 65: 55-63.

Damour, O., et al. (1992) "Cytotoxicity evalution of antiseptics and antibiotics on cultured human fibroblasts and keratinocytes," *Burns* 18:479-485.

Mikami, Y., et al. (1994) "Comparsion of in vitro antifungal activity of itraconazole and hydroxy-itraconazole by colorimetric MTT assay," *MYCOSES* 37:27-33.

Milewski, W. M. et al. (1996) "Overproduction of a 37-Kilodalton Cytoplasmic Protein Homologous to NAD+-Linked D-Lactate Dehydrogenase Associated with Vancomycin Resistance in *Staphylococcus aureus*," *Antimicrobial Agents and Chemotherapy* 40:166-172

Thompson, L. A. and Ellman, J. A. (1996) "Synthesis and Applications of Small Molecule Libraries," *Chem. Rev.* 96:555-600.

Gallop. M. A. et al. (1994) "Applications of Combinatorial Technologies to Drug Discovery. 1. Background and Peptide Combinatorial Libraries," *J. Med. Chem.* 37:1233-1251.

Gordon, E. M. et al. (1994) "Applications of Combinatorial Technologies to Drug Discovery. 2. Combinatorial Organic Synthesis, Library Screening Strategies, and Future Directions," *J. Med. Chemt* 37:1385-1401.

Terrett, N. K. et al. (1995) "Combinatorial Synthesis—The Design of Compound Libraries and their Application to Drug Discovery," *Tetrahedron* 51:8135-8173.

Betaneli, V. I. et al. (1982) "A Convenient Synthesis of 1,2-O-Ethylidene Derivatives of Carbohydrates," *Carbohydrate Research* 107:285-291.

Williams, D. H. et al. (1998) "An Analysis of the Origins of a Cooperative Binding Energy of Dimerization," *Science* 280: 711-714.

```
                       SEQUENCE LISTING

<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: synthetic
                        glycopepide
<220> FEATURE:
<221> NAME/KEY: PEPTIDE
<222> LOCATION: (1)..(7)
<223> OTHER INFORMATION: Amino acid residues 2, 4 and 6 each bear an
                        aromatic side chain, amino acids 1, 3, 5 and 7
                        may be any amino acid residue

<400> SEQUENCE: 1

Xaa Xaa Xaa Xaa Xaa Xaa Xaa
  1               5
```

Pankuch, G., et al. (1994) "Study of comparative antipneumococcal activities of penicillin G, RP 59500, erythromycin, sparfloxacin, and vancomycin by-using time-kill methodology," *Antimicrob. Agents Chemother.* 38: 2065-2072.

Zelenitsky, S., et al. (1997) "Time-kill curves for a semisynthetic glycopeptide, LY333328, against vancomycin-susceptible and vancomycin-resistant *Enterococcus faecium* strains," *Antimicrob. Agents Chemother.* 41:1407-1408.

Mercier, R-C., et al. (1997) "Pharmacodynamic evaluation of a new glycopeptide, LY333328, and in vitro activity against *Staphylococcus aureus* and *Enterococcus faecium,*" *Antimicrob. Agents Chemother.* 41:1307-1312.

Gerhard, U., et al. (1993) "The role of the sugar and chlorine substituents in the dimerization of vancomycin antibiotics," *J. Am. Chem. Soc.* 115: 232-237.

Solenberg, P. J. et al. (1997) "Production of hybrid glycopeptide antibiotics in vitro and in *Streptomyces toyocaensis,*" *Chem. Biol.* 4:195-202.

What is claimed is:

1. A glycopeptide of the formula $A_1$-$A_2$-$A_3$-$A_4$-$A_5$-$A_6$-$A_7$, wherein the groups $A_1$ to $A_7$ comprise the heptapeptide structure of naturally occurring vancomycin;

and wherein the group $A_4$ is linked via a glycosidic bond to a disaccharide having a glucose residue directly attached to said $A_4$ residue, wherein said glucose residue bears an N-substituted aminohexose residue selected from the group consisting of allyloxycarbonyl, N-decyl, and N-4-(4-chlorophenyl)benzyl and a substituent of the formula YXR, attached to the C-6 position of said glucose;

wherein the group Y is a single bond, the group X is O, $NR_1$, S, $SO_2$, C(O)O, C(O)S, C(S)O, C(S)S, C($NR_1$)O, C(O)$NR_1$, or halo (in which case Y and R are absent); and R and $R_1$ are independently hydrogen, alkyl, aryl, aralkyl, alkanoyl, aroyl, aralkanoyl, heterocyclic, heterocyclic-carbonyl, heterocyclic-alkyl, heterocyclic-alkyl-carbonyl, alkylsulfonyl or arylsulfonyl; and any pharmaceutically acceptable salts thereof provided that said substituent of the formula YXR is not hydroxyl.

2. The glycopeptide of claim 1 wherein Y is a single bond and X is O, $NR_1$, S or SO2.

3. The glycopeptide of claim 2 wherein X is $NR_1$.

4. The glycopeptide of claim 2 in which the N-substituted aminohexose residue is allyloxycarbonyl.

5. The glycopeptide of claim 3 in which the N-substituted aminohexose residue is N-decyl.

6. The glycopeptide of claim 2 in which said N-substituted aminohexose residue is N-4-(4-chlorophenyl)benzyl.

* * * * *